US011325889B2

(12) United States Patent
Ammirante et al.

(10) Patent No.: US 11,325,889 B2
(45) Date of Patent: May 10, 2022

(54) SUBSTITUTED 3-((3-AMINOPHENYL) AMINO)PIPERIDINE-2,6-DIONE COMPOUNDS, COMPOSITIONS THEREOF, AND METHODS OF TREATMENT THEREWITH

(71) Applicant: Celgene Corporation, Summit, NJ (US)

(72) Inventors: Massimo Ammirante, San Diego, CA (US); Sogole Bahmanyar, Rancho Santa Fe, CA (US); Matthew D. Correa, San Diego, CA (US); Virginia Grant, San Diego, CA (US); Joshua Hansen, San Diego, CA (US); Evan J. Horn, San Diego, CA (US); Timothy S. Kercher, Longmont, CO (US); Christopher Mayne, San Diego, CA (US); Mark A. Nagy, San Diego, CA (US); Rama Krishna Narla, San Diego, CA (US); Surendra Nayak, San Diego, CA (US); Stephen Norris, San Diego, CA (US); Patrick Papa, San Diego, CA (US); Veronique Plantevin-Krenitsky, San Francisco, CA (US); John J. Sapienza, San Diego, CA (US); Brandon W. Whitefield, San Diego, CA (US); Shuichan Xu, San Diego, CA (US)

(73) Assignee: Celgene Corporation, Summit, NJ (US)

(*) Notice: Subject to any disclaimer, the term of this patent is extended or adjusted under 35 U.S.C. 154(b) by 0 days.

(21) Appl. No.: 16/719,217

(22) Filed: Dec. 18, 2019

(65) Prior Publication Data

US 2020/0199074 A1 Jun. 25, 2020

Related U.S. Application Data

(63) Continuation of application No. 62/879,927, filed on Jul. 29, 2019.

(60) Provisional application No. 62/782,281, filed on Dec. 19, 2018.

(51) Int. Cl.
*C07D 211/94* (2006.01)
*C07D 233/86* (2006.01)
*C07D 211/98* (2006.01)
*C07D 233/30* (2006.01)

(52) U.S. Cl.
CPC .......... *C07D 211/94* (2013.01); *C07D 211/98* (2013.01); *C07D 233/30* (2013.01); *C07D 233/86* (2013.01)

(58) Field of Classification Search
CPC .................................................. C07D 211/94
USPC ....................................................... 546/210
See application file for complete search history.

(56) References Cited

U.S. PATENT DOCUMENTS

| 5,908,843 | A | 6/1999 | Gante et al. |
| 2008/0064876 | A1 | 3/2008 | Muller et al. |
| 2011/0306615 | A1 | 12/2011 | Tachibana et al. |
| 2013/0116269 | A1 | 5/2013 | Ivachtchenko et al. |
| 2014/0112922 | A1 | 4/2014 | DeLisa et al. |
| 2014/0356322 | A1 | 12/2014 | Crews et al. |
| 2015/0274738 | A1 | 10/2015 | Gray et al. |
| 2015/0291562 | A1 | 10/2015 | Crew et al. |
| 2016/0058872 | A1 | 3/2016 | Crew et al. |
| 2016/0096818 | A1 | 4/2016 | Muller et al. |
| 2016/0214972 | A1 | 7/2016 | Jin et al. |
| 2016/0272639 | A1 | 9/2016 | Crew et al. |
| 2017/0008904 | A1 | 1/2017 | Crew et al. |
| 2017/0065719 | A1 | 3/2017 | Qian et al. |
| 2018/0008587 | A1 | 1/2018 | Bignan |
| 2018/0085465 | A1 | 3/2018 | Bradner et al. |
| 2018/0093990 | A1 | 4/2018 | Gray et al. |
| 2018/0099940 | A1 | 4/2018 | Crew et al. |
| 2018/0100001 | A1 | 4/2018 | Verdine et al. |
| 2018/0179164 | A1 | 6/2018 | Ivachtchenko et al. |

(Continued)

FOREIGN PATENT DOCUMENTS

CN 109422725 A 3/2019
CN 109651256 A 4/2019

(Continued)

OTHER PUBLICATIONS

Venkatesh, J. Pharm. Sci. 89, 145-154 (2000) (p. 146.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Dorwald F. A. Side Reactions in Organic Synthesis, 2005, Wiley: VCH, Weinheim p. IX of Preface p. 1-15.*

(Continued)

*Primary Examiner* — Nizal S Chandrakumar
(74) *Attorney, Agent, or Firm* — Jones Day

(57) ABSTRACT

Provided herein are piperidine dione compounds having the following structure:

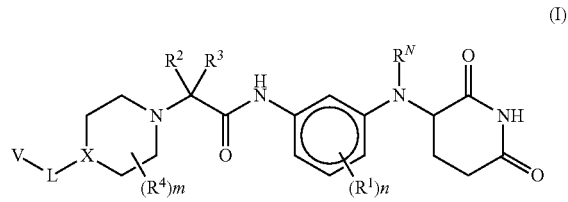

wherein $R^N$, $R^1$, $R^2$, $R^3$, $R^4$, X, L, V, m, and n are as defined herein, compositions comprising an effective amount of a piperidine dione compound, and methods for treating or preventing an androgen receptor mediated disease.

35 Claims, No Drawings

(56) References Cited

U.S. PATENT DOCUMENTS

| | | |
|---|---|---|
| 2018/0118733 A1 | 7/2018 | Harling et al. |
| 2018/0215731 A1 | 8/2018 | Crew et al. |
| 2018/0298021 A1 | 10/2018 | Bignan et al. |
| 2019/0071415 A1 | 3/2019 | Bradner et al. |
| 2019/0076542 A1 | 3/2019 | Phillips et al. |
| 2020/0199073 A1 | 6/2020 | Ammirante et al. |

FOREIGN PATENT DOCUMENTS

| | | |
|---|---|---|
| FR | 2768729 A1 | 3/1999 |
| FR | 2768728 A1 | 12/1999 |
| WO | WO 2007/044804 A2 | 4/2007 |
| WO | WO 2012/082837 A1 | 6/2012 |
| WO | WO 2014/120815 A1 | 8/2014 |
| WO | WO 2018/067764 A1 | 4/2018 |
| WO | WO 2018/089736 A1 | 5/2018 |
| WO | WO 2018/098280 A1 | 5/2018 |
| WO | WO 2018/113584 A1 | 6/2018 |
| WO | WO 2018/237026 A1 | 12/2018 |
| WO | WO 2019/106691 A1 | 6/2019 |
| WO | WO 2019/113006 A1 | 6/2019 |
| WO | WO 2019/228341 A1 | 12/2019 |

OTHER PUBLICATIONS

Brinkmann et al., "Mechanisms of androgen receptor activation and function," *J. Steroid Biochem. Mol. Biol.*, 69:307-313 (1999).

Chen et al., "Anti-androgens and androgen-depleting therapies in prostate cancer: new agents for an established target," *Lancet Oncol.*, 10:981-991 (2009).

Mills, Maintaining and reprogramming genomic androgen receptor activity in prostate cancer, *Nat. Rev. Cancer*, 14:187-198 (2014).

Murtha et al., "Androgen induction of a human prostate-specific kallikrein, hklk2: characterization of an androgen response element in the 5' promoter region of the gene," *Biochemistry*, 32:6459-6464 (1993).

Taplin, "Drug insight: role of the androgen receptor in the development and progression of prostate cancer," *Nat. Clin. Pract. Oncol.*, 4:236-244 (2007).

Tran et al., "Development of a second-generation antiandrogen for treatment of advanced prostate cancer," Science, 324:787-790 (2009).

Wirth et al., "Antiandrogens in the treatment of prostate cancer," *Eur. Urol.*, 51(2):306-313 (2007).

\* cited by examiner

SUBSTITUTED 3-((3-AMINOPHENYL)AMINO)PIPERIDINE-2,6-DIONE COMPOUNDS, COMPOSITIONS THEREOF, AND METHODS OF TREATMENT THEREWITH

RELATED APPLICATIONS

This application claims the benefit of U.S. Provisional Application Nos. 62/782,281, filed Dec. 19, 2018 and 62/879,927 filed Jul. 29, 2019, the disclosures of each of which are incorporated herein by reference in their entireties.

FIELD

Provided herein are certain 3-((3-aminophenyl)amino)piperidine-2,6-dione compounds, compositions comprising an effective amount of such compounds, and methods for treating or preventing androgen receptor mediated diseases, comprising administering an effective amount of such 3-((3-aminophenyl)amino)piperidine-2,6-dione compounds to a subject in need thereof. Also provided herein are the compounds and compositions for use in these methods.

BACKGROUND

Androgen receptor signaling is known to play a crucial role in the pathogenesis of prostate cancer and is involved in the development of other androgen receptor positive cancers (Chen Y et al., Lancet Oncol, 2009, 10:981-91; Mills I G, Nat Rev Cancer, 2014, 14:187-98; Taplin M E, Nat Clin Pract Oncol, 2007, 4:236-44; Wirth M P et al., Eur Urol, 2007, 51(2):306-13). The inhibition of androgen receptor signaling with anti-androgens that antagonize the androgen receptor has been used or proposed for the treatment of prostate cancer.

The androgen receptor normally resides in the cytoplasm bound to chaperones such as HSP90 (Brinkmann A O et al., J Steroid Biochem Mol Biol, 1999, 69:307-13). Upon binding of dihydrotestosterone (DHT) the androgen receptor changes its conformation and translocates to the nucleus, where it binds androgen responsive elements (AREs) driving the transcription of canonical targets such as KLK3 (also known as prostate specific antigen PSA), TMPRSS2 and KLK2 (Tran C et al., Science, 2009, 324:787-90; Murtha P et al., Biochemistry (Mosc.), 1993, 32:6459-64).

Prostate cancer (PCa) is one of the most frequently diagnosed non-cutaneous cancers among men in the US and is the second most common cause of cancer deaths with more than 200,000 new cases and over 30,000 deaths each year in the United States.

Androgen-deprivation therapy (ADT) is the standard of treatment for advanced PCa. Patients with advanced PCa undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

There remains a significant need for safe and effective methods of treating, preventing and managing AR mediated diseases, particularly for AR mediated diseases that are refractory to standard treatments, such as surgery, radiation therapy, chemotherapy and hormonal therapy, while reducing or avoiding the toxicities and/or side effects associated with conventional therapies.

Citation or identification of any reference in this section of this application is not to be construed as an admission that the reference is prior art to the present application.

SUMMARY

Provided herein are compounds having the following formula (I):

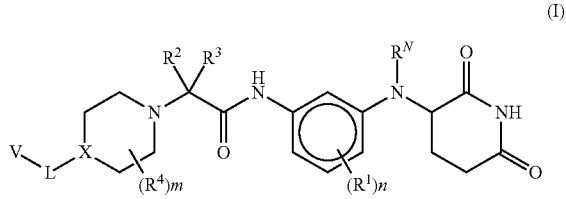

or a pharmaceutically acceptable salt, tautomer, isotopolog, or stereoisomer thereof, wherein $R^N$, $R^1$, $R^2$, $R^3$, $R^4$, X, L, V, m and n are as defined herein.

A compound of formula (I) or a pharmaceutically acceptable salt, tautomer, isotopolog, or stereoisomer thereof (each being referred to herein as a "Piperidine Dione Compound") is useful for treating or preventing androgen receptor mediated diseases in a subject.

In one aspect, provided herein are Piperidine Dione Compounds as described in the instant disclosure, such as, for example, in Table 1.

In one aspect, provided herein are pharmaceutical compositions comprising an effective amount of a compound as described herein, and a pharmaceutically acceptable carrier, excipient or vehicle. In one aspect, provided herein are pharmaceutical compositions comprising an effective amount of a Piperidine Dione Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing androgen receptor mediated diseases in a subject, comprising administering to a subject in need thereof an effective amount of a compound as described herein; and a pharmaceutically acceptable carrier, excipient or vehicle. In one aspect, provided herein are methods for treating or preventing androgen receptor mediated diseases in a subject, comprising administering to a subject in need thereof an effective amount of a Piperidine Dione Compound as described herein; and a pharmaceutically acceptable carrier, excipient or vehicle. In another aspect, provided herein are compounds for use in methods of treatment of androgen receptor mediated diseases. In another aspect, provided herein are Piperidine Dione Compounds for use in methods of treatment of androgen receptor mediated diseases.

In another aspect provided herein are methods for preparing compounds as described herein. In another aspect provided herein are methods for preparing Piperidine Dione Compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, the alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy; aryloxy; heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkyl alkylamino; imino; imido; amidino; guanidino; enamino; acylamino; sulfonylamino; urea; nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)$_2$. In certain embodiment, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d] oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocyclylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —$NH_2$, —$NH(R^{\#})$, or —$N(R^{\#})_2$, wherein each $R^{\#}$ is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or —N(alkyl)$_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

A "carboxy" group is a radical of the formula: —C(O)OH.

As used herein and unless otherwise specified, an "acyl" group is a radical of the formula: —C(O)(R$^\#$) or —C(O)H, wherein R$^\#$ is defined above. A "formyl" group is a radical of the formula: —C(O)H.

As used herein and unless otherwise specified, an "amido" group is a radical of the formula: —C(O)—NH$_2$, —C(O)—NH(R$^\#$), —C(O)—N(R$^\#$)$_2$, —NH—C(O)H, —NH—C(O)—(R$^\#$), —N(R$^\#$)—C(O)H, or —N(R$^\#$)—C(O)—(R$^\#$), wherein each R$^\#$ is independently defined above.

In one embodiment, an "amido" group is an "aminocarbonyl" group, which is a radical of the formula: —C(O)—NH$_2$, —C(O)—NH(R$^\#$), —C(O)—N(R$^\#$)$_2$, wherein each R$^\#$ is independently defined above.

In one embodiment, an "amido" group is an "acylamino" group, which is a radical of the formula: —NH—C(O)H, —NH—C(O)—(R$^\#$), —N(R$^\#$)—C(O)H, or —N(R$^\#$)—C(O)—(R$^\#$), wherein each R$^\#$ is independently defined above.

A "sulfonylamino" group is a radical of the formula: —NHSO$_2$(R$^\#$) or —N(alkyl)SO$_2$(R$^\#$), wherein each alkyl and R$^\#$ are defined above.

As used herein and unless otherwise specified, an "ester" group is a radical of the formula: —C(O)—O—(R$^\#$) or —O—C(O)—(R$^\#$), wherein R$^\#$ is defined above.

In one embodiment, an "ester" group is an "alkoxycarbonyl" group, which is a radical of the formula: —C(O)—O-(alkyl), wherein alkyl is defined above. The term "cycloalkyloxycarbonyl", "aryloxycarbonyl", "heterocyclyloxycarbonyl", "heteroaryloxycarbonyl", "heterocycloalkyloxycarbonyl", or the like, mirrors the above description for "alkoxycarbonyl" where the term "alkoxy" is replaced with "cycloalkyloxy", "aryloxy", "heterocyclyloxy", "heteroaryloxy", "heterocycloalkyloxy", or the like, respectively.

As used herein and unless otherwise specified, a "carbamate" group is a radical of the formula: —O—C(O)—NH$_2$, —O—C(O)—NH(R$^\#$), —O—C(O)—N(R$^\#$)$_2$, —NH—C(O)—O—(R$^\#$), or —N(R$^\#$)—C(O)—O—(R$^\#$), wherein each R$^\#$ is independently defined above.

A "urea" group is a radical of the formula: —N(alkyl)C(O)N(R$^\#$)$_2$, —N(alkyl)C(O)NH(R$^\#$), —N(alkyl)C(O)NH$_2$, —NHC(O)N(R$^\#$)$_2$, —NHC(O)NH(R$^\#$), or —NH(CO)NH$_2$, wherein each alkyl and R$^\#$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (═O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "Piperidine Dione Compound" refers to compounds of formula (I) as well as to further embodiments provided herein. In one embodiment, an "Piperidine Dione Compound" is a compound set forth in Table 1. The term "Piperidine Dione Compound" includes pharmaceutically acceptable salts, tautomers, isotopologues, and stereoisomers of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride, formic, and mesylate salts. Others are well-known in the art, see for example, *Remington's Pharmaceutical Sciences,* 18$^{th}$ eds., Mack Publishing, Easton Pa. (1990) or *Remington: The Science and Practice of Pharmacy,* 19$^{th}$ eds., Mack Publishing, Easton Pa. (1995).

As used herein and unless otherwise indicated, the term "stereoisomer" or "stereoisomerically pure" means one stereoisomer of a Piperidine Dione Compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Piperidine Dione Compounds can have chiral centers and can occur as racemates, individual enantiomers or diastereomers, and mixtures thereof. All such isomeric forms are included within the embodiments disclosed herein, including mixtures thereof.

The use of stereoisomerically pure forms of such Piperidine Dione Compounds, as well as the use of mixtures of those forms, are encompassed by the embodiments disclosed herein. For example, mixtures comprising equal or unequal amounts of the enantiomers of a particular Piperidine Dione Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuja, S., *Chiral Separation Methods for Pharmaceutical and Biotechnological Products* (John Wiley & Sons, 2011).

It should also be noted the Piperidine Dione Compounds can include E and Z isomers, or a mixture thereof, and cis and trans isomers or a mixture thereof. In certain embodiments, the Piperidine Dione Compounds are isolated as either the E or Z isomer. In other embodiments, the Piperidine Dione Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

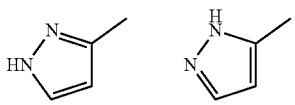

As readily understood by one skilled in the art, a wide variety of functional groups and other structures may exhibit tautomerism and all tautomers of compounds of formula (I) are within the scope of the present invention.

It should also be noted the Piperidine Dione Compounds can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the Piperidine Dione Compounds as described herein, whether radioactive or not, are intended to be encompassed within the scope of the embodiments provided herein. In some embodiments, there are provided isotopologues of the Piperidine Dione Compounds, for example, the isotopologues are deuterium, carbon-13, and/or nitrogen-15 enriched Piperidine Dione Compounds. As used herein, "deuterated", means a compound wherein at least one hydrogen (H) has been replaced by deuterium (indicated by D or $^2$H), that is, the compound is enriched in deuterium in at least one position.

It is understood that, independently of stereoisomerical or isotopic composition, each Piperidine Dione Compound referred to herein can be provided in the form of any of the pharmaceutically acceptable salts discussed herein. Equally, it is understood that the isotopic composition may vary independently from the stereoisomerical composition of each Piperidine Dione Compound referred to herein. Further, the isotopic composition, while being restricted to those elements present in the respective Piperidine Dione Compound or salt thereof, may otherwise vary independently from the selection of the pharmaceutically acceptable salt of the respective Piperidine Dione Compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is an androgen receptor mediated disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is an androgen receptor mediated disease, as described herein, or symptoms thereof.

The term "effective amount" in connection with a Piperidine Dione Compound means an amount capable of treating or preventing a disorder, disease or condition, or symptoms thereof, disclosed herein.

The term "subject" or "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an androgen receptor mediated disease, or a symptom thereof.

The term "androgen receptor" or "AR" or "NR3C4" as used herein refers to a nuclear hormone receptor activated by binding of the androgenic hormones, including testosterone or dihydrotestosterone. The term "androgen receptor" may refer to the nucleotide sequence or protein sequence of human androgen receptor (e.g., Entrez 367, Uniprot P10275, RefSeq NM_000044, or RefSeq NP_000035).

The term "AR-full length" (AR-FL) as used herein refers to AR protein that contains all four functional domains, including the N-terminal transactivation domain (NTD, exon 1), the DNA-binding domain (DBD, exons 2-3), the hinge domain (exon 4), and the C-terminal ligand binding domain (LBD, exons 4-8).

The term "castration resistant prostate cancer" (CRPC) refers to advanced prostate cancer that is worsening or progressing while the patient remains on androgen deprivation therapy or other therapies to reduce testosterone, or prostate cancer which is considered hormone refractory, hormone naive, androgen independent or chemical or surgical castration resistant. Castration resistant prostate cancer (CRPC) is an advanced prostate cancer which developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Piperidine Dione Compounds

Provided herein are compounds having the following formula (I):

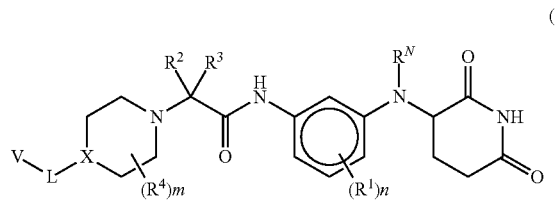

(I)

or a pharmaceutically acceptable salt, tautomer, isotopolog, or stereoisomer thereof,
wherein
$R^N$ is H;
each $R^1$ is independently selected from halogen, CN, and $C_{1-3}$ alkyl;
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;
each $R^4$ is independently selected from substituted or unsubstituted $C_{1-3}$ alkyl, and halogen, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
X is $CR^x$;
$R^x$ is H, halogen, or substituted or unsubstituted $C_{1-3}$ alkyl;
L is —O—, —O(CH$_2$)$_p$— or —(CH$_2$)$_p$—;
n is 0-4;
m is 0-8;
p is 1-3;

V is

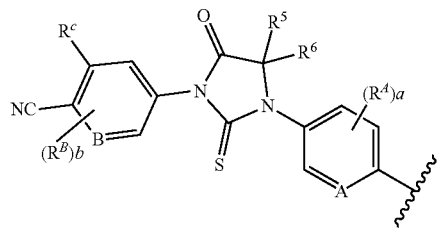

wherein
A is N, CH, or $CR^A$;
B is N, CH or $CR^B$;
each $R^A$ is independently selected from halogen, substituted or unsubstituted $C_{1-6}$ alkyl, and substituted and unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-5}$ cycloalkyl or a 3-5 membered heterocyclyl;
a is 0-3; and
b is 0-2.

In one embodiment of a compound of formula (I), the compound is

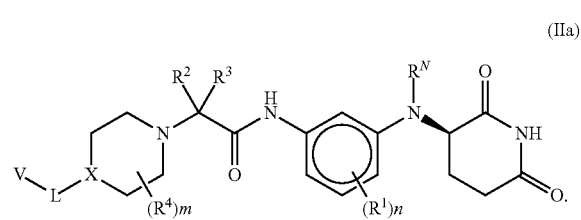

(IIa)

In another embodiment of a compound of formula (I), the compound is

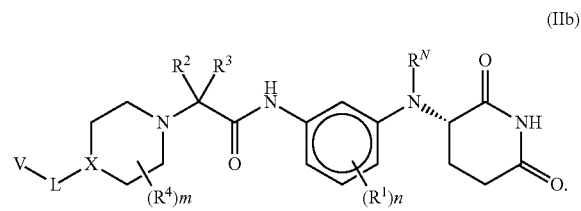

(IIb)

In some embodiments of compounds of formula (I), (IIa) and (IIb), each $R^1$ is independently selected from halogen, CN, and $C_{1-3}$ alkyl. In some embodiments of compounds of formula (I), (IIa) and (IIb), each $R^1$ is independently selected from Cl, F, Br, CN, —CH$_3$, and —CH$_2$CH$_3$. In other embodiments, each $R^1$ is independently selected from Cl, F, and CN.

In some embodiments of compounds of formula (I), n is 0. In other embodiments, n is 1.

In some embodiments of compounds of formula (I), the compound is

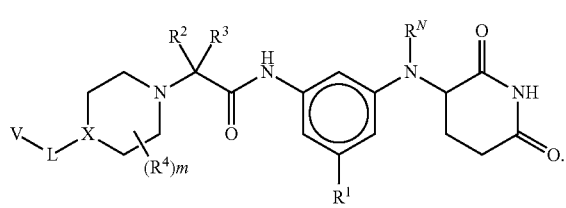

(III)

In other embodiments of compounds of formula (I), the compound is

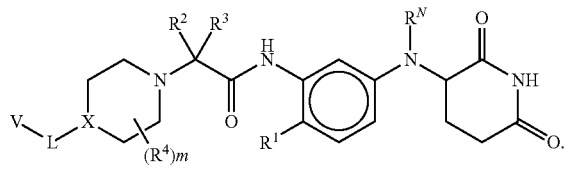

(IV)

In still other embodiments of compounds of formula (I), the compound is

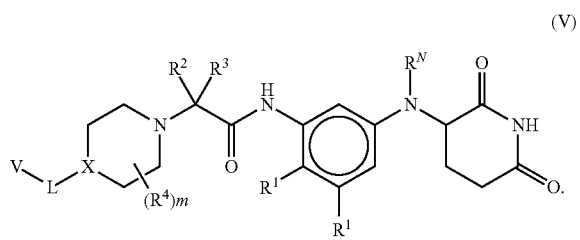

(V)

In some embodiments, the compound is a compound of formula (III), (IV) or (V), wherein each $R^1$ is independently selected from Cl, F, and CN. In some such embodiments, $R^1$ is F or Cl.

In some embodiments of compounds of formula (I), $R^2$ and $R^3$ are each independently selected from H, substituted or unsubstituted methyl, and ethyl, or $R^2$ and $R^3$ and the carbon to which they are attached form a substituted or unsubstituted cyclopropyl, cyclobutyl or cyclopentyl. In some such embodiments, $R^2$ and $R^3$ are each independently selected from H and methyl, or $R^2$ and $R^3$ and the carbon to which they are attached form an unsubstituted cyclopropyl. In some other embodiments, $R^2$ and $R^3$ are both H or methyl, or $R^2$ and $R^3$ and the carbon to which they are attached form an unsubstituted cyclopropyl.

In some embodiments of compounds of formula (I), each $R^4$ is independently selected from substituted or unsubstituted methyl and ethyl, or two $R^4$ groups, together with the same carbon atom to which they are attached, form a substituted or unsubstituted cyclopropyl or cyclobutyl. In some embodiments, each $R^4$ is independently selected from substituted or unsubstituted methyl, or two $R^4$ groups, together with the same carbon atom to which they are attached, form an unsubstituted cyclopropyl. In other embodiments, each $R^4$ is independently selected from methyl and $CH_2OH$, or two $R^4$ groups, together with the same carbon atom to which they are attached, form an unsubstituted cyclopropyl.

In some embodiments of compounds of formula (I), m is 0, 1, 2, 3 or 4. In some embodiments m is 0, 1, or 2.

In some embodiments of compounds of formula (I), two $R^4$ groups together with the non-adjacent carbon atoms to which they are attached form an unsubstituted 4-7-membered heterocyclyl. In some such embodiments, the compound is

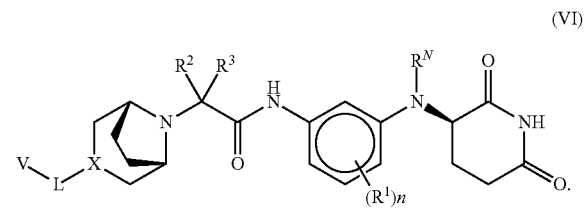

(VI)

In some embodiments of compounds of formula (I), $R^x$ is H. In other embodiments, $R^x$ is $CH_3$. In yet other embodiments, $R^x$ is F.

In some embodiments of compounds of formula (I), L is —O—, —O($CH_2$)—, or —O($CH_2$)($CH_2$)—.

In some embodiments of compounds of formula (I), A is CH. In some other embodiments of compounds of formula (I), B is CH. In still other embodiments, B is N.

In some embodiments of compounds of formula (I), a is 0, 1 or 2.

In some embodiments of compounds of formula (I), each $R^A$ is independently selected from Cl, Br, F, methyl, ethyl, n-propyl, isopropyl, n-butyl, isobutyl, sec-butyl, tert-butyl, n-pentyl, $CH_2CH_2CH(CH_3)_2$, $CH(CH_3)CH(CH_3)_2$, $CH_2C(CH_3)_3$, $CF_3$, $CF_2CH_3$, $CH_2CH_2F$, $CH_2CHF_2$, $CH_2CF_3$, $CH_2OH$, $CH(CH_3)OH$, $CH_2CH_2OH$, $CH(CH_3)CH_2OH$, $CH_2CH(CH_3)OH$, cyclopropyl, cyclobutyl, and cyclopentyl. In some such embodiments, each $R^A$ is independently selected from Cl, F, ethyl, isopropyl, $CF_2CH_3$, and $CH_2CH_2F$. In other embodiments, each $R^A$ is independently selected from Cl, F, ethyl, isopropyl, $CF_2CH_3$, and $CH_2CH_2F$. In yet other embodiments, each $R^A$ is independently selected from Cl, ethyl, isopropyl, $CF_2CH_3$ and $CH_2CH_2F$.

In some embodiments of compounds of formula (I), b is 0. In some embodiments of compounds of formula (I), $R^C$ is $CF_3$.

In some embodiments of compounds of formula (I), $R^5$ and $R^6$ are methyl, or $R^5$ and $R^6$, together with the carbon atom to which they are attached, form a cyclopropyl, cyclobutyl, tetrahydrofuranyl, or tetrahydropyranyl. In other embodiments, $R^5$ and $R^6$ are methyl, or $R^5$ and $R^6$, together with the carbon atom to which they are attached, form a cyclobutyl.

In some embodiments of compounds of formula (III), (IV) or (V), each $R^1$ is independently selected from Cl, F, and CN, and $R^2$ and $R^3$ are H or methyl. In some such embodiments, each $R^4$ is independently selected from methyl and $CH_2OH$, or two $R^4$ groups, together with the same carbon atom to which they are attached, form an unsubstituted cyclopropyl. In some such embodiments, $R^4$ is methyl. In some other such embodiments, L is —O—, —O($CH_2$)—, or —O($CH_2$)($CH_2$)—. In still other such embodiments, A is CH. In yet other such embodiments, B is CH, and each $R^A$ is independently selected from Cl, F, ethyl, isopropyl, $CF_2CH_3$, and $CH_2CH_2F$. In other such embodiments, B is N, and each $R^A$ is independently selected from Cl, ethyl, isopropyl, $CF_2CH_3$ and $CH_2CH_2F$. In some other such embodiments, each $R^A$ is Cl, F, ethyl, isopropyl, $CF_2CH_3$, and $CH_2CH_2F$. In still other such embodiments, $R^5$ and $R^6$ are methyl, or $R^5$ and $R^6$, together with the carbon atom to which they are attached, form a cyclobutyl.

In some embodiments of compounds of formula (I), (IIa), and (IIb), $R^N$ is H;

each $R^1$ is independently selected from Cl, F, Br, CN, —$CH_3$, and —$CH_2CH_3$;

$R^2$ and $R^3$ are each independently selected from H, substituted or unsubstituted methyl, and ethyl, or $R^2$ and $R^3$ and the carbon to which they are attached form a substituted or unsubstituted cyclopropyl, cyclobutyl or cyclopentyl;

each $R^4$ is independently selected from substituted or unsubstituted methyl and ethyl, or two $R^4$ groups, together with the same carbon atom to which they are attached, form a substituted or unsubstituted cyclopropyl or cyclobutyl;

X is $CR^x$;

$R^x$ is H, F, or $CH_3$;

L is —O—, —$O(CH_2)_p$— or —$(CH_2)_p$—;

n is 0-4;

m is 0-8;

p is 1-3;

V is

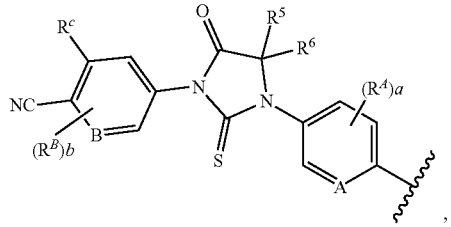

wherein

A is N, CH, or $CR^A$;

B is N, CH or $CR^B$;

each $R^A$ is independently selected from Cl, Br, F, methyl, ethyl, n-propyl, isopropyl, n-butyl, isobutyl, sec-butyl, tert-butyl, n-pentyl, $CH_2CH_2CH(CH_3)_2$, $CH(CH_3)CH(CH_3)_2$, $CH_2C(CH_3)_3$, $CF_3$, $CF_2CH_3$, $CH_2CH_2F$, $CH_2CHF_2$, $CH_2CF_3$, $CH_2OH$, $CH(CH_3)OH$, $CH_2CH_2OH$, $CH(CH_3)CH_2OH$, $CH_2CH(CH_3)OH$, cyclopropyl, cyclobutyl, and cyclopentyl;

each $R^B$ is independently selected from halogen, and methyl;

$R^C$ is halogen or $CF_3$;

$R^5$ and $R^6$ are methyl, or $R^5$ and $R^6$, together with the carbon atom to which they are attached, form a cyclopropyl, cyclobutyl, tetrahydrofuranyl, or tetrahydropyranyl;

a is 0-3; and b is 0-2.

In some embodiments of compounds of formula (III), (IV) and (V), $R^N$ is H;

each $R^1$ is independently selected from Cl, F, Br, CN, —$CH_3$, and —$CH_2CH_3$;

$R^2$ and $R^3$ are each independently selected from H, substituted or unsubstituted methyl, and ethyl, or $R^2$ and $R^3$ and the carbon to which they are attached form a substituted or unsubstituted cyclopropyl, cyclobutyl or cyclopentyl;

each $R^4$ is independently selected from substituted or unsubstituted methyl and ethyl, or two $R^4$ groups, together with the same carbon atom to which they are attached, form a substituted or unsubstituted cyclopropyl or cyclobutyl;

X is $CR^x$;

$R^x$ is H, F, or $CH_3$;

L is —O—, —$O(CH_2)_p$— or —$(CH_2)_p$—;

n is 0-4;

m is 0-8;

p is 1-3;

V is

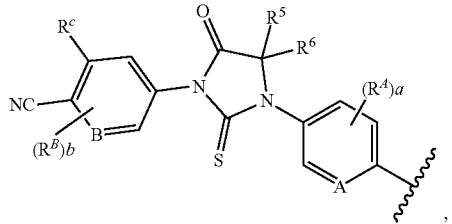

wherein

A is N, CH, or $CR^A$;

B is N, CH or $CR^B$;

each $R^A$ is independently selected from Cl, Br, F, methyl, ethyl, n-propyl, isopropyl, n-butyl, isobutyl, sec-butyl, tert-butyl, n-pentyl, $CH_2CH_2CH(CH_3)_2$, $CH(CH_3)CH(CH_3)_2$, $CH_2C(CH_3)_3$, $CF_3$, $CF_2CH_3$, $CH_2CH_2F$, $CH_2CHF_2$, $CH_2CF_3$, $CH_2OH$, $CH(CH_3)OH$, $CH_2CH_2OH$, $CH(CH_3)CH_2OH$, $CH_2CH(CH_3)OH$, cyclopropyl, cyclobutyl, and cyclopentyl;

each $R^B$ is independently selected from halogen, and methyl;

$R^C$ is halogen or $CF_3$;

$R^5$ and $R^6$ are methyl, or $R^5$ and $R^6$, together with the carbon atom to which they are attached, form a cyclopropyl, cyclobutyl, tetrahydrofuranyl, or tetrahydropyranyl;

a is 0-3; and b is 0-2.

Further embodiments provided herein include any combinations of one or more of the particular embodiments set forth above.

In some embodiments of compounds of formula (I), the compound is a compound from Table 1.

Representative compounds of formula (I), (II), (III), (IV), (V), and (VI), are set forth in Table 1.

Piperidine Dione Compounds set forth in Table 1 were tested in the AR mediated assays described herein and were found to have activity therein. In one embodiment, the Piperidine Dione Compound is a compound as described herein, wherein the compound at a concentration of 1 μM leads to degration of AR protein, by at least about 50% or more.

Methods for Making Piperidine Dione Compounds

The Piperidine Dione Compounds described herein can be made using conventional organic syntheses and commercially available starting materials, or the methods provided herein. By way of example and not limitation, Piperidine Dione Compounds of formula (I), wherein $R^N$, $R^1$, $R^2$, $R^3$, $R^4$, $R^5$, $R^6$, $R^A$, $R^B$, $R^C$, L, V, X, n, m, p, a and b are as defined herein, can be prepared as outlined in Schemes 1 and 6 shown below, as well as in the examples set forth herein. It should be noted that one skilled in the art would know how to modify the procedures set forth in the illustrative schemes and examples to arrive at the desired products.

Scheme 1

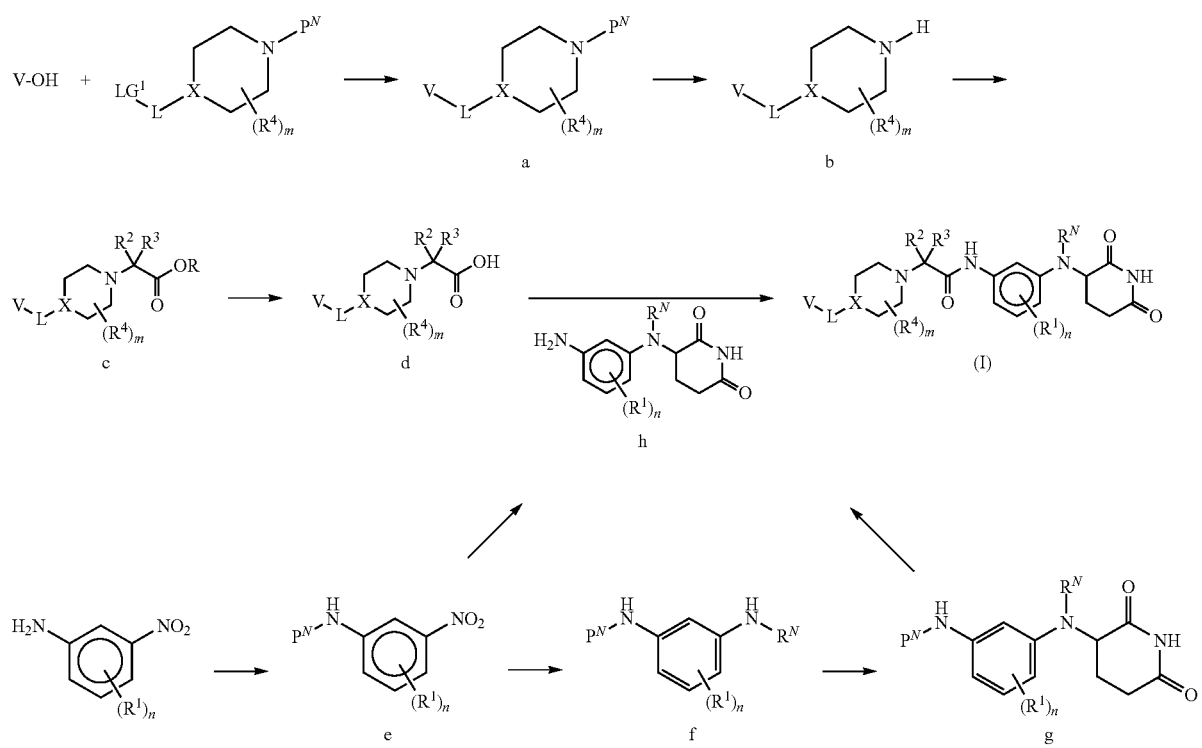

As shown in Scheme 1, Piperidine Dione Compounds of formula (I), wherein L is —O(CH$_2$)$_p$—, can be prepared starting by reacting the phenol derivative (A is CH or CR$^4$) or pyridinone (A is N) V—OH with the appropriately derivatized and N-protected piperidyl (for example, wherein P$^N$ is Boc and the leaving group LG$^1$ is Br, Cl, OTs, or OMs), in the presence of a base, in a solvent (for example, CsCO$_3$ in DMF, or K$_2$CO$_3$ in acetonitrile), at elevated temperature (for example, between about 40° C. and about 70° C.) to provide intermediate a. Alternatively, when LG$^1$ is —OH, V—OH is treated under Mitsunobu conditions (for example, with PPh$_3$ and DIAD or DEAD, in a solvent such as THF, at room temperature) to provide intermediate a. Removal of the N-protecting group P$^N$ from intermediate a, (for example, when P$^N$ is Boc, by treatment with an acid in a solvent, for example, HCl in dioxane or EtOAc, at room temperature, or with TFA in DCM, at room temperature), provides intermediate b. Reaction of intermediate b with Br—C(R$^2$)(R$^3$)COOR (wherein R is C$_{1-4}$ alkyl, for example, methyl, ethyl, or t-butyl), in the presence of a base, such as TEA, DBU, or DIEA, in a solvent, such as THF, NMP, or DMF, optionally at elevated temperature (for example, a temperature between about 20° C. and about 80° C.), optionally in the presence of NaI, provides intermediate c. Deprotection of the carboxylate in intermediate c, wherein R is methyl or ethyl, by treatment with a base, such as LiOH or NaOH, in a solvent, such as THF/H$_2$O mixtures or dioxane/H$_2$O mixtures; or when R is t-butyl, by treatment with an acid in a solvent, such as HCl in dioxane/DCM mixtures or TFA in DCM, provides intermediate d.

Appropriately derivatized 3-((3-aminophenyl)amino)piperidine-2,6-diones h are prepared from R$^1$-derivatized 3-nitroanilines, which are protected with an amine protecting group P$^N$ (wherein when P$^N$ is, for example Boc, by treatment with Boc$_2$O in the presence of a base, such as TEA, DIEA, or DBU, in a solvent, such as THF, NMP or DMF) to form intermediate e. The nitro group in intermediate e is reduced (by treatment with a reducing agent, for example H$_2$, in the presence of a catalyst, such as Pd/C, in a solvent, such as EtOH or MeOH; or Fe and NH$_4$Cl, in a solvent such as EtOH and H$_2$O) to provide the mono-protected derivatized dianiline intermediate f. Coupling of intermediate f with 3-bromopiperidine-2,6-dione in the presence of a base, in a solvent (for example, NaHCO$_3$, CsCO$_3$, or K$_2$CO$_3$, in DMF or NMP, at elevated temperature, for example between about 50° C. and about 80° C.; or DIEA in DMF or NMP, at elevated temperature, for example, about 150° C.), followed by removal of the protecting group P$^N$ (for example, when P$^N$ is Boc, treatment with an acid, in a solvent, such as TFA in DCM; or treatment with HCl in dioxane or EtOAc) provides intermediate h. Alternatively, intermediate h is obtained via iron-catalyzed reductive coupling of intermediate e and 3-bromopiperidine-2,6-dione (for example, by reaction in the presence of Zn, TMSCl, FeCl$_2$*4H$_2$O, in a solvent, such as NMP, at elevated temperature, for example between about 80° C. to about 100° C.), followed by removal of the protecting group P$^N$ (for example, when P$^N$ is Boc, treatment with an acid in a solvent, such as TFA in DCM; or treatment with HCl in dioxane or EtOAc).

Coupling of intermediate d with intermediate h, for example in the presence of a coupling agent, such as HATU, HBTU, EDC, or DCC, optionally in combination with HOBt, in the presence of a base, such as DIEA, NMM, or TEA, in a solvent, such as DCM, DMF, or NMP, or mixtures thereof, provides compounds of formula (I), wherein L is —O(CH$_2$)$_p$—.

Scheme 2

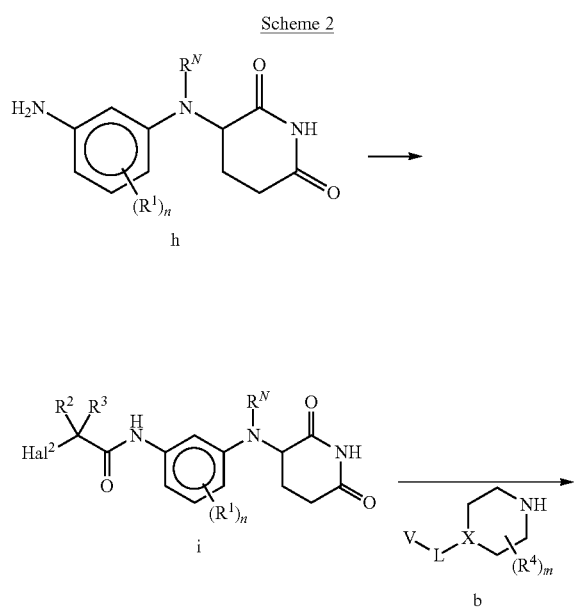

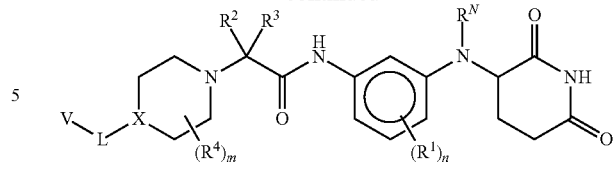

An alternate approach to the synthesis of compounds of formula (I) is shown in Scheme 2. In one approach, the common intermediate h is reacted with $Hal^2$-$C(R^2)(R^3)COY$ (wherein $Hal^2$ is Cl or Br), in the presence of, when Y is OH, a coupling agent (for example HATU, HBTU, or EDC or DCC, optionally in combination with HOBt), and a base (for example DIEA, TEA, or NMM), in a solvent, for example, DCM, DMF, NMP or mixtures thereof; or in the presence of, when Y is Cl, a base, such as TEA or DIEA, in a solvent, such as DMF or NMP, at a temperature between about 0° C. and about 25° C., to provide intermediate i. Treatment of intermediate i with intermediate b, in the presence of a base, such as DIEA, in a solvent, such as DMF, at elevated temperature, for example, between about 40° C. and about 60° C., optionally in the presence of NaI, provides the target compounds of formula (I).

Scheme 3

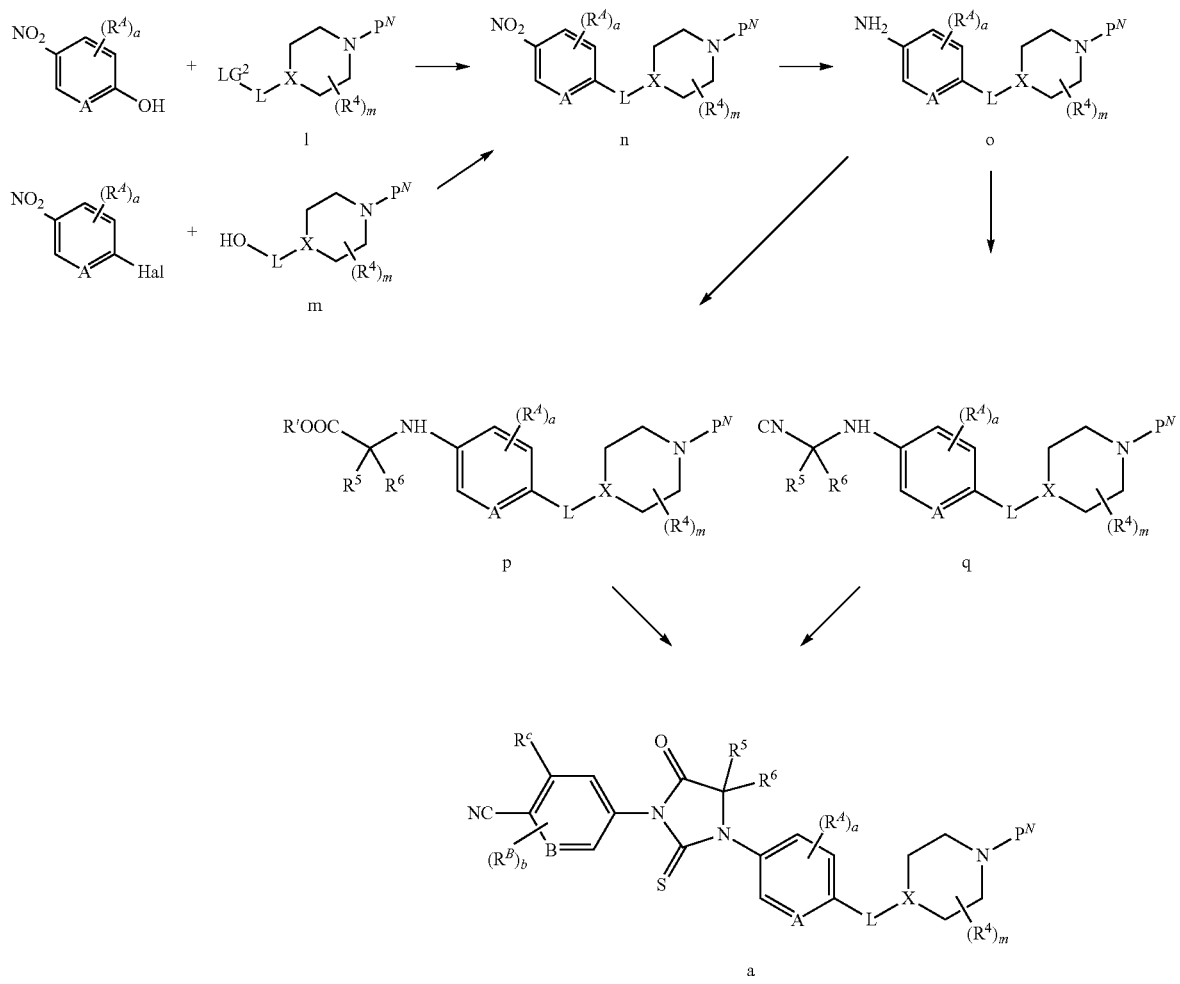

An alternate synthesis of intermediate a, wherein L is —O(CH$_2$)$_p$—, is shown in Scheme 3. Appropriately derivatized 4-nitrophenol or 5-nitropyridin-2-ol, is reacted with intermediate l (wherein LG$^2$ is Br, Cl or OH), and when LG$^2$ is Br or Cl, in the presence of a base, in a solvent, at elevated temperature (for example, the base is CsCO$_3$ or K$_2$CO$_3$, the solvent is acetonitrile, DMF or NMP, and the temperature is between about 50° C. and about 80° C.), to provide intermediate n. When LG$^2$ is OH, a Mitsunobu reaction is performed (using PPh$_3$ and DIAD or DEAD, in a solvent, such as THF, at room temperature) to provide intermediate n. Alternatively, when A is N, appropriately derivatized 2-halo-5-nitropyridine is reacted with intermediate m, in the presence of a base, such as CsCO$_3$ or K$_2$CO$_3$, in a solvent, such as acetonitrile, DMF, THF, or NMP, at elevated temperature, for example between about 50° C. and about 70° C., to provide intermediate n. Reduction of the nitro group in intermediate n with a reducing agent, in a solvent, (for example, H$_2$ in EtOH, in the presence of a catalyst, for example, Pd/C; or Fe and NH$_4$Cl, in EtOH and H$_2$O, at elevated temperature, for example about 80° C.) provides intermediate o. Reaction of intermediate o with R'OOC—C(R$^5$)(R$^6$)Hal (wherein Hal is Br or Cl and R' is C$_{1-3}$ alkyl) in the presence of a base (for example DIEA or TEA) at elevated temperature (for example, between 110° C. and about 130° C.) provides intermediate p. Reaction of intermediate p with an appropriately derivatized 4-isothiocyanatobenzonitrile or 5-isothiocyanatopicolinonitrile, in the presence of a base, such as TEA, in a solvent, such as EtOAc, at elevated temperature, for example, between about 70° C. and about 90° C., provides intermediates a, which can be further reacted to provide compounds of formula (I), wherein L is —O(CH$_2$)$_p$—, as described in the schemes above.

Alternatively, reaction of intermediate o with CN—C(R$^5$)(R$^6$)OH in the presence of MgSO$_4$, at elevated temperature, for example between 50° C. to about 70° C., provides intermediate q. Reagents CN—C(R$^5$)(R$^6$)OH can be formed by reaction of C(=O)(R$^5$)(R$^6$) with TMSCN and TMSOTf, in a solvent, such as DCM. Reaction of intermediate q, with an appropriately derivatized 4-isothiocyanatobenzonitrile or 5-isothiocyanatopicolinonitrile, in a solvent, such as DMF or DMA, followed by treatment with an acid, for example, HCl, in a solvent, such as MeOH or EtOH, at elevated temperature, for example between about 70° C. and about 80° C., provides intermediate a, to be used as described above to provide compounds of formula (I), wherein L is —O(CH$_2$)$_p$—.

Synthesis of intermediates V—OH, wherein R$^A$ is substituted or unsubstituted C$_{1-6}$ alkyl, or substituted or unsubstituted C$_{3-6}$ cycloalkyl, is shown in Schemes 4, 5, and 6.

Scheme 4

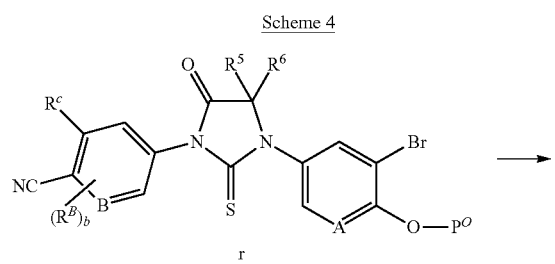

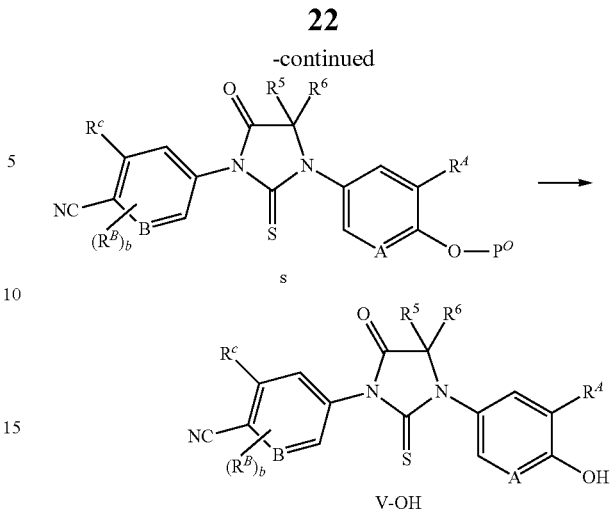

Intermediates r, wherein P$^O$ is a phenol protecting group, for example acetyl or benzyl, can be treated with R$^A$—Zn—Br, in the presence of a catalyst and a ligand, for example, CPhos PdG3 and CPhos in a solvent, for example, toluene, at lower temperature for example, between about 0° C. and about 25° C. to generate intermediates s. Removal of the protecting group P$^O$ (when P$^O$ is acetyl, by treatment with a base, such as K$_2$CO$_3$, in a solvent, such as MeOH or EtOH; or when P$^O$ is benzyl, by treatment with a reducing agent such as H$_2$, in the presence of a catalyst such as Pd/C, in a solvent, such as EtOH or MeOH), provides the intermediates V—OH, wherein R$^A$ is substituted or unsubstituted C$_{1-6}$ alkyl, or substituted or unsubstituted C$_{3-6}$ cycloalkyl, which can be used in the schemes above.

Scheme 5

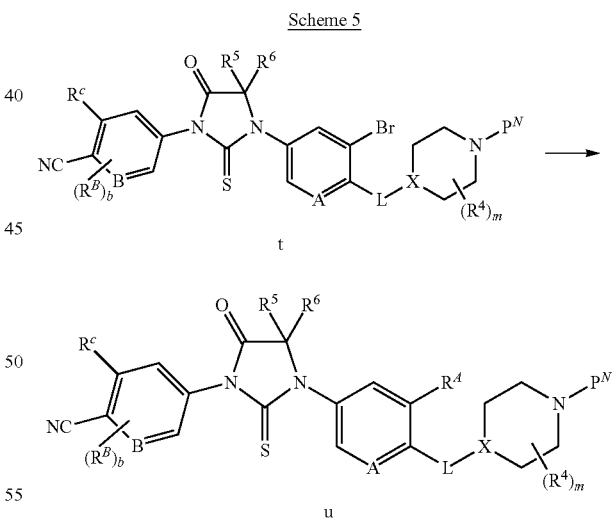

Alternatively, as shown in Scheme 5, R$^A$ can be incorporated by reaction of intermediate t with R$^A$—Zn—Br, in the presence of a catalyst and a ligand, for example, CPhos PdG3 and CPhos in a solvent, for example, toluene, at lower temperature for example, between about 0° C. and about 25° C. to generate intermediates u, wherein R$^A$ is substituted or unsubstituted C$_{1-6}$ alkyl, or substituted or unsubstituted C$_{3-6}$ cycloalkyl, and which can be used similarly to intermediate a in the schemes above.

Scheme 6

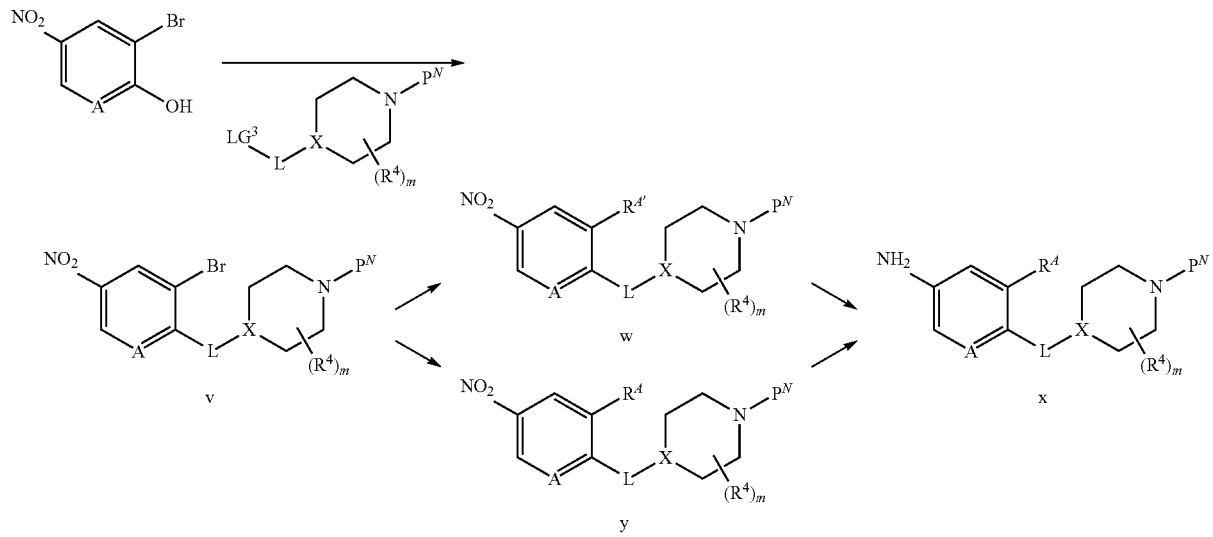

Intermediates x, wherein L is —O(CH$_2$)$_p$— and R$^A$ is defined below, for use in the schemes above, can be prepared as shown in Scheme 6. In a first step, 2-bromo-4-nitrophenol or 3-bromo-5-nitropyridin-2-ol, is reacted with the appropriately derivatized and N-protected piperidyl (for example, wherein P$^N$ is Boc and the leaving group LG$^3$ is Br, Cl, OTs, or OMs), in the presence of a base in a solvent (for example, CsCO$_3$ or K$_2$CO$_3$, in DMF, NMP, or acetonitrile), at elevated temperature (for example, between about 40° C. and about 70° C.) to provide intermediate v. Alternatively, when LG$^3$ is —OH, 2-bromo-4-nitrophenol or 3-bromo-5-nitropyridin-2-ol, is treated under Mitsunobu conditions (for example, with PPh$_3$ and DIAD or DEAD, in a solvent such as THF, at room temperature) to provide intermediate v. Introduction of R$^A$ is achieved by reaction of intermediate v with a boronate R$^{A'}$[B(OR$^+$)$_2$]$_2$, (wherein R$^{A'}$ is substituted or unsubstituted C$_{2-6}$ alkenyl, substituted or unsubstituted cyclopropyl, or substituted or unsubstituted C$_{5-6}$ cycloalkenyl, and R$^+$ together with the boron atom and the atoms to which they are attached, forms a cyclic boronate, for example, 4,4,4',4',5,5,5',5'-octamethyl-2,2'-bi(1,3,2-dioxaborolane), in the presence of a palladium catalyst (for example Pd(dppf)Cl$_2$) and a base (such as K$_3$PO$_4$) in a solvent (such as a 1,4-dioxane/water mixture), providing intermediate w, wherein R$^{A'}$ is substituted or unsubstituted C$_{2-6}$ alkenyl, substituted or unsubstituted cyclopropyl, or substituted or unsubstituted C$_{5-6}$ cycloalkenyl. Reduction of the nitro group and the R$^{A'}$ alkenyl group or cycloalkenyl in intermediate w, using a reducing agent, such as H$_2$, in the presence of a catalyst, such as Pd/C, in a solvent, such as MeOH or EtOH, at a temperature between about 20° C. and about 30° C., provides intermediates x, wherein R$^A$ is substituted or unsubstituted C$_{2-6}$ alkyl, substituted or unsubstituted cyclopropyl, or substituted or unsubstituted C$_{5-6}$ cycloalkyl, that can be used in the schemes above to provide compounds of formula (I), wherein L is —O(CH$_2$)$_p$— and R$^A$ is substituted or unsubstituted C$_{2-6}$ alkyl, substituted or unsubstituted cyclopropyl, or substituted or unsubstituted C$_{5-6}$ cycloalkyl. Alternatively, intermediate v is treated with R$^A$BF$_3$—K$^+$, wherein R$^A$ is substituted or unsubstituted C$_{1-6}$ alkyl, in the presence of a catalyst and a ligand (for example cataCXium® A Palladacycle Gen. 3 and butyldi-1-adamantylphosphine), in the presence of a base, such as Cs$_2$CO$_3$ or K$_2$CO$_3$, in a solvent, such as a toluene/water mixture, at elevated temperature, for example, between about 90° C. and about 110° C., to provide intermediate y, wherein R$^A$ is substituted or unsubstituted C$_{1-6}$ alkyl. As before, reduction of the nitro group in intermediate y, using a reducing agent, such as H$_2$, in the presence of a catalyst, such as Pd/C, in a solvent, such as MeOH or EtOH, at a temperature between about 20° C. and about 30° C., provides intermediates x, wherein R$^A$ is substituted or unsubstituted C$_{1-6}$ alkyl, that can be used in the schemes above to provide compounds of formula (I), wherein L is —O(CH$_2$)$_p$— and R$^A$ is substituted or unsubstituted C$_{1-6}$ alkyl.

In some embodiments, chiral separation (by standard methods and as described herein) of the enantiomers of compounds of formula (I) provides compounds of formula (IIa) and formula (IIb)

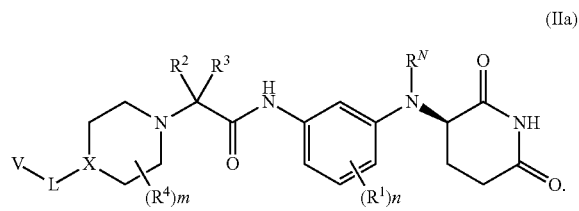

(IIa)

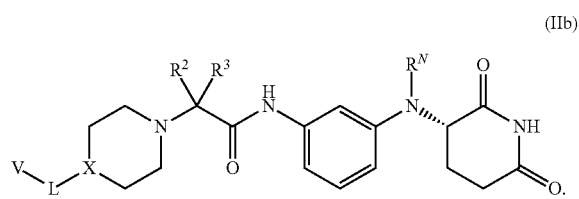

(IIb)

Alternatively, chiral separation by standard methods of intermediates h or i, used as described in the schemes above, provides compounds of formula (IIa) or (IIb).

The term "protected" with respect to amine and hydroxyl groups, refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., (5th Edition, 2014), which can be added or removed using the procedures set forth therein.

The term "protected" with respect to amine and hydroxyl groups, refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., (5th Edition, 2014), which can be added or removed using the procedures set forth therein.

In one aspect, provided herein are methods for preparing a compound of formula (I):

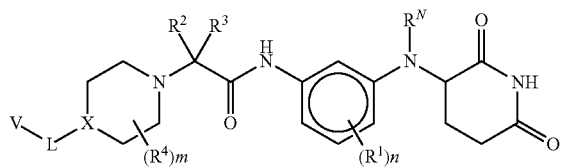

(I)

the methods comprising contacting a compound of formula (h)

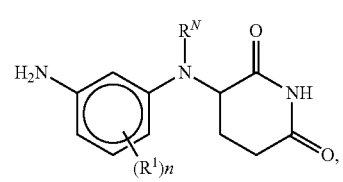

(h)

with a compound of formula (d)

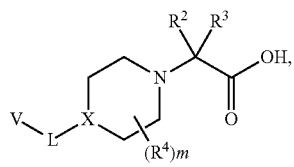

(d)

in the presence of a coupling agent, and a base, in a solvent, under conditions suitable to provide a compound of formula (I); wherein $R^N$ is H;

each $R^1$ is independently selected from halogen, CN, and $C_{1-3}$ alkyl;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

each $R^4$ is independently substituted or unsubstituted $C_{1-3}$ alkyl, and halogen, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

X is $CR^x$;

$R^x$ is H, halogen, or substituted or unsubstituted $C_{1-3}$ alkyl;

L is —O—, —O(CH$_2$)$_p$— or —(CH$_2$)$_p$—;

n is 0-4;

m is 0-8;

p is 1-3;

V is

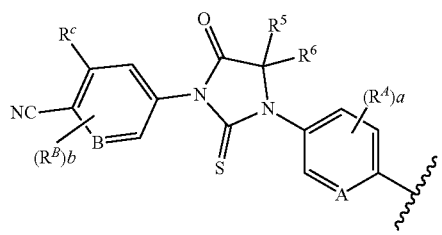

wherein

A is N, CH, or $CR^A$;

B is N, CH or $CR^B$;

each $R^A$ is independently selected from halogen, substituted or unsubstituted $C_{1-6}$ alkyl, or substituted and unsubstituted $C_{3-6}$ cycloalkyl;

each $R^B$ is independently selected from halogen, and substituted or unsubstituted $C_{1-6}$ alkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-5}$ cycloalkyl or a 3-5 membered heterocyclyl;

a is 0-3; and b is 0-2.

In one embodiment, the coupling agent is HATU, HBTU, EDC or DCC, optionally in combination with HOBt. In one embodiment, the coupling agent is HATU. In another embodiment, the base is DIEA, NMM or TEA. In one embodiment, the base is DIEA. In another embodiment, the solvent is DCM, DMF, NMP, or mixtures thereof. In one embodiment the solvent is DMF.

In the following embodiments, the variables $R^N$, $R^1$, $R^2$, $R^3$, $R^4$, $R^5$, $R^6$, $R^A$, $R^B$, $R^C$, L, V, A, B, n, m, p, a, and b are as defined herein, unless otherwise specified.

In some embodiments, the methods additionally comprise preparing a compound of formula (h)

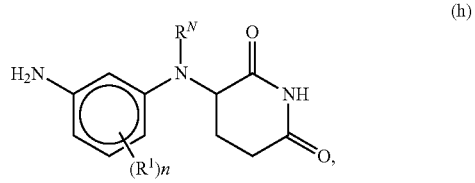

(h)

the methods comprising deprotecting a compound of formula (g)

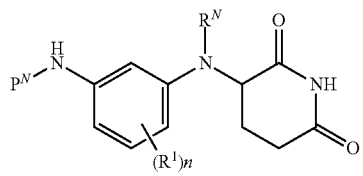

under conditions suitable to provide a compound of formula (h), wherein $P^N$ is an amine protecting group.

In some embodiments, $P^N$ is a Boc group. In some such embodiments, the deprotecting is performed by treatment with an acid, in a solvent. In some embodiments, acid is TFA and the solvent is DCM. In other embodiments, the acid is HCl, and the solvent is dioxane or EtOAc.

In some embodiments, the methods additionally comprise preparing a compound of formula (g)

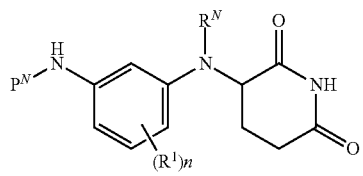

the methods comprising contacting a compound of formula (f)

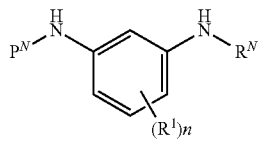

with 3-bromopiperidine-2,6-dione, in the presence of a base, in a solvent, at elevated temperature, under conditions suitable to provide a compound of formula (g).

In some such embodiments, the base is $NaHCO_3$, $CsCO_3$ or $K_2CO_3$ and the solvent is DMF or NMP. In one embodiment, base is $NaHCO_3$, and the solvent is DMF. In some such embodiments, the contacting is performed at a temperature of between about 50° C. and about 80° C. In other embodiments, the base is DIEA. In some such embodiments the solvent is DMF or NMP. In some such embodiments, the contacting is performed at a temperature of about 150° C.

In some embodiments, the methods additionally comprise preparing a compound of formula (f)

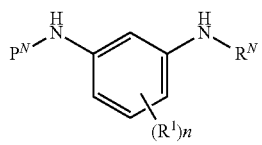

the methods comprising reduction of the nitro group in a compound of formula (e)

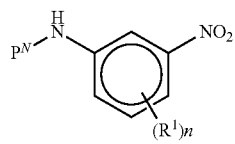

using a reducing agent, optionally in the presence of a catalyst, in a solvent, under conditions suitable to provide a compound of formula (f).

In some such embodiments, the reducing agent is $H_2$, and the catalyst is Pd/C. In some such embodiments, the solvent is EtOH or MeOH. In other embodiments, the reducing agent is Fe and $NH_4Cl$. In some such embodiments, the solvent is EtOH and $H_2O$.

In some embodiments, the methods additionally comprise preparing a compound of formula (e)

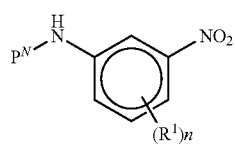

the methods comprising protecting a nitroaniline of formula

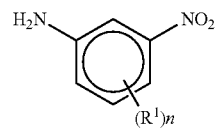

with an amine protecting group $P^N$, by reaction with a protecting agent in the presence of a base, in a solvent, under conditions suitable to provide a compound of formula (e).

In some such embodiments, amine protecting group $P^N$ is Boc and the protecting agent is $Boc_2O$. In some embodiments, the base is TEA, DIEA or DBU. In some embodiments, the base is TEA. In some such embodiments, the solvent is THF, NMP or DMF. In some embodiments, the solvent is THF.

In some other embodiments, the methods additionally comprise preparing a compound of formula (g)

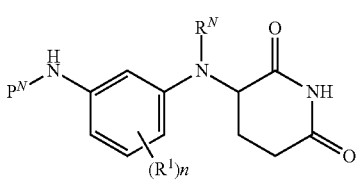

the methods comprising contacting a compound of formula (e)

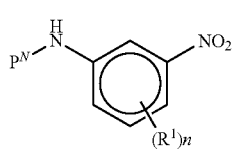
(e)

with 3-bromopiperidine-2,6-dione, in the presence of Zn, TMSCl, and $FeCl_2*4H_2O$, in a solvent, at elevated temperature, under conditions suitable to provide a compound of formula (g).

In some embodiments, the solvent is NMP. In some embodiments, the temperature is between about 80° C. to about 100° C.

In some embodiments, the methods additionally comprise preparing a compound of formula (d)

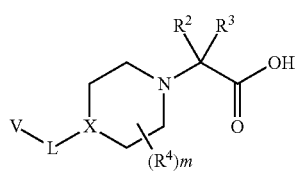
(d)

the methods comprising deprotecting a compound of formula (c)

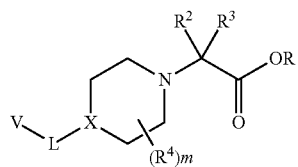
(c)

wherein R is $C_{1-4}$ alkyl, under conditions suitable to provide a compound of formula (d).

In some embodiments, wherein R is methyl or ethyl, the deprotecting is performed by treatment with a base, in a solvent. In some embodiments, the base is LiOH or NaOH. In other embodiments, the solvent is $THF/H_2O$ mixtures or dioxane/$H_2O$ mixtures. In other embodiments, wherein R is t-butyl, the deprotecting is performed by treatment with an acid in a solvent. In some such embodiments, the acid is HCl and the solvent is dioxane/DCM mixtures. In other embodiments, the acid is TFA and the solvent is DCM.

In some other embodiments, the methods additionally comprise preparing a compound of formula (c)

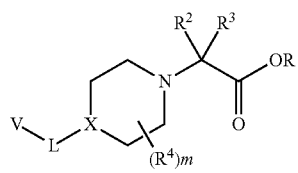
(c)

the methods comprising contacting a compound of formula (b)

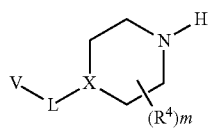
(b)

with $Br-C(R^2)(R^3)COOR$, in the presence of a base, in a solvent under conditions suitable to provide a compound of formula (c).

In some embodiments, the base is TEA, DBU, or DIEA. In some embodiments, the base is TEA. In other embodiments, the solvent is THF, NMP, or DMF. In some such embodiments, the solvent is THF. In some embodiments, the contacting is at elevated temperature, for example, a temperature between about 20° C. and about 80° C. In some embodiments, the contacting is in the presence of NaI.

In some embodiments, the methods additionally comprise preparing a compound of formula (b)

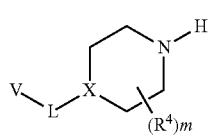
(b)

the methods comprising deprotecting a compound of formula (a)

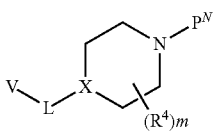
(a)

wherein $P^N$ is an amine protecting group, under conditions suitable to provide a compound of formula (b).

In some embodiments, the $P^N$ is Boc. In some such embodiments, the deprotecting is performed by treatment with an acid in a solvent. In some embodiments, the acid is HCl and the solvent is dioxane or EtOAc. In other embodiments, the acid is TFA and the solvent is DCM.

In some embodiments, the methods additionally comprise preparing a compound of formula (a)

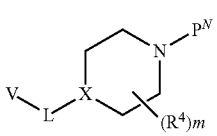
(a)

the methods comprising contacting a compound

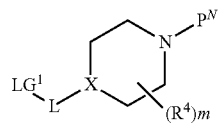

with V—OH, wherein $LG^1$ is a leaving group selected from OH, Br, Cl, OTs, and OMs, under conditions suitable to provide a compound of formula (a).

In some embodiments, $LG^1$ is Br, Cl, OTs, or OMs, and the contacting is performed in the presence of a base, in a solvent. In some such embodiments, the base is $CsCO_3$ and the solvent is DMF. In other embodiments, the base is $K_2CO_3$ and the solvent is acetonitrile. In some embodiments, the contacting is performed at elevated temperature. In some such embodiments, the temperature is between about 40° C. and about 70° C. In some embodiments, wherein $LG^1$ is —OH, and the contacting is performed in the presence of $PPh_3$ and DIAD or DEAD, in a solvent. In some such embodiments, the solvent is THF. In some embodiments, the contacting is performed at room temperature.

Also provided are methods of preparing compounds of formula (I)

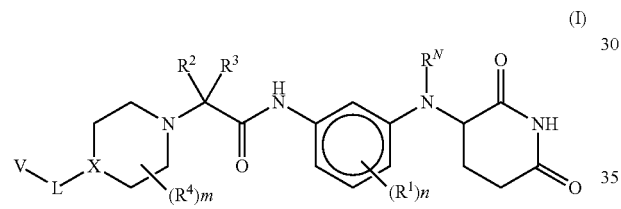

the methods comprising contacting a compound of formula (i)

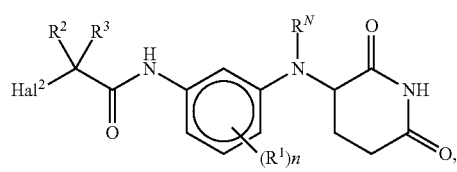

with a compound of formula (b)

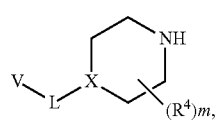

wherein $Hal^2$ is Br or Cl, in the presence of a base, in a solvent, under conditions suitable to provide a compound of formula (I); wherein $R^N$ is H;

each $R^1$ is independently selected from halogen, CN, and $C_{1-3}$ alkyl;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

each $R^4$ is independently substituted or unsubstituted $C_{1-3}$ alkyl, and halogen, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

X is $CR^x$;

$R^x$ is H, halogen, or substituted or unsubstituted $C_{1-3}$ alkyl;

L is —O—, —O(CH$_2$)$_p$— or —(CH$_2$)$_p$—;

n is 0-4;

m is 0-8;

p is 1-3;

V is

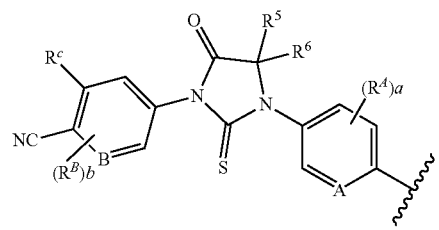

wherein

A is N, CH, or $CR^A$;

B is N, CH or $CR^B$;

each $R^A$ is independently selected from halogen, substituted or unsubstituted $C_{1-6}$ alkyl, or substituted and unsubstituted $C_{3-6}$ cycloalkyl;

each $R^B$ is independently selected from halogen, and substituted or unsubstituted $C_{1-6}$ alkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-5}$ cycloalkyl or a 3-5 membered heterocyclyl;

a is 0-3; and b is 0-2.

In one embodiment, the base is DIEA, TEA or NMM. In one embodiment, the base is DIEA. In another embodiment, the solvent is DMF or NMP. In one embodiment, the contacting is performed at elevated temperature. In one such embodiment, the temperature is between about 40° C. and about 60° C. In one embodiment, the contacting is performed in the presence of NaI.

In some embodiments, the methods additionally comprise preparing a compound of formula (i)

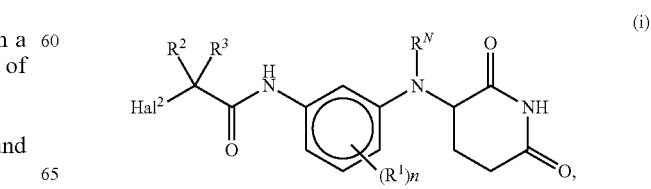

the methods comprising contacting a compound of formula (h)

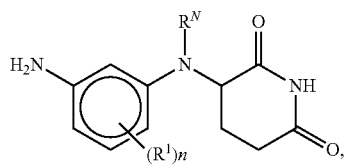

with Hal²-C(R²)(R³)COY, wherein Y is OH or Cl, under conditions suitable to provide a compound of formula (i).

In some embodiments, wherein Y is OH, the contacting is performed in the presence of a coupling agent, and a base, in a solvent. In one embodiment, the coupling agent is HATU, HBTU, EDC or DCC, optionally in combination with HOBt. In one embodiment, the coupling agent is HATU. In some embodiments, the base is DIEA, TEA, or NMM. In one embodiment, the base is DIEA. In one embodiment, the solvent is DCM, DMF, NMP or mixtures thereof. In one embodiment, the solvent is DMF. In other embodiments, wherein Y is Cl, the contacting is performed in the presence of a base, in a solvent. In some such embodiments, the base is TEA or DIEA. In other embodiments, the solvent is DMF or NMP. In some embodiments, the contacting is performed at a temperature between about 0° C. and about 25° C.

In some embodiments, the methods additionally comprise preparing a compound of formula (a)

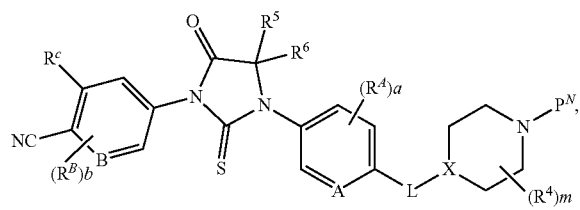

the methods comprising contacting a compound of formula (q)

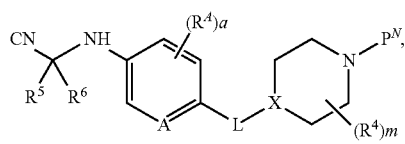

with a compound

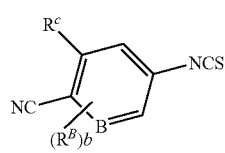

in a first solvent, followed by treatment with an acid, in a second solvent, under conditions suitable to provide a compound of formula (a), wherein L is —O(CH₂)$_p$—.

In some embodiments, the first solvent is DMF or DMA. In some embodiments, the acid is HCl. In some such embodiments, the second solvent is MeOH or EtOH. In some embodiments, the contacting with the acid is performed at elevated temperature. In some such embodiments, the temperature is between about 70° C. and about 80° C.

In some embodiments, the methods additionally comprise preparing a compound of formula (q)

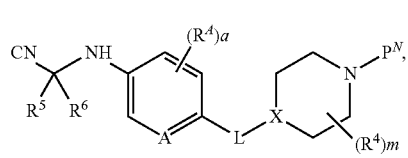

the methods comprising contacting a compound of formula (o)

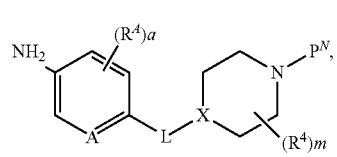

with CN—C(R⁵)(R⁶)OH, in the presence of a drying agent, under conditions suitable to provide a compound of formula (q).

In some embodiments, the drying agent is MgSO₄. In some embodiments, the contacting is performed at elevated temperature. In some such embodiments, the temperature is between about 50° C. and about 70° C.

In some embodiments, the methods additionally comprise preparing a compound of formula (a)

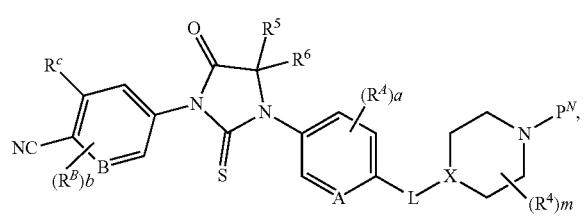

the methods comprising contacting a compound of formula (p)

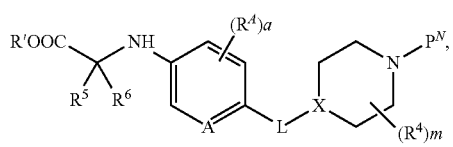

with a compound

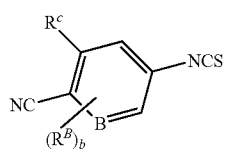

wherein R' is $C_{1-3}$ alkyl, in the presence of a base, in a solvent, under conditions suitable to provide a compound of formula (a), wherein L is —O(CH$_2$)$_p$—.

In some embodiments, the base is TEA. In other embodiments, the solvent is EtOAc. In some embodiments the contacting is performed at elevated temperature. In some such embodiments, the temperature is between about 70° C. and about 90° C.

In some embodiments, the methods additionally comprise preparing a compound of formula (p)

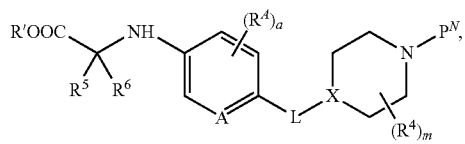

the methods comprising contacting a compound of formula (o)

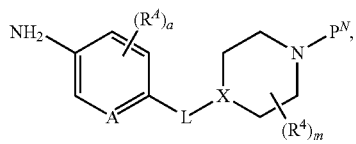

with R'OOC—C(R$^5$)(R$^6$)Hal, wherein Hal is Br or Cl, in the presence of a base, under conditions suitable to provide a compound of formula (p).

In some embodiments, Hal is Br. In some embodiments, the base is DIEA or TEA. In some embodiments the contacting is performed at elevated temperature. In some such embodiments, the temperature is between about 110° C. and about 130° C.

In some embodiments, the methods additionally comprise preparing a compound of formula (o)

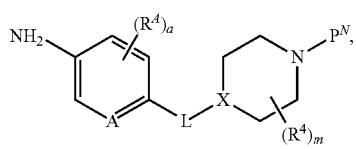

the methods comprising reducing a compound of formula (n)

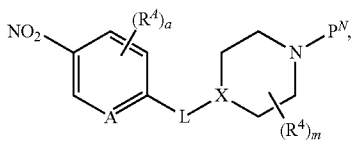

with a reducing agent, in a solvent, under conditions suitable to provide a compound of formula (o).

In some embodiments, the reducing agent is H$_2$. In some such embodiments, the contacting is performed in the presence of a catalyst. In some embodiments the catalyst is Pd/C. In some such embodiments, the solvent is EtOH. In other embodiments, the reducing agent is Fe and NH$_4$Cl. In some such embodiments, the solvent is EtOH and H$_2$O. In some such embodiments, the contacting is performed at elevated temperature. In some embodiments, the temperature is about 80° C.

In some embodiments, the methods additionally comprise preparing a compound of formula (n)

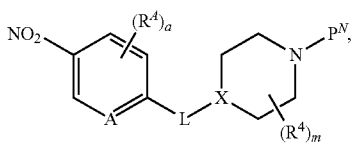

the methods comprising contacting a compound of formula (m)

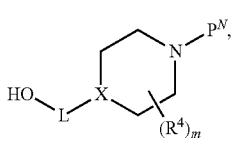

with a compound

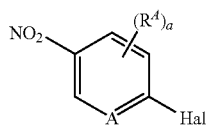

wherein A is N, in the presence of a base, in a solvent, under conditions suitable to provide a compound of formula (n), wherein A is N.

In some embodiments, the base is CsCO$_3$ or K$_2$CO$_3$. In some embodiments, the base is K$_2$CO$_3$. In some embodiments, the solvent is acetonitrile, DMF, THF, or NMP. In some embodiments, the solvent is acetonitrile. In some embodiments, the contacting is performed at elevated temperature. In some such embodiments, the temperature is between about 50° C. and about 70° C.

In some other embodiments, the methods additionally comprise preparing a compound of formula (n)

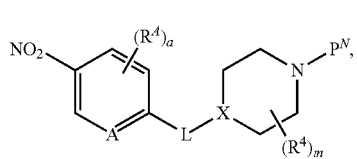

the methods comprising contacting a compound of formula (l)

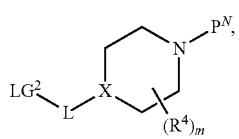

with a compound

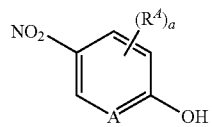

wherein $LG^2$ is Br, Cl or OH, under conditions suitable to provide a compound of formula (n), wherein A is N.

In some embodiments, $LG^2$ is Br or Cl, and the contacting is performed in the presence of a base, in a solvent. In some embodiments, the base is $CsCO_3$ or $K_2CO_3$. In some embodiments, the base is $CsCO_3$. In some embodiments, the solvent is acetonitrile, DMF or NMP. In some embodiments, the solvent is acetonitrile. In some embodiments, the contacting is performed at elevated temperature. In some embodiments the temperature is between about 50° C. and 80° C. In some embodiments, Hal is Br, the base is $CsCO_3$, the solvent is DMF and the temperature is about 70° C. In other embodiments, Hal is Cl, the base is $K_2CO_3$, the solvent is acetonitrile, and the temperature is about 60° C. In some embodiments, $LG^2$ is OH, and the contacting is performed in the presence of $PPh_3$ and DIAD or DEAD, in a solvent. In some embodiments, the solvent is THF. In some embodiments the contacting is performed at room temperature.

In some embodiments, the methods additionally comprise preparing a compound of formula V—OH

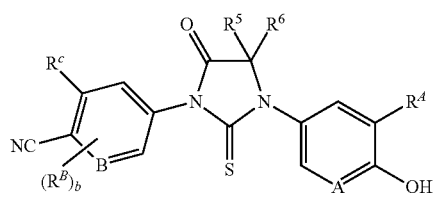

V-OH the methods comprising deprotecting a compound of formula (s)

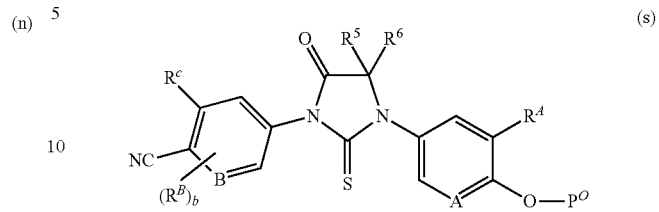

wherein $R^A$ is substituted or unsubstituted $C_{1-6}$ alkyl, or substituted or unsubstituted $C_{3-6}$ cycloalkyl and $P^O$ is a phenol protecting group, under conditions suitable to provide a compound of formula V—OH.

In some embodiments, $P^O$ is acetyl, and the deprotecting is performed by treatment with a base, in a solvent. In some such embodiments, the base is such as $K_2CO_3$. In some embodiments, the solvent is MeOH or EtOH. In other embodiments, $P^O$ is benzyl, and the deprotecting is performed by treatment with a reducing agent in a solvent. In some embodiments, the reducing agent is $H_2$, and the contacting is performed in the presence of a catalyst. In one embodiment, the catalyst is Pd/C. In some embodiments, the solvent is EtOH or MeOH.

In some embodiments, the methods additionally comprise preparing a compound of formula (s)

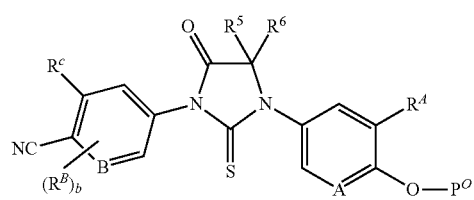

the methods comprising contacting a compound of formula (r)

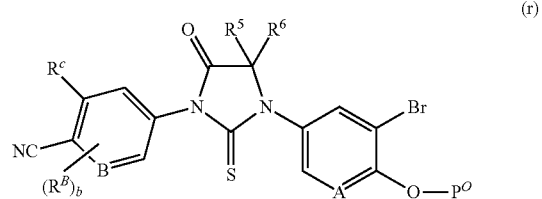

with $R^A$—Zn—Br, wherein $R^A$ is substituted or unsubstituted $C_{1-6}$ alkyl, or substituted or unsubstituted $C_{3-6}$ cycloalkyl, in the presence of a catalyst and a ligand, in a solvent, under conditions suitable to provide a compound of formula (s).

In some embodiments, the catalyst and the ligand are CPhosPdG3 and CPhos. In some embodiments, the solvent is toluene. In some embodiments, the contacting is performed at lower temperature. In some such embodiments, the temperature is between about 0° C. and about 25° C.

In some embodiments, the methods additionally comprise preparing a compound of formula (u)

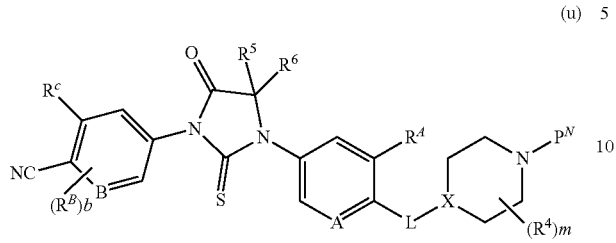

(u)

the methods comprising contacting a compound of formula (t)

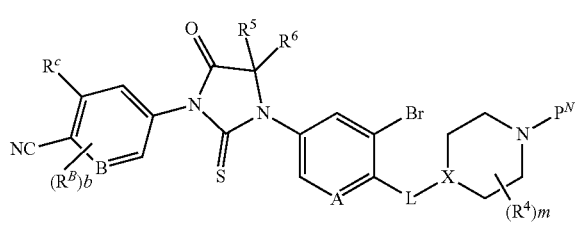

(t)

with $R^A$—Zn—Br, wherein $R^A$ is substituted or unsubstituted $C_{1-6}$ alkyl, or substituted or unsubstituted $C_{3-6}$ cycloalkyl, in the presence of a catalyst and a ligand, in a solvent, under conditions suitable to provide a compound of formula (u).

In some embodiments, the catalyst and the ligand are CPhosPdG3 and CPhos. In some embodiments, the solvent is toluene. In some embodiments, the contacting is performed at lower temperature. In some such embodiments, the temperature is between about 0° C. and about 25° C.

In some embodiments, the methods additionally comprise preparing a compound of formula (x)

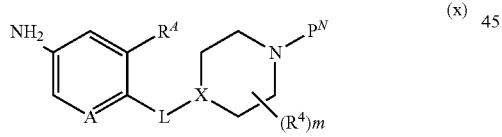

(x)

the methods comprising reducing a compound of formula (y)

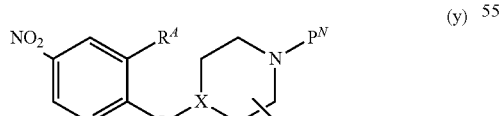

(y)

with a reducing agent, wherein L is —O(CH$_2$)$_p$—, and $R^A$ is substituted or unsubstituted $C_{1-6}$ alkyl, in a solvent, under conditions suitable to provide a compound of formula (x).

In some embodiments, the reducing agent is H$_2$, in the presence of a catalyst. In some embodiments the catalyst is Pd/C. In some embodiments, the solvent is MeOH or EtOH.

In some embodiments, the contacting is performed at a temperature between about 20° C. and about 30° C.

In some embodiments, the methods additionally comprise preparing a compound of formula (y)

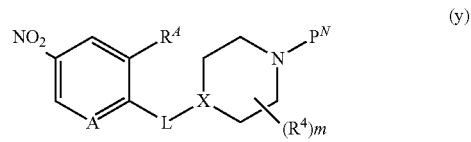

(y)

the methods comprising contacting a compound of formula (v)

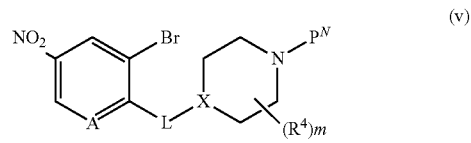

(v)

with $R^A$BF$_3$—K$^+$, wherein $R^A$ is substituted or unsubstituted $C_{1-6}$ alkyl, in the presence of a catalyst and a ligand, in the presence of a base, in a solvent, under conditions suitable to provide a compound of formula (y).

In some embodiments the catalyst and the ligand are cataCXium® A Palladacycle Gen. 3 and butyldi-1-adamantylphosphine. In some embodiments, the base is Cs$_2$CO$_3$ or K$_2$CO$_3$. In some embodiments the base is Cs$_2$CO$_3$. In some embodiments, the solvent is a toluene/water mixture. In some embodiments, the contacting is performed at elevated temperature. In some embodiments, the temperature is between about 90° C. and about 110° C.

In some embodiments, the methods additionally comprise preparing a compound of formula (x)

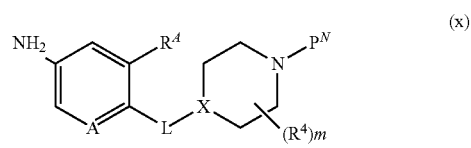

(x)

the methods comprising reducing a compound of formula (w)

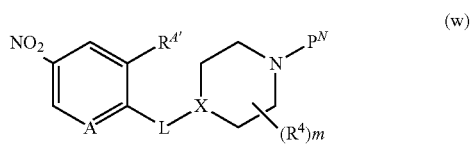

(w)

with a reducing agent, wherein L is —O(CH$_2$)$_p$—, and $R^{A'}$ is substituted or unsubstituted $C_{2-6}$ alkenyl, substituted or unsubstituted cyclopropyl, or substituted or unsubstituted $C_{5-6}$ cycloalkenyl, in a solvent, under conditions suitable to provide a compound of formula (x), wherein $R^A$ is substituted or unsubstituted $C_{2-6}$ alkyl, substituted or unsubstituted cyclopropyl or substituted or unsubstituted $C_{5-6}$ cycloalkyl.

In some embodiments, the reducing agent is H$_2$, in the presence of a catalyst. In some embodiments the catalyst is Pd/C. In some embodiments, the solvent is MeOH or EtOH.

In some embodiments, the contacting is performed at a temperature between about 20° C. and about 30° C.

In some embodiments, the methods additionally comprise preparing a compound of formula (w)

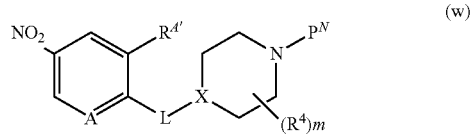

the methods comprising contacting a compound of formula (v)

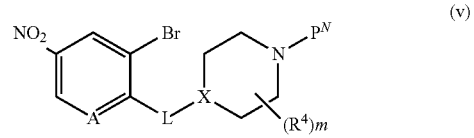

with $R^{A'}[B(OR^+)_2]_2$, wherein $R^{A'}$ is substituted or unsubstituted $C_{2-6}$ alkenyl, substituted or unsubstituted cyclopropyl, or substituted or unsubstituted $C_{5-6}$ cycloalkenyl, and $R^+$ together with the boron atom and the atoms to which they are attached, forms a cyclic boronate, for example, 4,4,4', 4',5,5,5',5'-octamethyl-2,2'-bi(1,3,2-dioxaborolane, in the presence of a catalyst and a base, in a solvent, under conditions suitable to provide a compound of formula (w).

In some embodiments, the catalyst is $Pd(dppf)Cl_2$. In some embodiments, the base is $K_3PO_4$. In some embodiments, the solvent is a 1,4-dioxane/water mixture.

In some embodiments, the methods additionally comprise preparing a compound of formula (v)

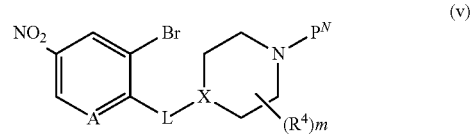

the methods comprising contacting a compound

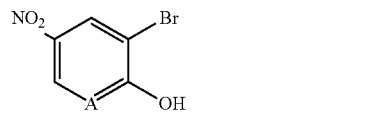

with a compound

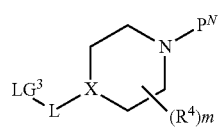

wherein $LG^3$ is OH, Br, Cl, OTs, or OMs, under conditions suitable to provide a compound of formula (v).

In some embodiments, $LG^3$ is Br, Cl, OTs, or OMs, and the contacting is performed in the presence of a base, in a solvent. In some embodiments, the base $CsCO_3$ or $K_2CO_3$. In some embodiments, the solvent is DMF, NMP, or acetonitrile. In some embodiments, the contacting is performed at elevated temperature. In some embodiments, the temperature is between about 40° C. and about 70° C. In other embodiments, $LG^3$ is —OH, and the contacting is performed in the presence of $PPh_3$ and DIAD or DEAD, in a solvent. In some embodiments, the solvent is THF. In some embodiments, the contacting is performed at room temperature.

In one embodiment, provided herein are compounds having the following formula (a):

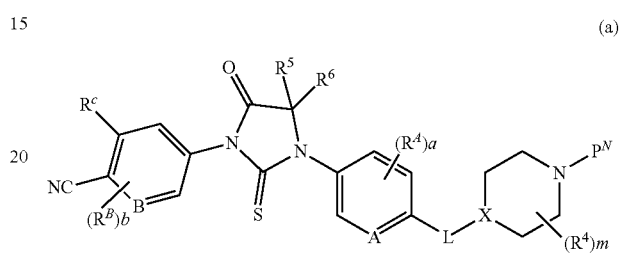

or a pharmaceutically acceptable salt, tautomer, isotopolog, or stereoisomer thereof, where the variables are as described elsewhere herein.

In one embodiment, provided herein is a compound of formula (a), wherein

A is N, CH, or $CR^A$;

B is N, CH, or $CR^B$;

each $R^A$ is independently selected from halogen, substituted or unsubstituted $C_{1-6}$ alkyl, and substituted or unsubstituted $C_{3-6}$ cycloalkyl;

each $R^B$ is independently selected from halogen, and substituted or unsubstituted $C_{1-6}$ alkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;

a is 0-3;

b is 0-2

X is $CR^x$;

$R^x$ is H, halogen, or substituted or unsubstituted $C_{1-3}$ alkyl;

L is —O—, —$O(CH_2)_p$— or —$(CH_2)_p$—;

m is 0-8;

p is 1-3;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl; and $P^N$ is an amine protecting group.

In one embodiment, $P^N$ is tert-butyloxycarbonyl or carboxybenzyl.

In one embodiment, provided herein are compounds having the following formula (b):

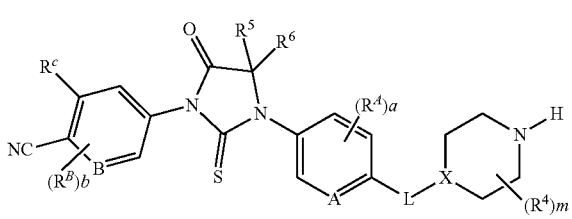

or a pharmaceutically acceptable salt, tautomer, isotopolog, or stereoisomer thereof, where the variables are as described elsewhere herein.

In one embodiment, provided herein is a compound of formula (b), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
X is $CR^x$;
$R^x$ is H, halogen, or substituted or unsubstituted $C_{1-3}$ alkyl;
L is —O—, —O(CH$_2$)$_p$— or —(CH$_2$)$_p$—;
m is 0-8;
p is 1-3; and
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl.

In one embodiment, provided herein are compounds having the following formula (c):

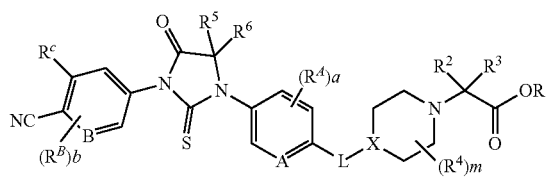

or a pharmaceutically acceptable salt, tautomer, isotopolog, or stereoisomer thereof, where the variables are as described elsewhere herein.

In one embodiment, provided herein is a compound of formula (c), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
X is $CR^x$;
$R^x$ is H, halogen, or substituted or unsubstituted $C_{1-3}$ alkyl;
L is —O—, —O(CH$_2$)$_p$— or —(CH$_2$)$_p$—;
m is 0-8;
p is 1-3;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
$R^2$ and $R^3$ are each independently selected from H, and $C_{1-3}$alkyl, or $R^2$ and
$R^3$ and the carbon to which they are attached form a substituted or unsubstituted $C_{3-6}$cycloalkyl; and
R is $C_{1-4}$ alkyl.

In one embodiment, provided herein are compounds having the following formula (d):

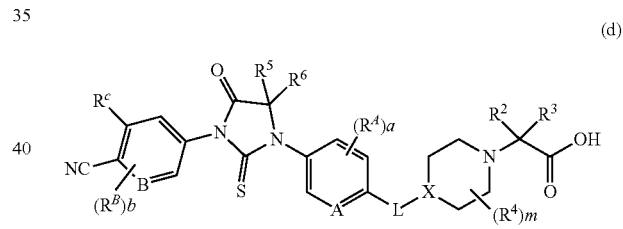

or a pharmaceutically acceptable salt, tautomer, isotopolog, or stereoisomer thereof, where the variables are as described elsewhere herein.

In one embodiment, provided herein is a compound of formula (d), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
X is $CR^x$;
$R^x$ is H, halogen, or substituted or unsubstituted $C_{1-3}$ alkyl;
L is —O—, —O(CH$_2$)$_p$— or —(CH$_2$)$_p$—;

m is 0-8;

p is 1-3;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl; and $R^2$ and $R^3$ are each independently selected from H, and $C_{1-3}$alkyl, or $R^2$ and $R^3$ and the carbon to which they are attached form a substituted or unsubstituted $C_{3-6}$cycloalkyl.

In one embodiment, provided herein are compounds having the following formula (t):

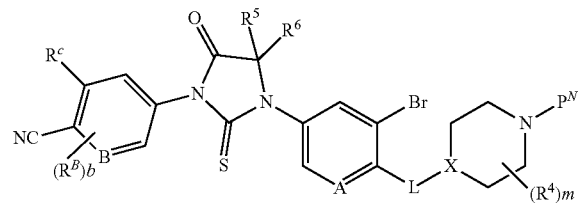

(t)

or a pharmaceutically acceptable salt, tautomer, isotopolog, or stereoisomer thereof, where the variables are as described elsewhere herein.

In one embodiment, provided herein is a compound of formula (t), wherein

A is N, CH, or $CR^A$;

B is N, CH, or $CR^B$;

each $R^B$ is independently selected from halogen, and substituted or unsubstituted $C_{1-6}$ alkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;

b is 0-2

X is $CR^x$;

$R^x$ is H, halogen, or substituted or unsubstituted $C_{1-3}$ alkyl;

L is —O—, —O(CH$_2$)$_p$— or —(CH$_2$)$_p$—;

m is 0-8;

p is 1-3;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl; and $P^N$ is an amine protecting group.

In one embodiment, $P^N$ is tert-butyloxycarbonyl or carboxybenzyl.

In one embodiment, provided herein are compounds having the following formula (u):

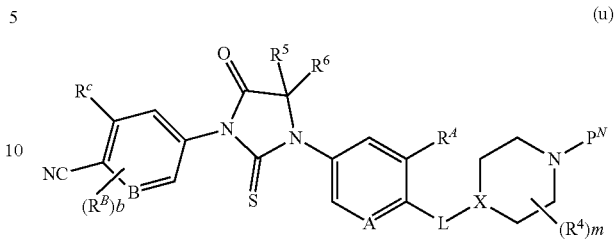

(u)

or a pharmaceutically acceptable salt, tautomer, isotopolog, or stereoisomer thereof, where the variables are as described elsewhere herein.

In one embodiment, provided herein is a compound of formula (u), wherein

A is N, CH, or $CR^A$;

B is N, CH, or $CR^B$;

each $R^B$ is independently selected from halogen, and substituted or unsubstituted $C_{1-6}$ alkyl;

$R^A$ is halogen, substituted or unsubstituted $C_{1-6}$ alkyl, or substituted or unsubstituted $C_{3-6}$ cycloalkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;

b is 0-2

X is $CR^x$;

$R^x$ is H, halogen, or substituted or unsubstituted $C_{1-3}$ alkyl;

L is —O—, —O(CH$_2$)$_p$— or —(CH$_2$)$_p$—;

m is 0-8;

p is 1-3;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl; and $P^N$ is an amine protecting group.

In one embodiment, $P^N$ is tert-butyloxycarbonyl or carboxybenzyl.

Methods of Use

In one embodiment, the compounds described herein have utility as pharmaceuticals to treat, prevent or improve conditions in animals or humans. The Piperidine Dione Compounds described herein have utility as pharmaceuticals to treat, prevent or improve conditions in animals or humans. Accordingly, provided herein are many uses of Piperidine Dione Compounds, including the treatment or prevention of those diseases set forth below. In one embodiment, the methods provided herein comprise the administration of an effective amount of a compound to a subject in need thereof.

The methods provided herein comprise the administration of an effective amount of one or more Piperidine Dione Compound(s) to a subject in need thereof.

Provided herein are methods for treating or preventing an androgen receptor (AR) mediated disease in a subject, the method comprising administering to a subject in need thereof an effective amount of a compound as described herein.

Provided herein are methods for treating or preventing an AR mediated disease in a subject, the method comprising administering to a subject in need thereof an effective amount of a Piperidine Dione Compound as described herein. For example, the Piperidine Dione Compound is a compound from Table 1.

In another aspect, provided herein are compounds for use in the treatment or prevention of an AR mediated disease in a subject, comprising administering to a subject in need thereof an effective amount of a Piperidine Dione Compound as described herein. In some embodiments, provided herein are compounds for use in the treatment of an AR mediated disease in a subject, comprising administering to a subject in need thereof an effective amount of a Piperidine Dione Compound as described herein. In some embodiments, provided herein are compounds for use in the prevention of an AR mediated disease in a subject, comprising administering to a subject in need thereof an effective amount of a Piperidine Dione Compound as described herein.

In some embodiments, the compound used in the methods herein is a Piperidine Dione Compound as described herein. In some embodiments, the compound is a compound of formula (I). In some embodiments, the compound is a compound of formula (II). In some embodiments, the compound is a compound of formula (III). In some embodiments, the compound is a compound of formula (IV). In some embodiments, the compound is a compound of formula (V). In some embodiments, the compound is a compound of formula (VI). In some embodiments, the compound is a compound from Table 1.

In some embodiments, the AR mediated disease is AR wild-type mediated disease. In other embodiments, the AR mediated disease is the result of AR amplification.

In certain embodiments, the AR mediated disease is prostate cancer. In some such embodiments, the prostate cancer is castration resistant prostate cancer (CRPC). In some such embodiments, the prostate cancer is metastatic castration resistant prostate cancer (mCRPC). In still another embodiment, the prostate cancer is non-metastatic CRPC (nmCRPC). In some embodiments, the prostate cancer is hormone refractory. In some embodiments, the prostate cancer is resistant to treatment with an AR antagonist. For example, the prostate cancer is resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

Provided herein are methods of reducing AR levels, the method comprising administering to a subject an effective amount of a Piperidine Dione Compound. Also provided herein are Piperidine Dione Compounds for use in methods of reducing AR levels in a cell in vivo, ex vivo or in vitro, comprising contacting the cell with an effective amount of a Piperidine Dione Compound. In one embodiment, the cell is in a patient. In one embodiment, the cell is not in a patient. In one embodiment, provided herein are methods of reducing levels of wild-type AR within a tumor, the method comprising administering a therapeutically effective amount of a Piperidine Dione Compound, to reduce the level of wild-type AR within the tumor. In one embodiment, provided herein are methods of reducing levels of AR-full length (AR-FL) within a tumor, the method comprising administering a therapeutically effective amount of a Piperidine Dione Compound, to reduce the level of AR-full length (AR-FL) within the tumor. In some embodiments, the AR levels are reduced compared to the AR levels prior to Piperidine Dione Compound administration. In some embodiments, the AR levels are reduced by 20%, 30%, 40%, 50%, 60%, 70%, 805, 90%, 95%, or 99% compared to the AR levels prior to Piperidine Dione Compound administration.

Also provided herein are methods for regulating protein activity of AR in a patient in need thereof, comprising administering to said patient an amount of a Piperidine Dione Compound. In some such embodiments, provided herein are methods for decreasing protein activity of AR in a patient in need thereof, comprising administering to said patient an amount of a Piperidine Dione Compound. In some embodiments, the protein activity of AR is reduced compared to the protein activity of AR prior to Piperidine Dione Compound administration. In some embodiments, the protein activity of AR is reduced by 20%, 30%, 40%, 50%, 60%, 70%, 805, 90%, 95%, or 99% compared to the protein activity of AR prior to Piperidine Dione Compound administration.

In some embodiments of the methods described herein, the methods additionally comprise administering one or more second agents selected from an AR antagonist (such as cyproterone acetate, spironolactone, bicalutamide, and enzalutamide), a 5α-reductase inhibitor (such as finasteride and dutasteride), a CYP17A1 inhibitor (such as abiraterone acetate), a gonadotropin-releasing hormone (GnRH) analog (such as leuprorelin and cetrorelix), and an anti-gonadotropin (such as megestrol acetate and medroxyprogesterone acetate).

In some embodiments, the compounds provided herein may be used in any of the above-mentioned methods.

In some embodiments, the Piperidine Dione Compound provided herein may be used in any of the above-mentioned methods.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The Piperidine Dione Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Piperidine Dione Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a Piperidine Dione Compound to be administered to a subject is rather widely variable and can be subject to the judgment of a health-care practitioner. In general, the Piperidine Dione Compounds can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Piperidine Dione Compound administered will depend on such factors as the solubility of the active component, the formulation used and the route of administration.

In another embodiment, provided herein are methods for the treatment or prevention of a disease or disorder comprising the administration of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day of a Piperidine Dione Compound to a subject in need thereof.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a Piperidine Dione Compound.

In a particular embodiment, provided herein are unit dosage formulations comprising about 0.1 mg or 100 mg of a Piperidine Dione Compound.

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Piperidine Dione Compound.

An Piperidine Dione Compound can be administered once, twice, three, four or more times daily. In a particular embodiment, doses of 100 mg or less are administered as a once daily dose and doses of more than 100 mg are administered twice daily in an amount equal to one half of the total daily dose.

An Piperidine Dione Compound can be administered orally for reasons of convenience. In one embodiment, when administered orally, a Piperidine Dione Compound is administered with a meal and water. In another embodiment, the Piperidine Dione Compound is dispersed in water or juice (e.g., apple juice or orange juice) or any other liquid and administered orally as a solution or a suspension.

The Piperidine Dione Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Piperidine Dione Compound without an additional carrier, excipient or vehicle.

In another embodiment, provided herein are compositions comprising an effective amount of a Piperidine Dione Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Piperidine Dione Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Piperidine Dione Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Piperidine Dione Compound can be delayed or prolonged by proper formulation. For example, a slowly soluble pellet of the Piperidine Dione Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Piperidine Dione Compound in oily or emulsified vehicles that allow it to disperse slowly in the serum.

EXAMPLES

The following Examples are presented by way of illustration, not limitation Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

Abbreviations Used

| Boc | tert-Butyloxycarbonyl |
|---|---|
| Boc$_2$O | di-tert-Butyl dicarbonate |

-continued

| | |
|---|---|
| nBuLi | n-Butyllithium |
| CataCXium ®A Palladacycle Gen. 3 | Methanesulfonato(diadamantyl-n-butylphosphino)-2'-amino-1,1'-biphenyl-2-yl)palladium(II) dichloromethane adduct |
| CPhos | 2-(2-Dicyclohexylphosphanylphenyl)-N$^1$,N$^1$,N$^3$,N$^3$-tetramethyl-benzene-1,3-diamine |
| CPhosPdG3 | [(2-Dicyclohexylphosphino-2',6'-bis(N,N-dimethylamino)-1,1'-biphenyl)-2-(2'-amino-1,1'-biphenyl)] palladium(II) methanesulfonate |
| DCM | Dichloromethane |
| DIAD | Diisopropyl azodicarboxylate |
| DEAD | Diethyl azodicarboxylate |
| DIEA | N,N-Diisopropylethylamine |
| DMA | N,N-Dimethylacetamide |
| DMF | N,N-Dimethylformamide |
| DMSO | Dimethylsulfoxide |

-continued

| | |
|---|---|
| ESI | Electrospray ionization |
| EtOH | Ethanol |
| EtOAc | Ethyl acetate |
| FeCl$_2$ | Iron(II) chloride |
| HATU | 1-[Bis(dimethylamino)methylene]-1H-1,2,3-triazolo[4,5-b]pyridinium 3-oxide hexafluorophosphate |
| HPLC | High performance liquid chromatography |
| HTRF | Homogeneous time resolved fluorescence |
| LCMS | Liquid chromatography mass spectrometry |
| MeOH | Methanol |
| MS | Mass spectrometry |
| MTBE | Methyl tert-butyl ether |
| NMP | N-Methylpyrrolidone |
| NMR | Nuclear magnetic resonance |
| OMs | Mesylate |
| OTs | Tosylate |
| PPh3 | Triphenylphosphine |
| TEA | Triethylamine |
| TFA | Trifluoroacetic acid |
| Tf$_2$O | Triflic anhydride |
| THF | Tetrahydrofuran |
| THP | Tetrahydropyrane |
| TLC | Thin layer chromatography |
| TMSCl | Trimethylsilyl chloride |
| TMSCN | Trimethylsilyl cyanide |
| TMSOTf | Trimethylsilyl trifluoromethanesulfonate |
| TsOH | p-Toluenesulfonic acid |

Compound Synthesis

Example 1: 2-(4-(4-(3-(4-Cyano-3-(trifluoromethyl) phenyl)-5,5-dimethyl-4-oxo-2-thioxoimidazolidin-1-yl)-2-fluorophenoxy)piperidin-1-yl)-N-(3-((2,6-dioxopiperidin-3-yl)amino)phenyl)acetamide formate

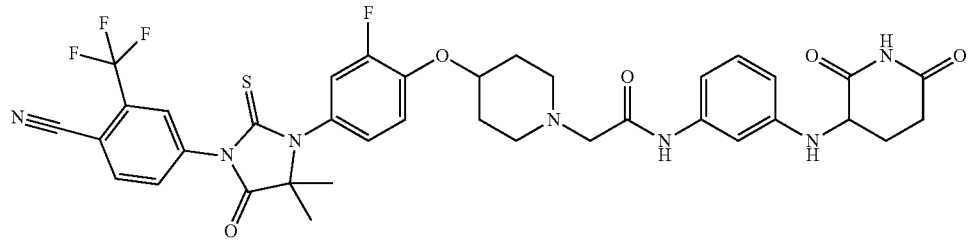 [SMILES: CC1(C)C(=O)N(c2ccc(C#N)c(C(F)(F)F)c2)C(=S)N1c1ccc(OC2CCN(CC(=O)Nc3cccc(NC4CCC(=O)NC4=O)c3)CC2)c(F)c1]

4-Isothiocyanato-2-(trifluoromethyl)benzonitrile

To a solution of thiocarbonyl dichloride (82.9 g, 0.72 mol) in water (1 L) was added 4-amino-2-(difluoromethyl-fluoranyl)benzonitrile (90 g, 0.48 mol) at 15° C. After addition, the reaction was stirred at 28° C. for 6 h. The reaction mixture was extracted with EtOAc (300 mL×3). Combined organic extracts were concentrated and purified by silica gel chromatography column (0-5% EtOAc in petroleum ether) to afford 4-isothiocyanato-2-(trifluoromethyl)benzonitrile (110 g, 99.7% yield) as a brown solid. $^1$H NMR (400 MHz, CDCl$_3$) δ ppm 7.85 (d, J=8.4 Hz, 1H), 7.59 (d, J=1.6 Hz, 1H), 7.50 (dd, J=1.6 Hz, 8.0 Hz, 1H).

2-(3-Fluoro-4-hydroxy-anilino)-2-methyl-propanenitrile

To a solution of 4-amino-2-fluoro-phenol (80 g, 0.63 mol) in acetaone (400 mL) and DCM (800 mL) was added trimethylsilylformonitrile (87.4 g, 0.88 mol) and trimethylsilyl trifluoromethanesulfonate (7.0 g, 0.03 mol). The reaction was stirred at 25° C. for 16 h, filtered, and the filtrate was concentrated. The residue was purified by silica gel column chromatography (10-25% EtOAc in petroleum ether) to afford 2-(3-fluoro-4-hydroxy-anilino)-2-methyl-propanenitrile (76 g, 62.2% yield) as a brown solid. $^1$H NMR (400 MHz, DMSO-d$_6$) δ ppm 9.18 (s, 1H), 6.82 (t, J=10.0 Hz, 1H), 6.67 (dd, J=2.4 Hz, 13.2 Hz, 1H), 6.57-6.55 (m, 1H), 1.55 (s, 6H).

4-[3-(3-Fluoro-4-hydroxy-phenyl)-4,4-dimethyl-5-oxo-2-thioxo-imidazolidin-1-yl]-2-(trifluoromethyl)benzonitrile To a solution of 2-(3-fluoro-4-hydroxy-anilino)-2-methyl-propanenitrile (80 g, 0.41 mol) in dimethylacetamide (1.2 L) was added 4-isothiocyanato-2-(trifluoromethyl)benzonitrile (113 g, 0.49 mol) and the reaction was stirred at 25° C. for 3 h. A 2.0 M solution of HCl in MeOH (800 mL) and MeOH (800 mL) were added between 0-10° C. After addition, the reaction was stirred at 70° C. for 2 h, then poured into ice-water (200 mL) and extracted with EtOAc (100 mL×3). The combined organic layers were concentrated and purified by silica gel chromatography column (10-15% EtOAc in petroleum ether) to afford 4-[3-(3-fluoro-4-hydroxy-phenyl)-4,4-dimethyl-5-oxo-2-thioxo-imidazolidin-1-yl]-2-(trifluoromethyl)benzonitrile (52.2 g, 29.9% yield) as a white solid. $^1$H NMR (400 MHz, DMSO-d$_6$) δ ppm 10.38 (s, 1H), 8.38 (d, J=8.4 Hz, 1H), 8.27 (s, 1H), 8.07-8.05 (m, 1H), 7.22 (dd, J=2.4 Hz, 11.6 Hz, 1H), 7.09 (t, J=8.8 Hz, 1H), 7.03-7.02 (m, 1H), 1.50 (s, 6H).

tert-Butyl 4-(4-(3-(4-Cyano-3-(trifluoromethyl)phenyl)-5,5-dimethyl-4-oxo-2-thioxoimidazolidin-1-yl)-2-fluorophenoxy)piperidine-1-carboxylate 4-(3-(3-Fluoro-4-hydroxyphenyl)-4,4-dimethyl-5-oxo-2-thioxoimidazolidin-1-yl)-2-(trifluoromethyl)benzonitrile (0.5 g, 1.181 mmol), tert-butyl 4-((methylsulfonyl)oxy)piperidine-1-carboxylate (0.660 g, 2.362 mmol) and cesium carbonate (1.154 g, 3.54 mmol) were combined in DMF (8 mL) and the mixture was heated to 80° C. in a screw cap vial. After 16 h, the solution was partitioned between water and a mixture of EtOAc (75%) and hexanes (25%). The combined organic extracts were dried over magnesium sulfate, filtered, and concentrated under reduced pressure to afford a yellow oil. The oil was purified by silica gel column chromatography (0-45% EtOAc in hexanes) to afford the title compound as a solid upon drying (0.558 g, 0.920 mmol, 78% yield). MS (ESI) m/z 629 [M+Na]$^+$.

4-(3-(3-Fluoro-4-(piperidin-4-yloxy)phenyl)-4,4-dimethyl-5-oxo-2-thioxoimidazolidin-1-yl)-2-(trifluoromethyl)benzonitrile hydrochloride To a solution of tert-Butyl 4-(4-(3-(4-cyano-3-(trifluoromethyl)phenyl)-5,5-dimethyl-4-oxo-2-thioxoimidazolidin-1-yl)-2-fluorophenoxy)piperidine-1-carboxylate (0.568 g, 0.936 mmol) in DCM (3 mL) was added a 4.0 M solution of HCl in dioxane (2.34 mL, 9.36 mmol). The mixture was stirred at ambient temperature. After 30 min, the solution was concentrated under reduced pressure to afford the title compound (0.569 g, 1.05 mmol, quant. yield). MS (ESI) m/z 543 [M+1]$^+$.

Methyl 2-(4-(4-(3-(4-cyano-3-(trifluoromethyl)phenyl)-5,5-dimethyl-4-oxo-2-thioxoimidazolidin-1-yl)-2-fluorophenoxy)piperidin-1-yl)acetate 4-(3-(3-Fluoro-4-(piperidin-4-yloxy)phenyl)-4,4-dimethyl-5-oxo-2-thioxoimidazolidin-1-yl)-2-(trifluoromethyl)benzonitrile hydrochloride (0.250 g, 0.460 mmol) was combined with TEA (0.193 mL, 1.38 mmol) in THF (2.5 mL). After stirring for 2 min, methyl 2-bromoacetate (0.047 mL, 0.460 mmol) was added and the mixture was stirred at ambient temperature in a screw cap flask. After 2 h, the solution was concentrated under reduced pressure to afford a white residue that was purified via silica gel column chromatography (0-100% EtOAc in hexanes then 0-5% MeOH in EtOAc) to afford the title compound (0.231 g, 0.399 mmol, 87% yield). MS (ESI) m/z 579 [M+1]$^+$.

2-(4-(4-(3-(4-Cyano-3-(trifluoromethyl)phenyl)-5,5-dimethyl-4-oxo-2-thioxoimidazolidin-1-yl)-2-fluorophenoxy)piperidin-1-yl)acetic acid Methyl 2-(4-(4-(3-(4-cyano-3-(trifluoromethyl)phenyl)-5,5-dimethyl-4-oxo-2-thioxoimidazolidin-1-yl)-2-fluorophenoxy)piperidin-1-yl)acetate (0.243 g, 0.420 mmol) was dissolved in THF (2 mL) and treated with a solution of lithium hydroxide hydrate (0.176 g, 4.20 mmol) dissolved in water (2.000 mL). The mixture was stirred at ambient temperature. After 1 h, the solution was acidified using a 2 M aqueous solution of HCl to pH 5. The mixture was then partitioned between water and 10% MeOH in DCM. The combined organic layers were washed with brine and the organic layer was dried over magnesium sulfate, filtered, and concentrated under reduced pressure to afford the title compound as a white solid (0.163 g, 0.289 mmol, 69% yield). MS (ESI) m/z 565 [M+1]$^+$.

2-(4-(4-(3-(4-Cyano-3-(trifluoromethyl)phenyl)-5,5-dimethyl-4-oxo-2-thioxoimidazolidin-1-yl)-2-fluorophenoxy)piperidin-1-yl)-N-(3-((2,6-dioxopiperidin-3-yl)amino)phenyl)acetamide formate To a mixture of 2-(4-(4-(3-(4-cyano-3-(trifluoromethyl)phenyl)-5,5-dimethyl-4-oxo-2-thioxoimidazolidin-1-yl)-2-fluorophenoxy)piperidin-1-yl)acetic acid (0.060 g, 0.106 mmol), 3-((3-aminophenyl)amino)piperidine-2,6-dione trifluoroacetate (0.034 g, 0.106 mmol) and DIEA (0.056 mL, 0.319 mmol) in DMF (1 mL) was added HATU (0.040 g, 0.106 mmol) at ambient temperature. After 1 h, the solution was purified by standard methods to afford 2-(4-(4-(3-(4-cyano-3-(trifluoromethyl)phenyl)-5,5-dimethyl-4-oxo-2-thioxoimidazolidin-1-yl)-2-fluorophenoxy)piperidin-1-yl)-N-(3-((2,6-dioxopiperidin-3-yl)amino)phenyl)acetamide formate (0.033 g, 0.043 mmol, 40.5% yield). MS (ESI) m/z 766 [M+1]$^+$; $^1$H NMR (400 MHz, DMSO-d$_6$) δ ppm 10.78 (s, 1H), 9.44 (s, 1H), 8.39 (d, J=8.19 Hz, 1H), 8.28 (d, J=1.71 Hz, 1H), 8.20 (s, 1H), 8.06 (dd, J=8.13, 1.77 Hz, 1H), 7.41 (t, J=9.17 Hz, 1H), 7.31 (dd, J=11.74, 2.45 Hz, 1H), 7.11-7.17 (m, 1H), 6.97-7.03 (m, 2H), 6.86 (d, J=8.07 Hz, 1H), 6.54 (s, 1H), 6.40 (dd, J=7.82, 1.59 Hz, 1H), 5.87 (d, J=7.82 Hz, 1H), 4.51-4.59 (m, 1H), 4.26 (br d, J=7.82 Hz, 1H), 3.13 (s, 2H), 2.80 (td, J=5.23, 1.77 Hz, 2H), 2.68-2.76 (m, 1H), 2.53-2.66 (m, 3H), 2.37-2.45 (m, 1H), 1.99-2.14 (m, 3H), 1.74-1.91 (m, 3H), 1.51 (s, 6H), 0.85 (br d, J=10.76 Hz, 1H), 0.01-0.02 (m, 2H), −0.03-−0.01 (m, 3H), −0.15 (s, 1H).

Example 2: 2-(4-((4-(3-(4-Cyano-3-(trifluoromethyl)phenyl)-5,5-dimethyl-4-oxo-2-thioxoimidazolidin-1-yl)-2-fluorophenoxy)methyl)piperidin-1-yl)-N-(3-((2,6-dioxopiperidin-3-yl)amino)phenyl) acetamide formate

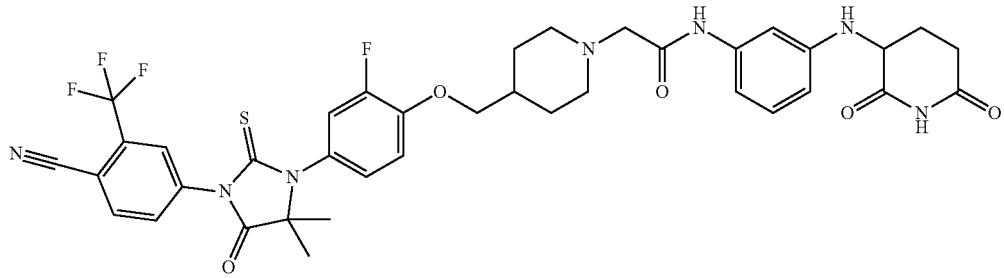 [SMILES: CC1(C)C(=O)N(c2ccc(C#N)c(C(F)(F)F)c2)C(=S)N1c1ccc(OCC2CCN(CC(=O)Nc3cccc(NC4CCC(=O)NC4=O)c3)CC2)c(F)c1]

tert-Butyl 4-((4-(3-(4-cyano-3-(trifluoromethyl)phenyl)-5,5-dimethyl-4-oxo-2-thioxoimidazolidin-1-yl)-2-fluorophenoxy)methyl)piperidine-1-carboxylate 4-(3-(3-Fluoro-4-hydroxyphenyl)-4,4-dimethyl-5-oxo-2-thioxoimidazolidin-1-yl)-2-(trifluoromethyl)benzonitrile (0.500 g, 1.18 mmol), tert-butyl 4-(((methyl sulfonyl)oxy)methyl)piperidine-1-carboxylate (0.693 g, 2.36 mmol) and cesium carbonate (1.154 g, 3.54 mmol) were combined in DMF (8 mL) and the mixture was heated to 70° C. in a screw cap vial. After 16 h, the solution was partitioned between water and a mixture of EtOAc (75%) and hexanes (25%). The aqueous phase was extracted with the same mixture of EtOAc (75%) and hexanes (25%). The combined organic layers were dried over magnesium sulfate, filtered, and concentrated under reduced pressure to afford a yellow oil. The oil was purified by silica gel column chromatography (0-45% EtOAc in hexanes) to afford the title compound as a foam that solidified upon drying (0.558 g, 0.899 mmol, 76% yield). MS (ESI) m/z 643 [M+Na]$^+$.

4-(3-(3-Fluoro-4-(piperidin-4-ylmethoxy)phenyl)-4,4-dimethyl-5-oxo-2-thioxoimidazolidin-1-yl)-2-(trifluoromethyl)benzonitrile hydrochloride tert-Butyl 4-((4-(3-(4-cyano-3-(trifluoromethyl)phenyl)-5,5-dimethyl-4-oxo-2-thioxoimidazolidin-1-yl)-2-fluorophenoxy)methyl)piperidine-1-carboxylate (0.558 g, 0.899 mmol) was dissolved in DCM (3 mL) and treated with a 4.0 M solution of HCl in dioxane (2.248 mL, 8.99 mmol). The mixture was stirred at ambient temperature. After 30 min, the solution was concentrated under reduced pressure to afford the title product as a solid (0.528 g, 0.948 mmol, quant. yield). MS (ESI) m/z 521 [M+1]$^+$.

Methyl 2-(4-((4-(3-(4-cyano-3-(trifluoromethyl)phenyl)-5,5-dimethyl-4-oxo-2-thioxoimidazolidin-1-yl)-2-fluorophenoxy)methyl)piperidin-1-yl)acetate 4-(3-(3-Fluoro-4-(piperidin-4-ylmethoxy)phenyl)-4,4-dimethyl-5-oxo-2-thioxoimidazolidin-1-yl)-2-(trifluoromethyl)benzonitrile hydrochloride (0.250 g, 0.449 mmol) was combined with TEA (0.188 mL, 1.346 mmol) in THF (2.5 mL). Methyl 2-bromoacetate (0.045 mL, 0.449 mmol) was then added and the mixture was stirred at ambient temperature in a screw cap vial. After 2 h, the solution was concentrated under reduced pressure to afford a white residue. The residue was purified by silica gel column chromatography (0-100% EtOAc in hexanes) to afford the title compound (0.166 g, 0.280 mmol, 62.4% yield). MS (ESI) m/z 593 [M+1]$^+$.

2-(4-((4-(3-(4-Cyano-3-(trifluoromethyl)phenyl)-5,5-dimethyl-4-oxo-2-thioxoimidazolidin-1-yl)-2-fluorophenoxy)methyl)piperidin-1-yl)acetic acid Methyl 2-(4-((4-(3-(4-cyano-3-(trifluoromethyl)phenyl)-5,5-dimethyl-4-oxo-2-thioxoimidazolidin-1-yl)-2-fluorophenoxy)methyl)piperidin-1-yl)acetate (0.166 g, 0.280 mmol) was dissolved in THF (2 mL) and was treated with a solution of lithium hydroxide hydrate (0.118 g, 2.80 mmol) in water (2.00 mL). The mixture was stirred at ambient temperature. After 1 h, the solution was acidified using a 2.0 M aqueous solution of HCl to pH=5 and was partitioned between water and a solution of 10% MeOH in DCM. The organic layers were combined, washed with brine, dried over magnesium sulfate, filtered, and concentrated under reduced pressure to afford the title compound as a white solid (0.122 g, 0.211 mmol, 75% yield). MS (ESI) m/z 579 [M+1]$^+$.

2-(4-((4-(3-(4-Cyano-3-(trifluoromethyl)phenyl)-5,5-dimethyl-4-oxo-2-thioxoimidazolidin-1-yl)-2-fluorophenoxy)methyl)piperidin-1-yl)-N-(3-((2,6-dioxopiperidin-3-yl)amino)phenyl)acetamide formate In a scintillation vial, 2-(4-((4-(3-(4-cyano-3-(trifluoromethyl)phenyl)-5,5-dimethyl-4-oxo-2-thioxoimidazolidin-1-yl)-2-fluorophenoxy)methyl)piperidin-1-yl)acetic acid (0.060 g, 0.104 mmol), 3-((3-aminophenyl)amino)piperidine-2,6-dione (0.033 g, 0.104 mmol) and DIEA (0.054 mL, 0.311 mmol) were combined in DMF (1 mL). HATU (0.039 g, 0.104 mmol) was added. After 1 h at ambient temperature, the solution was diluted with DMSO and purified by standard methods to afford 2-(4-((4-(3-(4-cyano-3-(trifluoromethyl)phenyl)-5,5-dimethyl-4-oxo-2-thioxoimidazolidin-1-yl)-2-fluorophenoxy)methyl)piperidin-1-yl)-N-(3-((2,6-dioxopiperidin-3-yl)amino)phenyl)acetamide formate (0.037 g, 0.047 mmol, 46% yield). MS (ESI) m/z 780 [M+1]$^+$; $^1$H NMR (400 MHz, DMSO-d$_6$) δ ppm 10.77 (s, 1H), 9.41 (br d, J=2.45 Hz, 1H), 8.39 (d, J=8.31 Hz, 1H), 8.27 (s, 1H), 8.13 (s, 1H), 8.06 (dd, J=8.38, 1.77 Hz, 1H), 7.28-7.38 (m, 2H), 7.16 (d, J=8.68 Hz, 1H), 6.97-7.02 (m, 2H), 6.81 (d, J=8.20 Hz, 1H), 6.52 (s, 1H), 6.38-6.41 (m, 1H), 5.88 (d, J=7.34 Hz, 1H), 4.22-4.30 (m, 1H), 4.00 (br d, J=5.87 Hz, 2H), 3.27-3.30 (m, 3H), 3.03-3.15 (m, 2H), 2.87-2.98 (m, 2H), 2.68-2.79 (m, 1H), 2.52-2.63 (m, 3H), 2.16-2.28 (m, 2H), 2.05-2.14 (m, 2H), 1.76-1.94 (m, 4H), 1.42-1.53 (m, 8H), 1.22-1.30 (m, 1H), 0.95 (d, J=6.60 Hz, 1H), 0.82-0.88 (m, 1H), 0.01-0.02 (m, 2H), −0.03-−0.01 (m, 4H), −0.15 (s, 1H).

Example 3: 2-[(2R,4S)-4-[2-[4-[3-[4-Cyano-3-(trifluoromethyl)phenyl]-5,5-dimethyl-4-oxo-2-thioxo-imidazolidin-1-yl]-2-ethyl-phenoxy]ethyl]-2-methyl-1-piperidyl]-N-[3-[(2,6-dioxo-3-piperidyl)amino]phenyl]acetamide hydrochloride

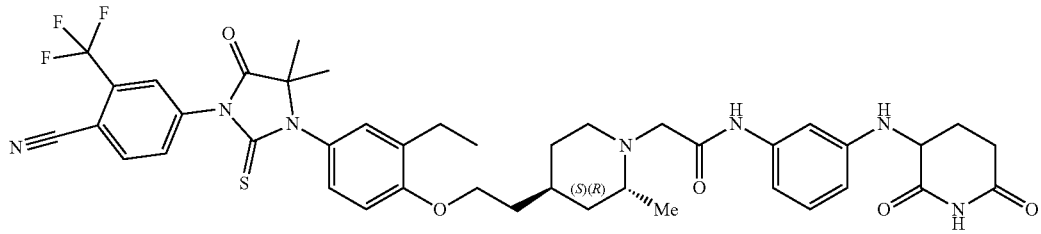

tert-Butyl (R,E)-4-(2-ethoxy-2-oxoethylidene)-2-methylpiperidine-1-carboxylate To a vial containing sodium hydride (0.281 g, 7.03 mmol, 1.50 eq) was added THF (4.69 mL, 1 M). The vial was placed in an ice bath and triethyl phosphonoacetate (1.40 mL, 7.03 mmol, 1.50 equiv) was added dropwise. After stirring for 10 min the flask was removed from the ice bath and warmed to room temperature. tert-butyl rac-(2R)-2-methyl-4-oxo-piperidine-1-carboxylate (1.00 g, 4.69 mmol, 1.00 eq) was added as a solution in THF (2.0 mL). The reaction solution was stirred at room temperature for 3 h, then was diluted with diethyl ether (75 mL) and washed with saturated aqueous sodium bicarbonate (2×100 mL) and brine (100 mL). The organic layer was dried over magnesium sulfate and concentrated to an orange oil that was purified by silica gel column chromatography (15-30% diethylether in hexanes) to give tert-butyl (R,E)-4-(2-ethoxy-2-oxoethylidene)-2-methylpiperidine-1-carboxylate (1.01 g, 3.56 mmol, 76.0% yield) as a colorless oil. MS (ESI) m/z 306.2 [M+1]$^+$; $^1$H NMR (400 MHz, CDCl$_3$) δ ppm 5.53 (br s, 1H), 5.49-5.44 (m, 1H), 4.57-4.35 (m, 2H), 4.24-4.19 (m, 1H), 4.18-4.09 (m, 4H), 3.54 (td, J=1.8, 18.6 Hz, 1H), 3.03-2.98 (m, 3H), 2.93-2.77 (m, 1H), 2.53-2.40 (m, 1H), 2.32-2.19 (m, 1H), 1.93 (br dd, J=3.2, 16.8 Hz, 1H), 1.85 (br d, J=16.8 Hz, 1H), 1.47 (s, 9H), 1.46 (s, 6H), 1.26 (dt, J=0.8, 7.1 Hz, 5H), 1.16 (d, J=6.7 Hz, 3H), 1.10 (d, J=6.7 Hz, 2H).

tert-Butyl (2R)-4-(2-Ethoxy-2-oxo-ethyl)-2-methyl-piperidine-1-carboxylate

To a solution of tert-butyl (R,E)-4-(2-ethoxy-2-oxoethylidene)-2-methylpiperidine-1-carboxylate (1.280 g, 4.52 mmol) in EtOH (18.1 mL, 0.25 M) followed by ~1 g of wetted palladium on carbon. The flask was evacuated under house vacuum and purged with a hydrogen balloon three times. The reaction was stirred under hydrogen atmosphere overnight. After 16 h, the reaction solution was filtered through celite and the filtrate was concentrated to provide a yellow oil. The crude material was taken up in chloroform, filtered through a syringe filter and concentrated to provide tert-butyl (2R)-4-(2-ethoxy-2-oxo-ethyl)-2-methyl-piperidine-1-carboxylate (1.183 g, 4.145 mmol, 91.7% yield) as a 2:3 mixture of diastereomers. MS (ESI) m/z 308.2 [M+Na]$^+$; $^1$H NMR (400 MHz, CDCl$_3$) δ ppm 4.21-4.05 (m, 4H), 4.02-3.84 (m, 1H), 3.77-3.62 (m, 1H), 3.06 (ddd, J=5.7, 10.3, 13.9 Hz, 1H), 2.94-2.79 (m, 1H), 2.21-2.13 (m, 3H), 2.10-2.02 (m, 1H), 1.99-1.86 (m, 1H), 1.85-1.75 (m, 1H), 1.73-1.53 (m, 3H), 1.45 (s, 6H), 1.45 (s, 8H), 1.26 (t, J=7.1 Hz, 6H), 1.17 (d, J=6.5 Hz, 2H), 1.15 (s, 3H).

Ethyl 2-[(2R)-2-methyl-4-piperidyl]acetate hydrochloride

To a vial containing tert-butyl (2R)-4-(2-ethoxy-2-oxo-ethyl)-2-methyl-piperidine-1-carboxylate (0.452 g, 1.58 mmol) added a 4.0 M solution of HCl in dioxane (7.92 mL, 31.68 mmol, 20 equiv). The reaction solution was stirred at room temperature for 45 min, then was concentrated under reduced pressure to provide ethyl 2-[(2R)-2-methyl-4-piperidyl]acetate hydrochloride (0.342 g, 1.542 mmol, 97.4% yield) as a white solid. The material was carried forward without further purification. MS (ESI) 186.2 [M+1]$^+$

Ethyl 2-[(2R)-1-[(4-methoxyphenyl)methyl]-2-methyl-4-piperidyl]acetate

To a 40 ml vial containing ethyl 2-[(2R)-2-methyl-4-piperidyl]acetate hydrochloride (1.00 g, 4.51 mmol) added DMF (15.034 mL) and DIEA (4.71 mL, 27.1 mmol) followed by 4-methoxybenzyl chloride (0.67 mL, 4.96 mmol). The reaction was heated to 50° C. The reaction solution was diluted with EtOAc (125 mL) and washed with saturated aqueous sodium bicarbonate (2×125 mL) and brine (125 mL). The organic layer was dried over magnesium sulfate and concentrated to provide an amber oil, which was purified by silica gel column chromatography (0.5-10% MeOH in DCM with 0.2% TEA) to give ethyl 2-[(2R)-1-[(4-methoxyphenyl)methyl]-2-methyl-4-piperidyl]acetate (1.09 g, 3.57 mmol, 79.1% yield) as a clear colorless oil. MS (ESI) m/z 306.2 [M+1]$^+$.

2-[(2R,4S)-1-[(4-Methoxyphenyl)methyl]-2-methyl-4-piperidyl]ethanol

A solution of ethyl 2-[(2R)-1-[(4-methoxyphenyl)methyl]-2-methyl-4-piperidyl]acetate (1.19 g, 3.9 mmol, 1.00 eq) in THF (19.5 mL, 0.1 M) was placed in an EtOH/water cooling bath at −20° C. A solution of diisobutylaluminum hydride (1.39 mL, 7.79 mmol, 2.00 eq) in THF (5 mL) was added dropwise. After 20 min, the reaction was quenched via the Fieser workup. To the solution was carefully added water dropwise (0.31 mL), followed by a 15% aqueous NaOH solution (0.31 mL) and water (1.1 mL). The solution was stirred for 2 min and then was diluted with diethylether (50 mL) and allowed to warm to room temperature. After 15 min at room temperature, anhydrous sodium sulfate was added and the slurry stirred for 30 min.

The slurry was filtered through celite and the solids were washed thoroughly with diethyl ether followed by EtOAc. The solution was concentrated to a clear, colorless oil. The crude material was purified by SFC (iridis BEH column, 10% MeOH with 10 mM ammonium acetate modifier) to give 2-[(2R,4S)-1-[(4-methoxyphenyl)methyl]-2-methyl-4-piperidyl]ethanol (0.380 g, 1.44 mmol, 37.0% yield). MS (ESI) m/z 264.2 [M+1]$^+$; $^1$H NMR (400 MHz, CDCl$_3$) δ ppm 7.37-7.29 (m, 2H), 6.87 (d, J=8.8 Hz, 2H), 3.93 (d, J=13.1 Hz, 1H), 3.80 (s, 3H), 3.71 (d, J=13.1 Hz, 1H), 3.67 (t, J=6.5 Hz, 2H), 3.34-3.22 (m, 1H), 2.94-2.83 (m, 1H), 2.72-2.60 (m, 1H), 1.92-1.79 (m, 1H), 1.79-1.65 (m, 2H), 1.64-1.55 (m, 1H), 1.54-1.40 (m, 3H), 1.22-1.16 (m, 3H).

tert-Butyl (2R,4S)-4-(2-hydroxyethyl)-2-methyl-piperidine-1-carboxylate

2-[(2R,4S)-1-[(4-Methoxyphenyl)methyl]-2-methyl-4-piperidyl]ethanol (0.545 g, 2.07 mmol), Boc$_2$O (0.903 g, 4.14 mmol, 2.00 eq), and 10% palladium hydroxide on carbon powder (0.145 g, 0.210 mmol, 0.10 eq) were combined in MeOH (20.7 mL, 0.1 M) and placed on the Parr Shaker at 60 psi. After 16 h, the reaction solution was filtered through celite and the celite was washed with MeOH and EtOAc. The filtrate was concentrated to provide a gel-like material, which was dissolved in MeOH (10 mL) and sonicated. Silica gel was added, along with EtOAc (30 mL) and the slurry was slowly concentrated to a fine powder that was loaded on a silica gel column for purification (30-100% diethylether in hexanes) to give tert-butyl (2R,4S)-4-(2-hydroxyethyl)-2-methyl-piperidine-1-carboxylate (0.442 g, 1.82 mmol, 87.8% yield). MS (ESI) m/z 266.2 [M+Na]$^+$; $^1$H NMR (400 MHz, CDCl$_3$) δ ppm 4.50-4.27 (m, 1H), 4.07-3.85 (m, 1H), 3.70 (t, J=6.7 Hz, 2H), 2.91-2.76 (m, 1H), 1.88-1.75 (m, 1H), 1.74-1.63 (m, 1H), 1.59-1.50 (m, 2H), 1.49-1.46 (m, 2H), 1.45 (s, 9H), 1.31 (dt, J=5.6, 12.8 Hz, 1H), 1.13 (d, J=7.0 Hz, 3H), 1.05 (dq, J=4.6, 12.7 Hz, 1H).

(2R,4S)-4-[2-[4-[3-[4-cyano-3-(trifluoromethyl)phenyl]-5,5-dimethyl-4-oxo-2-thioxo-imidazolidin-1-yl]-2-ethyl-phenoxy]ethyl]-2-methyl-piperidine-1-carboxylate To a vial containing triphenylphosphine (0.106 g, 0.400 mmol, 1.50 eq) and THF (1 mL) in an ice bath was added diisopropyl azodicarboxylate (0.070 mL, 0.370 mmol, 1.40 eq). The reaction solution was stirred at 0° C. for 10 min, at which time the homogenous solution had turned to a white slurry. A solution of tert-butyl (2R,4S)-4-(2-hydroxyethyl)-2-methyl-piperidine-1-carboxylate (0.070 g, 0.270 mmol) in THF (1 mL) was added at once, and the reaction solution was stirred at 0° C. for 5 min. A solution of 4-[3-(3-ethyl-4-hydroxy-phenyl)-4,4-dimethyl-5-oxo-2-thioxo-imidazolidin-1-yl]-2-(trifluoromethyl)benzonitrile (0.139 g, 0.320 mmol, 1.20 eq) (prepared as described herein) in THF (0.7 mL) was added. The reaction solution was stirred at 0° C. After 2 h, the reaction was slowly allowed to warm to room temperature overnight. After a total of 16 h, the reaction solution was concentrated and purified by silica gel column chromatography (10-50% EtOAc in hexanes) to give tert-butyl (2R,4S)-4-[2-[4-[3-[4-cyano-3-(trifluoromethyl)phenyl]-5,5-dimethyl-4-oxo-2-thioxo-imidazolidin-1-yl]-2-ethyl-phenoxy]ethyl]-2-methyl-piperidine-1-carboxylate (0.145 g, 0.145 mmol, 54.4% yield). MS (ESI) m/z 559.0 [M−Boc+H]$^+$; $^1$H NMR (400 MHz, CDCl$_3$) δ ppm 8.00-7.93 (m, 2H), 7.87-7.81 (m, 1H), 7.10-7.02 (m, 2H), 6.95-6.89 (m, 1H), 4.57-4.33 (m, 1H), 4.06 (t, J=6.2 Hz, 2H), 2.94-2.75 (m, 1H), 2.68 (q, J=7.6 Hz, 2H), 2.02-1.86 (m, 1H), 1.80-1.70 (m, 3H), 1.59-1.55 (m, 6H), 1.46 (s, 9H), 1.44-1.32 (m, 2H), 1.23 (t, J=7.5 Hz, 3H), 1.17-1.09 (m, 4H).

4-(3-(3-Ethyl-4-(2-((2R,4S)-2-methylpiperidin-4-yl)ethoxy)phenyl)-4,4-dimethyl-5-oxo-2-thioxoimidazolidin-1-yl)-2-(trifluoromethyl)benzonitrile To a vial containing tert-butyl (2R,4S)-4-[2-[4-[3-[4-cyano-3-(trifluoromethyl)phenyl]-5,5-dimethyl-4-oxo-2-thioxo-imidazolidin-1-yl]-2-ethyl-phenoxy]ethyl]-2-methyl-piperidine-1-carboxylate (0.142 g, 0.210 mmol) was added DCM (0.850 mL, 0.10 M) followed by TFA (0.5 mL, 6.53 mmol, 30 eq). The reaction solution was stirred at room temperature for 90 min, then was diluted with EtOAc (75 mL) and washed with saturated aqueous sodium bicarbonate solution (2×75 mL), water (75 mL), and brine. The organic layer was dried over magnesium sulfate and concentrated to give 4-(3-(3-ethyl-4-(2-((2R,4S)-2-methylpiperidin-4-yl)ethoxy)phenyl)-4,4-dimethyl-5-oxo-2-thioxoimidazolidin-1-yl)-2-(trifluoromethyl)benzonitrile as an amber oil that was carried forward without further purification. MS (ESI) m/z=559.2 [M+1]$^+$.

2-[(2R,4S)-4-[2-[4-[3-[4-Cyano-3-(trifluoromethyl)phenyl]-5,5-dimethyl-4-oxo-2-thioxo-imidazolidin-1-yl]-2-ethyl-phenoxy]ethyl]-2-methyl-1-piperidyl]-N-[3-[(2,6-dioxo-3-piperidyl)amino]phenyl]acetamide hydrochloride To a 2-dram vial containing 4-[3-[3-ethyl-4-[2-[(2R,4S)-2-methyl-4-piperidyl]ethoxy]phenyl]-4,4-dimethyl-5-oxo-2-thioxo-imidazolidin-1-yl]-2-(trifluoromethyl)benzonitrile (0.078 g, 0.140 mmol) and 2-chloro-N-[3-[(2,6-dioxo-3-piperidyl)amino]phenyl]acetamide (0.041 g, 0.140 mmol, 1.00 eq) was added DMF (0.347 mL, 0.4 M) followed by DIEA (0.15 mL, 0.830 mmol, 6.00 eq). The reaction solution was heated to 45° C. After 14 h, the reaction solution was diluted with DMSO to a total volume of 2 mL, filtered, and purified by standard methods to give 2-[(2R,4S)-4-[2-[4-[3-[4-cyano-3-(trifluoromethyl)phenyl]-5,5-dimethyl-4-oxo-2-thioxo-imidazolidin-1-yl]-2-ethyl-phenoxy]ethyl]-2-methyl-1-piperidyl]-N-[3-[(2,6-dioxo-3-piperidyl)amino]phenyl]acetamide hydrochloride (0.078 g, 0.090 mmol, 65% yield). MS (ESI) m/z 818.2 [M+1]$^+$; $^1$H NMR (400 MHz, CDCl$_3$) δ ppm 10.55-10.47 (m, 1H), 8.01-7.95 (m, 3H), 7.84 (dd, J=2.1, 8.3 Hz, 1H), 7.18-7.04 (m, 4H), 6.96-6.88 (m, 2H), 6.48 (br d, J=7.5 Hz, 1H), 4.13-4.04 (m, 3H), 3.96-3.82 (m, 2H), 3.81-3.68 (m, 1H), 3.48-3.33 (m, 1H), 3.14-3.02 (m, 1H), 2.88-2.78 (m, 2H), 2.65 (q, J=7.5 Hz, 2H), 2.60-2.48 (m, 1H), 2.06-1.99 (m, 3H), 1.95-1.77 (m, 5H), 1.59-1.55 (m, 6H), 1.52-1.37 (m, 3H), 1.22 (t, J=7.5 Hz, 3H).

Example 4: 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(5-((2,6-dioxopiperidin-3-yl)amino)-2-fluorophenyl)acetamide hydrochloride

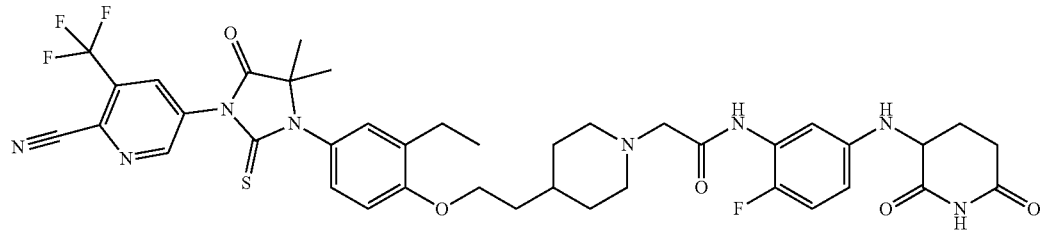 [SMILES: CCc1cc(N2C(=S)N(c3cnc(C#N)c(C(F)(F)F)c3)C(=O)C2(C)C)ccc1OCCC1CCN(CC(=O)Nc2cc(NC3CCC(=O)NC3=O)ccc2F)CC1]

1-(Benzyloxy)-2-bromo-4-nitrobenzene

To mixture of 2-bromo-4-nitrophenol (30.00 g, 137.61 mmol, 1 eq) and potassium carbonate (57.06 g, 412.8 mmol, 3.00 eq) in acetonitrile (300 mL) was added (bromomethyl)benzene (25.89 g, 151.4 mmol, 17.98 mL, 1.1 eq) under nitrogen. The reaction mixture was stirred at 80° C. for 2 h, filtered, and the filtrate was concentrated under vacuum. The residue was purified by silica gel column chromatography (5-20% EtOAc in petroleum ether) to give the product, 1-(benzyloxy)-2-bromo-4-nitrobenzene (35.80 g, 116.2 mmol, 84.4% yield) as a yellow solid. MS (ESI) m/z 332.0 [M+Na]$^+$; $^1$H NMR (400 MHz, DMSO-$d_6$) δ ppm 8.44 (d, J=2.7 Hz, 1H), 8.27 (dd, J=2.8, 9.2 Hz, 1H), 7.52-7.46 (m, 2H), 7.45-7.40 (m, 3H), 7.38-7.34 (m, 1H), 5.37 (s, 2H).

1-(Benzyloxy)-4-nitro-2-vinylbenzene

To a mixture of 1-(benzyloxy)-2-bromo-4-nitrobenzene (20.00 g, 64.91 mmol, 1.00 eq), 4,4,5,5-tetramethyl-2-vinyl-1,3,2-dioxaborolane (19.99 g, 129.8 mmol, 22.02 mL, 2.00 eq) and potassium phosphate (41.33 g, 194.7 mmol, 3.00 eq) in dioxane (300 mL) and water (150 mL) was added [1,1'-bis(diphenylphosphino)-ferrocene]dichloropalladium (II) (4.75 g, 6.49 mmol, 0.10 eq) at room temperature (25° C.). The reaction mixture was de-gassed and then heated to 100° C. for 12 h under nitrogen, filtered and the filtrate concentrated under vacuum. The residue was purified by silica gel column chromatography (0-1% EtOAc in petroleum ether) to give the product, 1-(benzyloxy)-4-nitro-2-vinylbenzene (12.5 g, 48.9 mmol, 75.4% yield) was obtained as a yellow solid. MS (ESI) m/z 278.1 [M+Na]$^+$.

4-Amino-2-ethylphenol

To a solution of 1-(benzyloxy)-4-nitro-2-vinylbenzene (12.50 g, 48.9 mmol, 1.00 eq) in MeOH (50 mL) and THF (50 mL) was added palladium on carbon (2.00 g, 10% purity) under nitrogen. The suspension was degassed under vacuum and purged with hydrogen. The mixture was stirred under hydrogen (50 psi) at 50° C. for 12 h, filtered, and the filtrate was concentrated under vacuum. The residue was purified by silica gel column chromatography (0-2% EtOAc in petroleum ether) to give the product, 4-amino-2-ethylphenol (6.40 g, 46.6 mmol, 95.3% yield) was obtained as a brown solid. MS (ESI) m/z 170.2 [M+Na]$^+$; $^1$H NMR (400 MHz, DMSO-$d_6$) δ ppm 8.13 (s, 1H), 6.46 (d, J=8.3 Hz, 1H), 6.34 (d, J=2.6 Hz, 1H), 6.23 (dd, J=2.8, 8.3 Hz, 1H), 4.28 (s, 1H), 2.41 (q, J=7.5 Hz, 2H), 1.07 (t, J=7.5 Hz, 3H).

5-Isothiocyanato-3-(trifluoromethyl)picolinonitrile

To a solution of 5-amino-3-(trifluoromethyl)picolinonitrile (20.00 g, 106.9 mmol, 1.00 eq) in toluene (200 mL) was added thiocarbonyl dichloride (24.58 g, 213.8 mmol, 16.39 mL, 2.00 eq). The reaction mixture was stirred at 110° C. for 12 h, then concentrated under reduced pressure. The residue was purified by silica gel column chromatography (0-5% EtOAc in petroleum ether) to give the product, 5-isothiocyanato-3-(trifluoromethyl)picolinonitrile (18.90 g, 82.47 mmol, 77.2% yield) as a yellow liquid. MS (ESI) m/z 230.1 [M+1]$^+$.

2-((3-Ethyl-4-hydroxyphenyl)amino)-2-methylpropanenitrile

To a solution of 2-hydroxy-2-methylpropanenitrile (18.64 g, 219.0 mmol, 20 mL, 4.69 eq) in 4-amino-2-ethylphenol (6.40 g, 46.6 mmol, 1.00 eq) was added magnesium sulfate (14.04 g, 116.6 mmol, 2.50 eq). The reaction mixture was stirred at 60° C. for 12 h, then poured into EtOAc-water (v/v=1/1, 100 mL) and stirred for 15 min. The organic phase was separated and the aqueous phase was extracted with EtOAc (100 mL×2). The combined organic extracts were washed with brine (200 mL×5), dried with anhydrous sodium sulfate, filtered, and concentrated under vacuum. 2-((3-Ethyl-4-hydroxyphenyl)amino)-2-methylpropanenitrile (12.00 g, crude) was obtained as a brown solid. MS (ESI) m/z 205.1 [M+1]$^+$.

5-(3-(3-Ethyl-4-hydroxyphenyl)-4,4-dimethyl-5-oxo-2-thioxoimidazolidin-1-yl)-3-(trifluoromethyl)picolinonitrile A solution of 2-((3-ethyl-4-hydroxyphenyl)amino)-2-methylpropanenitrile (9.50 g, 46.5 mmol, 1.00 eq) and 5-isothiocyanato-3-(trifluoromethyl)picolinonitrile (8.53 g, 37.2 mmol, 0.80 eq) in DMF (100 mL) was stirred at 20° C. for 1 h. Then, a 4.0 M solution of HCl in MeOH (100 mL, 2.15 eq) was added. The resulting mixture was stirred at 70° C. for 12 h, then was concentrated under reduced pressure to remove MeOH. The resulting mixture was diluted with water (200 mL) and extracted with EtOAc (200 mL×2). The combined organic extracts were washed with brine (50 mL×2), dried with anhydrous sodium sulfate, and concentrated under reduced pressure. The residue was purified by silica gel column chromatography (5-30% EtOAc in petroleum ether) to give the product, 5-(3-(3-ethyl-4-hydroxyphenyl)-4,4-dimethyl-5-oxo-2-thioxoimidazolidin-1-yl)-3-(trifluoromethyl)picolinonitrile (13.30 g, 30.61 mmol, 65.8% yield) was obtained as a brown solid. MS (ESI) m/z 457.2 [M+Na]$^+$ tert-Butyl 4-(2-(4-(3-(6-cyano-5-(trifluoromethyl) pyridin-3-yl)-5,5-dimethyl-4-oxo-2-thioxoimidazolidin-1-yl)-2-ethylphenoxy)ethyl)piperidine-1-carboxylate 5-(3-(3-Ethyl-4-hydroxyphenyl)-4,4-dimethyl-5-oxo-2-thioxoimidazolidin-1-yl)-3-(trifluoromethyl)picolinonitrile (3.95 g, 9.09 mmol), tert-butyl 4-(2-bromoethyl)piperidine-1-carboxylate (3.99 g, 13.6 mmol), and cesium carbonate (4.44 g, 13.6 mmol) were combined in DMF (64.9 mL). This mixture was heated to 60° C. for 2 h, then diluted with EtOAc (300 mL), water (75 mL), and brine (75 mL). The layers were separated, the organic layer was washed with brine (2×100 mL), dried over anhydrous magnesium sulfate, filtered, and concentrated to an oil. The oil was purified by silica gel column chromatography (0-45% EtOAc in hexanes). Product containing fractions were combined and concentrated to an oil that triturated and precipitated from a mixture of diethyl ether and hexanes. tert-Butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidine-1-carboxylate (4.67 g, 7.23 mmol, 80% yield) was collected by filtration and dried in a vacuum oven for 4 h. MS (ESI) m/z 546 [M-Boc+1]$^+$.

5-(3-(3-Ethyl-4-(2-(piperidin-4-yl)ethoxy)phenyl)-4,4-dimethyl-5-oxo-2-thioxoimidazolidin-1-yl)-3-(trifluoromethyl)picolinonitrile hydrochloride A solution of tert-butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidine-1-carboxylate (4.57 g, 7.08 mmol) in DCM (75 mL) was added. To this mixture was added a 4 N HCl solution in dioxane (20 mL). After stirring at ambient temperature for 1.5 h, the reaction mixture was concentrated under reduced pressure to an oil, that was then triturated in diethyl ether to give 5-(3-(3-ethyl-4-(2-(piperidin-4-yl)ethoxy)phenyl)-4,4-dimethyl-5-oxo-2-thioxoimidazolidin-1-yl)-3-(trifluoromethyl)picolinonitrile (1.5 g, 2.58 mmol, 36.4 yield). MS (ESI) m/z 546.2 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetic acid hydrochloride To a solution of 5-(3-(3-ethyl-4-(2-(piperidin-4-yl)ethoxy)phenyl)-4,4-dimethyl-5-oxo-2-thioxoimidazolidin-1-yl)-3-(trifluoromethyl)picolinonitrile hydrochloride (1.50 g, 2.58 mmol) in THF (15 mL) was added DIEA (1.800 mL, 10.31 mmol), followed by tert-butyl 2-bromoacetate (0.400 mL, 2.71 mmol). The reaction mixture was stirred overnight at ambient temperature. Another 0.25 equivalents of reagents were added and stirring continued overnight. The reaction mixture was diluted with EtOAc (125 mL), water (20 mL), and brine (20 mL). Layers were separated, the organic phase was dried over anhydrous magnesium sulfate, filtered, and concentrated to an oil. The oil was dissolved in DCM (50 mL) and treated with a 4.0 M solution of HCl in dioxane and stirred at ambient temperature overnight, then concentrated to an oil. The residue was triturated with diethyl ether for an hour to afford 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl) acetic acid hydrochloride (1.545 g, 2.414 mmol, 94% yield) as a solid, collected by filtration, washed with diethyl ether, and dried in a vacuum oven overnight at 45° C. MS (ESI) m/z 604.2 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(5-((2,6-dioxopiperidin-3-yl)amino)-2-fluorophenyl) acetamide hydrochloride 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetic acid hydrochloride (0.100 g, 0.156 mmol), 3-((3-amino-4-fluorophenyl)amino)piperidine-2,6-dione hydrochloride (0.050 g, 0.183 mmol), HATU (0.089 g, 0.234 mmol), and DIEA (0.109 mL, 0.625 mmol) were combined in DMF (1 mL) and stirred at room temperature overnight. The reaction mixture was diluted with DMSO (1 mL), filtered, and purified by standard methods to afford 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(5-((2,6-dioxopiperidin-3-yl)amino)-2-fluorophenyl)acetamide hydrochloride (0.028 g, 0.033 mmol, 20.9% yield). MS (ESI) m/z 823.3 [M+1]$^+$; $^1$H NMR (400 MHz, DMSO-d$_6$) δ ppm 10.79 (s, 1H) 10.27 (s, 1H) 9.25 (d, J=1.96 Hz, 1H) 8.83 (d, J=1.83 Hz, 1H) 7.09-7.22 (m, 4H) 6.98-7.08 (m, 1H) 6.51 (dt, J=8.65, 3.44 Hz, 1H) 4.14-4.31 (m, 4H) 4.06-4.13 (m, 2H) 3.65-3.75 (m, 1H) 3.05-3.20 (m, 2H) 2.58-2.80 (m, 4H) 2.06-2.15 (m, 1H) 1.71-2.02 (m, 7H) 1.57-1.70 (m, 2H) 1.52 (s, 6H) 1.11-1.20 (m, 3H).

Example 5: 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((2,6-dioxopiperidin-3-yl)amino)-5-fluorophenyl)acetamide formate

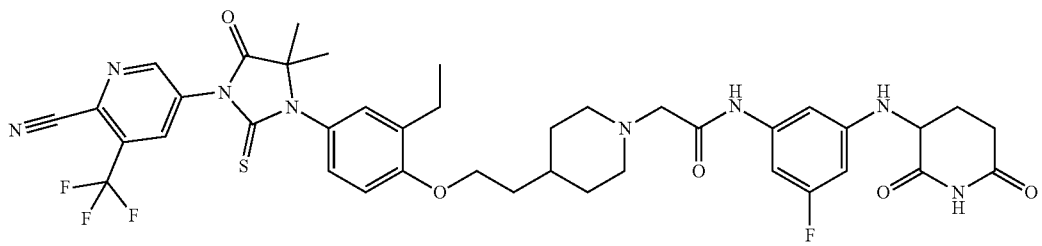 [SMILES: CCc1cc(N2C(=S)N(c3cnc(C#N)c(C(F)(F)F)c3)C(=O)C2(C)C)ccc1OCCC1CCN(CC(=O)Nc2cc(F)cc(NC3CCC(=O)NC3=O)c2)CC1]

3-((3-Amino-5-fluorophenyl)amino)piperidine-2,6-dione hydrochloride

3-Bromopiperidine-2,6-dione (4.57 g, 23.78 mmol), 5-fluorobenzene-1,3-diamine (1.50 g, 11.89 mmol) and DIEA (6.23 mL, 35.7 mmol) were combined in DMF (18 mL) and the mixture was heated to 150° C. in a screw cap vial. After 24 h, the solution was concentrated under reduced pressure partially and the residue was purified via reverse phase preparative HPLC (5-25% acetonitrile in water, 0.1% formic acid over 25 min). Pertinent fractions were diluted with a few drops of 2.0 M aqueous HCl and fractions concentrated under reduced pressure to afford the title compound as the hydrochloride salt (1.15 g, 3.71 mmol, 31% yield). MS (ESI) m/z 238 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((2,6-dioxopiperidin-3-yl)amino)-5-fluorophenyl)acetamide formate 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetic acid dihydrochloride (0.100 g, 0.148 mmol) (prepared as described herein), 3-((3-amino-5-fluorophenyl)amino)piperidine-2,6-dione hydrochloride (0.054 g, 0.163 mmol), and DIEA (0.129 mL, 0.739 mmol) were combined in DMF (0.75 mL) and the solution was stirred for 2 min. HATU (0.062 g, 0.163 mmol) was then added and the resulting mixture was stirred at ambient temperature. After 90 min, the solution was diluted with DMSO (1 mL) and purified by standard methods to afford 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((2,6-dioxopiperidin-3-yl)amino)-5-fluorophenyl)acetamide formate (0.018 g, 0.020 mmol, 13% yield). MS (ESI) m/z 823 [M+1]$^+$; $^1$H NMR (400 MHz, DMSO-d$_6$) δ ppm 10.80 (s, 1H), 9.53 (s, 1H), 9.24 (d, J=1.83 Hz, 1H), 8.82 (d, J=1.83 Hz, 1H), 8.20 (s, 1H), 7.07-7.17 (m, 3H), 6.73-6.80 (m, 2H), 6.18-6.25 (m, 2H), 4.30 (s, 1H), 4.09 (br t, J=6.24 Hz, 2H), 3.06 (s, 2H), 2.82-2.89 (m, 2H), 2.73 (s, 1H), 2.58-2.70 (m, 3H), 2.25-2.45 (m, 3H), 2.00-2.24 (m, 4H), 1.88 (br d, J=12.35 Hz, 2H), 1.63-1.79 (m, 5H), 1.44-1.58 (m, 8H), 1.29-1.42 (m, 3H), 1.24 (br s, 2H), 1.16 (t, J=7.52 Hz, 4H), 0.95 (d, J=6.60 Hz, 1H), 0.79-0.90 (m, 2H), 0.01-0.01 (m, 1H), −0.03--0.01 (m, 2H), −0.15 (s, 1H).

Example 6: (2R)—N-(3-Chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide hydrochloride

2-((3-Bromo-4-hydroxyphenyl)amino)-2-methylpropanenitrile

To a solution of 4-amino-2-bromophenol (5.00 g, 26.6 mmol) in DCM (177 mL) in acetone (89 mL) were added trimethylsilyl cyanide (4.66 mL, 37.2 mmol) and trimethylsilyl trifluoromethylsulphonate (0.241 mL, 1.330 mmol). The reaction mixture was stirred at room temperature for 1 h, then was concentrated to remove solvent. The crude material was purified by silica gel column chromatography (0-100% EtOAc in hexanes) to afford 2-((3-bromo-4-hydroxyphenyl)amino)-2-methylpropanenitrile (4.56 g, 17.87 mmol, 67.2% yield) as a brown solid. MS (ESI) m/z 256.2 [M+1]$^+$; $^1$H NMR (400 MHz, DMSO-d$_6$) δ ppm 9.55-9.66 (m, 1H), 7.05 (d, J=2.69 Hz, 1H), 6.83-6.87 (m, 1H), 6.77-6.81 (m, 1H), 5.51 (s, 1H), 1.55 (s, 6H).

4-(3-(3-bromo-4-hydroxyphenyl)-4,4-dimethyl-5-oxo-2-thioxoimidazolidin-1-yl)-2-(trifluoromethyl)benzonitrile 2-((3-Bromo-4-hydroxyphenyl)amino)-2-methylpropanenitrile (1.00 g, 3.92 mmol) and 4-isothiocyanato-2-(trifluoromethyl)benzonitrile (0.894 g, 3.92 mmol) were combined in DMA (13.07 mL) and stirred at room temperature overnight. MeOH (5 mL) and a 3.0 N aqueous solution of HCl (5 mL) were added and the reaction was heated at 70° C. After 2 h, the reaction mixture was partitioned between EtOAc and water. The aqueous layer was extracted with EtOAc before the combined organic layers were dried over magnesium sulfate, filtered, and concentrated under reduced pressure. The crude material was purified by silica gel column chromatgraphy (0-100% EtOAc in hexanes) to afford 4-(3-(3-bromo-4-hydroxyphenyl)-4,4-dimethyl-5-oxo-2-thioxoimidazolidin-1-yl)-2-(trifluoromethyl)benzonitrile (1.23 g, 2.42 mmol, 62.0% yield) as a white solid. MS (ESI) m/z 484.0 [M+1]$^+$.

2-Bromo-4-(3-(4-cyano-3-(trifluoromethyl)phenyl)-5,5-dimethyl-4-oxo-2-thioxoimidazolidin-1-yl)phenyl acetate To a solution of 4-(3-(3-bromo-4-hydroxyphenyl)-4,4-dimethyl-5-oxo-2-thioxoimidazolidin-1-yl)-2-(trifluoromethyl)benzonitrile (0.75 g, 1.55 mmol) in DCM (7.74 mL) was added DIEA (0.541 mL, 3.10 mmol) followed by acetyl chloride (0.132 mL, 1.858 mmol). After stirring at room temperature for 12 h, the reaction mixture was diluted with EtOAc (100 mL) and the organic layer was washed with a saturated aqueous solution of sodium bicarbonate (2×100 mL) and brine (100 mL). The organic layer was dried over magnesium sulfate and concentrated to provide a colorless oil which was purified by silica gel column chromatography (20-50% EtOAc in hexanes) to give 2-bromo-4-(3-(4-cyano-

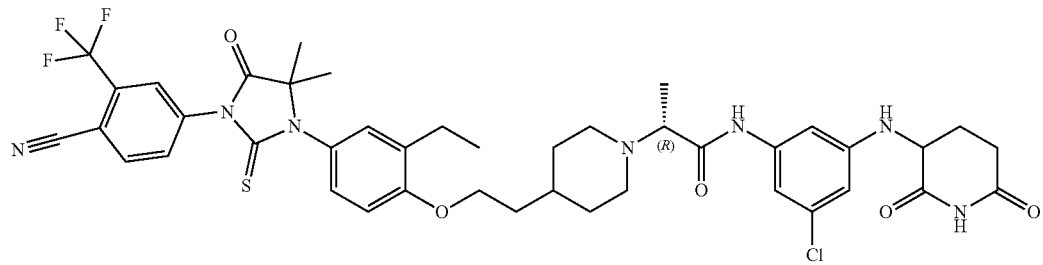

3-(trifluoromethyl)phenyl)-5,5-dimethyl-4-oxo-2-thioxoimidazolidin-1-yl)phenyl acetate (0.766 g, 1.455 mmol, 94% yield). MS (ESI) m/z 526.0 [M+H]$^+$; $^1$H NMR (400 MHz, CDCl$_3$) δ ppm 7.97 (s, 1H), 7.94 (s, 1H), 7.82 (dd, J=2.1, 8.2 Hz, 1H), 7.58 (d, J=2.3 Hz, 1H), 7.36-7.27 (m, 2H), 2.40 (s, 3H), 1.61 (s, 6H).

4-(3-(4-Cyano-3-(trifluoromethyl)phenyl)-5,5-dimethyl-4-oxo-2-thioxoimidazolidin-1-yl)-2-ethylphenyl acetate To a mixture of 2-bromo-4-(3-(4-cyano-3-(trifluoromethyl)phenyl)-5,5-dimethyl-4-oxo-2-thioxoimidazolidin-1-yl)phenyl acetate (2.00 g, 3.80 mmol), [(2-dicyclohexylphosphino-2',6'-bis(N,N-dimethylamino)-1,1'-biphenyl)-2-(2'-amino-1,1'-biphenyl)]palladium(II) methanesulfonate (0.311 g, 0.380 mmol) and 2-(2-dicyclohexylphosphanylphenyl)-N1,N1,N3,N3-tetramethyl-benzene-1,3-diamine (0.166 g, 0.380 mmol) combined in a schlenk flask and purged with argon, was added toluene (15.20 mL). The reaction mixture was placed in an ice bath for 5 min, then treated with a 0.5 M solution of ethylzinc(II) bromide in THF (6.08 mL, 3.04 mmol, 0.80 equiv). After 30 min, an additional 0.5 equivalent of ethylzinc(II) bromide solution was used (3.80 mL, 1.90 mmol) at 0° C. for 30 min, the reaction was quenched with the addition of a 2.0 M aqueous solution of HCl (2.470 mL, 4.94 mmol) and the mixture diluted with EtOAc (350 mL). The organic layer was washed twice with a saturated aqueous solution of sodium bicarbonate, dried over magnesium sulfate, filtered, and concentrated under reduced pressure to afford a brown solid. The crude material was purified by silica gel column chromatography (0-45% EtOAc in hexanes) to afford 4-(3-(4-cyano-3-(trifluoromethyl)phenyl)-5,5-dimethyl-4-oxo-2-thioxoimidazolidin-1-yl)-2-ethylphenyl acetate (0.986 g, 2.07 mmol, 55% yield). MS (ESI) m/z 476 [M+1]$^+$.

4-(3-(3-Ethyl-4-hydroxyphenyl)-4,4-dimethyl-5-oxo-2-thioxoimidazolidin-1-yl)-2-(trifluoromethyl)benzonitrile A suspension of 4-(3-(4-cyano-3-(trifluoromethyl)phenyl)-5,5-dimethyl-4-oxo-2-thioxoimidazolidin-1-yl)-2-ethylphenyl acetate (0.876 g, 1.842 mmol) and potassium carbonate (0.255 g, 1.84 mmol) in MeOH (20 mL) was stirred at ambient temperature. After 40 min, the solution diluted with EtOAc (200 mL) and partitioned with water (50 mL). The combined organic layers were dried over magnesium sulfate, filtered, and concentrated under reduced pressure to afford the title compound (0.766 g, 1.76 mmol, 96% yield). MS (ESI) m/z 434 [M+1]$^+$.

tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidine-1-carboxylate A mixture of 4-(3-(3-ethyl-4-hydroxyphenyl)-4,4-dimethyl-5-oxo-2-thioxoimidazolidin-1-yl)-2-(trifluoromethyl)benzonitrile (0.500 g, 1.154 mmol), tert-butyl 4-(2-bromoethyl)piperidine-1-carboxylate (0.506 g, 1.730 mmol), cesium carbonate (0.564 g, 1.730 mmol), and DMF (5.0 mL) was heated to 60° C. for 18 h. The reaction was partitioned between EtOAc and water. The organic layer was separated and the aqueous layer was extracted with EtOAc. The combined organic layers were washed with brine and dried over sodium sulfate, filtered, and concentrated under reduced pressure to give a dark red oil. The oil was taken up in EtOAc and purified by silica gel column chromatography (0-60% EtOAc in hexanes). Fractions containing the desired product were combined and concentrated under reduced pressure to give tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidine-1-carboxylate (0.680 g, 1.05 mmol, 91% yield) as a light pink foamy semi-solid material. MS (ESI) m/z 645.2 [M+1]$^+$.

4-(3-(3-Ethyl-4-(2-(piperidin-4-yl)ethoxy)phenyl)-4,4-dimethyl-5-oxo-2-thioxoimidazolidin-1-yl)-2-(trifluoromethyl)benzonitrile A solution of tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidine-1-carboxylate (0.680 g, 1.05 mmol) in DCM (5.0 mL) was treated with TFA (2.0 mL, 26.0 mmol). The reaction mixture was stirred at 25° C. for 18 h, then concentrated under reduced pressure to give a dark purple foamy solid. The solid was dissolved in MeOH and loaded onto a strong cation resin exchange column. The column was washed successively with water, MeOH, and then a 5% solution of ammonium hydroxide in MeOH which eluted the product. 4-(3-(3-Ethyl-4-(2-(piperidin-4-yl)ethoxy)phenyl)-4,4-dimethyl-5-oxo-2-thioxoimidazolidin-1-yl)-2-(trifluoromethyl)benzonitrile (0.530 g, 0.973 mmol, 92% yield) was isolated as a light green foamy solid upon removal of the solvents under reduced pressure as a light green foamy solid. MS (ESI) m/z 545.2 [M+1]$^+$.

(R)-Methyl 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanoate trifluroacetate A mixture of 4-(3-(3-ethyl-4-(2-(piperidin-4-yl)ethoxy)phenyl)-4,4-dimethyl-5-oxo-2-thioxoimidazolidin-1-yl)-2-(trifluoromethyl)benzonitrile (0.265 g, 0.487 mmol), (S)-methyl 2-chloropropanoate (0.089 g, 0.73 mmol), TEA (0.203 mL, 1.46 mmol), and THF (2.5 mL) was heated to 85° C. for 48 h, then concentrated under reduced pressure to give a dark yellow oil. The oil was dissolved in DMSO and purified by reverse-phase semi-preparative HPLC (5-95% acetonitrile+0.1% TFA in water+0.1% TFA, over 30 min). Fractions containing the desired product were combined and concentrated to the organic solvent component. The remaining liquid was frozen and lyophilized to give (R)-methyl 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanoate, trifluoroacetate (0.172 g, 0.231 mmol, 47.5% yield) as a white solid. MS (ESI) m/z 631.2 [M+1]$^+$.

(R)-2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperidin-1-yl)propanoic acid A solution of (R)-methyl 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanoate (0.172 g, 0.273 mmol) in THF (1.0 mL) and water (0.333 mL) was treated with lithium hydroxide (0.065 g, 2.73 mmol) and stirred at 25° C. for 18 h. The organic solvent was removed under reduced pressure. The aqueous phase was diluted with water and treated with a 1.0 N aqueous solution of HCl to adjust the pH to 4. The product precipitated as a tan sticky solid that was separated from the supernatant aqueous layer and was dried in an oven overnight to give (R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanoic acid (0.123 g, 0.199 mmol, 73.1% yield). MS (ESI) m/z 617.0 [M+1]$^+$.

3-((3-Amino-5-chlorophenyl)amino)piperidine-2,6-dione hydrochloride

A mixture of 3-bromopiperidine-2,6-dione (2.69 g, 14.0 mmol), 5-chlorobenzene-1,3-diamine (1.00 g, 7.01 mmol), DIEA (3.67 mL, 21.04 mmol) in DMF (12.0 mL) was heated to 150° C. for 24 h. The crude reaction mixture was purified by reverse phase semi preparative HPLC (5-25% acetonitrile+0.1% formic acid in water+0.1% formic acid, over 25 min). Fractions containing the desired product were combined and treated with a 1.0 N aqueous solution of HCl (5.0 mL). The organic solvent was removed under reduced pressure prior to lyophilization to give 3-((3-amino-5-chlorophenyl)amino)piperidine-2,6-dione hydrochloride (0.472 g, 1.63 mmol, 23.2% yield) as a dark brown solid. MS (ESI) m/z 254.0 [M+1]$^+$.

(2R)—N-(3-chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide hydrochloride A mixture of (R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanoic acid (0.123 g, 0.199 mmol), 3-((3-amino-5-chlorophenyl)amino)piperidine-2,6-dione hydrochloride (0.069 g, 0.24 mmol), DIEA (0.139 mL, 0.798 mmol), HATU (0.083 g, 0.219 mmol), and DMF (1.0 mL) was stirred at 25° C. for 1 h. The reaction was dissolved in DMSO and purified by standard methods to give (2R)—N-(3-chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide hydrochloride (0.079 g, 0.089 mmol, 44.6% yield). MS (ESI) m/z 853.2 [M+1]$^+$; $^1$H NMR (400 MHz, DMSO-d$_6$) δ ppm 10.75-10.86 (m, 1H), 10.59-10.69 (m, 1H), 8.35-8.42 (m, 1H), 8.25-8.31 (m, 1H), 8.04-8.10 (m, 1H), 7.07-7.20 (m, 3H), 6.96-7.02 (m, 1H), 6.79-6.87 (m, 1H), 6.53 (t, J=1.90 Hz, 1H), 4.34 (br dd, J=4.22, 11.55 Hz, 1H), 3.99-4.13 (m, 6H), 3.56-3.66 (m, 1H), 3.43 (br d, J=11.00 Hz, 1H), 3.06-3.19 (m, 1H), 2.92-3.05 (m, 1H), 2.69-2.79 (m, 1H), 2.55-2.66 (m, 3H), 1.62-2.12 (m, 8H), 1.52-1.58 (m, 3H), 1.49 (s, 5H), 1.13-1.19 (m, 3H).

Example 7: N-(3-Chloro-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)acetamide hydrochloride

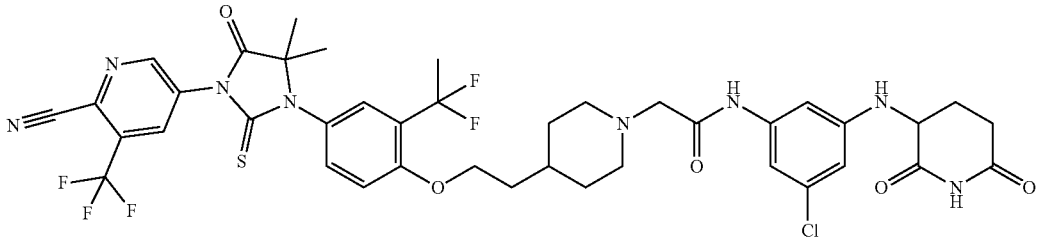 [SMILES: CC(F)(F)c1cc(N2C(=S)N(c3cnc(C#N)c(C(F)(F)F)c3)C(=O)C2(C)C)ccc1OCCC1CCN(CC(=O)Nc2cc(Cl)cc(NC3CCC(=O)NC3=O)c2)CC1]

2-(1,1-Difluoroethyl)-4-nitrophenol

A solution of 1-(2-hydroxy-5-nitrophenyl)ethanone (1.27 g, 7.00 mmol) in DCM (18 mL) was cooled to 0° C. and bis(2-methoxyethyl)aminosulfur trifluoride (Deoxo-Fluor®, 2.58 mL, 14.0 mmol) was added dropwise over 2 min. The mixture was stirred for 2.5 h during which time the temperature gradually rose to 20° C. The mixture was poured into ice water (30 mL) and mixed for 5 min. The organic layer was removed, the aqueous layer extracted with DCM, and the combined organic extracts dried over sodium sulfate and activated carbon. The solution was filtered, concentrated, and the residual solid purified by silica gel column chromatography (10-40% EtOAc in hexanes) to provide the title compound as a light beige solid (1.23 g, 86% yield). $^1$H NMR (400 MHz, CDCl$_3$) δ ppm 8.33 (d, J=2.57 Hz, 1H), 8.24 (dd, J=8.99, 2.63 Hz, 1H), 7.06 (d, J=9.05 Hz, 1H), 6.51-6.92 (br s, 1H), 2.08 (t, J=18.9 Hz, 3H).

tert-Butyl 4-(2-(2-(1,1-difluoroethyl)-4-nitrophenoxy)ethyl)piperidine-1-carboxylate To a solution of 2-(1,1-difluoroethyl)-4-nitrophenol (4.00 g, 19.69 mmol) and tert-butyl 4-(2-bromoethyl)piperidine-1-carboxylate (5.75 g, 19.69 mmol)) in dry DMF (20 mL) was added cesium carbonate (12.83 g, 39.4 mmol) and the mixture was stirred under an atmosphere of nitrogen at 65° C. for 4 h. The mixture was cooled to room temperature, poured into ice-water (60 mL) and mixed, then extracted with EtOAc (100 mL×2). The combined extracts were washed with water (100 mL), brine (100 mL) and dried over sodium sulfate. The combined organic layers were filtered through a silica gel plug and concentrated to give tert-butyl 4-(2-(2-(1,1-difluoroethyl)-4-nitrophenoxy)ethyl)piperidine-1-carboxylate (7.10 g, 17.1 mmol, 87% yield) as a light gold viscous oil. $^1$H NMR (400 MHz, CDCl$_3$) δ ppm 1.15-1.24 (m, 2H) 1.69-1.78 (m, 3H) 1.80-1.90 (m, 2H) 1.95-2.08 (m, 4H) 2.63-2.80 (m, 2H) 4.18-4.34 (m, 2H) 6.91-7.16 (m, 1H) 8.17-8.34 (m, 1H) 8.35-8.46 (m, 1H).

tert-Butyl 4-(2-(4-amino-2-(1,1-difluoroethyl)phenoxy)ethyl)piperidine-1-carboxylate To a solution of tert-butyl 4-(2-(2-(1,1-difluoroethyl)-4-nitrophenoxy)ethyl)piperidine-1-carboxylate (7.00 g, 16.89 mmol) in EtOH (200 mL) was added palladium/carbon (0.750 g, 10% purity). The mixture was degassed with hydrogen then stirred under an atmosphere of hydrogen maintained by a balloon at 25° C. for 12 h. The mixture was filtered and concentrated to give tert-butyl 4-(2-(4-amino-2-(1,1-difluoroethyl)phenoxy)ethyl)piperidine-1-carboxylate (6.50 g, 16.9 mmol, 100% yield) as a purple solid. MS (ESI) m/z 384.2 [M]+.

tert-Butyl 4-(2-(4-((2-cyanopropan-2-yl)amino)-2-(1,1-difluoroethyl)phenoxy)ethyl)piperidine-1-carboxylate A solution of tert-butyl 4-(2-(4-amino-2-(1,1-difluoroethyl)phenoxy)ethyl)piperidine-1-carboxylate (6.50 g, 16.91 mmol) in acetone (60 mL) was cooled to 0° C. and trimethylsilanecarbonitrile (2.52 g, 25.4 mmol) was added followed by trimethylsilyl trifluoromethanesulfonate (0.153 mL, 0.845 mmol). The mixture was stirred for 7 h during which time the temperature reached ambient temperature. After removal of the solvent under reduced pressure, the residue was dissolved in EtOAc (100 mL) and washed with a saturated aqueous solution of sodium bicarbonate (100 mL), dried over anhydrous sodium sulfate, and concentrated. The material was purified by silica gel column chromatography (0-70% EtOAc in hexanes) to give tert-butyl 4-(2-(4-((2-cyanopropan-2-yl)amino)-2-(1,1-difluoroethyl)phenoxy)ethyl)piperidine-1-carboxylate (4.00 g, 8.86 mmol, 52.4% yield) as a syrup. $^1$H NMR (400 MHz, CDCl$_3$) δ ppm 1.10-1.22 (m, 2H) 1.43-1.47 (m, 9H) 1.63 (s, 7H) 1.68-1.77 (m, 5H) 1.92-1.95 (m, 1H) 2.02-2.05 (m, 1H) 2.65-2.77 (m, 2H) 3.99-4.05 (m, 2H) 4.06-4.16 (m, 2H) 6.85-6.91 (m, 1H) 7.06-7.14 (m, 2H).

5-(3-(3-(1,1-Difluoroethyl)-4-(2-(piperidin-4-yl)ethoxy)phenyl)-4,4-dimethyl-5-oxo-2-thioxoimidazolidin-1-yl)-3-(trifluoromethyl)picolinonitrile A solution of tert-butyl 4-(2-(4-((2-cyanopropan-2-yl)amino)-2-(1,1-difluoroethyl)phenoxy)ethyl)piperidine-1-carboxylate (4 g, 8.84 mmol) and 5-isothiocyanato-3-(trifluoromethyl)picolinonitrile (2.03 g, 8.84 mmol) in DMF (20 mL) was stirred at 60° C. for 2 h. The mixture was cooled to room temperature and treated with MeOH (30 mL), water (8 mL), and a 6.0 M aqueous solution of hydrochloride acid (6.48 mL, 39.12 mmol). The resulting solution was stirred at 60° C. for 16 h, concentrated to remove the MeOH component, cooled to 0° C., and slowly treated with a saturated aqueous solution of sodium bicarbonate (20 mL) and EtOAc (100 mL). The material was further extracted from the aqueous phase with EtOAc (100 mL×2). The combined organic extracts were washed with brine (100 mL), dried over sodium sulfate, filtered, and concentrated to dryness. The residual orange foam was dissolved in DCM (10 mL), treated with TFA (30 mL), and stirred for 2 h. The solution was filtered, concentrated, and the residue was purified by silica gel column chromatography (0-10% MeOH in DCM). The collected fractions were concentrated to give 5-(3-(3-(1,1-difluoroethyl)-4-(2-(piperidin-4-yl)ethoxy)phenyl)-4,4-dimethyl-5-oxo-2-thioxoimidazolidin-1-yl)-3-(trifluoromethyl)picolinonitrile 2,2,2-trifluoroacetate (5.10 g, 7.33 mmol, 83% yield) as an orange solid. MS (ESI) m/z 582.1 [M+1]+.

2-(4-(2-(4-(3-(6-Cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl) acetic acid To a solution of 5-(3-(3-(1,1-difluoroethyl)-4-(2-(piperidin-4-yl)ethoxy)phenyl)-4,4-dimethyl-5-oxo-2-thioxoimidazolidin-1-yl)-3-(trifluoromethyl)picolinonitrile 2,2,2-trifluoroacetate (2.00 g, 2.88 mmol) in THF (15 mL) was added DIEA (3.01 mL, 17.25 mmol), followed by tert-butyl 2-bromoacetate (0.518 mL, 3.45 mmol) and the resulting mixture was stirred at ambient temperature for 16 h. The mixture was diluted with EtOAc (125 mL), water (20 mL), and brine (20 mL). Layers were separated and the organic layer was dried over anhydrous magnesium sulfate, filtered, and concentrated to an oil. To the oil dissolved in DCM (50 mL) was added hydrochloric acid (12.88 mL, 51.5 mmol) as a 4.0 M solution in dioxane and the reaction was stirred at ambient temperature for 16 h. The reaction mixture was concentrated to an oil that was triturated with diethyl ether for 1 h. The resulting solids were collected by filtration, washed with diethyl ether, and dried in a vacuum oven overnight at 45° C. to give 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)acetic acid hydrochloride (1.90 g, 2.81 mmol, 98% yield). MS (ESI) m/z 640.2 [M+1]+.

N-(3-Chloro-5-((2,6-dioxopiperidin-3-yl)amino) phenyl)-2-(4-(2-(4-(3-(6-cyano-5-(trifluoromethyl) pyridin-3-yl)-5,5-dimethyl-4-oxo-2-thioxoimidazolidin-1-yl)-2-(1,1-difluoroethyl)phenoxy)ethyl) piperidin-1-yl)acetamide hydrochloride A mixture of 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)acetic acid hydrochloride (0.200 g, 0.296 mmol), 3-((3-amino-5-chlorophenyl)amino)piperidine-2,6-dione hydrochloride (0.086 g, 0.296 mmol), and DIEA (0.310 mL, 1.775 mmol) in DMF (2 mL) was stirred for 5 min. HATU (0.169 g, 0.444 mmol) was added and the resulting mixture was stirred at ambient temperature for 16 h, then diluted with EtOAc (100 mL), water (100 mL), and brine (20 mL). The organic layer was separated layers, dried over anhydrous magnesium sulfate, filtered, and concentrated to an oil. The oil was purified by standard methods to afford N-(3-chloro-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl) piperidin-1-yl)acetamide hydrochloride (0.021 g, 0.024 mmol, 8.1% yield). MS (ESI) m/z 875.0 [M]+; $^1$H NMR (400 MHz, DMSO-d$_6$) δ ppm 0.71-0.92 (m, 1H) 1.15-1.32 (m, 4H) 1.48-1.61 (m, 7H) 1.72-2.15 (m, 10H) 2.64-2.84 (m, 2H) 3.99-4.40 (m, 4H) 6.26-6.43 (m, 1H) 6.45-6.57 (m, 1H) 6.77-6.91 (m, 1H) 6.93-7.04 (m, 1H) 7.26-7.57 (m, 3H) 8.72-8.90 (m, 1H) 9.18-9.32 (m, 1H) 9.73-10.02 (m, 1H) 10.75-10.89 (m, 1H).

Example 8: N-(3-Chloro-5-((2,6-dioxopiperidin-3-yl)amino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxamide hydrochloride

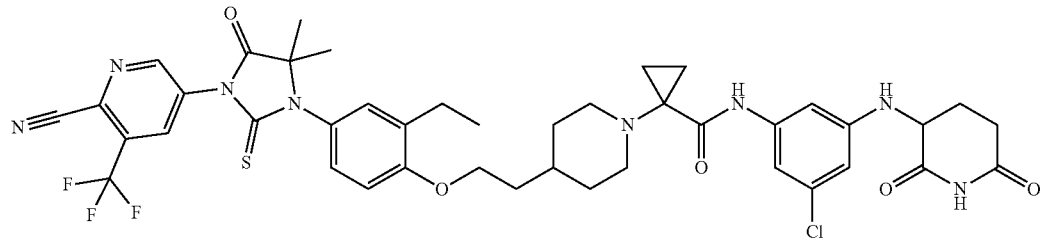 [SMILES: CCc1cc(N2C(=S)N(c3cnc(C#N)c(C(F)(F)F)c3)C(=O)C2(C)C)ccc1OCCC1CCN(C2(C(=O)Nc3cc(Cl)cc(NC4CCC(=O)NC4=O)c3)CC2)CC1]

1,1-Dimethyl-4-oxopiperidin-1-ium iodide

To a solution of 1-methylpiperidin-4-one (15.00 g, 132.56 mmol, 1.00 eq) in acetone (75 mL) was added iodomethane (20.70 g, 145.81 mmol, 1.1 eq) dropwise at 0° C. The reaction was stirred at 20° C. for 1 h, the resulting a white suspension was collected by filtration, washed with EtOAc (100 mL), and dried under reduced pressure to afford 1,1-dimethyl-4-oxopiperidin-1-ium iodide (32.80 g, 128.6 mmol, 97.0% yield) as an off-white solid. $^1$H NMR (400 MHz, DMSO-$d_6$) δ ppm 3.76 (t, J=6.4 Hz, 4H), 3.28 (s, 6H), 2.71 (br s, 4 h).

Methyl 1-(4-oxopiperidin-1-yl)cyclopropanecarboxylate

To a refluxing mixture of 1,1-dimethyl-4-oxopiperidin-1-ium iodide (25.24 g, 98.95 mmol, 1.50 eq), potassium carbonate (10.03 g, 72.56 mmol, 1.10 eq) and EtOH (200 mL) was added a solution of methyl 1-aminocyclopropanecarboxylate hydrochloride (10.00 g, 65.97 mmol, 1.00 eq) in water (50 mL) dropwise. The reaction was stirred at 85° C. for 1 h. The volatile solvents were removed under reduced pressure to yield a residue that was diluted with EtOAc (50 mL) and water (50 mL). After separation of the layers, the aqueous layer was extracted with EtOAc (30 mL). The combined organic extracts were washed with brine (50 mL), dried, filtered, and concentrated. The crude product was purified by fsilica gel column chromatography (0-8% EtOAc in petroleum ether) to give methyl 1-(4-oxopiperidin-1-yl)cyclopropanecarboxylate (2.10 g, 10.65 mmol, 16.1% yield) as a colorless oil. $^1$H NMR (400 MHz, CDCl$_3$) δ ppm 3.65 (s, 3H), 3.23 (br s, 4H), 2.34 (t, J=6.0 Hz, 1H), 1.36 (q, J=4.0 Hz, 2H), 1.07 (q, J=3.6 Hz, 2H).

Methyl 1-(4-(2-(tert-butoxy)-2-oxoethylidene)piperidin-1-yl)cyclopropanecarboxylate A solution of sodium hydride (0.639 g, 16.0 mmol, 60% purity, 1.50 eq) in THF (20 mL) treated with tert-butyl 2-(diethoxyphosphoryl)acetate (3.49 g, 13.84 mmol, 1.30 eq) added dropwise at 0° C., was stirred at 0° C. for 10 min. To this mixture was added a solution of methyl 1-(4-oxopiperidin-1-yl)cyclopropanecarboxylate (2.10 g, 10.65 mmol, 1.00 eq) in THF (10 mL) dropwise and the reaction was stirred at 20° C. for 1 h, then quenched with the addition of a saturated aqueous solution of ammonium chloride (50 mL). The mixture was extracted with EtOAc (30 mL×2). The organic extracts were washed with brine (50 mL), dried, filtered, and concentrated. The residue was purified by silica gel column chromatography (0-2% EtOAc in petroleum ether) to give methyl 1-(4-(2-(tert-butoxy)-2-oxoethylidene)piperidin-1-yl)cyclopropanecarboxylate (2.95 g, 9.99 mmol, 93.8% yield) as a white solid. $^1$H NMR (400 MHz, CDCl$_3$) δ ppm 5.56 (s, 1H), 3.64 (s, 3H), 3.03-2.84 (m, 6H), 2.17 (T, J=5.6 Hz, 2H), 1.30 (q, J=4.0 Hz, 2H), 0.98 (q, J=3.6 Hz, 2H).

Methyl 1-(4-(2-(tert-butoxy)-2-oxoethyl)piperidin-1-yl)cyclopropanecarboxylate A mixture of methyl 1-(4-(2-(tert-butoxy)-2-oxoethylidene)piperidin-1-yl)cyclopropanecarboxylate (2.95 g, 9.99 mmol, 1.00 eq), palladium on activated carbon (0.600 g, 10% purity) and THF (60 mL) was stirred at 20° C. under an atmosphere of hydrogen (15 psi) for 10 h. The catalyst was removed by filtration and the filtrate was concentrated to give methyl 1-(4-(2-(tert-butoxy)-2-oxoethyl)piperidin-1-yl)cyclopropanecarboxylate (2.69 g, 9.05 mmol, 90.6% yield) as a colorless oil. $^1$H NMR (400 MHz, CDCl$_3$) δ ppm 3.64 (s, 3H), 3.01 (td, J=11.6, 2.4 Hz, 2H), 2.83-2.80 (m, 2H), 2.10 (d, J=7.2 Hz, 2H), 1.85-1.73 (m, 1H), 1.65-1.62 (m, 1H), 1.44 (s, 9H), 1.26 (q, J=4.0 Hz, 2H), 1.08 (td, J=12.0, 4.4 Hz, 2H), 0.91 (q, J=3.6 Hz, 2H).

2-(1-(1-(Methoxycarbonyl)cyclopropyl)piperidin-4-yl)acetic acid

To a solution of methyl 1-(4-(2-(tert-butoxy)-2-oxoethyl)piperidin-1-yl)cyclopropanecarboxylate (2.49 g, 8.37 mmol, 1.00 eq) in DCM (10 mL) was added a 4.0 M solution of HCl in dioxane (10 mL, 4.78 eq). The reaction was stirred at 20° C. for 12 h and concentrated under reduced pressure. 2-(1-(1-(methoxycarbonyl)cyclopropyl)piperidin-4-yl)acetic acid hydrochloride (2.12 g, 7.63 mmol, 91.2% yield) was isolated as a white solid and was used in the next step without additional purification. $^1$H NMR (400 MHz, CH$_3$OD) δ ppm 3.86-3.78 (m, 5H), 3.55 (d, J=11.6 Hz, 2H), 2.32 (d, J=6.4 Hz, 2H), 2.10-2.03 (m, 3H), 1.76-1.63 (m, 6H).

Methyl 1-(4-(2-hydroxyethyl)piperidin-1-yl)cyclopropanecarboxylate

To a solution of 2-(1-(1-(methoxycarbonyl)cyclopropyl)piperidin-4-yl)acetic acid hydrochloride (2.12 g, 7.63 mmol, 1.00 eq) in THF (11 mL) was added 4-methylmorpholine (1.54 g, 15.27 mmol, 2.00 eq), followed by isobutyl carbonochloridate (1.04 g, 7.63 mmol, 1.00 eq) both added dropwise at −15° C. The mixture was stirred at this temperature for 10 min. The resulting suspension was separated by filtration and was washed with THF (2 mL). The filtrates were combined in a flask placed at −15° C. A solution of sodium borohydride (0.433 g, 11.45 mmol, 1.50 eq) in water (5 mL) was added in one portion. The reaction was stirred at 20° C. for 20 min. To the mixture was added a saturated aqueous solution of sodium bicarbonate (50 mL) and the resulting mixture was extracted with EtOAc (30 mL×2). The combined organic extracts were washed with brine (30 mL), dried, filtered, and concentrated to give methyl 1-(4-(2-hydroxyethyl)piperidin-1-yl)cyclopropanecarboxylate (1.59 g, 7.00 mmol, 91.6% yield) as a colorless oil and that was used to next step without purification. $^1$H NMR (400 MHz, CDCl$_3$) δ ppm 3.68 (t, J=6.4 Hz, 2H), 3.64 (s, 3H), 3.00 (td, J=11.6, 2.0 Hz, 2H), 2.84-2.81 (m, 2H), 1.64-1.61 (m, 2H), 1.52-1.44 (m, 3H), 1.28-1.24 (m, 2H), 1.06 (qd, J=12.4, 4.0 Hz, 2H), 0.92-0.90 (m, 2H).

Methyl 1-(4-(2-(4-(3-(6-cyano-5-(trifluoromethyl) pyridin-3-yl)-5,5-dimethyl-4-oxo-2-thioxoimidazolidin-1-yl)-2-ethylphenoxy)ethyl)piperidin-1-yl)cyclopropanecarboxylate To a mixture of methyl 1-(4-(2-hydroxyethyl)piperidin-1-yl)cyclopropanecarboxylate (0.525 g, 2.31 mmol, 1.00 eq), 5-(3-(3-ethyl-4-hydroxyphenyl)-4,4-dimethyl-5-oxo-2-thioxoimidazolidin-1-yl)-3-(trifluoromethyl)picolinonitrile (1.00 g, 2.31 mmol, 1.00 eq) and triphenylphosphine (0.909 g, 3.46 mmol, 1.5 eq) in toluene (10 mL) was added (E)-diisopropyl diazene-1,2-dicarboxylate (0.701 g, 3.460 mmol, 1.50 eq). The reaction was stirred at 110° C. for 12 h, then concentrated under reduced pressure. The residue was purified by semi-preparative reverse phase HPLC (33-63% acetonitrile in water+0.1% TFA, 27 min) to give methyl 1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxylate (0.854 g, 1.33 mmol, 57.4% yield) as an off-white solid. $^1$H NMR (400 MHz, CDCl$_3$) δ ppm 9.10 (d, J=2.0 Hz, 1H), 8.37 (d, J=2.0 Hz, 1H), 7.07-7.04 (m, 2H), 6.93 (d, J=8.4 Hz, 1H), 4.05 (t, J=6.4 Hz, 2H), 3.64 (s, 3H), 3.04 (t, J=10.0 Hz, 2H), 2.87 (d, J=11.2 Hz, 2H), 2.69 (q, J=7.2 Hz, 2H), 1.79-1.69 (m, 5H), 1.60 (s, 6H), 1.29-1.27 (m, 2H), 1.23 (t, J=11.6 Hz, 3H), 1.19-1.09 (m, 2H), 0.93 (q, J=3.6 Hz, 2H).

1-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxylic acid hydrochloride A solution of methyl 1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxylate (0.854 g, 1.33 mmol, 1.00 eq) dissolved in a 6.0 N aqueous solution of HCl (40 mL, 180.9 eq) was stirred at 100° C. for 36 h. The reaction mixture was cooled to room temperature and a biphasic mixture was observed. The supernatant solution was decanted and the solid deposited on the surface of the flask was dissolved in acetonitrile (20 mL) and the solution was concentrated under reduced pressure to afford 1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxylic acid hydrochloride (0.850 g, crude) as a white solid that was used in the next step without further purification. MS (ESI) m/z 630.2 [M+1]$^+$.

N-(3-Chloro-5-((2,6-dioxopiperidin-3-yl)amino) phenyl)-1-(4-(2-(4-(3-(6-cyano-5-(trifluoromethyl) pyridin-3-yl)-5,5-dimethyl-4-oxo-2-thioxoimidazolidin-1-yl)-2-ethylphenoxy)ethyl)piperidin-1-yl) cyclopropanecarboxamide hydrochloride A mixture of 1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxylic acid hydrochloride (0.850 g, 1.280 mmol, 1 eq), 3-((3-amino-5-chlorophenyl)amino)piperidine-2,6-dione hydrochloride (0.370 g, 1.28 mmol, 1.00 eq), HATU (0.582 g, 1.53 mmol, 1.20 eq), DIEA (0.660 g, 5.10 mmol, 4.00 eq) and DMF (6 mL) was stirred at 25° C. for 36 h, filtered, and the filtrate was purified by standard methods to give N-(3-chloro-5-((2,6-dioxopiperidin-3-yl)amino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy) ethyl)piperidin-1-yl)cyclopropanecarboxamide hydrochloride (0.302 g, 0.332 mmol, 26.0% yield). MS (ESI) m/z 865.2 [M+1]$^+$; $^1$H NMR (400 MHz, DMSO-d$_6$) δ ppm 10.80 (s, 1H), 10.54 (s, 1H), 9.53 (s, 1H), 9.24 (d, J=2.0 Hz, 1H), 8.82 (d, J=2.0 Hz, 1H), 7.16-7.09 (m, 3H), 6.90 (d, J=18.0 Hz, 2H), 6.50 (s, 1H), 4.32-4.30 (m, 1H), 4.09 (br s, 1H), 3.61-3.56 (m, 4H), 2.78-2.56 (m, 4H), 2.08-2.04 (m, 1H), 1.93-1.75 (m, 9H), 1.61-1.50 (m, 8H), 1.17-1.13 (m, 4H).

Examples 9 and 10: (2S)—N-(3-Chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide hydrochloride and (2R)—N-(3-chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide hydrochloride

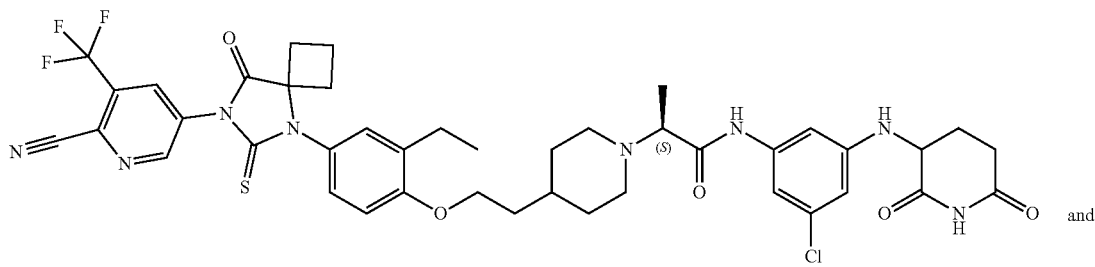

and

-continued

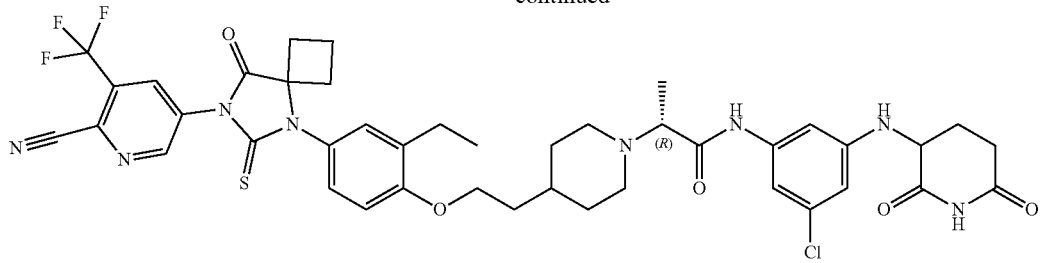

1-((3-Ethyl-4-hydroxyphenyl)amino)cyclobutanecarbonitrile

To a solution of 4-amino-2-ethyl-phenol (3.500 g, 25.51 mmol, 1 eq) and cyclobutanone (1.970 g, 28.07 mmol, 2.10 mL, 1.10 eq) in THF (70 mL) was added trimethylsilyl cyanide (3.040 g, 30.62 mmol, 3.83 mL, 1.20 eq) and scandium triflate (1.260 g, 2.550 mmol, 0.10 eq) under nitrogen. The reaction mixture was stirred at 25° C. for 16 h, concentrated, and then diluted with water (50 mL) and extracted with EtOAc (50 mL×3). The combined organic layers were washed with brine (30 mL×2), dried over anhydrous sodium sulfate, filtered, and concentrated under reduced pressure. The residue was purified by silica gel column chromatography (100% DCM) to afford 1-((3-ethyl-4-hydroxyphenyl)amino)cyclobutanecarbonitrile (2.650 g, 11.96 mmol, 46.9% yield) as a yellow solid. MS (ESI) m/z 217.2 [M+1]$^+$; $^1$HNMR (400 MHz, CDCl$_3$) δ ppm 6.68 (d, J=8.4 Hz, 1H), 6.51 (d, J=2.8 Hz, 1H), 6.42 (dd, J=2.8, 8.4 Hz, 1H), 4.61 (br s, 1H), 3.75 (br s, 1H), 2.83-2.68 (m, 2H), 2.64-2.53 (m, 2H), 2.43-2.30 (m, 2H), 2.27-2.09 (m, 2H), 1.22 (t, J=7.6 Hz, 3H).

4-(5-(3-Ethyl-4-hydroxyphenyl)-8-oxo-6-thioxo-5,7-diazaspiro[3.4]octan-7-yl)-2-(trifluoromethyl)benzonitrile To a solution of 1-((3-ethyl-4-hydroxyphenyl)amino)cyclobutanecarbonitrile (1.450 g, 6.70 mmol, 1.00 eq) and 4-isothiocyanato-2-(trifluoromethyl)benzonitrile (1.840 g, 8.050 mmol, 1.20 eq) in DMF (10 mL) was stirred at 25° C. for 1 h. Then a 4.0 M solution of HCl in MeOH (15 mL, 8.95 eq) and MeOH (5 mL) were added. The reaction mixture stirred at 70° C. for 12 h, and concentrated under reduced pressure. The residue was diluted with water (50 mL) and extracted with EtOAc (100 mL×3). The combined organic layers were washed with brine 60 mL (30 mL×2), dried over anhydrous sodium sulfate, filtered, and concentrated under reduced pressure. The residue was purified by silica gel column chromatography (0-35% EtOAc in petroleum ether) to afford 4-(5-(3-ethyl-4-hydroxyphenyl)-8-oxo-6-thioxo-5,7-diazaspiro[3.4]octan-7-yl)-2-(trifluoromethyl)benzonitrile (3.00 g, 6.35 mmol, 94.7% yield) as a grey solid. MS (ESI) m/z 446.1 [M+1]$^+$; $^1$H NMR (400 MHz, CDCl$_3$) δ ppm 8.03-7.94 (m, 2H), 7.90-7.83 (m, 1H), 7.08 (d, J=2.2 Hz, 1H), 7.05-6.99 (m, 1H), 6.91 (d, J=8.4 Hz, 1H), 5.44 (br s, 1H), 2.75-2.68 (m, 2H), 2.68-2.52 (m, 4H), 2.31-2.15 (m, 1H), 1.74-1.68 (m, 1H), 1.29 (t, J=7.6 Hz, 3H).

tert-Butyl 4-(2-(benzyloxy)ethyl)piperidine-1-carboxylate

To a solution of tert-butyl 4-(2-hydroxyethyl)piperidine-1-carboxylate (3.00 g, 13.08 mmol, 1.00 eq) in DMF (30 mL) was added sodium hydride (1.050 g, 26.16 mmol, 60% purity, 2.00 eq) at 0° C. under nitrogen. The reaction mixture was stirred at 25° C. for 1 h, then treated with benzyl bromide (3.360 g, 19.62 mmol, 2.33 mL, 1.5 eq), and stirred at 25° C. for 2 h. The reaction mixture was quenched with a saturated solution of ammonium chloride (40 mL) at 0° C., diluted with water (50 mL), and extracted with EtOAc (100 mL×3). The combined organic layers were washed with brine (30 mL×2), dried over anhydrous sodium sulfate, filtered, and concentrated under reduced pressure. The residue was purified by silica gel column chromatography (0-4% EtOAc in petroleum ether) to afford tert-butyl 4-(2-(benzyloxy)ethyl)piperidine-1-carboxylate (3.70 g, 11.58 mmol, 88.5% yield) isolated as a colorless oil. $^1$H NMR (400 MHz, CDCl$_3$) δ ppm 7.39-7.28 (m, 5H), 4.50 (s, 2H), 4.19-3.91 (m, 2H), 3.52 (t, J=6.2 Hz, 2H), 2.80-2.56 (m, 2H), 1.69-1.62 (m, 2H), 1.60-1.52 (m, 3H), 1.46 (s, 9H), 1.17-1.01 (m, 2H).

4-(2-(Benzyloxy)ethyl)piperidine

To a solution of tert-butyl 4-(2-(benzyloxy)ethyl)piperidine-1-carboxylate (3.70 g, 11.58 mmol, 1.00 eq) in dioxane (25 mL) was added a solution of a 4.0 M solution of HCl in dioxane (25 mL, 8.60 eq) under nitrogen. The reaction mixture was stirred at 25° C. for 2 h, concentrated under reduced pressure, diluted with EtOAc (50 mL), and the pH was adjusted to 9 with a saturated solution of sodium bicarbonate. The crude material was extracted by EtOAc (50 mL×3) and the organic layers were washed with brine, dried over anhydrous sodium sulfate, filtered, and concentrated to give 4-(2-(benzyloxy)ethyl)piperidine (3.00 g, crude) as a white solid. The material was used in the next step without additional purification. MS (ESI) m/z 220.2 [M+1]$^+$.

tert-Butyl 2-(4-(2-(benzyloxy)ethyl)piperidin-1-yl)propanoate

To a solution of 4-(2-(benzyloxy)ethyl)piperidine (3.00 g, 13.7 mmol, 1.00 eq) and tert-butyl 2-bromopropanoate (5.72 g, 27.4 mmol, 2.00 eq) in acetonitrile (30 mL) was added DIEA (8.84 g, 68.4 mmol, 11.91 mL, 5.00 eq) under nitrogen. The reaction mixture was stirred at 25° C. for 12 h, then was concentrated under reduced pressure. The residue was diluted with water (30 mL) and extracted with EtOAc (100 mL×3). The combined organic layers were washed with brine (50 mL×2), dried over anhydrous sodium sulfate, filtered, and concentrated under reduced pressure. The residue was purified by silica gel column chromatography (0-8% EtOAc in petroleum ether) to afford tert-butyl 2-(4-(2-(benzyloxy)ethyl)piperidin-1-yl)propanoate (3.68 g, 10.4 mmol, 75.9% yield) as a yellow oil. MS (ESI) m/z 348.2 [M+1]$^+$; $^1$H NMR (400 MHz, CDCl$_3$) δ ppm 7.39-7.25 (m, 4H), 4.50 (s, 2H), 3.50 (t, J=6.5 Hz, 2H), 3.17 (q, J=7.1 Hz, 1H), 2.95-2.84 (m, 2H), 2.34 (dt, J=2.4, 11.6 Hz, 1H), 2.22 (dt, J=2.1, 11.6 Hz, 1H), 1.72-1.63 (m, 2H), 1.56 (q, J=6.6 Hz, 2H), 1.47 (s, 9H), 1.46-1.38 (m, 1H), 1.35-1.27 (m, 1H), 1.25 (d, J=7.1 Hz, 3H), 1.23-1.13 (m, 1H).

Chiral Separation of (S)-tert-butyl 2-(4-(2-(benzyloxy)ethyl)piperidin-1-yl)propanoate and (R)-tert-Butyl 2-(4-(2-(benzyloxy)ethyl)piperidin-1-yl)propanoate The two enantiomers of tert-butyl 2-(4-(2-(benzyloxy)ethyl)piperidin-1-yl)propanoate (3.68 g, 10.6 mmol) were separated by chiral SFC using the following method (column: DAICEL CHIRALCEL OJ-H (250 mm×30 mm, 5 µm); mobile phase B: 0.1% aqueous ammonia in MeOH; gradient B=15%; 2.5 min) to give enantiomer 1 (0.550 g, 1.45 mmol, 91.6% purity) as a colorless oil, and enantiomer 2 (0.960 g, 2.73 mmol, 98.9% purity) was obtained as a colorless oil.

An assignment of (R) and (S) was not performed. Each enantiomer was used separately in the steps below.

Enantiomer 1 of tert-butyl 2-(4-(2-hydroxyethyl)piperidin-1-yl)propanoate

To a solution of the enantiomer 1 of tert-butyl 2-(4-(2-(benzyloxy)ethyl)piperidin-1-yl)propanoate (0.550 g, 1.580 mmol, 1.00 eq) in MeOH (10 mL) was added Pd on carbon (0.050 g, 10% purity) under nitrogen. The suspension was degassed under vacuum and purged with hydrogen several times. The mixture was stirred under hydrogen (50 psi) at 25° C. for 16 h. The catalyst was removed by filtration and the filtrate was concentrated under reduced pressure. To a solution of the residue (0.550 g, crude) in MeOH (10 mL) was added Pd on carbon (0.050 g, 10% purity) under nitrogen. The suspension was degassed under vacuum and purged with hydrogen several times. The mixture was stirred under hydrogen (50 Psi) at 25° C. for another 16 h. The catalyst was removed by filtration and the filtrate was concentrated under reduced pressure to provide enantiomer 1 of tert-butyl 2-(4-(2-hydroxyethyl)piperidin-1-yl)propanoate (0.420 g, crude) was obtained as a yellow oil and was used into the next step without further purification.

Enantiomer 1 of tert-butyl 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl) piperidin-1-yl)propanoate To a solution of 5-(5-(3-ethyl-4-hydroxyphenyl)-8-oxo-6-thioxo-5,7-diazaspiro[3.4]octan-7-yl)-3-(trifluoromethyl) picolinonitrile (0.300 g, 0.672 mmol, 1.00 eq), enantiomer 1 of tert-butyl 2-(4-(2-hydroxyethyl)piperidin-1-yl)propanoate (0.208 g, 0.806 mmol, 1.2 eq) and triphenylphosphine (0.212 g, 0.806 mmol, 1.20 eq) in toluene (2 mL) was added diisopropyl diazene-1,2-dicarboxylate (0.163 g, 0.806 mmol, 0.157 mL, 1.20 eq) under nitrogen. The reaction mixture was stirred at 110° C. for 12 h, then was diluted with water (30 mL), and the crude product was extracted with EtOAc (50 mL×3). The combined organic layers were washed with brine, dried over anhydrous sodium sulfate, filtered, and concentrated under reduced pressure. The residue was purified by silica gel column chromatography (100% EtOAc, 0-10% MeOH in DCM) followed by preparative silica gel TLC (50% EtOAc in petroleum ether). Enantiomer 1 of tert-butyl 2-(4-(2-(4-(7-(6-cyano-5-(trifluoromethyl)pyridin-3-yl)-8-oxo-6-thioxo-5,7-diazaspiro[3.4] octan-5-yl)-2-ethylphenoxy)ethyl)piperidin-1-yl)propanoate (0.240 g, 0.345 mmol, 51.4% yield) was obtained as a yellow solid. MS (ESI) m/z 686.1 [M+1]$^+$.

Enantiomer 1 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoic acid To a solution of enantiomer 1 of tert-butyl 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoate (0.240 g, 0.350 mmol, 1.00 eq) in DCM (2 mL) was added a 4.0 M solution of HCl in dioxane (10 mL). The reaction mixture was stirred at 25° C. for 16 h then was concentrated under reduced pressure to give enantiomer 1 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoic acid (0.220 g, crude) as a yellow oil which was used into the next step without further purification. MS (ESI) m/z 630.1 [M+1]$^+$.

Diastereomer 1 of N-(3-chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl) piperidin-1-yl)propanamide hydrochloride To a solution of enantiomer 1 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl) propanoic acid (0.220 g, 0.349 mmol, 1.00 eq) and 3-((3-amino-5-chlorophenyl)amino)piperidine-2,6-dione hydrochloride (0.152 g, 0.524 mmol, 1.50 eq) in DMF (3 mL) was added DIEA (0.226 g, 1.75 mmol, 0.304 mL, 5.00 eq) and HATU (0.133 g, 0.349 mmol, 1.00 eq) under nitrogen. The reaction mixture was stirred at 25° C. for 12 h and filtered. The filtrate was purified by semi-preparative reverse phase HPLC (40-70% acetonitrile+0.225% formic acid in water, over 9 min). The collected fraction was concentrated to remove most of the acetonitrile and was treated with a 1.0 M aqueous solution of HCl (5 mL), and lyophilized. The solid was diluted with EtOAc (50 mL) and the pH was adjusted to 9 with a saturated aqueous solution of sodium bicarbonate. The mixture was extracted with EtOAc (50 mL×3) and the organic layers were washed with brine, dried with anhydrous sodium sulfate, filtered, and concentrated under reduced pressure. The residue was purified by standard methods to afford diastereomer 1 of N-(3-chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy) ethyl)piperidin-1-yl)propanamide hydrochloride (0.047 g, 0.052 mmol, 14.8% yield). MS (ESI) m/z 865.2 [M+1]$^+$; $^1$H NMR (400 MHz, DMSO-d$_6$) δ ppm 10.90-10.68 (m, 2H), 9.90 (br s, 1H), 9.22 (s, 1H), 8.76 (s, 1H), 7.25-7.12 (m, 3H), 7.00 (s, 1H), 6.91-6.83 (m, 1H), 6.53 (s, 1H), 4.40-4.30 (m, 1H), 4.18-4.00 (m, 3H), 3.62 (br d, J=7.8 Hz, 1H), 3.16 (br s, 1H), 3.00 (br d, J=10.8 Hz, 1H), 2.81-2.70 (m, 1H), 2.69-2.56 (m, 6H), 2.44 (br s, 2H), 2.12-1.89 (m, 6H), 1.87-1.73 (m, 3H), 1.72-1.62 (m, 1H), 1.56 (br d, J=6.6 Hz, 5H), 1.22-1.15 (m, 3H).

Enantiomer 2 of tert-butyl 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl) piperidin-1-yl)propanoate To a solution of 5-(5-(3-ethyl-4-hydroxyphenyl)-8-oxo-6-thioxo-5,7-diazaspiro[3.4]octan-7-yl)-3-(trifluoromethyl)

picolinonitrile (0.300 g, 0.672 mmol, 1.00 eq), enantiomer 2 of tert-butyl 2-(4-(2-hydroxyethyl)piperidin-1-yl)propanoate (0.208 g, 0.806 mmol, 1.20 eq) (prepared as described above) and triphenylphosphine (0.264 g, 1.01 mmol, 1.50 eq) in toluene (2 mL) was added diisopropyl diazene-1,2-dicarboxylate (0.204 g, 1.01 mmol, 0.196 mL, 1.5 eq) under nitrogen. The reaction mixture was stirred at 110° C. for 12 h, then was concentrated under reduced pressure. The residue was added triphenylphosphine (0.264 g) and diisopropyl diazene-1,2-dicarboxylate (0.196 mL). The reaction mixture was stirred at 110° C. for another 16 h, then concentrated under reduced pressure. The residue was purified by silica gel column chromatography (21% EtOAc in petroleum ether) followed by silica gel preparative TLC (50% EtOAc in petroleum ether) to afford enantiomer 2 of tert-butyl 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoate (0.120 g, 0.162 mmol, 24.2% yield) as a yellow oil. MS (ESI) m/z 686.3 [M+1]+

Enantiomer 2 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoic acid To a solution of enantiomer 2 of tert-butyl 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoate (0.120 g, 0.175 mmol, 1.00 eq) in DCM (2 mL) was added a 4.0 M solution of HCl in dioxane (10 mL, 229 eq). The reaction mixture was stirred at 25° C. for 12 h, then was concentrated under reduced pressure. Enantiomer 2 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoic acid (0.120 g, 0.190 mmol, 1.00 eq) was obtained as a yellow oil which was used into the next step without further purification. MS (ESI) m/z 630.2 [M+1]+.

Diastereomer 2 of N-(3-chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide hydrochloride To a solution of enantiomer 2 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanoic acid (0.120 g, 0.190 mmol, 1.00 eq) and 3-((3-amino-5-chlorophenyl)amino)piperidine-2,6-dione hydrochloride (0.100 g, 0.343 mmol, 1.80 eq) in DMF (2 mL) was added HATU (0.072 g, 0.190 mmol, 1.00 eq) and DIEA (0.123 g, 0.953 mmol, 0.166 mL, 5.00 eq). The reaction mixture was stirred at 25° C. for 16 h, filtered. The filtrate was purified by standard methods to afford diastereomer 2 of N-(3-chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide hydrochloride (0.030 g, 0.033 mmol, 17.5% yield). MS (ESI) m/z 865.3 [M+1]+; 1H NMR (400 MHz, DMSO-$d_6$) δ ppm 1.15-1.21 (m, 3H), 1.53 (br s, 1H), 1.56 (br d, J=6.85 Hz, 3H), 1.68 (br d, J=12.72 Hz, 1H), 1.74-2.14 (m, 9H), 2.37-2.45 (m, 2H), 2.57-2.68 (m, 6H), 2.70-2.81 (m, 1H), 3.00 (br d, J=11.86 Hz, 1H), 3.10-3.23 (m, 1H), 3.61 (br d, J=12.23 Hz, 1H), 4.12 (br s, 3H), 4.34 (br d, J=6.97 Hz, 1H), 6.36 (br s, 1H), 6.53 (s, 1H), 6.85-6.94 (m, 1H), 7.01 (s, 1H), 7.15 (br d, J=3.55 Hz, 2H), 7.18-7.24 (m, 1H), 8.76 (d, J=1.59 Hz, 1H), 9.22 (s, 1H), 10.08 (br s, 1H), 10.80 (s, 1H), 10.85 (br s, 1H).

Example 11: N-(3-Cyano-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide trifluoroacetate

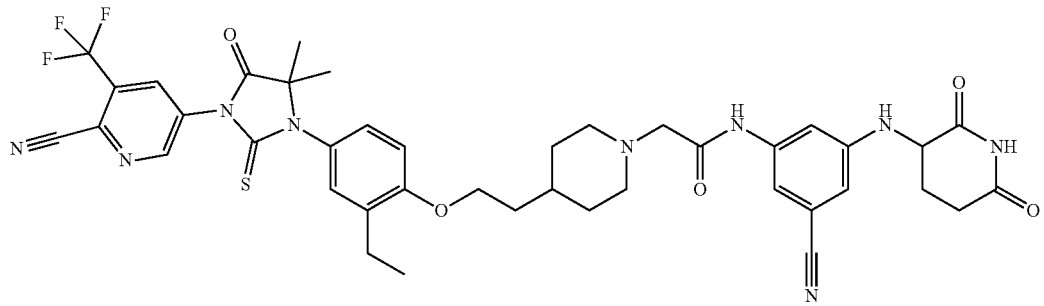 [SMILES: CCc1cc(N2C(=S)N(c3cnc(C#N)c(C(F)(F)F)c3)C(=O)C2(C)C)ccc1OCCC1CCN(CC(=O)Nc2cc(C#N)cc(NC3CCC(=O)NC3=O)c2)CC1]

tert-Butyl N-(3-bromo-5-nitrophenyl)-N-tert-butoxycarbonyl-carbamate

To a solution of 3-bromo-5-nitro-aniline (5.500 g, 25.34 mmol, 1.00 eq) in pyridine (50 mL) was added Boc$_2$O (27.66 g, 126.7 mmol, 5.00 eq). The mixture was stirred at 25° C. for 12 h, then diluted with water (30 mL) and EtOAc (60 mL×3). The combined organic extracts were washed with brine (20 mL×2), dried with anhydrous sodium sulfate, filtered, and concentrated under vacuum. The residue was purified by silica gel column chromatography (3% EtOAc in petroleum ether) to afford tert-butyl N-(3-bromo-5-nitrophenyl)-N-tert-butoxycarbonyl-carbamate (8.00 g, 19.2 mmol, 76.0% yield) as a yellow solid. 1H NMR (400 MHz, DMSO-$d_6$) δ ppm 8.37 (t, J=1.8 Hz, 1H), 8.20 (t, J=1.8 Hz, 1H), 8.12 (t, J=1.6 Hz, 1H), 1.40 (s, 18H).

tert-Butyl (3-cyano-5-nitrophenyl)carbamate

A mixture of tert-butyl N-(3-bromo-5-nitro-phenyl)-N-tert-butoxycarbonyl-carbamate (4.300 g, 10.31 mmol, 1.00 eq) in DMF (5 mL) was added zinc cyanide (2.420 g, 20.61 mmol, 2.00 eq), and tetrakis[triphenylphosphine]palladium (0) (2.380 g, 2.060 mmol, 0.20 eq), and the mixture was stirred at 100° C. for 10 h under nitrogen. The reaction mixture was diluted with water (25 mL) and the product was extracted with EtOAc (30 mL×3). The combined organic extracts were washed with brine (15 mL×2), dried with anhydrous sodium sulfate, filtered, and concentrated in vacuo. The residue was purified by silica gel column chromatography (4% EtOAc in petroleum ether) to afford tert-butyl (3-cyano-5-nitrophenyl)carbamate (1.10 g, 4.09 mmol, 30.0% yield) as a yellow solid. $^1$H NMR (400 MHz, DMSO-d$_6$) δ ppm 10.24 (s, 1H), 8.64 (s, 1H), 8.31 (s, 1H), 8.13 (s, 1H), 1.50 (s, 9H).

tert-Butyl (3-amino-5-cyanophenyl)carbamate

To a mixture of tert-butyl N-(3-cyano-5-nitro-phenyl) carbamate (1.100 g, 4.180 mmol, 1.00 eq) in EtOH (30 mL) and water (10 mL) was added ferric nitrate (1.400 g, 25.07 mmol, 6.00 eq) and ammonium chloride (2.240 g, 41.79 mmol, 10.00 eq) at 25° C. The mixture was heated to 80° C., stirred for 10 h under nitrogen, and filtered. The filtrate was concentrated under reduced pressure to afford tert-butyl (3-amino-5-cyanophenyl)carbamate (0.950 g, 4.07 mmol, 97.0% yield) as a black brown oil. MS (ESI) m/z 178.1 [M−55]$^+$.

3,5-Diaminobenzonitrile

To a solution of tert-butyl (3-amino-5-cyanophenyl)carbamate (0.200 g, 0.857 mmol, 1.00 eq) in EtOAc (2 mL) was added a 4.0 M solution of HCl in 1,4-dioxane (4 M, 10.00 eq). The mixture was stirred at 25° C. for 1 h, then poured into a saturated aqueous solution of sodium bicarbonate (50 mL) and the mixture was extracted with EtOAc (50 mL×3).

The combine organic extracts were washed with brine (50 mL×3), dried over anhydrous sodium sulfate, filtered, and concentrated under vacuum. Compound 3,5-diaminobenzonitrile (0.100 g, 0.751 mmol, 88.0% yield) was obtained as a white solid.

3-Amino-5-((2,6-dioxopiperidin-3-yl)amino)benzonitrile

To a solution of 3,5-diaminobenzonitrile (0.100 g, 0.751 mmol, 1.00 eq) and 3-bromopiperidine-2,6-dione (0.288 g, 1.50 mmol, 2.00 eq) in DMF (1 mL) was added sodium hydrogen carbonate (0.094 g, 1.13 mmol, 1.50 eq). The mixture was stirred at 50° C. for 12 h. The mixture was poured into ice-water (20 mL), and the aqueous phase was extracted with EtOAc (20 mL×3). The combined organic extracts were washed with brine (20 mL), dried with anhydrous sodium sulfate, filtered, and concentrated under vacuum. The mixture was purified by preparative TLC (50% EtOAc petroleum ether). Compound 3-amino-5-((2,6-dioxopiperidin-3-yl)amino)benzonitrile (0.050 g, 0.20 mmol, 27% yield) was obtained as a white solid. MS (ESI) m/z 245.2 [M+1]$^+$.

N-(3-Cyano-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide trifluoroacetate 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetic acid dihydrochloride (0.100 g, 0.148 mmol), 3-amino-5-((2,6-dioxopiperidin-3-yl)amino)benzonitrile (0.047 g, 0.192 mmol), HATU (0.062 g, 0.163 mmol) and DIEA (0.103 mL, 0.591 mmol) were combined in DMF (1 mL) and the mixture was stirred at ambient temperature in a screw cap vial. After 2 h, the solution was diluted with DMSO (1 mL) and purified by standard methods to afford the title compound (0.041, 0.049 mmol, 33.4% yield). MS(ESI) m/z 830 [M+1]$^+$; $^1$H NMR (400 MHz, DMSO-d$_6$) δ ppm 10.84 (s, 1H), 9.24 (d, J=1.96 Hz, 1H), 8.82 (d, J=1.96 Hz, 1H), 7.25 (s, 1H), 7.08-7.19 (m, 4H), 6.82 (br s, 1H), 6.53 (s, 2H), 4.40 (br s, 1H), 3.99-4.22 (m, 3H), 2.74 (s, 1H), 2.52-2.69 (m, 4H), 2.07 (br s, 2H), 1.93 (br dd, J=12.23, 4.28 Hz, 3H), 1.65-1.84 (m, 4H), 1.51 (s, 9H), 1.16 (t, J=7.52 Hz, 4H), 0.83 (s, 1H), −0.04−−0.01 (m, 1H).

Example 12: (S)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(((S)-2,6-dioxopiperidin-3-yl)amino)phenyl)propanamide hydrochloride

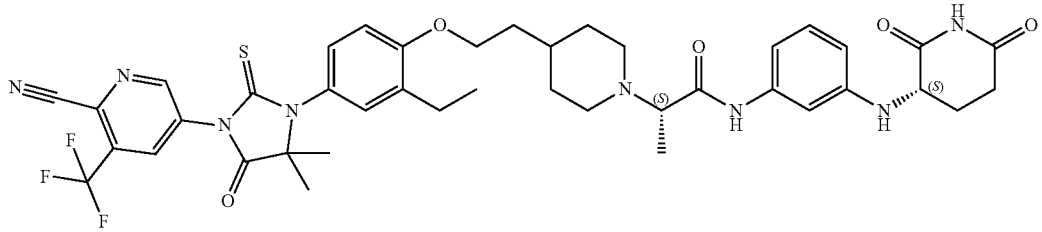

tert-Butyl N-[3-[(2,6-dioxo-3-piperidyl)amino]phenyl]carbamate

To a solution of tert-butyl N-(3-aminophenyl)carbamate (10.90 g, 52.1 mmol) and 3-bromopiperidine-2,6-dione (10.00 g, 52.1 mmol) in DMF (50 mL) was added sodium bicarbonate (4.38 g, 52.1 mmol). The reaction mixture was stirred at 80° C. for 16 h, then was cooled to room temperature, and poured into ice water (800 mL). The resulting solid was collected by filtration, then washed with a 1:1 mixture of EtOAc and petroleum ether (100 mL) and dried under vacuum to give tert-butyl N-[3-[(2,6-dioxo-3-piperidyl)amino]phenyl]carbamate (14.00 g, 84.2% yield) as a blue solid. $^1$H NMR (400 MHz, DMSO-d$_6$) δ ppm 10.77 (s, 1H), 9.03 (s, 1H), 6.93 (t, J=8.0 Hz, 1H), 6.85 (d, J=6.8 Hz, 1H), 6.65 (d, J=8.0 Hz, 1H), 6.31-6.29 (m, 1H), 5.78 (d, J=8.0 Hz, 1H), 4.24-4.18 (m, 1H), 2.74-2.60 (m, 2H), 2.30-2.19 (m, 1H), 1.95-1.80 (m, 1H), 1.47 (s, 9H).

3-(3-Aminoanilino)piperidine-2,6-dione

To a solution of tert-butyl N-[3-[(2,6-dioxo-3-piperidyl)amino]phenyl]carbamate (12.00 g, 37.6 mmol) in DCM (60 mL) was added TFA (61.6 g, 540 mmol, 40 mL) at 0° C. The reaction mixture was stirred at 20° C. for 3 h, then was concentrated under reduced pressure. The residue was diluted with MTBE (60 mL) and stirred at 20° C. for 30 min. The solid was collected by filtration and dissolved in water (400 mL) prior to adjusting the pH to 7 with the addition of a saturated aqueous solution of sodium bicarbonate. The material was extracted with EtOAc (500 mL×3). The combined organic layers were dried over anhydrous sodium sulfate, filtered, and concentrated under recued pressure to give 3-(3-aminoanilino)piperidine-2,6-dione (8.00 g, 97.1% yield) as orange solid. $^1$H NMR (400 MHz, DMSO-d$_6$) δ ppm 10.83 (s, 1H), 6.81-6.77 (m, 1H), 5.97-5.83 (m, 3H), 5.47 (d, J=7.6 Hz, 1H), 4.78 (s, 2H), 4.26-4.22 (m, 1H), 2.78-2.61 (m, 2H), 2.15-2.14 (m, 1H), 1.91-1.85 (m, 1H).

(R)-3-((3-Aminophenyl)amino)piperidine-2,6-dione and (S)-3-((3-aminophenyl)amino)piperidine-2,6-dione The two enantiomers of 3-((3-aminophenyl)amino)piperidine-2,6-dione (8 g) were separated by chiral SFC and the fractions were concentrated at a temperature below 35° C. to give two peaks. The absolute configuration was determined by vibrational circular dichroism spectroscopy (VCD). (R)-3-((3-Aminophenyl)amino)piperidine-2,6-dione (2.80 g, 35.0% yield, 97.7% ee) and (S)-3-((3-aminophenyl)amino)piperidine-2,6-dione (2.90 g, 36.3% yield, 97.1% ee) were isolated as brown solids. SFC purification conditions (Column: Chiralpak IC-H, 250×30 mm i.d. 5 μm; mobile phase: A for CO$_2$ and B for EtOH:acetonitrile=2:1; gradient: B %=40%; flow rate: 75 g/min).

(R)-Methyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoate (R)-Methyl 2-chloropropanoate (0.179 mL, 1.65 mmol, 2.40 eq) was added to a stirred mixture of 5-(3-(3-ethyl-4-(2-(piperidin-4-yl)ethoxy)phenyl)-4,4-dimethyl-5-oxo-2-thioxoimidazolidin-1-yl)-3-(trifluoromethyl)picolinonitrile hydrochloride (0.400 g, 0.687 mmol, 1.00 eq) (prepared as described herein) and TEA (0.383 mL, 2.75 mmol, 4.00 eq) in THF (5.87 mL, 0.117 molar). The reaction mixture was stirred for 2 d at 85° C., then was concentrated and purified by silica gel column chromatography (0-100% EtOAc/hexanes) to give (S)-methyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoate (0.331 g, 0.524 mmol, 76% yield, 94.3% ee) as a yellow solid. MS (ESI) m/z 632.2 [M+1]$^+$.

(S)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid A suspension of (S)-methyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoate (0.231 g, 0.366 mmol, 1.00 eq) in a 3:1 mixture of THF (3.52 mL) and water (1.2 mL) (0.078 molar) was treated by the addition of lithium hydroxide (0.091 g, 3.81 mmol, 10.4 eq), and was stirred at room temperature for 18 h. The reaction was diluted with EtOAc and water and then the pH was adjusted to 3 with the addition of a 6.0 N aqueous solution of HCl. The organic layer was extracted with EtOAc, dried over sodium sulfate, filtered, and concentrated to afford (S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid hydrochloride (0.222 g, 0.359 mmol, 98% yield) as a beige solid. MS (ESI) m/z 618.2 [M+1]$^+$.

(S)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(((S)-2,6-dioxopiperidin-3-yl)amino)phenyl)propanamide hydrochloride (S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid hydrochloride (0.111 g, 0.180 mmol, 1.00 eq) was combined with (S)-3-((3-aminophenyl)amino)piperidine-2,6-dione (0.039 g, 0.180 mmol, 1.00 eq), HATU (0.075 g, 0.2 mmol, 1.10 eq), DIEA (0.094 mL, 0.54 mmol, 300. eq) in DMF (0.899 mL, 0.2 M). The reaction was stirred at 25° C. for 2 h, then quenched with water and diluted with EtOAc, and the aqueous layer was extracted by EtOAc. The combined organic layers were concentrated, and the residue was purified by standard methods to afford (2S)-2-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]-1-piperidyl]-N-[3-[[(3 S)-2,6-dioxo-3-piperidyl]amino]phenyl] propanamide hydrochloride (0.056 g, 0.063 mmol, 35% yield). MS (ESI) m/z 819.4 [M+1]$^+$; $^1$H NMR (400 MHz, DMSO-d$_6$) δ ppm 10.79 (s, 1H), 10.52 (s, 1H), 9.88 (q, 1H, J=7.6 Hz), 9.24 (d, 1H, J=1.8 Hz), 8.82 (d, 1H, J=2.0 Hz), 7.1-7.2 (m, 3H), 7.05 (t, 1H, J=8.1 Hz), 6.97 (t, 1H, J=1.7 Hz), 6.85 (br d, 1H, J=7.9 Hz), 6.47 (dd, 1H, J=1.8, 8.0 Hz), 4.27 (br dd, 1H, J=4.9, 11.5 Hz), 4.10 (br t, 2H, J=5.7 Hz), 4.05 (quin, 1H, J=6.8 Hz), 3.43 (br d, 1H, J=11.0 Hz), 3.27 (br s, 1H), 3.1-3.2 (m, 1H), 2.9-3.0 (m, 1H), 2.7-2.8 (m, 1H), 2.63 (q, 2H, J=7.6 Hz), 2.6-2.6 (m, 1H), 2.1-2.1 (m, 1H), 1.98 (br d, 2H, J=13.3 Hz), 1.91 (br dq, 1H, J=4.5, 12.1 Hz), 1.82 (br s, 1H), 1.76 (q, 2H, J=5.6 Hz), 1.6-1.7 (m, 1H), 1.55 (br d, 3H, J=6.8 Hz), 1.53 (br s, 1H), 1.51 (s, 6H), 1.16 (t, 3H, J=7.5 Hz).

Example 13: (2R)-2-[4-[2-[4-[3-[6-Cyano-5-(trifluoromethyl)-3-pyridyl]-5,5-dimethyl-4-oxo-2-thioxo-imidazolidin-1-yl]-2-ethyl-phenoxy]ethyl]-1-piperidyl]-N-[3-[[(3S)-2,6-dioxo-3-piperidyl]amino]phenyl]propanamide hydrochloride

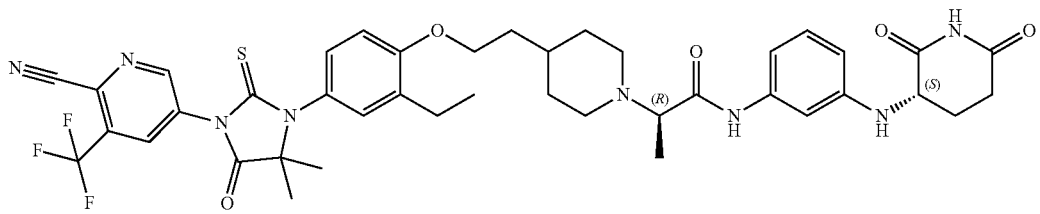

(R)-Methyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoate (S)-Methyl 2-chloropropanoate (0.101 g, 0.825 mmol, 1.20 eq) was added to a stirred mixture of 5-(3-(3-ethyl-4-(2-(piperidin-4-yl)ethoxy)phenyl)-4,4-dimethyl-5-oxo-2-thioxoimidazolidin-1-yl)-3-(trifluoromethyl)picolinonitrile hydrochloride (0.400 g, 0.687 mmol, 1.00 eq) and TEA (0.383 mL, 2.75 mmol, 4.00 eq) in THF (5.87 mL, 0.117 molar). The reaction mixture was stirred for 5 d at 85° C., then was concentrated and purified by silica gel column chromatography (0-100% EtOAc in hexanes) to give (R)-methyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoate (0.296 g, 0.469 mmol, 68.2% yield, 94% ee) as a yellow solid. MS (ESI) m/z 632.2 [M+1]$^+$.

(R)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid A suspension of (R)-methyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoate (0.194 g, 0.307 mmol, 1.00 eq) in a 3:1 mixture of THF (2.95 mL) and water (0.984 mL) (0.078 molar) was treated with lithium hydroxide (0.077 g, 3.2 mmol, 10.4 eq). The reaction mixture was stirred at room temperature for 18 h, was diluted with EtOAc and water, and the pH was adjusted to 3 with the addition of a 6.0 N aqueous HCl. The organic layer was extracted with EtOAc, dried over sodium sulfate, filtered, and concentrated to afford (R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid (0.195 g, 0.259 mmol, 84% yield) as a beige solid. MS (ESI) m/z 618.2 [M+1]$^+$.

(R)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(((S)-2,6-dioxopiperidin-3-yl)amino)phenyl)propanamide hydrochloride (R)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid (0.097 g, 0.158 mmol, 1.00 eq) was combined with (S)-3-((3-aminophenyl)amino)piperidine-2,6-dione (prepared as described herein) (0.035 g, 0.158 mmol, 1.00 eq), HATU (0.066 g, 0.174 mmol, 1.10 eq), and DIEA (0.083 mL, 0.474 mmol, 4.00 eq) in DMF (0.789 mL, 0.200 molar), and the reaction was stirred at 25° C. for 2 h. Additional (S)-3-((3-aminophenyl)amino)piperidine-2,6-dione (0.035 g, 0.158 mmol, 1.00 eq), HATU (0.066 g, 0.174 mmol, 1.10 eq) and DIEA (0.083 mL, 0.474 mmol, 4.00 eq) were used, and the reaction was stirred an additional 18 h, then quenched with water and diluted with EtOAc, and the aqueous layer was extracted with EtOAc. The combined organic layers were concentrated, and the residue was purified by standard methods to afford (2R)-2-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]-1-piperidyl]-N-[3-[[(3 S)-2,6-dioxo-3-piperidyl]amino]phenyl]propanamide hydrochloride (0.027 g, 0.031 mmol, 19.7% yield). MS (ESI) m/z 819.4 [M+1]$^+$; $^1$H NMR (400 MHz, DMSO-d$_6$) δ ppm 10.80 (s, 1H), 10.52 (s, 1H), 9.87 (q, 1H, J=7.0 Hz), 9.24 (d, 1H, J=1.8 Hz), 8.82 (d, 1H, J=2.1 Hz), 7.1-7.2 (m, 3H), 7.05 (t, 1H, J=7.9 Hz), 6.97 (t, 1H, J=1.8 Hz), 6.85 (dd, 1H, J=0.8, 7.8 Hz), 6.47 (dd, 1H, J=1.9, 8.0 Hz), 4.27 (br dd, 1H, J=4.8, 11.3 Hz), 4.10 (br t, 2H, J=5.9 Hz), 4.05 (quin, 1H, J=6.8 Hz), 3.43 (br d, 2H, J=8.4 Hz), 3.07 (qd, 2H, J=12.7, 59.9 Hz), 2.7-2.8 (m, 1H), 2.63 (q, 2H, J=7.6 Hz), 2.6-2.6 (m, 1H), 2.0-2.1 (m, 1H), 1.99 (br d, 2H, J=12.6 Hz), 1.91 (br dq, 1H, J=4.2, 12.3 Hz), 1.82 (br s, 1H), 1.76 (q, 2H, J=5.6 Hz), 1.6-1.7 (m, 1H), 1.55 (d, 3H, J=6.8 Hz), 1.53 (br s, 1H), 1.51 (s, 6H), 1.16 (t, 3H, J=7.6 Hz).

Example 14: 2-(4-((4-(3-(6-Cyano-5-(trifluoromethyl)pyridin-3-yl)-5,5-dimethyl-4-oxo-2-thioxoimidazolidin-1-yl)phenoxy)methyl)piperidin-1-yl)-N-(3-((2,6-dioxopiperidin-3-yl)amino)phenyl)acetamide hydrochloride

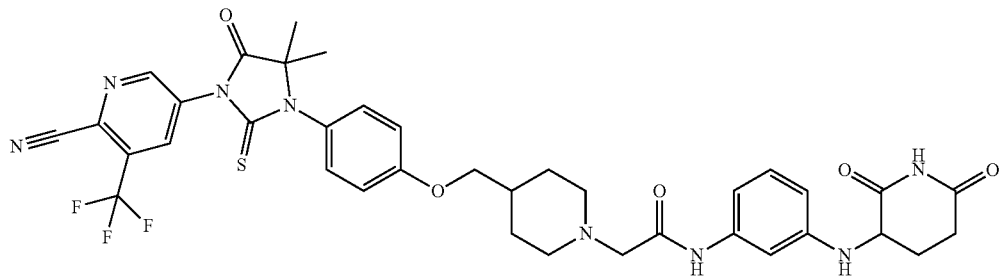 [SMILES: CC1(C)C(=O)N(c2cnc(C#N)c(C(F)(F)F)c2)C(=S)N1c1ccc(OCC2CCN(CC(=O)Nc3cccc(NC4CCC(=O)NC4=O)c3)CC2)cc1]

5-Isothiocyanato-3-(trifluoromethyl)picolinonitrile

To a solution of 5-amino-3-(trifluoromethyl)picolinonitrile (1.00 g, 5.34 mmol, 1.00 eq) in toluene (15 mL) was added thiophosgene (0.922 g, 8.020 mmol, 1.50 eq) in one portion under nitrogen. The mixture was stirred at 110° C. for 2 h, then was cooled to 25° C., and concentrated under reduced pressure at 40° C. The residue was purified by silica gel column chromatography (0-1% EtOAc in petroleum ether) to get 5-isothiocyanato-3-(trifluoromethyl)picolinonitrile (0.870 g, 3.80 mmol, 71.0% yield) as a light yellow oil. MS (ESI) m/z 230.1 [M+1]$^+$; $^1$H NMR (400 MHz, DMSO-d$_6$) δ ppm 9.11 (d, J=2.2 Hz, 1H), 8.66 (d, J=2.1 Hz, 1H).

tert-Butyl 4-((4-nitrophenoxy)methyl)piperidine-1-carboxylate

To a solution of 4-nitrophenol (1.290 g, 9.29 mmol, 1.00 eq) and tert-butyl 4-(hydroxymethyl)piperidine-1-carboxylate (2.000 g, 9.29 mmol, 1.00 eq) in THF (8 mL) was added triphenylphosphine (6.090 g, 23.22 mmol, 2.50 eq) and diisopropyl azodicarboxylate (3.76 g, 18.6 mmol, 3.61 mL, 2.00 eq) over 1 h at 0° C. under nitrogen. The reaction mixture was stirred at 25° C. for 9 h, then was diluted with EtOAc (10 mL), and concentrated under reduced pressure. The residue was purified by silica gel column chromatography (0-15% EtOAc in petroleum ether). Fractions were concentrated and the material was triturated (2% EtOAc in petroleum ether (50 mL×2) to afford tert-butyl 4-((4-nitrophenoxy)methyl)piperidine-1-carboxylate (1.070 g, 3.15 mmol, 33.9% yield) as a white solid. MS (ESI) m/z 281.0 [M+1]$^+$; $^1$H NMR (400 MHz, DMSO-d$_6$) δ ppm 8.25-8.15 (m, 2H), 7.24-7.08 (m, 2H), 4.10-3.90 (m, 4H), 2.92-2.58 (m, 2H), 2.04-1.92 (m, 1H), 1.81-1.70 (m, 2H), 1.39 (s, 9H), 1.21-1.14 (m, 2H).

tert-Butyl 4-((4-aminophenoxy)methyl)piperidine-1-carboxylate

To a mixture of tert-butyl 4-((4-nitrophenoxy)methyl)piperidine-1-carboxylate (6.50 g, 19.3 mmol, 1.00 eq) in MeOH (80 mL) was added palladium on carbon (1.00 g, 10% purity), The mixture was degassed with hydrogen three times and stirred at 25° C. under hydrogen (15 psi) for 10 h. The catalyst was removed by filtration and the filtrate was concentrated under reduced pressure to get tert-butyl 4-((4-aminophenoxy)methyl)piperidine-1-carboxylate (5.50 g, 17.9 mmol, 93% yield) as a black solid. $^1$H NMR (400 MHz, DMSO-d$_6$) δ ppm 6.63 (d, J=8.7 Hz, 2H), 6.48 (d, J=8.8 Hz, 2H), 4.58 (s, 2H), 4.02-3.90 (m, 2H), 3.66 (d, J=6.4 Hz, 2H), 2.82-2.61 (m, 2H), 1.89-1.78 (m, 1H), 1.70 (br s, 2H), 1.40-1.38 (m, 9H), 1.17-1.04 (m, 2H).

tert-Butyl 4-((4-((1-methoxy-2-methyl-1-oxopropan-2-yl)amino)phenoxy)methyl)piperidine-1-carboxylate To a solution of tert-butyl 4-((4-aminophenoxy)methyl)piperidine-1-carboxylate (5.50 g, 17.9 mmol, 1.00 eq) in DIEA (55 mL) and 1-methyl-2-pyrrolidinone (5 mL) was added methyl 2-bromo-2-methyl-propanoate (9.75 g, 53.8 mmol, 6.96 mL, 3.00 eq). After 12 h at 140° C., the reaction mixture was poured into a 1:1 mixture of EtOAc and water (100 mL) and stirred for 15 min. The organic phase was separated and the aqueous phase was extracted with EtOAc (80 mL×3). The combined organic phase was washed with brine (80 mL×2), dried with anhydrous sodium sulfate, filtered, and concentrated under reduced pressure. The residue was purified by silica gel column chromatography to get tert-butyl 4-((4-((1-methoxy-2-methyl-1-oxopropan-2-yl)amino)phenoxy)methyl)piperidine-1-carboxylate (4.60 g, 10.2 mmol, 56.7% yield) as a yellow oil. MS (ESI) m/z 407.1 [M+1]$^+$; $^1$H NMR (400 MHz, DMSO-d$_6$) δ ppm 6.67 (d, J=8.9 Hz, 2H), 6.40 (d, J=9.0 Hz, 2H), 5.40 (s, 1H), 3.99-3.86 (m, 2H), 3.68 (d, J=6.4 Hz, 2H), 3.58 (s, 3H), 2.81-2.62 (m, 2H), 1.90-1.78 (m, 1H), 1.69 (br s, 2H), 1.41-1.36 (m, 15H), 1.13-1.04 (m, 2H).

tert-Butyl 4-((4-(3-(6-cyano-5-(trifluoromethyl)pyridin-3-yl)-5,5-dimethyl-4-oxo-2-thioxoimidazolidin-1-yl)phenoxy)methyl)piperidine-1-carboxylate To a solution of tert-butyl 4-((4-((1-methoxy-2-methyl-1-oxopropan-2-yl)amino)phenoxy)methyl)piperidine-1-carboxylate (5.00 g, 12.3 mmol, 1.00 eq) and 5-isothiocyanato-3-(trifluoromethyl)picolinonitrile (5.64 g, 24.6 mmol, 2.00 eq) in EtOAc (50 mL) was added TEA (2.49 g, 24.6 mmol, 3.42 mL, 2.00 eq) in one portion under nitrogen. The mixture was stirred at 60° C. for 10 h, then was concentrated under vacuum. The residue was purified by silica gel column chromatography (0-50% EtOAc in petroleum ether) to get the tert-butyl 4-((4-(3-(6-cyano-5-(trifluoromethyl)pyridin-3-yl)-5,5-dimethyl-4-oxo-2-thioxoimidazolidin-1-yl)phenoxy)methyl)piperidine-1-carboxylate (3.900 g) as a yellow foam and tert-butyl 4-((4-(3-(6-cyano-5-(trifluoromethyl)pyridin-3-yl)-5,5-dimethyl-4-oxo-2-thioxoimizolidin-1-yl)phenoxy)methyl)piperidine-1-carboxylate (2.54 g) as a crude red oil. MS (ESI) m/z 504.1 [M-Boc+1]$^+$; $^1$H NMR (400 MHz, DMSO-d$_6$) δ ppm 9.25 (d, J=1.8 Hz, 1H), 8.82 (d, J=1.8 Hz, 1H), 7.26 (s, 2H), 7.11 (s, 2H), 4.01 (br s, 2H), 3.93-3.88 (m, 2H), 2.90-2.69 (m, 2H), 1.99 (s, 1H), 1.82-1.73 (m, 2H), 1.51 (s, 6H), 1.41 (s, 9H), 1.18 (s, 2H)

5-(4,4-Dimethyl-5-oxo-3-(4-(piperidin-4-ylmethoxy)phenyl)-2-thioxoimidazolidin-1-yl)-3-(trifluoromethyl)picolinonitrile hydrochloride A solution of tert-butyl 4-((4-(3-(6-cyano-5-(trifluoromethyl)pyridin-3-yl)-5,5-dimethyl-4-oxo-2-thioxoimidazolidin-1-yl)phenoxy)methyl)piperidine-1-carboxylate (2.80 g, 4.64 mmol, 1.00 eq) in THF (10 mL) was treated with a 4.0 M solution of HCl in dioxane (10 mL) and stirred at 25° C. for 2 h. After concentration under reduced pressure, 5-(4,4-dimethyl-5-oxo-3-(4-(piperidin-4-ylmethoxy)phenyl)-2-thioxoimidazolidin-1-yl)-3-(trifluoromethyl)picolinonitrile hydrochloride (2.80 g, crude) was isolated as a yellow foam. MS (ESI) m/z 504.0 [M+1]$^+$ 2-(4-((4-(3-(6-Cyano-5-(trifluoromethyl)pyridin-3-yl)-5,5-dimethyl-4-oxo-2-thioxoimidazolidin-1-yl)phenoxy)methyl)piperidin-1-yl)-N-(3-((2,6-dioxopiperidin-3-yl)amino)phenyl)acetamide hydrochloride To a mixture of 5-(4,4-dimethyl-5-oxo-3-(4-(piperidin-4-ylmethoxy)phenyl)-2-thioxoimidazolidin-1-yl)-3-(trifluoromethyl)picolinonitrile hydrochloride (0.130 g, 0.241 mmol, 1.00 eq) and 2-chloro-N-(3-((2,6-dioxopiperidin-3-yl)amino)phenyl)acetamide (0.072 g, 0.241 mmol, 1.00 eq) in DMF (2 mL) was added DIEA (0.156 g, 1.20 mmol, 5.00 eq), The mixture was stirred at 50° C. for 10 h, concentrated under reduced pressure and the residue was purified by standard methods to get 2-(4-((4-(3-(6-cyano-5-(trifluoromethyl)pyridin-3-yl)-5,5-dimethyl-4-oxo-2-thioxoimidazolidin-1-yl)phenoxy)methyl)piperidin-1-yl)-N-(3-((2,6-dioxopiperidin-3-yl)amino)phenyl)acetamide hydrochloride (0.114 g, 0.138 mmol, 57.3% yield). MS (ESI) m/z 763.3 [M+1]$^+$; $^1$H NMR (400 MHz, DMSO-d$_6$) δ ppm 10.80 (s, 1H), 10.53 (br s, 1H), 10.02-9.78 (m, 1H), 9.24 (d, J=1.8 Hz, 1H), 8.82 (d, J=1.8 Hz, 1H), 7.28 (d, J=8.8 Hz, 2H), 7.11 (d, J=8.9 Hz, 2H), 7.04 (s, 1H), 6.96 (br s, 1H), 6.85 (br d, J=7.8 Hz, 1H), 6.45 (br d, J=8.6 Hz, 1H), 4.25 (br dd, J=4.9, 11.5 Hz, 1H), 4.11 (br d, J=4.3 Hz, 2H), 3.93 (br d, J=6.0 Hz, 2H), 3.66-3.07 (m, 4H), 2.81-2.68 (m, 1H), 2.64-2.52 (m, 2H), 2.15-1.87 (m, 5H), 1.72 (br s, 2H), 1.50 (s, 6H).

Example 15: 2-(4-((4-(3-(4-Cyano-3-(trifluoromethyl)phenyl)-5,5-dimethyl-4-oxo-2-thioxoimidazolidin-1-yl)-2-ethylphenoxy)methyl)piperidin-1-yl)-N-(3-((2,6-dioxopiperidin-3-yl)amino)phenyl) acetamide hydrochloride

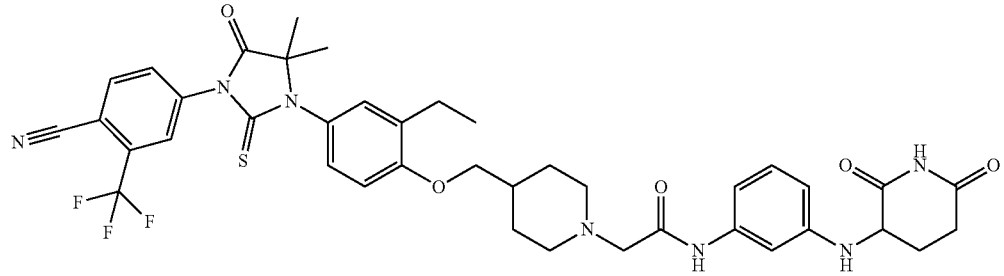 [SMILES: CCc1cc(N2C(=S)N(c3ccc(C#N)c(C(F)(F)F)c3)C(=O)C2(C)C)ccc1OCC1CCN(CC(=O)Nc2cccc(NC3CCC(=O)NC3=O)c2)CC1]

tert-Butyl 4-((4-(3-(4-cyano-3-(trifluoromethyl)phenyl)-5,5-dimethyl-4-oxo-2-thioxoimidazolidin-1-yl)-2-ethylphenoxy)methyl)piperidine-1-carboxylate 4-(3-(3-Ethyl-4-hydroxyphenyl)-4,4-dimethyl-5-oxo-2-thioxoimidazolidin-1-yl)-2-(trifluoromethyl)benzonitrile (0.100 g, 0.23 mmol) (prepared as described herein), tert-butyl 4-(bromomethyl)piperidine-1-carboxylate (0.064 g, 0.23 mmol) and cesium carbonate (0.113 g, 0.35 mmol) were combined in DMF (1.54 mL) and the solution was stirred at 40° C. overnight. The reaction was diluted with EtOAc (100 mL), water (20 mL), and brine (20 mL). The layers were separated and the organic layer was washed with brine (2×50 mL), dried over anhydrous magnesium sulfate, filtered, and concentrated under reduced pressure to an oil that was purified using silica gel chromatography (0-20% DCM in MeOH) to afford tert-butyl 4-((4-(3-(4-cyano-3-(trifluoromethyl)phenyl)-5,5-dimethyl-4-oxo-2-thioxoimidazolidin-1-yl)-2-ethylphenoxy)methyl)piperidine-1-carboxylate (0.146 g, 0.230 mmol, quantitative yield). MS (ESI) m/z 631.2 [M+1]$^+$.

4-(3-(3-Ethyl-4-(piperidin-4-ylmethoxy)phenyl)-4,4-dimethyl-5-oxo-2-thioxoimidazolidin-1-yl)-2-(trifluoromethyl)benzonitrile hydrochloride.

To a solution of tert-butyl 4-((4-(3-(4-cyano-3-(trifluoromethyl)phenyl)-5,5-dimethyl-4-oxo-2-thioxoimidazolidin-1-yl)-2-ethylphenoxy)methyl)piperidine-1-carboxylate (0.146 g, 0.23 mmol) in DCM (10 mL) was added TFA (2.0 mL, 26.0 mmol) and the mixture was stirred at ambient temperature, concentrated to an oil under reduced pressure after 3 h, and treated with a 4 N solution of HCl in dioxane (5 mL) and DCM (5 mL). The suspension was sonicated and concentrated under reduced pressure to an oil that was triturated with diethyl ether and hexanes. 4-(3-(3-Ethyl-4-(piperidin-4-ylmethoxy)phenyl)-4,4-dimethyl-5-oxo-2-thioxoimidazolidin-1-yl)-2-(trifluoromethyl)benzonitrile hydrochloride was isolated upon removal of the solvent under reduced pressure (0.103 g, 0.18 mmol, 78% yield). MS (ESI) m/z 531.2 [M+1]$^+$.

2-(4-((4-(3-(4-Cyano-3-(trifluoromethyl)phenyl)-5,5-dimethyl-4-oxo-2-thioxoimidazolidin-1-yl)-2-ethylphenoxy)methyl)piperidin-1-yl)-N-(3-((2,6-dioxopiperidin-3-yl)amino)phenyl)acetamide hydrochloride 4-(3-(3-Ethyl-4-(piperidin-4-ylmethoxy)phenyl)-4,4-dimethyl-5-oxo-2-thioxoimidazolidin-1-yl)-2-(trifluoromethyl)benzonitrile hydrochloride (0.083 g, 0.15 mmol), 2-chloro-N-(3-((2,6-dioxopiperidin-3-yl)amino)phenyl)acetamide (0.043 g, 0.15 mmol), and DIEA (0.103 mL, 0.59 mmol) were combined in DMF (1.0 mL) and the mixture was stirred at ambient temperature overnight. The mixture was purified by standard methods to afford 2-(4-((4-(3-(4-cyano-3-(trifluoromethyl)phenyl)-5,5-dimethyl-4-oxo-2-thioxoimidazolidin-1-yl)-2-ethylphenoxy)methyl)piperidin-1-yl)-N-(3-((2,6-dioxopiperidin-3-yl)amino)phenyl) acetamide hydrochloride (0.028 g, 0.034 mmol, 23% yield). MS (ESI) m/z 790.4 [M+1]$^+$; $^1$H NMR (400 MHz, DMSO-$d_6$) δ ppm 10.77-10.84 (m, 1H), 10.40-10.46 (m, 1H), 9.77-9.90 (m, 1H), 8.36-8.42 (m, 1H), 8.26-8.32 (m, 1H), 8.05-8.10 (m, 1H), 7.02-7.21 (m, 4H), 6.93-6.97 (m, 1H), 6.81-6.87 (m, 1H), 6.43-6.51 (m, 1H), 4.22-4.29 (m, 1H), 4.07-4.16 (m, 2H), 3.92-3.98 (m, 2H), 3.54-3.63 (m, 2H), 3.10-3.23 (m, 2H), 2.61-2.75 (m, 3H), 1.74-2.19 (m, 8H), 1.49 (s, 6H), 1.13-1.22 (m, 3H).

Example 16: 2-(4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-((2,6-dioxopiperidin-3-yl)amino)phenyl) acetamide hydrochloride

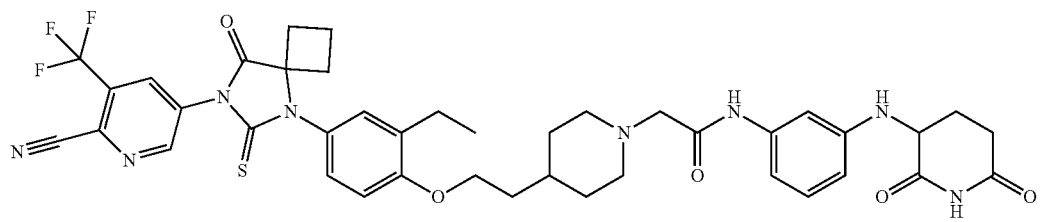 [SMILES: CCc1cc(N2C(=S)N(c3cnc(C#N)c(C(F)(F)F)c3)C(=O)C23CCC3)ccc1OCCC1CCN(CC(=O)Nc2cccc(NC3CCC(=O)NC3=O)c2)CC1]

tert-Butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidine-1-carboxylate To a solution of 5-(5-(3-ethyl-4-hydroxyphenyl)-8-oxo-6-thioxo-5,7-diazaspiro[3.4]octan-7-yl)-3-(trifluoromethyl)picolinonitrile (0.700 g, 1.57 mmol, 1.00 eq) (prepared as described herein) tert-butyl 4-(2-hydroxyethyl)piperidine-1-carboxylate (0.431 g, 1.88 mmol, 1.20 eq) and triphenylphosphine (0.494 g, 1.88 mmol, 1.20 eq) in toluene (7 mL) was added diisopropyl diazene-1,2-dicarboxylate (0.380 g, 1.88 mmol, 0.366 mL, 1.20 eq) under nitrogen. The reaction mixture was stirred at 110° C. for 12 h, then diluted with water (50 mL) and extracted with EtOAc (100 mL×3). The combined organic layers were washed with brine (30 mL×2), dried over anhydrous sodium sulfate, filtered, and concentrated under reduced pressure to give a residue. The residue was purified by silica gel column chromatography (0-9.4% EtOAc in petroleum ether) to afford tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidine-1-carboxylate (1.61 g, 1.50 mmol, 95.4% yield) as a red solid and tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidine-1-carboxylate (0.290 g, 0.638 mmol, 40.9% yield) as a grey solid. MS (ESI) m/z 680.3 [M+23]$^+$.

5-(5-(3-Ethyl-4-(2-(piperidin-4-yl)ethoxy)phenyl)-8-oxo-6-thioxo-5,7-diazaspiro[3.4]octan-7-yl)-3-(trifluoromethyl)picolinonitrile To a solution of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidine-1-carboxylate (1.61 g, 1.50 mmol, 1.00 eq) in DCM (3 mL) was added a 4.0 M solution of HCl in dioxane (15 mL, 40.12 eq) under nitrogen. The reaction mixture was stirred at 25° C. for 2 h, then was concentrated under reduced pressure. The residue was purified by semi-preparative reverse phase HPLC (30-60% acetonitrile+0.225% formic acid in water, over 22 min). Then the collected fractions were concentrated to remove most of the acetonitrile and treated with a 1.0 M aqueous solution of hydrochloric acid (5 mL). The product was lyophilized. 5-(5-(3-Ethyl-4-(2-(piperidin-4-yl)ethoxy)phenyl)-8-oxo-6-thioxo-5,7-diazaspiro[3.4]octan-7-yl)-3-(trifluoromethyl)picolinonitrile hydrochloride (0.515 g, 0.858 mmol, 57.4% yield) was obtained as a white solid. MS (ESI) m/z 558.2 [M+1]$^+$; $^1$H NMR (400 MHz, DMSO-d$_6$) δ 9.21 (d, J=2.0 Hz, 1H), 8.97 (br s, 1H), 8.81-8.62 (m, 2H), 7.22-7.09 (m, 3H), 4.10 (t, J=5.9 Hz, 2H), 3.25 (br d, J=12.5 Hz, 2H), 2.93-2.75 (m, 2H), 2.70-2.57 (m, 4H), 2.47-2.37 (m, 2H), 2.02-1.92 (m, 1H), 1.89 (br d, J=13.8 Hz, 2H), 1.85-1.70 (m, 3H), 1.61-1.50 (m, 1H), 1.49-1.36 (m, 2H), 1.17 (t, J=7.5 Hz, 3H).

2-(4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-((2,6-dioxopiperidin-3-yl)amino)phenyl)acetamide hydrochloride To a solution of 5-(5-(3-ethyl-4-(2-(piperidin-4-yl)ethoxy)phenyl)-8-oxo-6-thioxo-5,7-diazaspiro[3.4]octan-7-yl)-3-(trifluoromethyl)picolinonitrile hydrochloride (0.150 g, 0.252 mmol, 1.00 eq) and 2-chloro-N-(3-((2,6-dioxopiperidin-3-yl)amino)phenyl)acetamide (0.101 g, 0.303 mmol, 1.20 eq) in DMF (2 mL) was added DIEA (0.163 g, 1.26 mmol, 0.220 mL, 5.00 eq) under nitrogen. The reaction mixture was stirred at 50° C. for 16 h, filtered, and purified by standard methods to afford 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-((2,6-dioxopiperidin-3-yl)amino)phenyl)acetamide hydrochloride (0.172 g, 0.200 mmol, 79.2% yield). MS (ESI) m/z 817.3 [M+1]$^+$; $^1$H NMR (400 MHz, DMSO-d$_6$) δ ppm 10.82 (s, 1H), 10.70-10.50 (m, 1H), 10.06-9.81 (m, 1H), 9.22 (d, J=1.8 Hz, 1H), 8.77 (d, J=1.8 Hz, 1H), 7.28-7.11 (m, 3H), 7.09-7.02 (m, 1H), 6.99 (s, 1H), 6.86 (br d, J=8.1 Hz, 1H), 6.47 (br d, J=8.3 Hz, 1H), 4.27 (br dd, J=4.7, 11.3 Hz, 1H), 4.12 (br d, J=4.5 Hz, 4H), 3.56 (br s, 2H), 3.32 (br s, 1H), 3.23-3.04 (m, 2H), 2.81-2.69 (m, 1H), 2.69-2.55 (m, 5H), 2.49-2.39 (m, 2H), 2.15-2.06 (m, 1H), 2.05-1.83 (m, 5H), 1.78 (br d, J=5.7 Hz, 2H), 1.72-1.58 (m, 2H), 1.58-1.46 (m, 1H), 1.24-1.15 (m, 2H), 1.24-1.15 (m, 1H).

Example 17: N-(3-Chloro-5-((2,6-dioxopiperidin-3-yl)amino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)acetamide hydrochloride

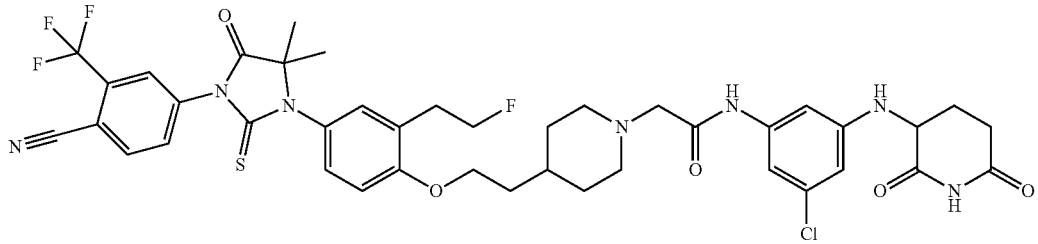 [SMILES: CC1(C)C(=O)N(c2ccc(C#N)c(C(F)(F)F)c2)C(=S)N1c1ccc(OCCC2CCN(CC(=O)Nc3cc(Cl)cc(NC4CCC(=O)NC4=O)c3)CC2)c(CCF)c1]

A. 1-(Benzyloxy)-4-nitro-2-vinylbenzene

To a solution of 1-(benzyloxy)-2-bromo-4-nitrobenzene (20.00 g, 64.91 mmol, 1.00 eq) and 4,4,5,5-tetramethyl-2-vinyl-1,3,2-dioxaborolane (12.00 g, 77.89 mmol, 13.21 mL, 1.20 eq) in dioxane (200 mL) and water (20 mL) was added 1,1'-bis(diphenylphosphino)ferrocene-palladium(II)dichloride DCM complex (5.300 g, 6.490 mmol, 0.1 eq) and potassium carbonate (17.94 g, 129.82 mmol, 2 eq). The mixture was stirred at 85° C. for 26 h under nitrogen atmosphere, then filtered, and concentrated under reduced pressure. The residue was diluted with water (300 mL) and extracted with EtOAc (100 mL×3). The combined organic layers were washed with brine (50 mL×3), dried over anhydrous sodium sulfate, filtered, and concentrated under reduced pressure to give a residue. The residue was purified by silica gel column chromatography (0-3% EtOAc in petroleum ether) to afford 1-(benzyloxy)-4-nitro-2-vinylbenzene (10.00 g, 39.17 mmol, 60.3% yield) as a yellow oil. MS (ESI) m/z 256.1 [M+1]+; 1H NMR (400 MHz, CH3OD) δ ppm 8.27 (d, J=2.8 Hz, 1H), 8.05 (dd, J=2.8, 9.0 Hz, 1H), 7.43-7.31 (m, 5H), 7.10 (d, J=9.2 Hz, 1H), 6.99 (dd, J=11.2, 17.8 Hz, 1H), 5.84 (dd, J=0.9, 17.7 Hz, 1H), 5.35 (dd, J=0.9, 11.2 Hz, 1H), 5.17 (s, 2H).

2-(2-(Benzyloxy)-5-nitrophenyl)ethanol

To a solution of 1-(benzyloxy)-4-nitro-2-vinylbenzene (8.35 g, 32.7 mmol, 1.00 eq) in THF (200 mL) was added borane dimethyl sulfide complex (10 M, 8.18 mL, 2.5 eq) dropwise at 0° C. The mixture was stirred at 20° C. for 2 h under nitrogen atmosphere. To the reaction mixture was added sodium perborate tetrahydrate (15.10 g, 98.13 mmol, 3 eq) at 0° C. followed by water (60 mL) added dropwise at 0° C. The resulting mixture was stirred at 20° C. for 12 h. The reaction was quenched by addition saturated sodium thiosulfate solution (400 mL) and the crude was extracted with EtOAc (100 mL×3). The combined organic layers were washed with brine (50 mL×3), dried over anhydrous sodium sulfate, filtered, and concentrated under reduced pressure to give a residue. The residue was purified by silica gel column chromatography (3-20% EtOAc in petroleum ether) to afford 2-(2-(benzyloxy)-5-nitrophenyl)ethanol (4.50 g, 16.5 mmol, 50.3% yield) as a yellow gum. MS (ESI) m/z 274.0 [M+1]+.

1-(Benzyloxy)-2-(2-fluoroethyl)-4-nitrobenzene

To a solution of 2-(2-(benzyloxy)-5-nitrophenyl)ethanol (4.50 g, 16.5 mmol, 1.00 eq) in DCM (50 mL) was added diethylaminosulfur trifluoride (7.96 g, 49.4 mmol, 6.53 mL, 3.00 eq) at 0° C. The mixture was stirred at 20° C. for 12 h under nitrogen atmosphere. The reaction mixture was poured into ice-water (200 mL) and the pH was adjusted to 7-8 with the addition of a saturated solution of sodium bicarbonate, then extracted with EtOAc (50 mL×3). The combined organic layers were washed with brine (20 mL×3), dried over anhydrous sodium sulfate, filtered, and concentrated under reduced pressure. The residue was purified by silica gel column chromatography (0-5% EtOAc in petroleum ether to afford 1-(benzyloxy)-2-(2-fluoroethyl)-4-nitrobenzene (3.150 g, 11.44 mmol, 69.5% yield) as a light yellow solid. MS (ESI) m/z 276.0 [M+1]+; 1H NMR (400 MHz, CH3OD) δ ppm 8.19-8.13 (m, 2H), 7.49-7.45 (m, 2H), 7.43-7.38 (m, 2H), 7.37-7.32 (m, 1H), 7.21 (d, J=8.7 Hz, 1H), 5.26 (s, 2H), 4.70 (t, J=6.2 Hz, 1H), 4.58 (t, J=6.2 Hz, 1H), 3.15 (t, J=6.2 Hz, 1H), 3.09 (t, J=6.2 Hz, 1H).

4-Amino-2-(2-fluoroethyl)phenol

To a solution of 1-(benzyloxy)-2-(2-fluoroethyl)-4-nitrobenzene (3.78 g, 13.7 mmol, 1.00 eq) in EtOAc (50 mL) was added palladium/carbon (1.460 g, 1.370 mmol, 10% purity, 0.1 eq). The mixture was stirred at 30° C. for 16 h under a hydrogen (50 psi) atmosphere then was stirred at 30° C. for another 16 h under hydrogen (50 psi) atmosphere. The catalyst was removed by filtration and the filtrate was treated with palladium/carbon (1.460 g, 1.370 mmol, 10% purity, 0.1 eq). The resulting mixture was stirred at 40° C. for another 16 h under hydrogen (50 Psi) atmosphere, then filtered and concentrated under reduced pressure. The residue was suspended in MTBE (20 mL) and stirred at 20° C. for 1 h. The solid was collected by filtration, affording 4-amino-2-(2-fluoroethyl)phenol (1.73 g, crude) as a brown solid. (ESI) m/z 156.1 [M+1]+; 1H NMR (400 MHz, CH3OD) δ ppm 6.66-6.56 (m, 2H), 6.56-6.48 (m, 1H), 4.60 (t, J=6.9 Hz, 1H), 4.48 (t, J=6.9 Hz, 1H), 2.97-2.86 (m, 2H).

2-((3-(2-Fluoroethyl)-4-hydroxyphenyl)amino)-2-methylpropanenitrile

To a solution of 4-amino-2-(2-fluoroethyl)phenol (1.100 g, 7.090 mmol, 1.00 eq) in 2-hydroxy-2-methylpropanenitrile (13.98 g, 164.27 mmol, 15 mL, 23.20 eq) was added magnesium sulfate (2.130 g, 17.72 mmol, 2.50 eq). The mixture was stirred at 60° C. for 12 h, then diluted with water (50 mL) and extracted with EtOAc (30 mL×3). The combined organic layers were washed with brine (20 mL×3), dried over anhydrous sodium sulfate, filtered, and concentrated under reduced pressure. The crude product, 2-((3-(2-fluoroethyl)-4-hydroxyphenyl)amino)-2-methylpropanenitrile (1.500 g, crude) obtained as a brown gum, was used into the next step without further purification. MS (ESI) m/z 196.1 [M−26]+.

4-(3-(3-(2-Fluoroethyl)-4-hydroxyphenyl)-4,4-dimethyl-5-oxo-2-thioxoimidazolidin-1-yl)-2-(trifluoromethyl)benzonitrile To a solution of 2-((3-(2-fluoroethyl)-4-hydroxyphenyl)amino)-2-methylpropanenitrile (1.500 g, 6.750 mmol, 1.00 eq) in DMF (15 mL) was added 4-isothiocyanato-2-(trifluoromethyl)benzonitrile (1.080 g, 4.720 mmol, 0.70 eq). The mixture was stirred at 20° C. for 1 h then was treated with a 4.0 M solution of HCl in MeOH (8.44 mL, 5 eq) and stirred at 70° C. for 12 h under nitrogen atmosphere. Following concentration under reduced pressure, the residue was diluted with water (50 mL) and extracted with EtOAc (30 mL×5). The combined organic layers were washed with brine (20 mL×3), dried over anhydrous sodium sulfate, filtered, and concentrated under reduced pressure. The residue was purified by silica gel column chromatography (5-20% EtOAc in petroleum ether to afford 4-(3-(3-(2-fluoroethyl)-4-hydroxyphenyl)-4,4-dimethyl-5-oxo-2-thioxoimidazolidin-1-yl)-2-(trifluoromethyl)benzonitrile (1.47 g, 3.26 mmol, 48.2% yield) as a yellow gum. MS (ESI) m/z 452.1 [M+1]+; 1H NMR (400 MHz, CH3OD) δ ppm 8.16-8.12 (m, 2H), 7.98 (br d, J=2.0 Hz, 1H), 7.14 (d, J=2.6 Hz, 1H), 7.07 (dd, J=2.6, 8.4 Hz, 1H), 6.91 (d, J=8.4 Hz, 1H), 4.68 (t, J=6.5 Hz, 1H), 4.56 (t, J=6.5 Hz, 1H), 3.09-3.00 (m, 2H), 1.53 (s, 6H), 1.56-1.50 (m, 1H).

tert-Butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidine-1-carboxylate To a solution of tert-butyl 4-(2-bromoethyl)piperidine-1-carboxylate (0.777 g, 2.66 mmol, 3.00 eq) in DMF (4 mL) was added sodium iodide (0.398 g, 2.660 mmol, 3.00 eq). After stirring at 90° C. for 0.5 h, potassium carbonate (0.367 g, 2.66 mmol, 3.00 eq), 18-crown-6 (0.703 g, 2.660 mmol, 3.00 eq), and 4-(3-(3-(2-fluoroethyl)-4-hydroxyphenyl)-4,4-dimethyl-5-oxo-2-thioxoimidazolidin-1-yl)-2-(trifluoromethyl)benzonitrile (0.400 g, 0.886 mmol, 1.00 eq) were added and the resulting mixture was stirred at 90° C. for 16 h, filtered, and the filtrate was purified by semi-preparative reverse phase HPLC (78-98% acetonitrile in water+0.225% formic acid, over 7.8 min) to afford tert-butyl 4-(2-(4-(3-(4- cyano-3-(trifluoromethyl)phenyl)-5,5-dimethyl-4-oxo-2-thioxoimidazolidin-1-yl)-2-(2-fluoroethyl)phenoxy)ethyl)piperidine-1-carboxylate (0.140 g, 0.211 mmol, 23.8% yield) as a yellow gum. MS (ESI) m/z 563.2 [M−99]$^+$.

4-(3-(3-(2-Fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile hydrochloride To tert-butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidine-1-carboxylate (0.140 g, 0.211 mmol, 1.00 eq) was added a 4.0 M solution of HCl in dioxane (5.0 mL, 95 eq). The mixture was stirred at 20° C. for 2 h, then was concentrated under reduced pressure to give a residue (0.126 g). A portion of 4-(3-(3-(2-fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile (0.063 g) was purified by semi-preparative reverse phase HPLC (25-45% acetonitrile in water+0.05% hydrochloric acid, over 10 min). Then 0.063 g of 4-(3-(3-(2-fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile was used into the next step without further purification. The purified solution was lyophilized to give 4-(3-(3-(2-fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile hydrochloride (0.025 g, 0.042 mmol, 19.9% yield) isolated as a yellow solid. Compound 4-(3-(3-(2-fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile hydrochloride (0.063 g, crude) was obtained as a yellow solid. MS (ESI) m/z 563.2 [M+1]$^+$; $^1$H NMR (400 MHz, DMSO-d$_6$) δ ppm 8.84 (br s, 1H), 8.57 (br d, J=8.2 Hz, 1H), 8.39 (d, J=8.3 Hz, 1H), 8.29 (d, J=1.5 Hz, 1H), 8.07 (dd, J=1.7, 8.1 Hz, 1H), 7.25-7.19 (m, 2H), 7.17-7.12 (m, 1H), 4.69 (t, J=6.3 Hz, 1H), 4.58 (t, J=6.3 Hz, 1H), 4.10 (br t, J=5.9 Hz, 2H), 3.25 (br d, J=12.7 Hz, 2H), 3.03 (t, J=6.2 Hz, 1H), 2.97 (t, J=6.2 Hz, 1H), 2.90-2.80 (m, 2H), 1.88 (br d, J=14.3 Hz, 2H), 1.82-1.70 (m, 3H), 1.48 (s, 6H), 1.45-1.35 (m, 2H).

N-(3-Chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)acetamide hydrochloride To a solution of crude 4-(3-(3-(2-fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile hydrochloride (0.063 g, 0.105 mmol, 1.00 eq) and 2-chloro-N-(3-chloro-5-((2,6-dioxopiperidin-3-yl)amino)phenyl)acetamide (0.042 g, 0.126 mmol, 1.20 eq) in DMF (2 mL) was added DIEA (0.054 g, 0.421 mmol, 0.073 mL, 4.00 eq). The mixture was stirred at 60° C. for 12 h, then filtered. The filtrate was purified by standard methods to afford N-(3-chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)acetamide hydrochloride (0.055 g, 0.061 mmol, 57.7% yield). MS (ESI) m/z 856.2 [M+1]$^+$; $^1$H NMR (400 MHz, DMSO-d$_6$) δ ppm 10.82-10.77 (m, 1H), 10.73 (s, 1H), 10.00-9.75 (m, 1H), 8.39 (d, J=8.2 Hz, 1H), 8.29 (d, J=1.5 Hz, 1H), 8.07 (dd, J=1.5, 8.3 Hz, 1H), 7.26-7.20 (m, 2H), 7.19-7.12 (m, 1H), 6.98 (s, 1H), 6.84 (s, 1H), 6.51 (s, 1H), 4.71 (t, J=6.3 Hz, 1H), 4.59 (t, J=6.3 Hz, 1H), 4.33 (br dd, J=4.8, 11.6 Hz, 1H), 4.25-4.08 (m, 4H), 3.53 (br d, J=11.1 Hz, 1H), 3.32 (br s, 1H), 3.18-2.95 (m, 4H), 2.79-2.68 (m, 1H), 2.62-2.57 (m, 1H), 2.11-2.03 (m, 1H), 1.98-1.73 (m, 6H), 1.68-1.55 (m, 2H), 1.49 (s, 6H).

Example 18: 2-(4-(2-(4-(3-(4-Cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)-N-(3-((2,6-dioxopiperidin-3-yl)amino)phenyl)acetamide hydrochloride

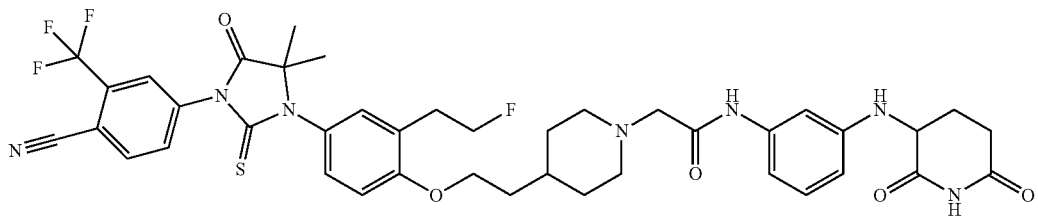 [SMILES: CC1(C)C(=O)N(c2ccc(C#N)c(C(F)(F)F)c2)C(=S)N1c1ccc(OCCC2CCN(CC(=O)Nc3cccc(NC4CCC(=O)NC4=O)c3)CC2)c(CCF)c1]

1-((3-(2-Fluoroethyl)-4-hydroxyphenyl)amino)cyclobutanecarbonitrile

To a solution of 4-amino-2-(2-fluoroethyl)phenol (1.00 g, 6.44 mmol, 1.00 eq) (prepared as described herein) and cyclobutanone (0.542 g, 7.73 mmol, 0.578 mL, 1.20 eq) in THF (20 mL) was added trimethylsilyl cyanide (0.767 g, 7.73 mmol, 0.968 mL, 1.20 eq) and scandium triflate (0.634 g, 1.29 mmol, 0.20 eq). The mixture was stirred at 20° C. for 16 h under nitrogen atmosphere, then was diluted with water (50 mL) and extracted with EtOAc (30 mL×3). The combined organic layers were washed with brine (20 mL×3), dried over anhydrous sodium sulfate, filtered, and concentrated under reduced pressure. The residue was purified by silica gel column chromatography (6-20% EtOAc in petroleum ether) to give 1-((3-(2-fluoroethyl)-4-hydroxyphenyl)amino)cyclobutanecarbonitrile (0.950 g, 4.06 mmol, 62.9% yield) as a yellow gum. MS (ESI) m/z 235.1 [M+1]$^+$.

5-(5-(3-(2-Fluoroethyl)-4-hydroxyphenyl)-8-oxo-6-thioxo-5,7-diazaspiro[3.4]octan-7-yl)-3-(trifluoromethyl)picolinonitrile To a solution of 1-((3-(2-fluoroethyl)-4-hydroxyphenyl)amino)cyclobutanecarbonitrile (0.400 g, 1.71 mmol, 1.00 eq) in DMF (5 mL) was added 5-isothiocyanato-3-(trifluoromethyl)picolinonitrile (0.391 g, 1.71 mmol, 1.00 eq). The mixture was stirred at 20° C. for 1 h, then was treated with a 4.0 M solution of HCl in MeOH (2.13 mL, 5 eq) and stirred at 70° C. for 12 h under nitrogen atmosphere. The reaction mixture was concentrated under reduced pressure, the residue was dissolved in water (40 mL), and the pH was adjusted to 7-8 with a saturated aqueous solution of sodium bicarbonate. The material was extracted with EtOAc (30 mL×3) and the combined organic layers were washed with brine (20 mL×3), dried over anhydrous sodium sulfate, filtered, and concentrated under reduced pressure. The residue was purified by silica gel column chromatography (10-20% EtOAc in petroleum ether) to give 5-(5-(3-(2-fluoroethyl)-4-hydroxyphenyl)-8-oxo-6-thioxo-5,7-diazaspiro[3.4]octan-7-yl)-3-(trifluoromethyl)picolinonitrile (0.720 g, 1.55 mmol, 90.8% yield) as a yellow gum. MS (ESI) m/z 465.1 [M+1]⁺.

tert-Butyl 4-(2-(4-(3-(4-cyano-3-(trifluoromethyl) phenyl)-5,5-dimethyl-4-oxo-2-thioxoimidazolidin-1-yl)-2-(2-fluoroethyl)phenoxy)ethyl)piperidine-1-carboxylate A mixture of 4-(3-(3-(2-fluoroethyl)-4-hydroxyphenyl)-4,4-dimethyl-5-oxo-2-thioxoimidazolidin-1-yl)-2-(trifluoromethyl)benzonitrile (0.300 g, 0.664 mmol, 1.00 eq), tert-butyl 4-(2-hydroxyethyl)piperidine-1-carboxylate (0.198 g, 0.863 mmol, 1.30 eq) and triphenylphosphine (0.261 g, 0.996 mmol, 1.50 eq) in THF (3 mL) was concentrated under reduced pressure, then dissolved in THF (3 mL) under nitrogen and cooled to 0° C. Diisopropyl azodicarboxylate (0.201 g, 0.996 mmol, 0.193 mL, 1.5 eq) was added. The solution was stirred at 50° C. for 12 h under nitrogen. The reaction mixture was diluted with water (100 mL), extracted with EtOAc (100 mL×3), and the combined organic layers were washed with brine (50 mL×3), dried, filtered, and concentrated under reduced pressure. The residue was purified by silica gel column chromatography (0-60% EtOAc in petroleum ether) to afford tert-butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidine-1-carboxylate (0.320 g, 0.448 mmol, 67.4% yield) as a brown oil. MS (ESI) m/z 563.2 [M−100+1]⁺.

4-(3-(3-(2-Fluoroethyl)-4-(2-(piperidin-4-yl)ethoxy) phenyl)-4,4-dimethyl-5-oxo-2-thioxoimidazolidin-1-yl)-2-(trifluoromethyl)benzonitrile A mixture of tert-butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidine-1-carboxylate (0.300 g, 0.452 mmol, 1.00 eq) in a 4.0 M solution of HCl in EtOAc (3.4 mL, 30 eq) was stirred at 25° C. for 1 h, and then concentrated under reduced pressure and diluted with EtOAc (100 mL). The pH of the solution was adjusted to 8 with a saturated aqueous solution of sodium bicarbonate. The solution was washed with brine (30 mL×3), dried, filtered, and concentrated under reduced pressure. The residue was purified by silica gel thin layer chromatography (9% MeOH in DCM) to afford 4-(3-(3-(2-fluoroethyl)-4-(2-(piperidin-4-yl)ethoxy)phenyl)-4,4-dimethyl-5-oxo-2-thio-xoimidazolidin-1-yl)-2-(trifluoromethyl)benzonitrile (0.100 g, 0.177 mmol, 39.1% yield) as a light yellow oil. MS (ESI) m/z 563.1 [M+1]⁺.

2-(4-(2-(4-(3-(4-Cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)-N-(3-((2,6-dioxopiperidin-3-yl)amino)phenyl)acetamide hydrochloride To a mixture of 4-(3-(3-(2-fluoroethyl)-4-(2-(piperidin-4-yl)ethoxy)phenyl)-4,4-dimethyl-5-oxo-2-thioxoimidazolidin-1-yl)-2-(trifluoromethyl)benzonitrile (0.080 g, 0.142 mmol, 1.00 eq) and 2-chloro-N-(3-((2,6-dioxopiperidin-3-yl)amino)phenyl)acetamide (0.041 g, 0.140 mmol, 0.98 eq) in DMF (1 mL) was added DIEA (0.051 g, 0.400 mmol, 0.069 mL, 2.82 eq) and the solution was stirred at 50° C. for 10 h. The reaction mixture was filtered and the filtrate was purified by standard methods to afford 2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl) piperidin-1-yl)-N-(3-((2,6-dioxopiperidin-3-yl)amino) phenyl)acetamide hydrochloride (0.064 g, 0.073 mmol, 52.0% yield). MS (ESI) m/z 822.1 [M+1]⁺; ¹H NMR (400 MHz, DMSO-d₆) δ ppm 10.80 (s, 1H), 10.70-10.50 (m, 1H), 9.91 (s, 1H), 8.39 (d, J=8.4 Hz, 1H), 8.29 (d, J=1.6 Hz, 1H), 8.08 (dd, J=1.6, 8.4 Hz, 1H), 7.26-7.19 (m, 2H), 7.19-7.13 (m, 1H), 7.08-7.02 (m, 1H), 6.99 (s, 1H), 6.86 (d, J=7.2 Hz, 1H), 6.47 (d, J=8.0 Hz, 1H), 4.71 (t, J=6.4 Hz, 1H), 4.59 (t, J=6.4 Hz, 1H), 4.26 (dd, J=4.8, 11.6 Hz, 1H), 3.54 (d, J=11.6 Hz, 2H), 3.31 (s, 1H), 3.20-3.08 (m, 2H), 3.05 (t, J=6.4 Hz, 1H), 2.99 (bt, J=6.4 Hz, 1H), 2.80-2.66 (m, 1H), 2.65-2.54 (m, 1H), 2.16-2.05 (m, 1H), 2.01-1.85 (m, 4H), 1.77 (s, 3H), 1.70-1.55 (m, 2H), 1.49 (s, 6H).

Example 19: N-(3-Chloro-5-((2,6-dioxopiperidin-3-yl)amino)phenyl)-2-(4-(4-(3-(4-cyano-3-(trifluoromethyl)phenyl)-5,5-dimethyl-4-oxo-2-thioxoimidazolidin-1-yl)-2-ethylphenoxy)piperidin-1-yl)acetamide hydrochloride

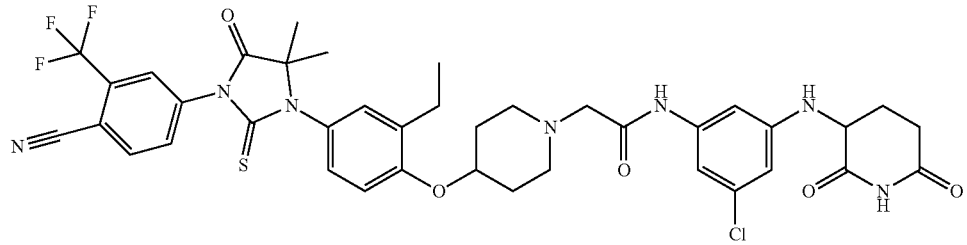 [SMILES: CCc1cc(N2C(=S)N(c3ccc(C#N)c(C(F)(F)F)c3)C(=O)C2(C)C)ccc1OC1CCN(CC(=O)Nc2cc(Cl)cc(NC3CCC(=O)NC3=O)c2)CC1]

tert-Butyl 4-(4-(3-(4-cyano-3-(trifluoromethyl)phenyl)-5,5-dimethyl-4-oxo-2-thioxoimidazolidin-1-yl)-2-ethylphenoxy)piperidine-1-carboxylate A mixture of 4-[3-(3-ethyl-4-hydroxy-phenyl)-4,4-dimethyl-5-oxo-2-thioxo-imidazolidin-1-yl]-2-(trifluoromethyl) benzonitrile (0.832 g, 1.92 mmol, 1.00 eq) in DMF (13.5 mL, 0.141 molar), tert-butyl 4-(methylsulfonyloxy)piperidine-1-carboxylate (1.29 g, 4.61 mmol, 2.40 eq), and cesium carbonate (0.943 g, 2.88 mmol, 1.50 eq) was heated to 60° C. and stirred overnight. The reaction was quenched with water and diluted with EtOAc, and the aqueous phase was extracted with EtOAc. The combined organic phases were washed with brine, dried over sodium sulfate, filtered, and concentrated. The crude residue was purified by silica gel column chromatography (0-100% EtOAc/hexanes). The fractions were concentrated, and the residue was triturated with DCM and hexanes to afford a mixture of tert-butyl 4-[4-[3-[4-cyano-3-(trifluoromethyl)phenyl]-5,5-dimethyl-4-oxo-2-thioxo-imidazolidin-1-yl]-2-ethyl-phenoxy]piperidine-1-carboxylate (1.19 g, 1.930 mmol, 100% yield) and the corresponding hydantoin byproduct as a beige solid. MS (ESI) m/z 637.7 [M+Na]$^+$.

4-(3-(3-Ethyl-4-(piperidin-4-yloxy)phenyl)-4,4-dimethyl-5-oxo-2-thioxoimidazolidin-1-yl)-2-(trifluoromethyl)benzonitrile dihydrochloride A suspension of tert-butyl 4-[4-[3-[4-cyano-3-(trifluoromethyl)phenyl]-5,5-dimethyl-4-oxo-2-thioxo-imidazolidin-1-yl]-2-ethyl-phenoxy]piperidine-1-carboxylate (1.19 g, 1.93 mmol, 1.00 eq) in DCM (8.53 mL, 0.226 molar) was treated with a 4.0 M solution of HCl in dioxane (7.23 mL, 28.92 mmol, 15 eq), and stirred at room temperature for 2 h. The reaction mixture was then concentrated to afford 4-[3-[3-ethyl-4-(4-piperidyloxy)phenyl]-4,4-dimethyl-5-oxo-2-thioxo-imidazolidin-1-yl]-2-(trifluoromethyl)benzonitrile dihydrochloride (1.15 g, 1.95 mmol, 101% yield) as a cream solid. MS (ESI) m/z 516.0 [M+H]$^+$.

2-Chloro-N-(3-chloro-5-((2,6-dioxopiperidin-3-yl)amino)phenyl)acetamide 3-((3-Amino-5-chlorophenyl)amino)piperidine-2,6-dione (3.74 g, 14.74 mmol, 1.00 eq), 2-chloroacetic acid (1.06 mL, 17.7 mmol, 1.20 eq) (prepared as described herein), HATU (8.41 g, 22.11 mmol, 1.5 eq), and DIEA (7.72 mL, 44.2 mmol, 3.00 eq) were combined in DMF (42.1 mL, 0.350 molar) and stirred at room temperature. After 10 min, the reaction mixture was partitioned between EtOAc and brine. The organic extracts were dried over sodium sulfate, filtered, and concentrated. The crude material was purified by silica gel column chromatography (50-100% EtOAc in hexanes) to afford a green oily, that was triturated in DCM and hexanes. Following the removal of the solvents under reduced pressure and further drying under high vacuum, 2-chloro-N-(3-chloro-5-((2,6-dioxopiperidin-3-yl)amino)phenyl)acetamide (3.25 g, 9.84 mmol, 66.7% yield) was isolated as a light green solid. MS (ESI) m/z 330.0 [M]$^+$; $^1$H NMR (DMSO-d$_6$, 400 MHz) δ ppm 10.80 (s, 1H), 10.19 (s, 1H), 6.92 (t, 1H, J=1.7 Hz), 6.82 (t, 1H, J=1.8 Hz), 6.47 (t, 1H, J=1.9 Hz), 6.32 (d, 1H, J=8.1 Hz), 4.3-4.4 (m, 1H), 4.22 (s, 2H), 2.7-2.8 (m, 1H), 2.5-2.6 (m, 1H), 2.0-2.1 (m, 1H), 1.90 (dq, 1H, J=4.7, 12.4 Hz).

N-(3-Chloro-5-((2,6-dioxopiperidin-3-yl)amino)phenyl)-2-(4-(4-(3-(4-cyano-3-(trifluoromethyl)phenyl)-5,5-dimethyl-4-oxo-2-thioxoimidazolidin-1-yl)-2-ethylphenoxy)piperidin-1-yl)acetamide hydrochloride 2-Chloro-N-[3-chloro-5-[(2,6-dioxo-3-piperidyl)amino]phenyl]acetamide (0.126 g, 0.38 mmol, 1.50 eq) was added to a stirred mixture of 4-[3-[3-ethyl-4-(4-piperidyloxy)phenyl]-4,4-dimethyl-5-oxo-2-thioxo-imidazolidin-1-yl]-2-(trifluoromethyl)benzonitrile dihydrochloride (0.150 g, 0.25 mmol, 1.00 eq), sodium iodide (0.058 g, 0.38 mmol, 1.50 eq), DMF (2.12 mL, 0.120 molar) and DIEA (0.22 mL, 1.27 mmol, 5 eq). The reaction mixture was stirred for 1 h at 60° C., and then the solution was filtered and purified by standard methods to afford N-[3-chloro-5-[(2,6-dioxo-3-piperidyl)amino]phenyl]-2-[4-[4-[3-[4-cyano-3-(trifluoromethyl)phenyl]-5,5-dimethyl-4-oxo-2-thioxo-imidazolidin-1-yl]-2-ethyl-phenoxy]-1-piperidyl]acetamide hydrochloride (0.067 g, 0.08 mmol, 30% yield). MS (ESI) m/z 810.2 [M+1]$^+$; $^1$H NMR (400 MHz, DMSO-d$_6$) δ ppm 10.82 (s, 1H), 10.6-10.7 (m, 1H), 10.1-10.3 (m, 1H), 8.39 (d, 1H, J=8.2 Hz), 8.29 (d, 1H, J=1.7 Hz), 8.07 (dd, 1H, J=1.6, 8.2 Hz), 7.16 (s, 3H), 7.00 (s, 1H), 6.82 (br s, 1H), 6.52 (t, 1H, J=1.8 Hz), 4.6-4.9 (m, 1H), 4.33 (dd, 1H, J=4.9, 11.5 Hz), 4.21 (br d, 2H, J=14.4 Hz), 3.63 (br d, 1H, J=12.1 Hz), 3.3-3.4 (m, 4H), 2.6-2.8 (m, 4H), 1.9-2.3 (m, 6H), 1.49 (s, 6H), 1.19 (td, 3H, J=7.4, 14.4 Hz).

Example 20: 2-(4-(2-(4-(3-(6-Cyano-5-(trifluoromethyl)pyridin-3-yl)-5,5-dimethyl-4-oxo-2-thioxoimidazolidin-1-yl)-2-isopropylphenoxy)ethyl)piperidin-1-yl)-N-(3-((2,6-dioxopiperidin-3-yl)amino)phenyl)acetamide hydrochloride

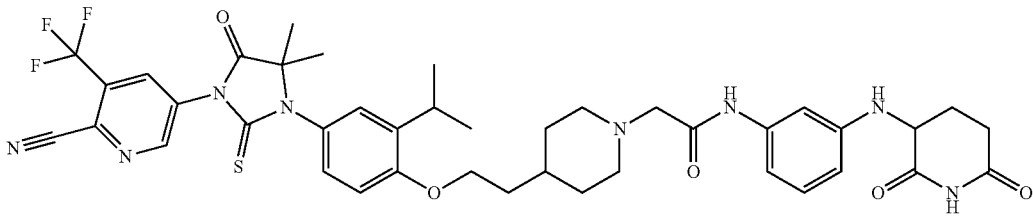 [SMILES: CC(C)c1cc(N2C(=S)N(c3cnc(C#N)c(C(F)(F)F)c3)C(=O)C2(C)C)ccc1OCCC1CCN(CC(=O)Nc2cccc(NC3CCC(=O)NC3=O)c2)CC1]

tert-Butyl 4-(2-(2-bromo-4-nitrophenoxy)ethyl)piperidine-1-carboxylate

To a mixture of 2-bromo-4-nitrophenol (10.00 g, 45.87 mmol, 1.00 eq), tert-butyl 4-(2-hydroxyethyl)piperidine-1-carboxylate (10.52 g, 45.87 mmol, 1.00 eq), triphenylphosphine (14.44 g, 55.04 mmol, 1.20 eq) and THF (50 mL) was added (E)-diisopropyl diazene-1,2-dicarboxylate (11.13 g, 55.04 mmol, 10.70 mL, 1.20 eq) dropwise under nitrogen at 0° C. The reaction was stirred at 60° C. for 10 h, then concentrated under reduced pressure. The crude product was purified by semi-preparative reverse phase HPLC (50-80% acetonitrile in water+0.1% TFA) to give tert-butyl 4-(2-(2-bromo-4-nitrophenoxy)ethyl)piperidine-1-carboxylate (14.6 g, 33.9 mmol, 73.9% yield) as a yellow oil. $^1$H NMR (400 MHz, CDCl$_3$) δ 8.46 (d, J=2.4 Hz, 1H), 8.19 (dd, J=9.2, 2.8 Hz, 1H), 6.93 (d, J=9.2 Hz, 1H), 4.18 (t, J=6.0 Hz, 2H), 4.12 (q, J=7.2 Hz, 2H), 2.73 (t, J=12.4 Hz, 2H), 1.85 (q, J=6.0 Hz, 2H), 1.79-1.73 (m, 3H), 1.46 (s, 9H), 1.24-1.16 (m, 2H).

tert-Butyl 4-(2-(4-nitro-2-(prop-1-en-2-yl)phenoxy) ethyl)piperidine-1-carboxylate A mixture of tert-butyl 4-(2-(2-bromo-4-nitrophenoxy) ethyl)piperidine-1-carboxylate (3.00 g, 6.99 mmol, 1.00 eq), 2-isopropenyl-4,4,5,5-tetramethyl-1,3,2-dioxaborolane (2.350 g, 13.98 mmol, 2.00 eq), [1,1'-bis(diphenylphosphino)ferrocene]dichloropalladium(II) (0.256 g, 0.349 mmol, 0.05 eq), potassium phosphate (4.45 g, 20.96 mmol, 3.00 eq), dioxane (30 mL) and water (15 mL) was stirred at 90° C. under nitrogen for 12 h, then diluted with brine (50 mL), and layers were separated. The aqueous layer was extracted with EtOAc (30 mL). The combined organic extracts were washed with brine (20 mL), dried, filtered, and concentrated. The crude product was purified by flash silica gel column chromatography (0-20% EtOAc in petroleum ether) to give tert-butyl 4-(2-(4-nitro-2-(prop-1-en-2-yl)phenoxy)ethyl)piperidine-1-carboxylate (2.39 g, 6.12 mmol, 87.6% yield) as a yellow oil. $^1$H NMR (400 MHz, CDCl$_3$) δ ppm 8.15 (dd, J=8.80, 2.80 Hz, 1H), 8.09 (d, J=1.20 Hz, 1H), 6.90 (d, J=8.80 Hz, 1H), 5.23 (t, J=1.20 Hz, 1H), 5.14 (d, J=0.80 Hz, 1H), 4.15-4.10 (m, 4H), 2.70 (t, J=12.00 Hz, 2H), 2.11 (s, 3H), 1.81 (q, J=6.40 Hz, 2H), 1.73-1.68 (m, 3H), 1.46 (s, 9H), 1.30-1.23 (m, 1H), 1.21-1.15 (m, 2H).

tert-Butyl 4-(2-(4-amino-2-isopropylphenoxy)ethyl) piperidine-1-carboxylate

A mixture of tert-butyl 4-(2-(4-nitro-2-(prop-1-en-2-yl) phenoxy)ethyl)piperidine-1-carboxylate (2.39 g, 6.12 mmol, 1.00 eq), palladium on activated carbon (0.500 g, 10% purity) and MeOH (30 mL) was stirred at 30° C. under an atmosphere of hydrogen (50 psi) for 24 h. The catalyst was removed by filtration and the filtrate was concentrated to give tert-butyl 4-(2-(4-amino-2-isopropylphenoxy)ethyl)piperidine-1-carboxylate (2.05 g, 5.66 mmol, 92.4% yield) as a yellow oil. $^1$H NMR (400 MHz, CDCl$_3$) δ ppm 6.67 (d, J=8.8 Hz, 1H), 6.60 (d, J=2.8 Hz, 1H), 6.49 (dd, J=8.4, 2.8 Hz, 1H), 4.09 (s, 2H), 3.93 (t, J=6.0 Hz, 2H), 3.48-3.08 (m, 3H), 2.70 (t, J=12.0 Hz, 2H), 1.73-1.68 (m, 5H), 1.46 (s, 9H), 1.18 (d, J=6.4 Hz, 8H).

tert-Butyl 4-(2-(4-((2-cyanopropan-2-yl)amino)-2-isopropylphenoxy)ethyl)piperidine-1-carboxylate A mixture of tert-butyl 4-(2-(4-amino-2-isopropylphenoxy)ethyl)piperidine-1-carboxylate (2.39 g, 6.12 mmol, 1.00 eq), 2-hydroxy-2-methyl-propanenitrile (1.860 g, 21.90 mmol, 2 mL, 7.94 eq) and magnesium sulfate (0.830 g, 6.90 mmol, 2.50 eq) was stirred at 60° C. for 12 h. To the mixture was added water (10 mL) and EtOAc (10 mL) and the layers were separated. The aqueous layer was extracted with EtOAc (10 mL). The combined organic extracts were washed with brine (10 mL×4), dried, filtered, and concentrated to give tert-butyl 4-(2-(4-((2-cyanopropan-2-yl) amino)-2-isopropylphenoxy)ethyl)piperidine-1-carboxylate (1.30 g, crude) as a brown oil. MS (ESI) m/z 403.2 [M+1-27]$^+$.

5-(3-(3-Isopropyl-4-(2-(piperidin-4-yl)ethoxy)phenyl)-4,4-dimethyl-5-oxo-2-thioxoimidazolidin-1-yl)-3-(trifluoromethyl)picolinonitrile hydrochloride To a solution of tert-butyl 4-(2-(4-((2-cyanopropan-2-yl) amino)-2-isopropylphenoxy)ethyl)piperidine-1-carboxylate (0.500 g, 1.16 mmol, 1.00 eq) and 5-isothiocyanato-3-(trifluoromethyl)pyridine-2-carbonitrile (0.266 g, 1.16 mmol, 1.00 eq) in DMF (5 mL) stirred at 25° C. for 1 h was added a 4.0 M solution of HCl in MeOH (1.45 mL, 5 eq) and the reaction was stirred at 80° C. for 1 h. After concentration under reduced pressure, the residue was purified by semi-preparative reverse phase HPLC (30-60% acetonitrile in water+0.05% HCl, 25 min) to give 5-(3-(3-isopropyl-4-(2-(piperidin-4-yl)ethoxy)phenyl)-4,4-dimethyl-5-oxo-2-thioxoimidazolidin-1-yl)-3-(trifluoromethyl)picolinonitrile hydrochloride (0.342 g, 0.574 mmol, 49.5% yield) as a yellow oil. MS (ESI) m/z 560.2 [M+1]$^+$; $^1$H NMR (400 MHz, CDCl$_3$) δ ppm 9.10 (d, J=2.0 Hz, 1H), 8.37 (d, J=2.0 Hz, 1H), 7.07-7.04 (m, 2H), 6.93 (d, J=8.4 Hz, 1H), 4.07 (t, J=5.6 Hz, 2H), 3.39-3.29 (m, 1H), 3.22 (d, J=12.0 Hz, 2H), 2.73-2.67 (m, 2H), 1.88-1.73 (m, 5H), 1.59 (s, 6H), 1.42-1.32 (m, 2H), 1.24-1.22 (m, 6H).

2-(4-(2-(4-(3-(6-Cyano-5-(trifluoromethyl)pyridin-3-yl)-5,5-dimethyl-4-oxo-2-thioxoimidazolidin-1-yl)-2-isopropylphenoxy)ethyl)piperidin-1-yl)-N-(3-((2,6-dioxopiperidin-3-yl)amino)phenyl)acetamide hydrochloride A mixture of 5-(3-(3-isopropyl-4-(2-(piperidin-4-yl) ethoxy)phenyl)-4,4-dimethyl-5-oxo-2-thioxoimidazolidin-1-yl)-3-(trifluoromethyl)picolinonitrile hydrochloride (0.245 g, 0.411 mmol, 1.00 eq), 2-chloro-N-(3-((2,6-dioxopiperidin-3-yl)amino)phenyl)acetamide (0.129 g, 0.390 mmol, 0.95 eq), DIEA (0.170 g, 1.310 mmol, 3.2 eq) and DMF (1.5 mL) was stirred at 50° C. for 10 h, then was filtered. The filtrate was purified by standard methods to give 2-(4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperidin-1-yl)-N-(3-((2,6-dioxopiperidin-3-yl)amino)phenyl)acetamide hydrochloride (0.177 g, 0.199 mmol, 48.6% yield). MS (ESI) m/z 819.3 [M+1]$^+$; $^1$H NMR (400 MHz, DMSO-d$_6$) δ ppm 10.82 (s, 1H), 10.51-10.47 (m, 1H), 9.81-9.76 (m, 1H), 9.25 (d, J=2.0 Hz, 1H), 8.83 (d, J=2.0 Hz, 1H), 7.17-7.10 (m, 3H), 7.05 (t, J=8.0 Hz, 1H), 6.95 (s, 1H), 6.86-6.82 (m, 1H), 6.46 (d, J=8.0 Hz, 1H), 4.26 (dd, J=11.2, 4.8 Hz, 1H), 4.22-4.09 (m, 4H), 3.32-3.24 (m, 2H), 3.18-3.06 (m, 2H), 2.78-2.69 (m, 1H), 2.63-2.56 (m, 1H), 2.13-2.07 (m, 1H), 1.98-1.74 (m, 6H), 1.70-1.56 (m, 2H), 1.51 (s, 6H), 1.19 (d, J=6.8 Hz, 6H).

Example 21 and 22: 2-((R)-4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-((2,6-dioxopiperidin-3-yl)amino)phenyl)acetamide hydrochloride and 2-((S)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-((2,6-dioxopiperidin-3-yl)amino)phenyl)acetamide hydrochloride

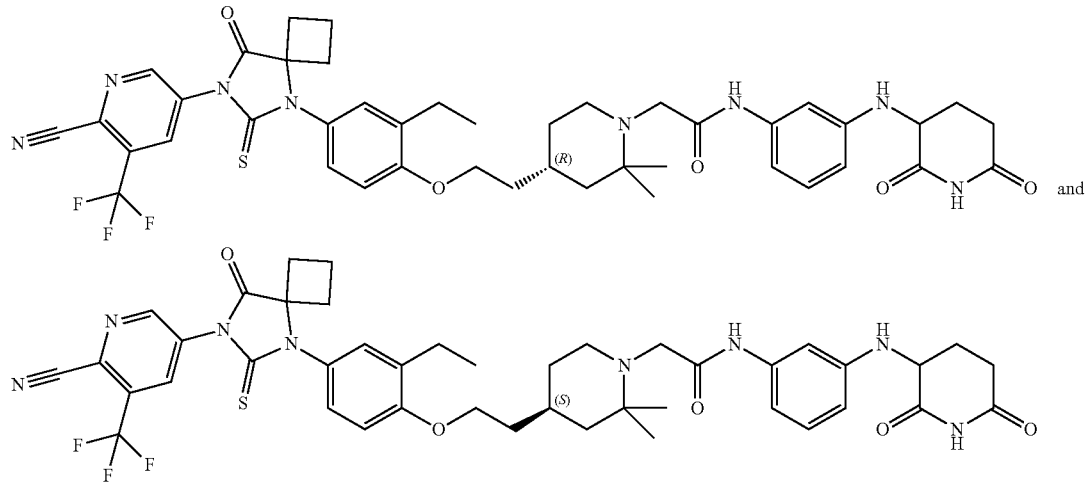

Ethyl 2-(1-benzyl-2,2-dimethylpiperidin-4-ylidene)acetate

To a solution of sodium hydride (0.885 g, 22.130 mmol, 60% purity, 1.30 eq) in THF (40 mL) was added ethyl 2-(diethoxyphosphoryl)acetate (4.20 g, 18.73 mmol, 1.01 eq) dropwise at 0° C. After 10 min, a solution of 1-benzyl-2,2-dimethylpiperidin-4-one (3.70 g, 17.0 mmol, 1.00 eq) in THF (20 mL) was added dropwise stirring was continued at 20° C. for 1 h. The reaction was quenched with the addition of a saturated aqueous solution of ammonium chloride (50 mL) and the product was extracted with EtOAc (30 mL×2). The organic extracts were washed with brine (50 mL), dried, filtered, and concentrated. The residue was purified by silica gel column chromatography (0-1% EtOAc in petroleum ether) to give ethyl 2-(1-benzyl-2,2-dimethylpiperidin-4-ylidene)acetate (3.99 g, 13.9 mmol, 81.5% yield) as a colorless oil. $^1$H NMR (400 MHz, CDCl$_3$) δ ppm 7.37 (d, J=7.2 Hz, 2H), 7.31 (t, J=7.2 Hz, 2H), 7.23 (t, J=7.2 Hz, 1H), 5.70-5.60 (m, 1H), 4.18-4.10 (m, 2H), 3.54 (s, 2H), 2.90-2.84 (m, 2H), 2.55-2.49 (m, 2H), 2.22-2.18 (m, 2H), 1.31-1.26 (m, 3H), 1.16-1.13 (m, 6H).

Methyl 2-(1-benzyl-2,2-dimethylpiperidin-4-yl)acetate

To a solution of ethyl 2-(1-benzyl-2,2-dimethylpiperidin-4-ylidene)acetate (2.00 g, 6.96 mmol, 1.99 eq) in MeOH (70 mL) were added magnesium turnings (6.77 g, 278.36 mmol, 40 eq) in portions. The reaction was stirred at 25° C. for 4 h. The temperature was cooled to 0° C. before adding concentrated HCl to form a clear solution. To the solution was added sodium bicarbonate to adjust the pH to 8. The alkaline solution was extracted with EtOAc (50 mL×2). The combined organic extracts were washed with brine (30 mL), dried, filtered, and concentrated. The crude product was purified by silica gel column chromatography (0-3% EtOAc in petroleum ether) to give methyl 2-(1-benzyl-2,2-dimethylpiperidin-4-yl)acetate (1.40 g, 5.08 mmol, 73.0% yield) as a light-yellow oil. $^1$H NMR (400 MHz, CDCl$_3$) δ ppm 7.35-7.27 (m, 4H), 7.21 (d, J=7.6 Hz, 1H), 4.05 (d, J=14.0 Hz, 1H), 3.67 (s, 3H), 2.96 (d, J=14.0 Hz, 1H), 2.56-2.51 (m, 1H), 2.26 (td, J=12.4, 2.8 Hz, 1H), 2.19 (d, J=6.8 Hz, 2H), 2.09-2.03 (m, 1H), 1.61-1.55 (m, 1H), 1.53-1.48 (m, 1H), 1.29-1.26 (m, 1H), 1.23 (s, 3H), 1.11 (qd, J=12.8, 4.8 Hz, 1H), 1.05 (s, 3H).

2-(1-Benzyl-2,2-dimethylpiperidin-4-yl)ethanol

To a solution of methyl 2-(1-benzyl-2,2-dimethyl-4-piperidyl)acetate (1.120 g, 4.070 mmol, 100 eq) in THF (25 mL) was added lithium aluminum hydride (0.232 g, 6.10 mmol, 1.50 eq) in portions at 0° C. The reaction mixture was stirred at 25° C. for 1 h then diluted with THF (20 mL) and treated with sodium sulfate (15 g) and cooled to 0° C. To the stirred mixture was added water (3 mL) dropwise and the mixture was stirred at 30° C. for 0.5 h. The suspension was filtered and the filtrate was concentrated under reduced to afford 2-(1-benzyl-2,2-dimethylpiperidin-4-yl)ethanol (0.990 g, crude) as a colorless oil. $^1$H NMR (400 MHz, CDCl$_3$) δ ppm 7.36-7.27 (m, 4H), 7.21 (t, J=7.2 Hz, 1H), 4.06 (d, J=14.0 Hz, 1H), 3.68 (t, J=6.8 Hz, 1H), 2.96 (d, J=14.0 Hz, 1H), 2.56-2.52 (m, 1H), 2.23 (td, J=12.4, 2.8 Hz, 1H), 1.70-1.65 (m, 1H), 1.61-1.56 (m, 1H), 1.51-1.43 (m, 3H), 1.28-1.20 (m, 4H), 1.12-1.03 (m, 4H).

Chiral Separation of enantiomers (S)-2-(1-benzyl-2,2-dimethylpiperidin-4-yl)ethanol and (R)-2-(1-benzyl-2,2-dimethylpiperidin-4-yl)ethanol The enantiomers of 2-(1-benzyl-2,2-dimethylpiperidin-4-yl)EtOH (0.980 g, 3.960 mmol, 1.00 eq) were separated by chiral SFC (column: DAICEL CHIRALPAK AD-H (250 mm×30 mm, 5 μm); mobile phase: A:CO$_2$, B:0.1% aqueous ammonia in 2-propanol; B=30%, 2.5 min) to give enantiomer 1 of 2-(1-benzyl-2,2-dimethylpiperidin-4-yl)EtOH (0.421 g, 1.62 mmol, 40.8% yield, $t_{R1}$=1.192 min, ee=99.3%) and enantiomer 2 of 2-(1-benzyl-2,2-dimethylpiperidin-4-yl)EtOH (0.463 g, 1.76 mmol, 44.3% yield, $t_{R2}$=1.338 min, ee=99.0%, 93.8% purity) as a yellow oils.

Enantiomer 1:
$^1$H NMR (400 MHz, CDCl$_3$) δ ppm 7.36-7.27 (m, 4H), 7.21 (t, J=7.2 Hz, 1H), 4.06 (d, J=14.0 Hz, 1H), 3.68 (t, J=6.8 Hz, 1H), 2.96 (d, J=14.0 Hz, 1H), 2.56-2.52 (m, 1H), 2.23 (td, J=12.4, 2.8 Hz, 1H), 1.70-1.65 (m, 1H), 1.61-1.56 (m, 1H), 1.51-1.43 (m, 3H), 1.28-1.20 (m, 4H), 1.12-1.03 (m, 4H).

Enantiomer 2:
$^1$H NMR (400 MHz, CDCl$_3$) δ ppm 7.36-7.27 (m, 4H), 7.21 (t, J=7.2 Hz, 1H), 4.06 (d, J=14.0 Hz, 1H), 3.68 (t, J=6.8 Hz, 1H), 2.96 (d, J=14.0 Hz, 1H), 2.56-2.52 (m, 1H), 2.23 (td, J=12.4, 2.8 Hz, 1H), 1.70-1.65 (m, 1H), 1.61-1.56 (m, 1H), 1.51-1.43 (m, 3H), 1.28-1.20 (m, 4H), 1.12-1.03 (m, 4H).

An assignment of (R) and (S) was not performed. Each enantiomer was used separately in the steps described below.

Enantiomer 1 of tert-butyl 4-(2-hydroxyethyl)-2,2-dimethylpiperidine-1-carboxylate A mixture of enantiomer 1 of 2-(1-benzyl-2,2-dimethyl-4-piperidyl)ethanol (0.420 g, 1.70 mmol, 1.00 eq), Boc$_2$O (0.741 g, 3.40 mmol, 2.00 eq), palladium hydroxide on activated carbon (0.150 g, 10% purity) and MeOH (10 mL) was stirred at 25° C. under hydrogen (50 psi) for 12 h. The catalyst was removed by filtration and the filtrate was concentrated. The crude product was purified by silica gel column chromatography (0-10% EtOAc in petroleum ether) to give enantiomer 1 of tert-butyl 4-(2-hydroxyethyl)-2,2-dimethylpiperidine-1-carboxylate (0.202 g, 0.785 mmol, 46.2% yield) as a light yellow oil. $^1$H NMR (400 MHz, CDCl$_3$) δ 3.78-3.68 (m, 3H), 3.14-3.08 (m, 1H), 1.82-1.74 (m, 2H), 1.49-1.46 (m, 15H), 1.34-1.24 (m, 5H), 1.17-1.08 (m, 1H).

Enantiomer 1 of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidine-1-carboxylate To a solution of enantiomer 1 of tert-butyl 4-(2-hydroxyethyl)-2,2-dimethylpiperidine-1-carboxylate (0.170 g, 0.661 mmol, 1.00 eq), 5-(5-(3-ethyl-4-hydroxyphenyl)-8-oxo-6-thioxo-5,7-diazaspiro[3.4]octan-7-yl)-3-(trifluoromethyl)picolinonitrile (0.324 g, 0.726 mmol, 1.10 eq) (prepared as described herein) in THF (1 mL) was added triphenylphosphine (0.260 g, 0.991 mmol, 1.50 eq) followed by the addition of (E)-diisopropyl diazene-1,2-dicarboxylate (0.200 g, 0.991 mmol, 1.50 eq) dropwise at 0° C. The reaction was stirred at 60° C. for 10 h. The volatile solvents were removed under reduced pressure. The crude product was purified by silica gel column chromatography (0-8% ethyl acetate in petroleum ether) to give enantiomer 1 of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidine-1-carboxylate (0.180 g, 0.262 mmol, 39.7% yield) as a yellow oil. $^1$H NMR (400 MHz, CDCl$_3$) δ 9.11 (d, J=2.0 Hz, 1H), 8.38 (d, J=2.0 Hz, 1H), 7.11-7.07 (m, 2H), 6.99 (d, J=8.8 Hz, 1H), 4.08 (t, J=6.4 Hz, 2H), 3.81 (dt, J=13.6, 5.2 Hz, 1H), 3.17-3.10 (m, 1H), 2.74-2.56 (m, 6H), 2.30-2.16 (m, 1H), 1.97-1.84 (m, 2H), 1.78 (q, J=6.0 Hz, 2H), 1.72-1.62 (m, 1H), 1.53 (s, 3H), 1.46 (s, 9H), 1.30 (s, 1H), 1.26-1.22 (m, 5H).

Enantiomer 1 of 5-(5-(4-(2-(2,2-dimethylpiperidin-4-yl)ethoxy)-3-ethylphenyl)-8-oxo-6-thioxo-5,7-diazaspiro[3.4]octan-7-yl)-3-(trifluoromethyl)picolinonitrile hydrochloride To a solution of enantiomer 1 of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidine-1-carboxylate (0.180 g, 0.262 mmol, 1.00 eq) in DCM (1 mL) was added a 4.0 M solution of HCl in dioxane (0.33 mL, 5.00 eq). The reaction was stirred at 25° C. for 3 h, concentrated under reduced pressure. The crude product was purified by semi-preparative reverse phase HPLC (37-57% acetonitrile in water+0.05% HCl). The collected fractions were concentrated under reduced pressure to a suspension. The suspension was freeze-dried to give enantiomer 1 of 5-(5-(4-(2-(2,2-dimethylpiperidin-4-yl)ethoxy)-3-ethylphenyl)-8-oxo-6-thioxo-5,7-diazaspiro[3.4]octan-7-yl)-3-(trifluoromethyl)picolinonitrile hydrochloride (0.067 g, 0.108 mmol, 41.1% yield) as a white solid. MS (ESI) m/z 586.3 [M+1]$^+$; $^1$H NMR (400 MHz, DMSO-d$_6$) δ 9.21 (d, J=2.4 Hz, 1H), 8.89-8.48 (m, 3H), 7.21-7.19 (m, 1H), 7.15-7.13 (m, 2H), 4.11 (t, J=5.6 Hz, 2H), 3.11-3.07 (m, 2H), 2.67-2.62 (m, 4H), 2.43-2.40 (m, 2H), 2.01-1.88 (m, 3H), 1.81-1.66 (m, 3H), 1.55-1.53 (m, 1H), 1.33-1.29 (m, 8H), 1.18 (t, J=7.6 Hz, 3H).

Diastereomer 1 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-((2,6-dioxopiperidin-3-yl)amino)phenyl)acetamide hydrochloride A mixture of enantiomer 1 of 5-(5-(4-(2-(2,2-dimethylpiperidin-4-yl)ethoxy)-3-ethylphenyl)-8-oxo-6-thioxo-5,7-diazaspiro[3.4]octan-7-yl)-3-(trifluoromethyl)picolinonitrile hydrochloride (0.254 g, 0.434 mmol, 1.00 eq), 2-chloro-N-(3-((2,6-dioxopiperidin-3-yl)amino)phenyl)acetamide hydrochloride (0.144 g, 0.434 mmol, 1.00 eq), DIEA (0.196 g, 1.52 mmol, 0.264 mL, 3.50 eq) and DMF (3.5 mL) was stirred at 70° C. for 48 h. The reaction mixture was concentrated under reduced pressure to remove solvent. The residue was purified by standard methods to give diastereomer 1 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-((2,6-dioxopiperidin-3-yl)amino)phenyl)acetamide hydrochloride (0.191 g, 0.216 mmol, 49.8% yield). MS (ESI) m/z 845.3 [M+1]$^+$; $^1$H NMR (400 MHz, DMSO-d$_6$) δ 10.80 (s, 1H), 10.54 (s, 1H), 9.37-9.35 (m, 1H), 9.21 (d, J=1.6 Hz, 1H), 8.75 (d, J=2.0 Hz, 1H), 7.21-7.14 (m, 3H), 7.13-7.04 (m, 1H), 6.95 (d, J=1.6 Hz, 1H), 6.86 (d, J=7.6 Hz, 1H), 6.46 (dd, J=8.0, 1.6 Hz, 1H), 6.06-5.98 (m, 1H), 4.37-4.33 (m, 1H), 4.26-4.23 (m, 1H), 4.11 (t, J=5.6 Hz, 2H), 3.79 (dd, J=14.8, 7.6 Hz, 1H), 3.49-3.45 (m, 1H), 3.25-3.20 (m, 1H), 2.71-2.64 (m, 6H), 2.45-2.42 (m, 3H), 2.08-2.06 (m, 1H), 2.04-1.93 (m, 4H), 1.83 (d, J=8.0 Hz, 2H), 1.81-1.57 (m, 5H), 1.44 (s, 3H), 1.33 (s, 3H), 1.18 (t, J=7.6 Hz, 3H).

Enantiomer 2 of tert-butyl 4-(2-hydroxyethyl)-2,2-dimethylpiperidine-1-carboxylate A mixture of enantiomer 2 of 2-(1-benzyl-2,2-dimethylpiperidin-4-yl)EtOH (0.460 g, 1.860 mmol, 1 eq), Boc$_2$O (0.812 g, 3.720 mmol, 2 eq), palladium hydroxide (0.150 g, 10% purity) and MeOH (10 mL) was stirred at 25° C. under hydrogen (50 psi) for 12 h. The catalyst was removed by filtration and the filtrate was concentrated. The crude product was purified by silica gel column chromatography (0-10% EtOAc in petroleum ether) to give enantiomer 2 of tert-butyl 4-(2-hydroxyethyl)-2,2-dimethylpiperidine-1-carboxylate (0.295 g, 1.15 mmol, 61.6% yield) as a colorless oil. $^1$H NMR (400 MHz, CDCl$_3$) δ ppm 3.78-3.68 (m, 3H), 3.14-3.08 (m, 1H), 1.81-1.78 (m, 2H), 1.52-1.44 (m, 15H), 1.34-1.26 (m, 5H), 1.17-1.08 (m, 1H).

Enantiomer 2 of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidine-1-carboxylate To a solution of enantiomer 2 of tert-butyl 4-(2-hydroxyethyl)-2,2-dimethylpiperidine-1-carboxylate (0.288 g, 1.12 mmol, 1.00 eq), 5-(5-(3-ethyl-4-hydroxyphenyl)-8-oxo-6-thioxo-5,7-diazaspiro[3.4]octan-7-yl)-3-(trifluoromethyl)picolinonitrile (0.500 g, 1.12 mmol, 1.00 eq) (prepared as described herein) in THF (3 mL) was added triphenylphosphine (0.440 g, 1.68 mmol, 1.50 eq), followed by the addition of (E)-diisopropyl diazene-1,2-dicarboxylate (0.339 g, 1.680 mmol, 1.50 eq) dropwise at 0° C. The reaction was stirred at 60° C. for 10 h then concentrated. The crude product was purified by preparative reverse phase HPLC (60-90% acetonitrile in water+0.05% HCl, 40 min) to give enantiomer 2 of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidine-1-carboxylate (0.504 g, 0.735 mmol, 65.6% yield) as a yellow oil. $^1$H NMR (400 MHz, CDCl$_3$) δ ppm 9.11 (d, J=2.0 Hz, 1H), 8.37 (d, J=2.0 Hz, 1H), 7.12-7.07 (m, 2H), 6.98 (d, J=8.4 Hz, 1H), 4.08 (t, J=6.0 Hz, 2H), 3.81 (dt, J=13.6, 5.2 Hz, 1H), 3.17-3.10 (m, 1H), 2.74-2.56 (m, 6H), 2.29-2.17 (m, 1H), 1.95-1.85 (m, 2H), 1.78 (q, J=6.0 Hz, 2H), 1.74-1.65 (m, 1H), 1.58-1.53 (m, 4H), 1.47-1.36 (m, 10H), 1.31 (s, 1H), 1.27-1.25 (m, 3H).

Enantiomer 2 of 5-(5-(4-(2-(2,2-dimethylpiperidin-4-yl)ethoxy)-3-ethylphenyl)-8-oxo-6-thioxo-5,7-diazaspiro[3.4]octan-7-yl)-3-(trifluoromethyl)picolinonitrile hydrochloride To a solution of enantiomer 2 of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidine-1-carboxylate (0.500 g, 0.729 mmol, 1.00 eq) in DCM (3 mL) was added a 4.0 M solution of HCl in dioxane (0.91 mL, 5.00 eq). The reaction was stirred at 25° C. for 1 h, concentrated under reduced pressure. The residue was triturated with EtOAc (5 mL) to form a white suspension. The suspension was collected by filtration and washed with (EtOAc (5 mL×2). The collected solid was suspended in acetonitrile (10 mL), the suspension concentrated and dried under reduced pressure to give enantiomer 2 of 5-(5-(4-(2-(2,2-dimethylpiperidin-4-yl)ethoxy)-3-ethylphenyl)-8-oxo-6-thioxo-5,7-diazaspiro[3.4]octan-7-yl)-3-(trifluoromethyl)picolinonitrile hydrochloride (0.402 g, 0.637 mmol, 87.4% yield) as a white solid. MS (ESI) m/z 586.3 [M+1]$^+$; $^1$H NMR (400 MHz, DMSO-d$_6$) δ ppm 9.21 (d, J=2.4 Hz, 1H), 8.95-8.75 (m, 3H), 7.21-7.18 (m, 1H), 7.15-7.13 (m, 2H), 4.10 (t, J=6.0 Hz, 2H), 3.12-3.00 (m, 2H), 2.67-2.59 (m, 4H), 2.45-2.40 (m, 2H), 2.02-1.93 (m, 2H), 1.90-1.86 (m, 1H), 1.80-1.65 (m, 3H), 1.58-1.50 (m, 1H), 1.39-1.29 (m, 8H), 1.17 (t, J=7.6 Hz, 3H).

Diastereomer 2 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-((2,6-dioxopiperidin-3-yl)amino)phenyl)acetamide hydrochloride A mixture of enantiomer 2 of 5-(5-(4-(2-(2,2-dimethylpiperidin-4-yl)ethoxy)-3-ethylphenyl)-8-oxo-6-thioxo-5,7-diazaspiro[3.4]octan-7-yl)-3-(trifluoromethyl)picolinonitrile hydrochloride (0.200 g, 0.321 mmol, 1.00 eq), 2-chloro-N-(3-((2,6-dioxopiperidin-3-yl)amino)phenyl)acetamide hydrochloride (0.107 g, 0.321 mmol, 1 eq), DIEA (0.145 g, 1.130 mmol, 3.50 eq) and DMF (2 mL) was stirred at 50° C. for 72 h. The reaction mixture was filtered. The filtrate was purified by standard methods to give diastereomer 2 of 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-((2,6-dioxopiperidin-3-yl)amino)phenyl)acetamide hydrochloride (0.093 g, 0.105 mmol, 32.5% yield). MS (ESI) m/z 845.3 [M+1]$^+$; $^1$H NMR (400 MHz, DMSO-d$_6$) δ ppm 10.80 (s, 1H), 10.60 (s, 1H), 9.37 (br, 1H), 9.21 (d, J=2.0 Hz, 1H), 8.76 (d, J=2.0 Hz, 1H), 7.21-7.13 (m, 3H), 7.05 (t, J=8.0 Hz, 1H), 6.96-6.95 (m, 1H), 6.86 (d, J=8.0 Hz, 1H), 6.46 (dd, J=8.0, 1.2 Hz, 1H), 6.36 (d, J=15.6 Hz, 1H), 4.26-4.23 (m, 1H), 4.10 (t, J=6.0 Hz, 1H), 3.81 (dd, J=15.2, 8.0 Hz, 1H), 3.22-3.17 (m, 2H), 2.77-2.62 (m, 6H), 2.45-2.39 (m, 2H), 2.11-1.90 (m, 5H), 1.83 (d, J=8.0 Hz, 2H), 1.78-1.69 (m, 2H), 1.61-1.52 (m, 2H), 1.44 (s, 3H), 1.33 (s, 3H), 1.18 (t, J=7.6 Hz, 3H).

Example 23: 2-(4-(2-(4-(7-(4-Cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-((2,6-dioxopiperidin-3-yl)amino)-2-fluorophenyl)acetamide hydrochloride

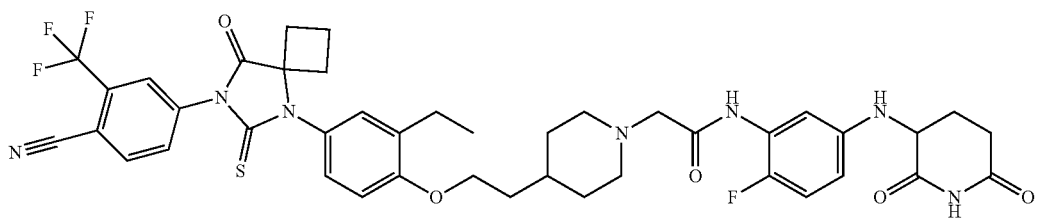 [SMILES: CCc1cc(N2C(=S)N(c3ccc(C#N)c(C(F)(F)F)c3)C(=O)C23CCC3)ccc1OCCC1CCN(CC(=O)Nc2cc(NC3CCC(=O)NC3=O)ccc2F)CC1]

2-Ethyl-4-((1-isocyanocyclobutyl)amino)phenol

To a solution of 4-amino-2-ethylphenol (8.600 g, 62.69 mmol, 1 eq) and cyclobutanone (6.590 g, 94.04 mmol, 7.03 mL, 1.50 eq) (prepared as described herein), in THF (100 mL) was added trimethylsilyl cyanide (15.55 g, 156.7 mmol, 19.61 mL, 2.50 eq) and scandium(III) trifluoromethanesulfonate (3.09 g, 6.27 mmol, 0.1 eq). The reaction mixture was stirred at 25° C. for 12 h, then was diluted with water (100 mL) and extracted with EtOAc (100 mL×2). The combined organic phases were dried with anhydrous sodium sulfate, filtered, and concentrated under vacuum. The residue was purified by flash silica gel column chromatography (3-25% EtOAc in petroleum ether), then by semi-preparative reverse phase HPLC (20-50% acetonitrile+0.225% formic acid in water, 32 min). The selected fraction was concentrated to remove most of the acetonitrile and the resulting suspension was treated with diluted HCl and was lyophilized to afford 2-ethyl-4-((1-isocyanocyclobutyl)amino)phenol (2.050 g, 9.480 mmol, 15.1% yield) as a brown solid. MS (ESI+) m/z 217.1 [M+1]$^+$; $^1$H NMR (400 MHz, CDCl$_3$) δ ppm 6.68 (d, J=8.4 Hz, 1H), 6.51 (d, J=2.8 Hz, 1H), 6.43 (dd, J=2.8, 8.4 Hz, 1H), 2.81-2.68 (m, 2H), 2.60 (q, J=7.6 Hz, 2H), 2.41-2.33 (m, 2H), 2.25-2.14 (m, 2H), 1.23 (t, J=7.5 Hz, 3H).

4-(5-(3-Ethyl-4-hydroxyphenyl)-8-oxo-6-thioxo-5,7-diazaspiro[3.4]octan-7-yl)-2-(trifluoromethyl)benzonitrile A solution of 4-isothiocyanato-2-(trifluoromethyl)benzonitrile (0.850 g, 3.730 mmol, 1.30 eq) and 2-ethyl-4-((1-isocyanocyclobutyl)amino)phenol (0.620 g, 2.87 mmol, 1.00 eq) in DMF (10 mL) was stirred at 25° C. for 1 h, then treated with a 4.0 M solution of HCl in MeOH (10 mL, 13.95 eq), and stirred at 70° C. for 12 h. The mixture was concentrated under vacuum to remove MeOH, then was diluted with water (200 mL) and extracted with EtOAc (200 mL×2). The combined organic phase was washed with brine (50 mL×2), dried with anhydrous sodium sulfate, and concentrated under reduced pressure. The residue was purified by silica gel column chromatography (5-15% EtOAc in petroleum ether) to give 4-(5-(3-ethyl-4-hydroxyphenyl)-8-oxo-6-thioxo-5,7-diazaspiro[3.4]octan-7-yl)-2-(trifluoromethyl)benzonitrile (0.200 g, 0.449 mmol, 15.7% yield) as a brown oil. MS (ESI) m/z 468.0 [M+Na]$^+$.

tert-Butyl 4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidine-1-carboxylate A mixture of 4-(5-(3-ethyl-4-hydroxyphenyl)-8-oxo-6-thioxo-5,7-diazaspiro[3.4]octan-7-yl)-2-(trifluoromethyl)benzonitrile (0.200 g, 0.449 mmol, 1.00 eq), tert-butyl 4-(2-hydroxyethyl)piperidine-1-carboxylate (0.103 g, 0.449 mmol, 0 eq) and triphenylphosphine (0.236 g, 0.898 mmol, 2.0 eq) in THF (2 mL) was treated with diisopropyl azodicarboxylate (0.182 g, 0.898 mmol, 0.17 mL, 2.00 eq) at 0° C., and the reaction mixture was stirred at 25° C. for 2 h, then was concentrated under vacuum. The residue was purified by silica gel column chromatography (3-25% EtOAc in petroleum ether) to give the product, tert-butyl 4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidine-1-carboxylate (0.230 g, 0.413 mmol, 92.0% yield) as a brown solid. MS (ESI) m/z 679.3 [M+1]$^+$.

4-(5-(3-Ethyl-4-(2-(piperidin-4-yl)ethoxy)phenyl)-8-oxo-6-thioxo-5,7-diazaspiro[3.4]octan-7-yl)-2-(trifluoromethyl)benzonitrile To a solution of tert-butyl 4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidine-1-carboxylate (0.230 g, 0.350 mmol, 1.00 eq) in dioxane (5 mL) was added a 4.0 M solution of HCl in dioxane (5 mL, 57.11 eq) and the resulting mixture was stirred at 25° C. for 1 h, then concentrated under reduced pressure to give 4-(5-(3-ethyl-4-(2-(piperidin-4-yl)ethoxy)phenyl)-8-oxo-6-thioxo-5,7-diazaspiro[3.4]octan-7-yl)-2-(trifluoromethyl)benzonitrile hydrochloride (0.205 g, 0.346 mmol, 98.7% yield) as a yellow oil and used into the next step without further purification. MS (ESI) m/z 557.3 [M+1]$^+$.

2-Chloro-N-(5-((2,6-dioxopiperidin-3-yl)amino)-2-fluorophenyl)acetamide

To a solution of 2-chloroacetic acid (0.478 g, 5.060 mmol, 1.20 eq) in DMF (10 mL) was added HATU (1.920 g, 5.060 mmol, 1.20 eq) in one portion at 25° C. under nitrogen and the mixture was stirred at 25° C. for 1 h. To this solution were added, 3-((3-amino-4-fluorophenyl)amino)piperidine-2,6-dione (1.00 g, 4.22 mmol, 1.00 eq) (prepared as described herein), and DIEA (1.63 g, 12.6 mmol, 2.2 mL, 3.00 eq) and stirring continued at 25° C. for 1 h. One main peak with desired mass was shown on LCMS. The reaction mixture was diluted with water (150 mL) and extracted with EtOAc (50 mL×4). The combined organic layers were washed with brine (100 mL×3), dried over anhydrous sodium sulfate, filtered, and concentrated under reduced pressure. The residue was purified by silica gel column chromatography (30-45% EtOAc in petroleum ether) to afford 2-chloro-N-(5-((2,6-dioxopiperidin-3-yl)amino)-2-fluorophenyl)acetamide (0.510 g, 1.53 mmol, 36.3% yield) as a brown solid. MS (ESI) m/z 314.1 [M+1]$^+$.

2-(4-(2-(4-(7-(4-Cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-((2,6-dioxopiperidin-3-yl)amino)-2-fluorophenyl)acetamide hydrochloride To a solution of 4-(5-(3-ethyl-4-(2-(piperidin-4-yl)ethoxy)phenyl)-8-oxo-6-thioxo-5,7-diazaspiro[3.4]octan-7-yl)-2-(trifluoromethyl)benzonitrile hydrochloric acid (0.200 g, 0.337 mmol, 1.00 eq) in DMF (3 mL) was added 2-chloro-N-(5-((2,6-dioxopiperidin-3-yl)amino)-2-fluorophenyl)acetamide (0.106 mg, 0.337 mmol, 1 eq) and DIEA (0.131 g, 1.01 mmol, 0.18 mL, 3.00 eq). The reaction mixture was stirred at 50° C. for 12 h, cooled to room temperature and the pH was adjusted to 6 with formic acid. The mixture was purified by standard methods to afford 2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-((2,6-dioxopiperidin-3-yl)amino)-2-fluorophenyl)acetamide hydrochloride (0.159 g, 0.181 mmol, 53.6% yield). MS (ESI+) m/z 834.4 [M+1]$^+$; $^1$H NMR (400 MHz, DMSO-d$_6$) δ ppm 10.78 (s, 1H), 10.52-10.28 (m, 1H), 10.22-9.97 (m, 1H), 8.37 (d, J=8.3 Hz, 1H), 8.25 (d, J=1.5 Hz, 1H), 8.05 (dd, J=1.7, 8.3 Hz, 1H), 7.23-7.10 (m, 4H), 7.06-6.98 (m, 1H), 6.60-6.43 (m, 1H), 4.25 (d, J=6.5 Hz, 1H), 4.18 (d, J=4.0 Hz, 2H), 4.11 (t, J=5.6 Hz, 2H), 3.54 (br d, J=10.9 Hz, 2H), 3.30-3.03 (m, 2H), 2.78-2.65 (m, 2H), 2.64-2.52 (m, 4H), 2.49-2.42 (m, 2H), 2.42-2.37 (m, 1H), 2.13-2.05 (m, 1H), 2.00-1.88 (m, 4H), 1.81-1.74 (m, 2H), 1.73-1.60 (m, 2H), 1.57-1.48 (m, 1H), 1.18 (t, J=7.5 Hz, 3H).

Example 24: 2-[4-[2-[4-[3-[6-Cyano-5-(trifluoromethyl)-3-pyridyl]-5,5-dimethyl-4-oxo-2-thioxo-imidazolidin-1-yl]-2-ethyl-phenoxy]ethyl]-4-methyl-1-piperidyl]-N-[3-[(2,6-dioxo-3-piperidyl)amino]phenyl]acetamide hydrochloride

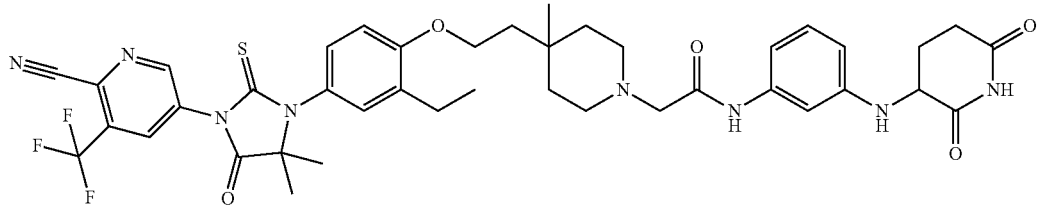 [SMILES: CCc1cc(N2C(=S)N(c3cnc(C#N)c(C(F)(F)F)c3)C(=O)C2(C)C)ccc1OCCC1(C)CCN(CC(=O)Nc2cccc(NC3CCC(=O)NC3=O)c2)CC1]

tert-Butyl 4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]-4-methyl-piperidine-1-carboxylate A mixture of 5-[3-(3-ethyl-4-hydroxy-phenyl)-4,4-dimethyl-5-oxo-2-thioxo-imidazolidin-1-yl]-3-(trifluoromethyl)pyridine-2-carbonitrile (0.230 g, 0.530 mmol) (prepared as described herein), tert-butyl 4-(2-hydroxyethyl)-4-methyl-piperidine-1-carboxylate (0.142 g, 0.580 mmol), triphenylphosphine (0.208 g, 0.790 mmol), in THF (2.5 mL) was stirred at 0° C. for 15 min before adding diisopropyl azodicarboxylate (0.160 g, 0.790 mmol) dropwise. The reaction mixture was stirred for an additional 45 min at 0° C. then for 18 h at room temperature. The solvent was removed under reduced pressure. The solid residue was dissolved in EtOAc and purified by silica gel column chromatography (0-50% EtOAc in hexanes). Fractions containing the desired product were combined and concentrated under reduced pressure to give tert-butyl 4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]-4-methyl-piperidine-1-carboxylate (0.295 g, 0.447 mmol, 84.5% yield) as a foamy orange semi-solid. MS (ESI) m/z 560.2 [M-Boc]+.

5-[3-[3-Ethyl-4-[2-(4-methyl-4-piperidyl)ethoxy]phenyl]-4,4-dimethyl-5-oxo-2-thioxo-imidazolidin-1-yl]-3-(trifluoromethyl)pyridine-2-carbonitrile hydrochloride Tert-Butyl 4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]-4-methyl-piperidine-1-carboxylate (0.295 g, 0.450 mmol) was dissolved in a 4.0 M solution of HCl in dioxane (2.00 mL, 8.00 mmol). The reaction mixture was stirred at 25° C. for 18 h, then concentrated under reduced pressure to give 5-[3-[3-ethyl-4-[2-(4-methyl-4-piperidyl)ethoxy]phenyl]-4,4-dimethyl-5-oxo-2-thioxo-imidazolidin-1-yl]-3-(trifluoromethyl)pyridine-2-carbonitrile; hydrochloride (0.286 g, 0.480 mmol, 107% yield) as a foamy white semi-solid. MS (ESI) m/z 560.0 [M+1]+.

2-[4-[2-[4-[3-[6-Cyano-5-(trifluoromethyl)-3-pyridyl]-5,5-dimethyl-4-oxo-2-thioxo-imidazolidin-1-yl]-2-ethyl-phenoxy]ethyl]-4-methyl-1-piperidyl]-N-[3-[(2,6-dioxo-3-piperidyl)amino]phenyl]acetamide hydrochloride A mixture of 5-[3-[3-ethyl-4-[2-(4-methyl-4-piperidyl)ethoxy]phenyl]-4,4-dimethyl-5-oxo-2-thioxo-imidazolidin-1-yl]-3-(trifluoromethyl)pyridine-2-carbonitrile hydrochloride (0.143 g, 0.240 mmol), 2-chloro-N-[3-[(2,6-dioxo-3-piperidyl)amino]phenyl]acetamide (0.071 g, 0.240 mmol), DIEA (0.13 mL, 0.720 mmol) in DMF (1 mL) was heated to 60° C. for 18 h, then diluted with DMSO, and purified by standard methods to give 2-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]-4-methyl-1-piperidyl]-N-[3-[(2,6-dioxo-3-piperidyl)amino]phenyl]acetamide hydrochloride (0.077 g, 0.086 mmol, 36% yield). MS (ESI) m/z 819.2 [M+1]+; $^1$H NMR (400 MHz, DMSO-$d_6$) δ ppm 10.80 (s, 1H), 10.47-10.57 (m, 1H), 9.66-9.97 (m, 1H), 9.25 (d, J=2.08 Hz, 1H), 8.82 (d, J=2.08 Hz, 1H), 7.09-7.20 (m, 3H), 7.01-7.08 (m, 1H), 6.97 (br s, 1H), 6.85 (br d, J=7.58 Hz, 1H), 6.46 (dd, J=1.59, 8.19 Hz, 1H), 4.22-4.29 (m, 1H), 4.09-4.21 (m, 4H), 3.20-3.48 (m, 4H), 2.69-2.80 (m, 1H), 2.56-2.66 (m, 3H), 2.06-2.15 (m, 1H), 1.85-2.05 (m, 3H), 1.74-1.83 (m, 3H), 1.64 (br d, J=13.69 Hz, 1H), 1.51 (s, 6H), 1.11-1.20 (m, 5H), 1.07 (s, 1H).

Example 25 and 26: 2-((1R,3r,5S)-3-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-((2,6-dioxopiperidin-3-yl)amino)phenyl)acetamide and 2-((1R,3s,5S)-3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-((2,6-dioxopiperidin-3-yl)amino)phenyl)acetamide

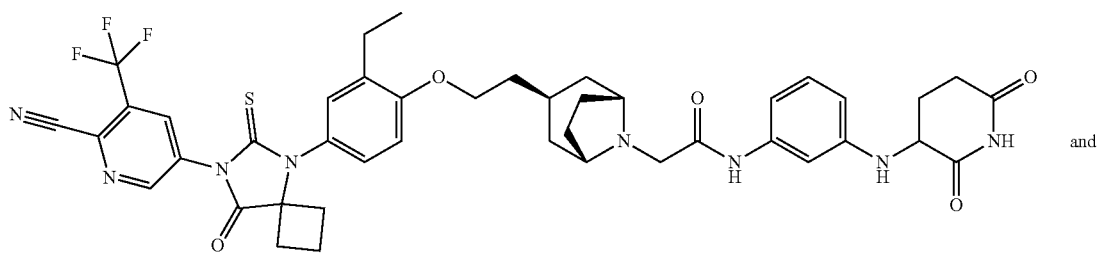

and

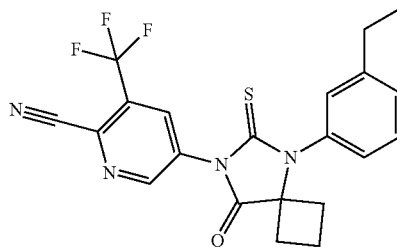

-continued

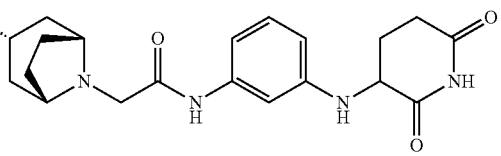

tert-Butyl (1R,5S)-3-(2-hydroxyethyl)-8-azabicyclo[3.2.1]octane-8-carboxylate To a solution containing 2-(8-azabicyclo[3.2.1]octan-3-yl)EtOH (1.00 g, 6.44 mmol) in DCM (20 mL) was added Boc$_2$O (1.54 g, 7.08 mmol) and DIEA (2.47 mL, 14.1 mmol). The solution was stirred at room temperature in a screw cap vial. After 30 min, the solution was partitioned between EtOAc and water (3×). The aqueous layer was extracted with EtOAc and the combined organic extracts were dried over magnesium sulfate, filtered, and concentrated under reduced pressure to afford a colorless oil. The oil was purified by silica gel column chromatography (0-60% EtOAc in hexanes) to afford the title compound as a slightly yellow oil (1.14 g, 4.46 mmol, 69.3% yield). MS (ESI) m/z 256 [M+1]$^+$.

tert-Butyl (1R,3r,5S)-3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octane-8-carboxylate 5-[5-(3-Ethyl-4-hydroxy-phenyl)-8-oxo-6-thioxo-5,7-diazaspiro[3.4]octan-7-yl]-3-(trifluoromethyl)pyridine-2-carbonitrile (0.550 g, 1.23 mmol), tert-butyl rac-(1R,5 S)-3-(2-hydroxyethyl)-8-azabicyclo[3.2.1]octane-8-carboxylate (0.377 g, 1.47 mmol) and triphenylphosphine (0.355, 1.35 mmol) (prepared as described herein), were combined in THF (6.2 mL). To the solution was added dropwise diisopropylazodicarboxylate (0.26 mL, 1.35 mmol) and the mixture was stirred at ambient temperature in a screw cap vial. After stirring over 2 d, the solution was concentrated under reduced pressure. The resulting red oil was purified by silica gel column chromatography (0-35% EtOAc in hexanes) to afford a mixture of diastereomers (0.950 g). The solid was resolved via chiral reverse phase preparative HPLC (95% MeOH in water isocratic, 0.1% TFA, Cosmosil 5PYE, 20×150 mm) to afford diastereomer 1 (0.132 g, 0.193 mmol, 15.7% yield) and diastereomer 2 (0.428 g, 0.626 mmol, 50.8% yield). MS (ESI) m/z 628 [M-(t-Butyl)]$^+$.

An assignment of chiral centers was not performed. Each diastereomer was used separately in the steps described below.

Diastereomer 1 of 5-(5-(4-(2-(8-azabicyclo[3.2.1]octan-3-yl)ethoxy)-3-ethylphenyl)-8-oxo-6-thioxo-5,7-diazaspiro[3.4]octan-7-yl)-3-(trifluoromethyl)picolinonitrile hydrochloride To a solution of diastereomer 1 of tert-butyl 3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octane-8-carboxylate (0.127 g, 0.185 mmol) in DCM (1 mL) was added a 4.0 M solution of HCl in dioxane (1.16 mL, 4.64 mmol). The mixture was stirred at ambient temperature, and after 2 h, was concentrated under reduced pressure to afford the title compound (0.126 g, 0.191 mmol, quant. yield). MS (ESI) m/z 584 [M+1]$^+$.

Diastereomer 1 of 2-(3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-((2,6-dioxopiperidin-3-yl)amino)phenyl)acetamide A mixture of diastereomer 1 of 5 5-(5-(4-(2-(8-azabicyclo[3.2.1]octan-3-yl)ethoxy)-3-ethylphenyl)-8-oxo-6-thioxo-5,7-diazaspiro[3.4]octan-7-yl)-3-(trifluoromethyl)picolinonitrile hydrochloride (0.063 g, 0.108 mmol), 2-chloro-N-[3-[(2,6-dioxo-3-piperidyl)amino]phenyl]acetamide (0.033 g, 0.110 mmol), sodium iodide (0.016 g, 0.108 mmol) and DIEA (0.055 g, 0.431 mmol) in DMF (1 mL) was stirred at 50° C. After 3 h, the solution was diluted with DMSO and purified by standard methods to afford the title compound (0.034 g, 0.040 mmol, 37% yield). MS (ESI) m/z 843 [M+1]$^+$; $^1$H NMR (400 MHz, DMSO-d$_6$) δ ppm 10.79 (s, 1H), 9.63 (s, 1H), 9.24 (d, J=1.83 Hz, 1H), 8.82 (d, J=2.20 Hz, 1H), 7.09-7.15 (m, 3H), 6.98 (t, J=1.71 Hz, 1H), 6.92 (s, 1H), 6.45 (t, J=1.90 Hz, 1H), 6.25 (d, J=7.83 Hz, 1H), 4.26-4.40 (m, 1H), 4.08 (br t, J=5.81 Hz, 2H), 3.25-3.30 (m, 2H), 3.17 (br s, 2H), 3.04 (s, 2H), 2.67 (t, J=1.90 Hz, 2H), 2.61 (d, J=7.34 Hz, 2H), 2.52-2.52 (m, 1H), 2.44 (br d, J=2.93 Hz, 2H), 2.33 (dt, J=3.67, 1.83 Hz, 2H), 2.12-2.21 (m, 3H), 1.91-2.00 (m, 5H), 1.70 (br d, J=7.83 Hz, 3H), 1.51 (s, 7H), 1.22-1.28 (m, 4H), 1.15 (t, J=7.46 Hz, 4H), 0.95 (d, J=6.60 Hz, 1H), 0.81-0.88 (m, 4H), 0.01-0.01 (m, 3H), −0.03--0.01 (m, 6H), −0.15 (s, 1H).

Diastereomer 2 of 5-(5-(4-(2-(8-azabicyclo[3.2.1]octan-3-yl)ethoxy)-3-ethylphenyl)-8-oxo-6-thioxo-5,7-diazaspiro[3.4]octan-7-yl)-3-(trifluoromethyl)picolinonitrile hydrochloride A solution of diastereomer 2 of tert-butyl 3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octane-8-carboxylate (0.365 g, 0.533 mmol) in DCM (2.7 mL) was treated with a 4.0 M solution of HCl in dioxane (3.33 mL, 13.3 mmol). The mixture was stirred at ambient temperature for 2 h, and concentrated under reduced pressure to afford the title compound as the HCl salt (0.361 g, 0.549 mmol, quant. yield). MS (ESI) m/z 584 [M+1]$^+$.

Diastereomer 2 of 2-(3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-((2,6-dioxopiperidin-3-yl)amino)phenyl)acetamide A mixture of diastereomer 2 of 5-(5-(4-(2-(8-azabicyclo[3.2.1]octan-3-yl)ethoxy)-3-ethylphenyl)-8-oxo-6-thioxo-5, 7-diazaspiro[3.4]octan-7-yl)-3-(trifluoromethyl)picolinonitrile (0.100 g, 0.171 mmol), 2-chloro-N-[3-[(2,6-dioxo-3-piperidyl)amino]phenyl]acetamide hydrochloride (0.053 g, 0.179 mmol), sodium iodide (0.026 g, 0.171 mmol) and DIEA (0.119 mL, 0.685 mmol) in DMF (1.7 mL) was stirred at 50° C. for 4 h. The solution diluted with DMSO and purified by standard methods to afford the title compound (0.059 g, 0.070 mmol, 41% yield). MS (ESI) m/z 843 [M+1]$^+$; $^1$H NMR (400 MHz, DMSO-d$_6$) δ ppm 10.77 (s, 1H), 9.52 (s, 1H), 9.22 (d, J=1.96 Hz, 1H), 8.76 (d, J=1.83 Hz, 1H), 7.12-7.21 (m, 3H), 6.98-7.04 (m, 2H), 6.79 (dd, J=7.95, 0.98 Hz, 1H), 5.90 (d, J=7.83 Hz, 1H), 4.21-4.35 (m, 1H), 4.10 (br t, J=5.87 Hz, 2H), 3.25-3.30 (m, 1H), 3.19 (br s, 2H), 3.02 (s, 2H), 2.57-2.68 (m, 6H), 2.39-2.47 (m, 3H), 2.33 (s, 1H), 2.14-2.25 (m, 2H), 1.97 (br d, J=6.85 Hz, 7H), 1.85-1.91 (m, 1H), 1.71 (br d, J=7.95 Hz, 3H), 1.47 (br d, J=13.57 Hz, 3H), 1.21-1.31 (m, 5H), 1.17 (t, J=7.46 Hz, 4H), 0.95 (d, J=6.72 Hz, 1H), 0.81-0.89 (m, 3H), 0.80-0.91 (m, 1H), 0.01-0.01 (m, 1H), −0.03-−0.01 (m, 2H).

Example 27: 2-((2S,4S)-4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide and 2-((2S,4R)-4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide column chromatography (0-1% EtOAc/petroleum ether) to give (S)-tert-butyl 4-(2-ethoxy-2-oxoethylidene)-2-methylpiperidine-1-carboxylate (5.60 g, 19.7 mmol, 84.3% yield) as a colorless oil. $^1$H NMR (400 MHz, CDCl$_3$) δ 5.52-5.46 (m, 1H), 4.50 (br s, 1H), 4.21-4.00 (m, 3H), 3.67-3.51 (m, 1H), 2.97-2.84 (m, 1H), 2.57-2.44 (m, 1H), 2.32-2.22 (m, 1H), 1.95-1.82 (m, 1H), 1.47-1.46 (m, 9H), 1.30-1.24 (m, 3H), 1.16-1.06 (m, 3H).

(2S)-tert-Butyl 4-(2-ethoxy-2-oxoethyl)-2-methylpiperidine-1-carboxylate

A mixture of (S)-tert-butyl 4-(2-ethoxy-2-oxoethylidene)-2-methylpiperidine-1-carboxylate (5.19 g, 18.3 mmol), Pd/C (1.00 g, 10% wt) and MeOH (80 mL) was stirred at 25° C. under hydrogen atmosphere (15 psi) for 12 h. The suspension was filtered, and the filtrate was concentrated to give (2S)-tert-butyl 4-(2-ethoxy-2-oxoethyl)-2-methylpiperidine-1-carboxylate (5.50 g, crude) as a colorless oil. $^1$H NMR (400 MHz, CDCl$_3$) δ 4.15-4.09 (m, 2H), 3.95-3.86 (m, 1H), 3.73-3.67 (m, 1H), 3.10-3.02 (m, 1H), 2.35-2.24 (m, 1H), 2.18-2.04 (m, 2H), 1.97-1.87 (m, 1H), 1.81-1.76 (m, 1H), 1.70-1.68 (m, 1H), 1.60-1.53 (m, 1H), 1.45 (s, 9H), 1.37-1.31 (m, 1H), 1.25 (t, J=7.6 Hz, 3H), 1.18-1.13 (m, 3H), 1.09-1.03 (m, 1H).

(2S)-tert-Butyl 4-(2-hydroxyethyl)-2-methylpiperidine-1-carboxylate

To a solution of (2S)-tert-butyl 4-(2-ethoxy-2-oxoethyl)-2-methylpiperidine-1-carboxylate (5.50 g, 19.2 mmol) in

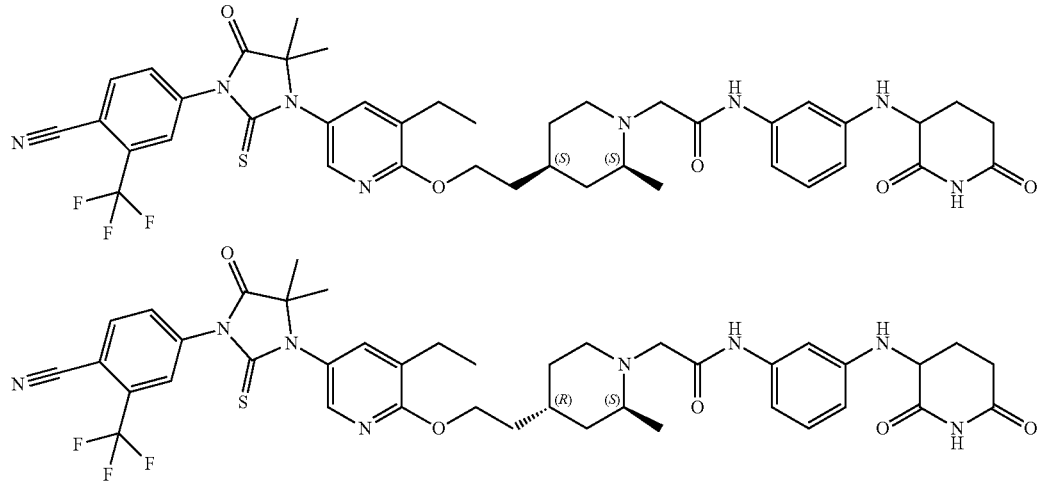

(S)-tert-Butyl 4-(2-ethoxy-2-oxoethylidene)-2-methylpiperidine-1-carboxylate

To a solution of sodium hydride (1.13 g, 28.1 mmol, 60% wt) in THF (50 mL) was added ethyl 2-(diethoxyphosphoryl)acetate (5.78 g, 25.7 mmol) dropwise at 0° C. The cold mixture was stirred at 0° C. for 10 min before a solution of (S)-tert-butyl 2-methyl-4-oxopiperidine-1-carboxylate (5.00 g, 23.4 mmol) in THF (15 mL) was added dropwise and the reaction was stirred at 20° C. for 1 h. The reaction was quenched by the addition of an aqueous solution of ammonium chloride (50 mL), and the mixture was extracted with EtOAc (30 mL×2). The organic layers were washed with brine (50 mL), dried over anhydrous sodium sulfate, filtered and concentrated. The residue was purified by flash silica gel THF (80 mL) was added lithium aluminum hydride (0.87 g, 23.1 mmol) portionwise at 0° C. The reaction was stirred at 25° C. for 1 h. To the reaction was added THF (50 mL) and sodium sulfate (20 g), and then the flask was placed in an ice-bath. To the stirred mixture was added water (2.5 mL) dropwise, and the mixture was stirred at 30° C. for 0.5 h. The suspension was filtered, and the filter cake was washed with ethyl acetate (50 mL). The filtrate was concentrated under reduced pressure to give (2S)-tert-butyl 4-(2-hydroxyethyl)-2-methylpiperidine-1-carboxylate (4.61 g, 18.9 mmol, 98.3% yield) as a crude colorless oil. $^1$H NMR (400 MHz, CDCl$_3$) δ 3.91-3.86 (m, 1H), 3.75-3.67 (m, 7H), 3.08-3.01 (m, 1H), 1.60-1.49 (m, 6H), 1.42-1.40 (m, 9H), 1.31-1.27 (m, 1H), 1.17-1.15 (m, 3H).

(2S)-tert-Butyl 4-(2-((3-bromo-5-nitropyridin-2-yl)oxy)ethyl)-2-methylpiperidine-1-carboxylate To a solution of (2S)-tert-butyl 4-(2-hydroxyethyl)-2-methylpiperidine-1-carboxylate (4.60 g, 18.9 mmol, 1 eq) in THF (40 mL) was added sodium hydride (1.13 g, 28.4 mmol, 60% purity, 1.5 eq) at 0° C. The mixture was gradually warmed to 25° C. and stirred for 1 h. To the mixture was added a solution of 3-bromo-2-chloro-5-nitropyridine (6.73 g, 28.4 mmol, 1.5 eq) in THF (10 mL) dropwise at 25° C., and then the reaction was stirred at 25° C. for 1 h. The reaction was quenched by addition of a saturated aqueous solution of sodium bicarbonate (100 mL). The mixture was extracted with EtOAc (50 mL×2), and the combined organic layers were washed with brine (100 mL), dried, filtered and concentrated. The crude product was purified by flash silica gel column chromatography (0-7% EtOAc/petroleum ether) to give (2S)-tert-butyl 4-(2-((3-bromo-5-nitropyridin-2-yl)oxy)ethyl)-2-methylpiperidine-1-carboxylate (6.01 g, 12.9 mmol, 68.7% yield, 96% purity) was as a yellow oil. MS (ESI) m/z 344.1 [M−100+1]$^+$; $^1$H NMR (400 MHz, CDCl$_3$) δ 8.95-9.01 (m, 1H), 8.59-8.64 (m, 1H), 4.30-4.59 (m, 3H), 3.86-4.07 (m, 1H), 3.66-3.78 (m, 1H), 3.01-3.16 (m, 1H), 1.68-1.93 (m, 4H), 1.58-1.67 (m, 1H), 1.46 (s, 9H), 1.33-1.43 (m, 1H), 1.17-1.21 (d, J=6.4 Hz, 1H), 1.11-1.16 (d, J=7.2 Hz, 1H).

(2S,4S)-tert-Butyl 4-(2-((3-bromo-5-nitropyridin-2-yl)oxy)ethyl)-2-methylpiperidine-1-carboxylate and (2S,4R)-tert-butyl 4-(2-((3-bromo-5-nitropyridin-2-yl)oxy)ethyl)-2-methylpiperidine-1-carboxylate The diastereoisomers of (2S)-tert-butyl 4-(2-((3-bromo-5-nitropyridin-2-yl)oxy)ethyl)-2-methylpiperidine-1-carboxylate (7.29 g, 16.4 mmol, 1 eq) were separated by SFC, and then further separated by chiral SFC (DAICEL CHIRALPAK AD-H (250 mm×30 mm, 5 μm); mobile phase: 35% MeOH+0.1% ammonia; 3 min) to give tert-butyl (2S,4S)-4-[2-[(3-bromo-5-nitro-2-pyridyl)oxy]ethyl]-2-methyl-piperidine-1-carboxylate (2.50 g, 5.61 mmol, 34.2% yield, 99.7% purity) as a yellow oil. $^1$H NMR (400 MHz, CDCl$_3$) δ 8.96-9.01 (d, J=2.4 Hz, 1H), 8.59-8.64 (m, J=2.4 Hz, 1H), 4.50-4.59 (t, J=6.4 Hz, 2H), 3.88-3.98 (m, 1H), 3.70-3.78 (m, 1H), 3.04-3.14 (m, 1H), 1.92-2.03 (m, 1H), 1.76-1.91 (m, 4H), 1.46 (s, 9H), 1.24-1.33 (m, 2H), 1.17-1.21 (d, J=6.4 Hz, 1H). tert-Butyl (2S,4R)-4-[2-[(3-bromo-5-nitro-2-pyridyl)oxy]ethyl]-2-methyl-piperidine-1-carboxylate (3.600 g, 8.040 mmol, 48.99% yield, 99.2% purity) was isolated as a yellow oil. $^1$H NMR (400 MHz, CDCl$_3$) δ 8.96-9.03 (d, J=2.8 Hz, 1H), 8.59-8.65 (m, J=2.4 Hz, 1H), 4.35-4.65 (m, 3H), 3.99 (br s, 1H), 2.74-2.95 (t, J=11.2 Hz, 1H), 1.84-1.98 (m, 1H), 1.60-1.84 (m, 4H), 1.33-1.50 (m, 11H), 1.13-1.16 (d, J=7.2 Hz, 1H).

(2S,4S)-tert-Butyl 2-methyl-4-(2-((5-nitro-3-vinylpyridin-2-yl)oxy)ethyl)piperidine-1-carboxylate and (2S,4R)-tert-butyl 2-methyl-4-(2-((5-nitro-3-vinylpyridin-2-yl)oxy)ethyl)piperidine-1-carboxylate To a mixture of 4,4,5,5-tetramethyl-2-vinyl-1,3,2-dioxaborolane (0.19 g, 1.28 mmol, 0.37 eq) in dioxane (20 mL) and water (10 mL) was added (2S,4S)-tert-butyl 4-(2-((3-bromo-5-nitropyridin-2-yl)oxy)ethyl)-2-methylpiperidine-1-carboxylate (1.50 g, 3.37 mmol, 1 eq), tetrakis(triphenylphosphine)palladium (0.19 g, 0.17 mmol, 0.05 eq) and sodium carbonate (1.07 g, 10.1 mmol, 3 eq) in one portion at 25° C. under nitrogen. The mixture was heated to 100° C. and stirred for 12 h. Additional 4,4,5,5-tetramethyl-2-vinyl-1,3,2-dioxaborolane (0.52 g, 3.37 mmol, 1 eq) was added, and the reaction was stirred for 12 h. The residue was poured into water (50 mL), the aqueous phase was extracted with EtOAc (30 mL×3), and the combined organic layers were washed with brine (30 mL), dried with anhydrous sodium sulfate, filtered and concentrated in vacuo. The residue was purified by silica gel chromatography (0-20% EtOAc/petroleum ether) to give (2S,4S)-tert-butyl 2-methyl-4-(2-((5-nitro-3-vinylpyridin-2-yl)oxy)ethyl)piperidine-1-carboxylate (0.62 g, 1.58 mmol, 47.0% yield) as a yellow oil. $^1$H NMR (400 MHz, CDCl$_3$) δ 8.88-9.01 (d, J=2.8 Hz, 1H), 8.39-8.53 (d, J=2.8 Hz, 1H), 6.77-6.92 (dd, J=17.6 Hz, J=10.8 Hz, 1H), 5.89-6.05 (d, J=17.6 Hz, 1H), 5.48-5.62 (d, J=15.2 Hz, 1H), 4.45-4.60 (t, J=6.8 Hz, 2H), 3.85-4.00 (m, 1H), 3.65-3.82 (m, 1H), 3.00-3.19 (m, 1H), 1.90-2.03 (m, 1H), 1.73-1.90 (m, 4H), 1.46 (s, 9H), 1.23-1.32 (m, 2H), 1.16-1.21 (d, J=2.4 Hz, 3H).

The same method was used to synthesize (2S,4S)-tert-butyl 2-methyl-4-(2-((5-nitro-3-vinylpyridin-2-yl)oxy)ethyl)piperidine-1-carboxylate (0.640 g, 1.630 mmol, 78.7% yield) as a light yellow solid. MS (ESI) m/z 336.5 [M+1]$^+$; $^1$H NMR (400 MHz, CDCl$_3$) δ 8.96 (d, J=2.8 Hz, 1H), 8.46 (d, J=2.8 Hz, 1H), 6.85 (dd, J=17.6, 11.2 Hz, 1H), 5.98 (d, J=17.6 Hz, 1H), 5.54 (d, J=11.6 Hz, 1H), 4.53 (t, J=6.8 Hz, 2H), 4.30-4.48 (m, 1H), 3.85-4.10 (m, 1H), 2.77-2.94 (m, 1H), 1.81-1.95 (m, 1H), 1.68-1.80 (m, 3H), 1.59-1.66 (m, 1H), 1.47 (s, 9H), 1.34-1.43 (m, 1H), 1.09-1.17 (m, 4H).

(2S,4S)-tert-Butyl 4-(2-((5-amino-3-ethylpyridin-2-yl)oxy)ethyl)-2-methylpiperidine-1-carboxylate and (2S,4R)-tert-butyl 4-(2-((5-amino-3-ethylpyridin-2-yl)oxy)ethyl)-2-methylpiperidine-1-carboxylate To a solution of (2S,4S)-tert-butyl 2-methyl-4-(2-((5-nitro-3-vinylpyridin-2-yl)oxy)ethyl)piperidine-1-carboxylate (0.62 g, 1.58 mmol, 1 eq) in THF (10 mL) was added Pd/C (0.15 g, 10% wt) under nitrogen. The suspension was degassed under vacuum and purged with hydrogen several times, and the mixture was stirred under hydrogen atmosphere (50 psi) at 25° C. for 12 h. The reaction was filtered and concentrated in vacuo to give crude (2S,4S)-tert-butyl 4-(2-((5-amino-3-ethylpyridin-2-yl)oxy)ethyl)-2-methylpiperidine-1-carboxylate (0.42 g, 1.16 mmol, 72.9% yield) as a yellow oil. MS (ESI) m/z 364.6 [M+1]$^+$; $^1$H NMR (400 MHz, CDCl3) δ 7.46-7.50 (d, J=2.8 Hz, 1H), 6.87-6.90 (d, J=2.8 Hz, 1H), 4.23-4.28 (t, J=5.6 Hz, 2H), 3.85-3.95 (m, 1H), 3.67-3.75 (m, 1H), 3.30 (s, 2H), 3.03-3.13 (m, 1H), 2.49-2.57 (m, 2H), 1.88-2.00 (m, 1H), 1.73-1.87 (m, 4H), 1.46 (s, 9H), 1.07-1.25 (m, 8H).

The same method, including 0.96 eq of 28% pure ammonium hydroxide in addition and an elevated temperature of 45° C., was used to form (2S,4R)-tert-butyl 4-(2-((5-amino-3-ethylpyridin-2-yl)oxy)ethyl)-2-methylpiperidine-1-carboxylate (0.500 g, 1.380 mmol, 91.3% yield) as a light yellow oil. MS (ESI) m/z 364.5 [M+1]$^+$; $^1$H NMR (400 MHz, CDCl$_3$) δ 7.48 (d, J=2.8 Hz, 1H), 6.89 (d, J=2.8 Hz, 1H), 4.35-4.55 (m, 1H), 4.20-4.31 (m, 2H), 3.85-4.05 (m, 1H), 3.05-3.60 (m, 2H), 2.75-2.95 (m, 1H), 2.53 (q, J=7.6 Hz, 2H), 1.82-1.96 (m, 1H), 1.63-1.76 (m, 4H), 1.46 (s, 9H), 1.30-1.40 (m, 1H), 1.15-1.20 (m, 3H), 1.00-1.14 (m, 4H).

(2S,4S)-tert-Butyl 4-(2-((3-ethyl-5-((1-methoxy-2-methyl-1-oxopropan-2-yl)amino) pyridin-2-yl)oxy)ethyl)-2-methylpiperidine-1-carboxylate and (2S,4R)-tert-butyl 4-(2-((3-ethyl-5-((1-methoxy-2-methyl-1-oxopropan-2-yl)amino)pyridin-2-yl)oxy)ethyl)-2-methylpiperidine-1-carboxylate A mixture of (2S,4S)-tert-butyl 4-(2-((5-amino-3-ethylpyridin-2-yl)oxy)ethyl)-2-methylpiperidine-1-carboxylate (0.42 g, 1.16 mmol, 1 eq), methyl 2-bromo-2-methyl-propanoate (1.05 g, 5.78 mmol, 5 eq) and N-ethyl-N-isopropylpropan-2-amine (0.75 g, 5.78 mmol, 5 eq) was stirred at 100° C. for 24 h. A saturated aqueous solution of ammonium chloride (30 mL) and EtOAc (30 mL) were added, and the layers were separated. The aqueous layer was extracted with EtOAc (30 mL), and the combined organic layers were washed with brine (20 mL), dried, filtered and concentrated. The crude product was purified by silica gel chromatography (0-50% EtOAc/petroleum ether) to afford (2S,4S)-tert-butyl 4-(2-((3-ethyl-5-((1-methoxy-2-methyl-1-oxopropan-2-yl)amino)pyridin-2-yl)oxy)ethyl)-2-methylpiperidine-1-carboxylate (0.42 mg, 0.91 mmol, 78.4% yield) as a yellow oil. MS (ESI) m/z 464.3 [M+1]$^+$; $^1$H NMR (400 MHz, CDCl3) δ 7.46-7.49 (d, J=2.4 Hz, 1H), 6.92-6.95 (d, J=2.4 Hz, 1H), 4.22-4.29 (t, J=6.0 Hz, 2H), 3.86-3.96 (m, 1H), 3.66-3.76 (m, 5H), 3.02-3.12 (m, 1H), 2.48-2.56 (m, 2H), 1.89-1.99 (m, 1H), 1.74-1.87 (m, 4H), 1.45-1.49 (m, 14H), 1.24-1.31 (m, 2H), 1.14-1.19 (m, 6H).

(2S,4R)-tert-Butyl 4-(2-((3-ethyl-5-((1-methoxy-2-methyl-1-oxopropan-2-yl)amino)pyridin-2-yl)oxy)ethyl)-2-methylpiperidine-1-carboxylate (0.141 g, 0.295 mmol, 44.68% yield, 97% purity) was made following the same procedure to give a brown oil. MS (ESI) m/z 464.1 [M+1]$^+$.

(2S,4S)-tert-Butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidine-1-carboxylate and (2S,4R)-tert-butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidine-1-carboxylate A mixture of (2S,4S)-tert-butyl 4-(2-((3-ethyl-5-((1-methoxy-2-methyl-1-oxopropan-2-yl)amino)pyridin-2-yl)oxy)ethyl)-2-methylpiperidine-1-carboxylate (0.42 g, 0.91 mmol, 1 eq), 4-isothiocyanato-2-(trifluoromethyl)benzonitrile (0.31 g, 1.36 mmol, 1.5 eq), TEA (0.27 g, 2.72 mmol, 378 µL, 3 eq) and EtOAc (5 mL) was stirred at 60° C. for 10 h. LCMS showed 40% desired product was detected, the residue was poured into water (50 mL), and the aqueous phase was extracted with EtOAc (30 mL×3). The combined organic layers were washed with brine (50 mL), dried over anhydrous sodium sulfate, filtered and concentrated in vacuo. The residue was purified by semi-preparative, reverse-phase HPLC (78-100% acetonitrile in water+ 0.225% formic acid, 11 min) to give (2S,4S)-tert-butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidine-1-carboxylate (0.19 g, 0.29 mmol, 32.6% yield) as a colorless oil. MS (ESI) m/z 560.4 [M–100+1]$^+$; $^1$H NMR (400 MHz, CDCl$_3$) δ 7.89-8.03 (m, 3H), 7.81-7.87 (dd, J=8.4 Hz, J=1.6 Hz, 1H), 7.30-7.35 (m, 1H), 4.34-4.44 (t, J=6.0 Hz, 2H), 3.85-3.97 (m, 1H), 3.67-3.78 (m, 2H), 3.04-3.14 (m, 1H), 2.59-2.68 (m, 2H), 1.91-2.03 (m, 1H), 1.69-1.89 (m, 5H), 1.51-1.59 (m, 2H), 1.46 (s, 10H), 1.18-1.30 (m, 9H).

The same procedure provided (2S,4R)-tert-butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidine-1-carboxylate (0.080 g, 0.112 mmol, 37.12% yield, 98.9% purity, formic acid) as yellow oil. MS (ESI) m/z 682.3 [M+Na]$^+$.

4-(3-(5-Ethyl-6-(2-((2S,4S)-2-methylpiperidin-4-yl)ethoxy)pyridin-3-yl)-4,4-dimethyl-5-oxo-2-thioxoimidazolidin-1-yl)-2-(trifluoromethyl)benzonitrile and 4-(3-(5-ethyl-6-(2-((2S,4R)-2-methylpiperidin-4-yl)ethoxy)pyridin-3-yl)-4,4-dimethyl-5-oxo-2-thioxoimidazolidin-1-yl)-2-(trifluoromethyl)benzonitrile To a mixture of (2S,4S)-tert-butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidine-1-carboxylate (0.19 g, 0.29 mmol, 1 eq) in DCM (2 mL) was added hydrogen chloride/MeOH (4 M, 0.3 mL, 4.17 eq) in one portion. The mixture was stirred at 25° C. for 1 h. The reaction was concentrated in vacuo, and the residue was poured into saturated aqueous solution of sodium bicarbonate (20 mL) and stirred for 10 min. The aqueous phase was extracted with EtOAc (10 mL×3), and the combined organic layers were washed with brine (20 mL×1), dried with anhydrous sodium sulfate, filtered and concentrated in vacuo. Compound 4-(3-(5-ethyl-6-(2-((2S,4S)-2-methylpiperidin-4-yl)ethoxy)pyridin-3-yl)-4,4-dimethyl-5-oxo-2-thioxoimidazolidin-1-yl)-2-(trifluoromethyl)benzonitrile (0.13 g, crude) was obtained as a yellow oil. MS (ESI) m/z 560.4 [M+1]$^+$.

A lower temperature of 10° C. and 8 h of stirring was required for the synthesis of 4-(3-(5-ethyl-6-(2-((2S,4R)-2-methylpiperidin-4-yl)ethoxy)pyridin-3-yl)-4,4-dimethyl-5-oxo-2-thioxoimidazolidin-1-yl)-2-(trifluoromethyl)benzonitrile (0.067 g, 0.112 mmol, 99.16% yield, hydrogen chloride) as a yellow solid by the same procedure. MS (ESI) m/z 560.3 [M+1]$^+$.

2-((2S,4S)-4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide and 2-((2S,4R)-4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide To a mixture of 4-(3-(5-ethyl-6-(2-((2S,4S)-2-methylpiperidin-4-yl)ethoxy)pyridin-3-yl)-4,4-dimethyl-5-oxo-2-thioxoimidazolidin-1-yl)-2-(trifluoromethyl)benzonitrile (0.13 g, 0.23 mmol, 1 eq) and 2-chloro-N-(3-((2,6-dioxopiperidin-3-yl)amino)phenyl)acetamide (0.10 g, 0.34 mmol, 1.5 eq) in DMF (3 mL) was added N-ethyl-N-isopropylpropan-2-amine (0.09 g, 0.68 mmol, 3 eq). The mixture was heated to 70° C. and stirred for 12 h. The mixture was poured into water (30 mL) and stirred for 10 min. The aqueous phase was extracted with EtOAc (30 mL×3), and the combined organic layers were washed with brine (50 mL×5), dried with anhydrous sodium sulfate, filtered and concentrated in vacuo. The residue was purified by standard methods to provide 2-((2S,4S)-4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide (0.06 g, 0.07 mmol, 31.1% yield, 98% purity). MS (ESI) m/z 819.3 [M+1]$^+$; $^1$H NMR (400 MHz, DMSO-d$_6$) δ 10.77 (s, 1H), 9.35 (s, 1H), 8.36-8.43 (d, J=8.4 Hz, 1H), 8.27-8.32 (d, J=1.6 Hz, 1H), 8.05-8.10 (dd, J=8.0 Hz, J=1.6 Hz, 1H), 7.95-8.05 (d, J=2.4 Hz, 1H), 7.50-7.60 (d, J=2.4 Hz, 1H), 6.93-7.08 (m, 2H), 6.75-6.85 (d, J=8.4 Hz, 1H), 6.32-6.46 (d, J=8.4 Hz, 1H), 5.80-5.96 (d, J=7.6 Hz, 1H), 4.36-4.44 (t, J=6.4 Hz, 2H), 4.21-4.33 (m, 1H), 3.35-3.38 (m, 1H), 2.93-3.01 (d, J=16.4 Hz, 1H), 2.85-2.93 (d, J=11.6 Hz, 1H), 2.68-2.77 (m, 1H), 2.56-2.64 (m, 4H), 2.35-2.41 (d, J=11.2 Hz, 1H), 2.07-2.12 (m, 1H), 1.58-1.93 (m, 1H), 1.64-1.77 (m, 4H), 1.58 (br s, 1H), 1.51 (s, 6H), 1.27-1.38 (m, 1H), 1.13-1.21 (t, J=7.6 Hz, 3H), 0.96-1.12 (m, 4H). The same synthesis, except with a 48 h reaction time, was used to provide 2-((2S,4R)-4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide (0.045 g, 0.054 mmol, 48.13% yield, 98.18% purity) as a white solid. MS (ESI) m/z 819.3 [M+1]$^+$; $^1$H NMR (400 MHz, DMSO-d$_6$) δ 10.76 (s, 1H), 9.37 (s, 1H), 8.39 (d, J=8.4 Hz, 1H), 8.29 (d, J=2.8 Hz, 1H), 8.08 (d, J=8.0 Hz, 1H), 7.55 (d, J=2.4 Hz, 1H), 7.02-6.98 (m, 2H), 6.81 (d, J=7.6 Hz, 1H), 6.40 (d, J=8.0 Hz, 1H), 5.88 (d, J=8.0 Hz, 1H), 4.40 (t, J=6.4 Hz, 2H), 4.30-4.24 (m, 1H), 3.18 (d, J=16.0 Hz, 1H), 3.05-3.01 (m, 2H), 2.77-2.69 (m, 1H), 2.62-2.57 (m, 5H), 2.12-2.07 (m, 1H), 1.93-1.70 (m, 5H), 1.58-1.51 (m, 8H), 1.39-1.34 (m, 1H), 1.17 (t, J=7.6 Hz, 3H), 1.00 (d, J=6.8 Hz, 3H).

Assays

Cell Based Assays

VCAP AR Degradation Assay.

Test compounds were pre-dispensed into a Corning Cell-Bind 96-well clear bottom plate (Cat #3300) using an acoustic dispenser to make a 10-point concentration series at 1:3 dilution for each compound. The final top concentration of each compound was 5 M. DMSO at a final concentration of 0.1% was used as a control. VCaP cells cultured in DMEM with 8% fetal bovine serum (FBS) were seeded at 50K cells per well in a 200 μL volume into the compound plate and incubated at 37° C. in a CO$_2$ incubator for 24 h. The medium was carefully removed from the cells and the plate was placed on ice. One hundred L of ice-cold 1× cell lysis buffer from Cell Signaling Technologies (Cat #9803) was added to each well of the cells and the plate was incubated at 4° C. on a shaker for 1 h. Fifteen L of cell lysate was used for AR ELISA detection using a PathScan Total Sandwich AR ELISA kit (Cell Signaling Technology, Cat #12580). AR levels in compound-treated wells were normalized to that of DMSO control and expressed as percent of control (PoC) (y). A Four Parameter Logistic Model (Sigmoidal Dose-Response Model) was used to determine the compound's DC$_{50}$, and EC$_{50}$, using the following equation:

$$y=(A+((B-A)/(1+((C/x)^D))))$$

A=Y$_{Min}$ (lowest AR level normalized to DMSO control in response to compound treatment, as determined by curve fit)

B=Y$_{Max}$ (maximum AR level as determined by curve fit)

C=EC$_{50}$

D=Hill Slope x=compound concentration

EC$_{50}$=the concentration of compound when y=(Y$_{Max}$-Y$_{Min}$)/2

DC$_{50}$=the concentration of the compound when y=50% of DMSO control (50% AR degradation)

y=AR protein level normalized to DMSO control

The lowest measured AR level normalized to DMSO control in response to compound treatment, termed Y value, was used to characterize the compound-mediated AR degradation efficiency.

Each of the Piperidine Dione Compounds in Table 1, was tested in the VCAP AR degradation assay, and was found to have activity therein. All of the compounds in Table 1 were shown to have an DC$_{50}$<1 μM and Y<50% of DMSO control.

Prostate Cancer Cell Proliferation Assay.

VCAP or ENZR cells were plated at 10K cells per well in 96-well CellBind (Costar) plates using DMEM+8% FBS media. Cells were incubated overnight at 37° C. and test compound was serially diluted and added to the well. Following seven-day incubation, the assay media was removed by inversion and the plate was frozen overnight at −80° C. Plates were thawed at room temperature and 100 μL deionized water (ddH$_2$O) was added to each well. Plates were incubated at 37° C. in non-CO$_2$ incubator for 1 h and then frozen at −80° C. overnight. Plates were thawed to room temperature and 100 μL TNE buffer (NaCl, Tris, EDTA)+Hoescht dye (1.0 mg/ml, 1:400) was added to each well. Fluorescent signal was measured at 460 nm. All data were normalized as a percentage of the DMSO control. A Four Parameter Logistic Model (Sigmoidal Dose-Response Model) was used to determine the compound's GI$_{50}$ value, using the following equation:

$$y=(A+((B-A)/(1+((C/x)^D))))$$

A=Y$_{Min}$ (lowest cell viability in luminescence unit normalized to DMSO control in response to compound treatment determined by curve fit)

B=Y$_{Max}$ (maximum cell viability measured as luminescence unit normalized to DMSO control as determined by curve fit)

C=EC$_{50}$

D=Hill Slope

GI$_{50}$=the concentration of the compound when Y=(Y$_{Max}$+Y$_{t_o}$)/2

EC$_{50}$=the concentration of compound when y=(Y$_{Max}$-Y$_{Min}$)/2

IC$_{50}$=the concentration of the compound when Y=50% of DMSO control y=cell viability measured as luminescence unit and normalized as percentage of the DMSO control t$_0$=time when compound was added Piperidine Dione Compounds have been, or will be tested in the prostate cancer cell proliferation assay, and have shown, or will be shown, to have activity therein.

In Vivo Assays

AR Degradation Assay.

In vivo AR degradation assays were performed in NSG mice bearing VCaP prostate cancer xenograft tumors. Male NSG mice were inoculated with VCaP cells in the flank region above the right leg. Following inoculation of the animals, the tumors were allowed to grow to approximately 500 mm$^3$ prior to randomization. The randomized animals were administered with test compounds formulated in 20% Labrasol, 80% 25 mM citrate buffer pH 3. The compounds were administered orally once daily for 3 days. After the last dose of compound administration, the plasma and tumors were collected and processed for AR degradation assays. Intratumoral AR levels were measured using western blot analysis. Statistical analysis was performed using a one-way analysis of variance (ANOVA).

Piperidine Dione Compounds have been, or will be tested in the in vivo AR degradation assay, and have shown, or will be shown, to have activity therein.

VCaP Prostate Cancer Xenograft Model.

The xenograft study was conducted with male NSG mice bearing VCaP prostate cancer xenograft tumors. Male NSG mice were inoculated subcutaneously with VCaP cells in the flank region above the right hind leg. Following inoculation of the animals, the tumors were allowed to grow to approximately 200 mm$^3$ prior to randomization. During randomization, the mice bearing VCaP tumors ranging between 75 and 250 mm$^3$ were pooled together and randomized into various treatment groups. Test compounds formulated in 20% Labrasol, 80% 25 mM citrate buffer pH 3 were administered in a dose volume of 5 mL/kg. The compounds were administered orally once daily for the duration of the study. Tumors were measured twice a week using calipers and tumor volumes were calculated using the formula W$^2$×L/2. Statistical analysis was performed using a one-way or 2-way analysis of variance (ANOVA).

Piperidine Dione Compounds have been, or will be tested in the VCAP prostate cancer xenograft model and have shown, or will be shown, to be effective as treatments of prostate cancer in the models.

ACTIVITY TABLES

Each of the Piperidine Dione Compounds in Table 1, was tested in one or more of the AR degradation assays shown above, for example, the VCAP AR Degradation Assay assay, and was found to have activity therein.

All of the compounds in Table 1 were shown to have an $DC_{50}<1$ μM and Y<50% of DMSO control, with some compounds having an $DC_{50}$ value C: $DC_{50} \leq 0.10$ μM, some an $DC_{50}$ value B: $0.10$ μM$<DC_{50} \leq 0.50$ μM, and others an $DC_{50}$ value A: $0.50$ μM$<DC_{50} \leq 1.0$ M.

Additionally the compounds were shown to have an AR degradation efficiency Y value <50% of DMSO control, with some compounds having $0<Y<=25\%$ (shown as *), some compounds having $25\%<Y<=35\%$ (shown as ), and others having $35\%<Y<50\%$ (shown as *).

TABLE 1

| Cmpd No. | Cmpd Structure | Cmpd Name | MH+ Obs. | DC50 | Y |
|---|---|---|---|---|---|
| 1 | | 2-(4-(4-(3-cyano-4-(trifluoromethyl)phenyl)-5,5-dimethyl-4-oxo-2-thioxoimidazolidin-1-yl)-2-fluorophenoxy)piperidin-1-yl)-N-(3-(2,6-dioxopiperidin-3-ylamino)phenyl)acetamide | 766.0 | C | ** |

TABLE 1-continued
| Cmpd No. | Cmpd Structure | Cmpd Name | MH+ Obs. | DC50 | Y |
|---|---|---|---|---|---|
| 2 | 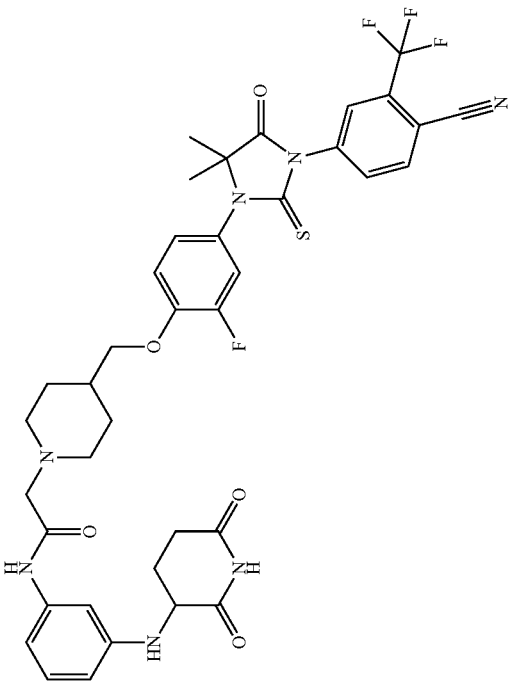 | 2-(4-((4-(3-(4-cyano-3-(trifluoromethyl)phenyl)-5,5-dimethyl-4-oxo-2-thioxoimidazolidin-1-yl)-2-fluorophenoxy)methyl)piperidin-1-yl)-N-(3-(2,6-dioxopiperidin-3-ylamino)phenyl)acetamide | 780.0 | B | ** |

| Cmpd No. | Cmpd Structure | Cmpd Name | MH+ Obs. | DC50 | Y |
|---|---|---|---|---|---|
| 3 | | 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperidin-1-yl)-N-(3-(2,6-dioxopiperidin-3-ylamino)phenyl)acetamide | 794.0 | B | ** |

TABLE 1-continued

| Cmpd No. | Cmpd Structure | Cmpd Name | MH+ Obs. | DC50 | Y |
|---|---|---|---|---|---|
| 4 | | 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperidin-1-yl)-N-(3-(2,6-dioxopiperidin-3-ylamino)phenyl)acetamide | 810.6 | B | ** |

TABLE 1-continued

| Cmpd No. | Cmpd Structure | Cmpd Name | MH+ Obs. | DC50 | Y |
|---|---|---|---|---|---|
| 5 | | 2-(4-(2-(2-chloro-4-(3-(6-cyano-5-(trifluoromethyl)pyridin-3-yl)-5,5-dimethyl-4-oxo-2-thioxoimidazolidin-1-yl)phenoxy)ethyl)piperidin-1-yl)-N-(3-(2,6-dioxopiperidin-3-ylamino)phenyl)acetamide | 811.1 | C | * |
| 6 | | 2-(4-((4-(3-(6-cyano-5-(trifluoromethyl)pyridin-3-yl)-5,5-dimethyl-4-oxo-2-thioxoimidazolidin-1-yl)phenoxy)methyl)piperidin-1-yl)-N-(3-(2,6-dioxopiperidin-3-ylamino)phenyl)acetamide | 763.2 | B | ** |

TABLE 1-continued

| Cmpd No. | Cmpd Structure | Cmpd Name | MH+ Obs. | DC50 | Y |
|---|---|---|---|---|---|
| 7 | | 2-(4-(2-chloro-4-(3-(6-cyano-5-(trifluoromethyl)pyridin-3-yl)-5,5-dimethyl-4-oxo-2-thioxoimidazolidin-1-yl)phenoxy)methyl)piperidin-1-yl)-N-(3-(2,6-dioxopiperidin-3-ylamino)phenyl)acetamide | 797.3 | A | ** |
| 8 | | 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperidin-1-yl)-N-(3-chloro-5-(2,6-dioxopiperidin-3-ylamino)phenyl)acetamide | 845.2 | B | * |

TABLE 1-continued

| Cmpd No. | Cmpd Structure | Cmpd Name | MH+ Obs. | DC50 | Y |
|---|---|---|---|---|---|
| 9 | | 2-(4-((2-chloro-4-(3-(4-cyano-3-(trifluoromethyl)phenyl)-5,5-dimethyl-4-oxo-2-thioxoimidazolidin-1-yl)phenoxy)methyl)piperidin-1-yl)-N-(3-chloro-5-(2,6-dioxopiperidin-3-ylamino)phenyl)acetamide | 832.2 | A | *** |

TABLE 1-continued

| Cmpd No. | Cmpd Structure | Cmpd Name | MH+ Obs. | DC50 | Y |
|---|---|---|---|---|---|
| 10 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperidin-1-yl)acetamide | 828.2 | B | ** |

TABLE 1-continued

| Cmpd No. | Cmpd Structure | Cmpd Name | MH+ Obs. | DC50 | Y |
|---|---|---|---|---|---|
| 11 | | 2-(4-((4-(3-(4-cyano-3-(trifluoromethyl)phenyl)-5,5-dimethyl-4-oxo-2-thioxoimidazolidin-1-yl)-2-ethylphenoxy)methyl)piperidin-1-yl)-N-(3-(2,6-dioxopiperidin-3-ylamino)phenyl)acetamide | 790.4 | B | ** |
| 12 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)acetamide | 825.2 | C | * |

TABLE 1-continued

| Cmpd No. | Cmpd Structure | Cmpd Name | MH+ Obs. | DC$_{50}$ | Y |
|---|---|---|---|---|---|
| 13 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide | 839.3 | C | * |

| Cmpd No. | Cmpd Structure | Cmpd Name | MH+ Obs. | DC$_{50}$ | Y |
|---|---|---|---|---|---|
| 14 | | N-(2-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide | 839.2 | B | * |

TABLE 1-continued

| Cmpd No. | Cmpd Structure | Cmpd Name | MH+ Obs. | DC50 | Y |
|---|---|---|---|---|---|
| 15 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(5-(2,6-dioxopiperidin-3-ylamino)-2-fluorophenyl)acetamide | 823.3 | C | * |

TABLE 1-continued
| Cmpd No. | Cmpd Structure | Cmpd Name | MH+ Obs. | DC50 | Y |
|---|---|---|---|---|---|
| 16 | 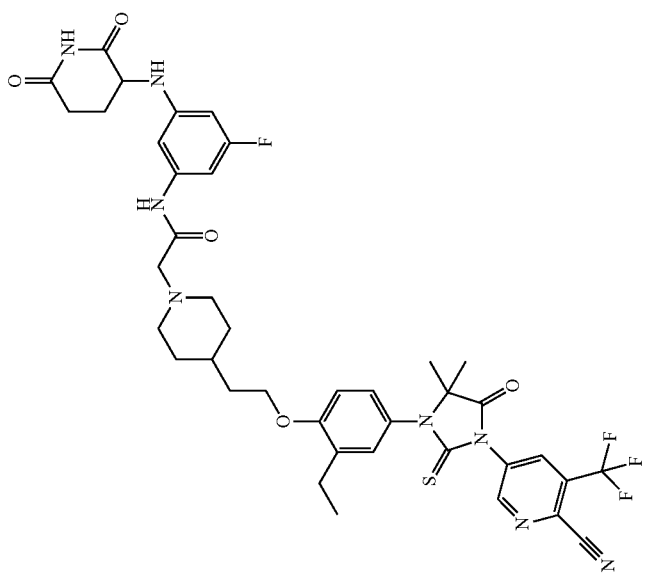 | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)-5-fluorophenyl)acetamide | 823.0 | C | * |

TABLE 1-continued

| Cmpd No. | Cmpd Structure | Cmpd Name | MH+ Obs. | DC$_{50}$ | Y |
|---|---|---|---|---|---|
| 17 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)acetamide | 804.4 | C | * |

TABLE 1-continued

| Cmpd No. | Cmpd Structure | Cmpd Name | MH+ Obs. | DC$_{50}$ | Y |
|---|---|---|---|---|---|
| 18 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(5-(2,6-dioxopiperidin-3-ylamino)-2-fluorophenyl)acetamide | 822.4 | B | * |

| Cmpd No. | Cmpd Structure | Cmpd Name | MH+ Obs. | DC50 | Y |
|---|---|---|---|---|---|
| 19 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)-5-fluorophenyl)acetamide | 822.2 | B | * |

TABLE 1-continued
| Cmpd No. | Cmpd Structure | Cmpd Name | MH+ Obs. | DC50 | Y |
|---|---|---|---|---|---|
| 20 | 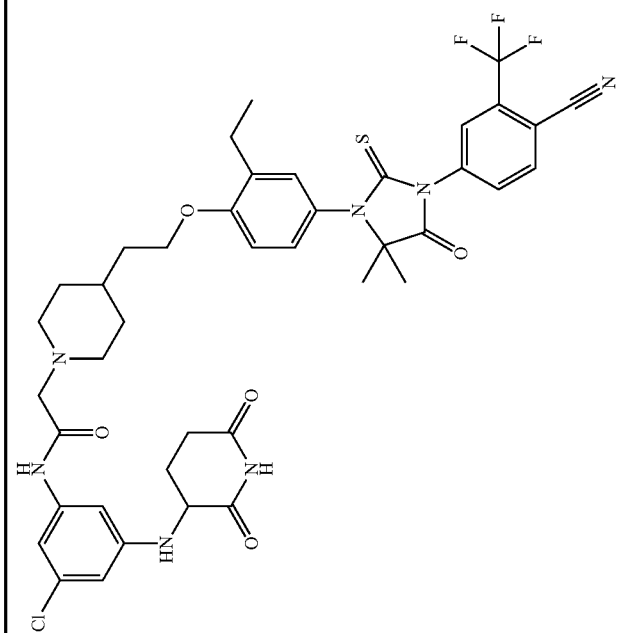 | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)acetamide | 838.2 | C | * |

TABLE 1-continued
| Cmpd No. | Cmpd Structure | Cmpd Name | MH+ Obs. | DC50 | Y |
|---|---|---|---|---|---|
| 21 | 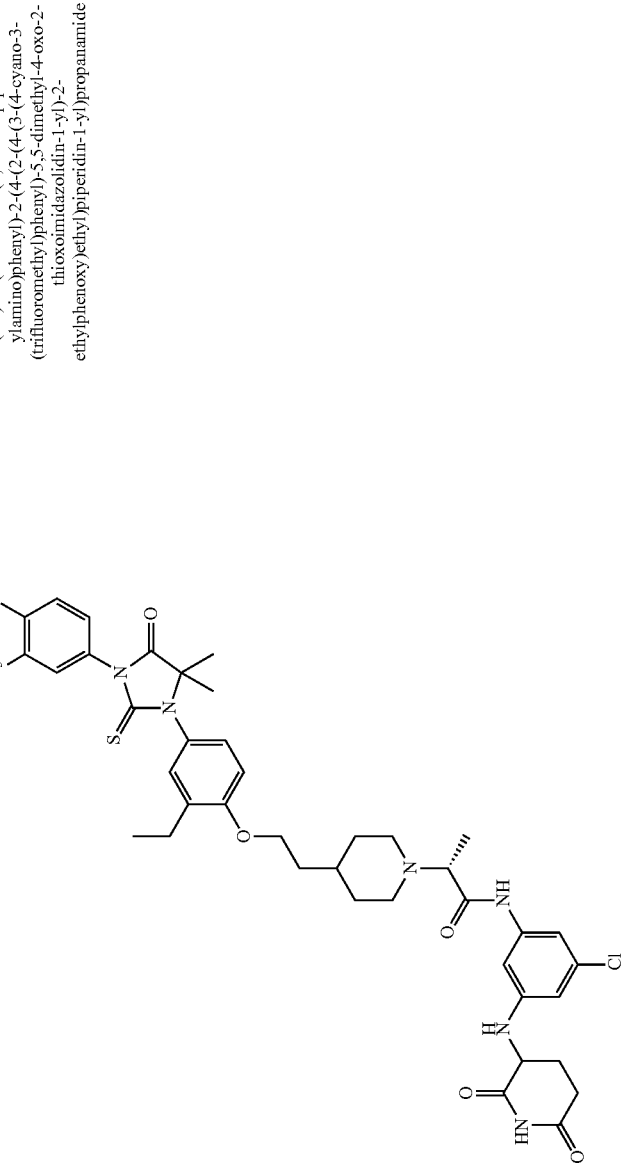 | (2R)-N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide | 853.2 | B | * |

| Cmpd No. | Cmpd Structure | Cmpd Name | MH+ Obs. | DC₅₀ | Y |
|---|---|---|---|---|---|
| 22 | | 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)-N-(3-(2,6-dioxopiperidin-3-ylamino)-5-fluorophenyl)acetamide | 859.2 | C | * |

TABLE 1-continued

| Cmpd No. | Cmpd Structure | Cmpd Name | MH+ Obs. | DC$_{50}$ | Y |
|---|---|---|---|---|---|
| 23 | | (2S)-N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide | 853.6 | C | * |

TABLE 1-continued
| Cmpd No. | Cmpd Structure | Cmpd Name | MH+ Obs. | DC50 | Y |
|---|---|---|---|---|---|
| 24 | 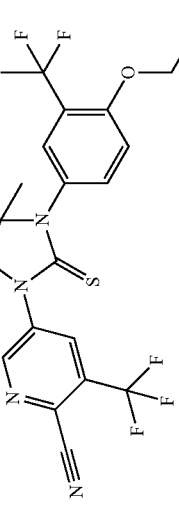 | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)acetamide | 875.0 | B | * |

TABLE 1-continued
| Cmpd No. | Cmpd Structure | Cmpd Name | MH+ Obs. | DC50 | Y |
|---|---|---|---|---|---|
| 25 | 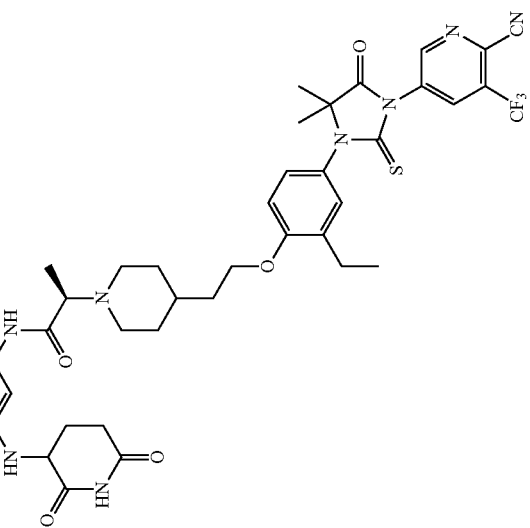 | (2R)-N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide | 853.7 | C | * |

TABLE 1-continued

| Cmpd No. | Cmpd Structure | Cmpd Name | MH+ Obs. | DC50 | Y |
|---|---|---|---|---|---|
| 26 | | (2S)-N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide | 853.2 | B | * |
| 27 | | N-(3-chloro-5-(2,6-dioxopiperidin-3-ylamino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)acetamide | 851.3 | C | * |

TABLE 1-continued

| Cmpd No. | Cmpd Structure | Cmpd Name | MH+ Obs. | DC50 | Y |
|---|---|---|---|---|---|
| 28 | | N-(3-chloro-5-(2,6-dioxopiperidin-3-ylamino)phenyl)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)acetamide | 851.3 | B | * |
| 29 | | 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)acetamide | 817.3 | C | * |

TABLE 1-continued

| Cmpd No. | Cmpd Structure | Cmpd Name | MH+ Obs. | DC50 | Y |
|---|---|---|---|---|---|
| 30 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(1,1-difluoroethyl)phenoxy)ethyl)piperidin-1-yl)acetamide | 874.2 | B | * |
| 31 Diast 1 | | (2R)-N-(3-chloro-5-(2,6-dioxopiperidin-3-ylamino)phenyl)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)propanamide | 864.3 | B | * |

TABLE 1-continued

| Cmpd No. | Cmpd Structure | Cmpd Name | MH+ Obs. | DC50 | Y |
|---|---|---|---|---|---|
| 32 Diast 2 | | or (2S)-N-(3-chloro-5-(2,6-dioxopiperidin-3-ylamino)phenyl)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)propanamide | 864.3 | B | ** |

TABLE 1-continued

| Cmpd No. | Cmpd Structure | Cmpd Name | MH+ Obs. | DC50 | Y |
|---|---|---|---|---|---|
| 33 | (structure shown) | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)acetamide | 856.2 | C | * |

TABLE 1-continued

| Cmpd No. | Cmpd Structure | Cmpd Name | MH+ Obs. | DC50 | Y |
|---|---|---|---|---|---|
| 34 | | N-(3-chloro-5-(2,6-dioxopiperidin-3-ylamino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxamide | 865.2 | A | *** |
| 35 Diast 1 | | (2S)-N-(3-chloro-5-(2,6-dioxopiperidin-3-ylamino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide | 865.2 | B | * | or

TABLE 1-continued

| Cmpd No. | Cmpd Structure | Cmpd Name | MH+ Obs. | DC$_{50}$ | Y |
|---|---|---|---|---|---|
| 36 Diast 2 | | (2R)-N-(3-chloro-5-(2,6-dioxopiperidin-3-ylamino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide | 865.3 | B | * |
| 37 | | (2S)-N-(3-cyano-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide | 844.0 | C | * |

TABLE 1-continued

| Cmpd No. | Cmpd Structure | Cmpd Name | MH+ Obs. | DC50 | Y |
|---|---|---|---|---|---|
| 38 | (structure) | (2R)-N-(3-cyano-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide | 844.0 | C | ** |

TABLE 1-continued

| Cmpd No. | Cmpd Structure | Cmpd Name | MH+ Obs. | DC50 | Y |
|---|---|---|---|---|---|
| 39 | (structure) | N-(3-cyano-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide | 830.0 | C | ** |

TABLE 1-continued

| Cmpd No. | Cmpd Structure | Cmpd Name | MH+ Obs. | DC50 | Y |
|---|---|---|---|---|---|
| 40 | (structure) | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-cyano-5-(2,6-dioxopiperidin-3-ylamino)phenyl)acetamide | 829.0 | B | ** |

TABLE 1-continued

| Cmpd No. | Cmpd Structure | Cmpd Name | MH+ Obs. | DC50 | Y |
|---|---|---|---|---|---|
| 41 | | (2S)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)propanamide | 818.2 | C | * |

| Cmpd No. | Cmpd Structure | Cmpd Name | MH+ Obs. | DC50 | Y |
|---|---|---|---|---|---|
| 42 | | (2R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)propanamide | 818.2 | B | ** |

TABLE 1-continued

| Cmpd No. | Cmpd Structure | Cmpd Name | MH+ Obs. | DC50 | Y |
|---|---|---|---|---|---|
| 43 | | 2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)acetamide | 838.3 (M + Na+) | C | * |
| 44 | | (S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((R)-2,6-dioxopiperidin-3-ylamino)phenyl)propanamide | 819.4 | C | * |

TABLE 1-continued

| Cmpd No. | Cmpd Structure | Cmpd Name | MH+ Obs. | DC$_{50}$ | Y |
|---|---|---|---|---|---|
| 45 |  | (R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((R)-2,6-dioxopiperidin-3-ylamino)phenyl)propanamide | 818.6 | C | * |
| 46 |  | (S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((S)-2,6-dioxopiperidin-3-ylamino)phenyl)propanamide | 819.4 | C | * |

TABLE 1-continued
| Cmpd No. | Cmpd Structure | Cmpd Name | MH+ Obs. | DC₅₀ | Y |
|---|---|---|---|---|---|
| 47 | 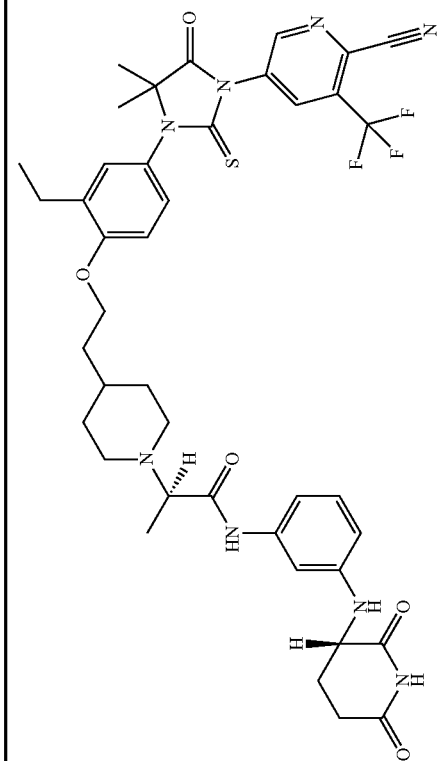 | (R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((S)-2,6-dioxopiperidin-3-ylamino)phenyl)propanamide | 819.4 | C | * |

TABLE 1-continued
| Cmpd No. | Cmpd Structure | Cmpd Name | MH+ Obs. | DC50 | Y |
|---|---|---|---|---|---|
| 48 | 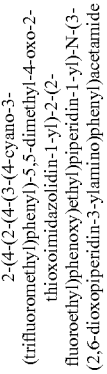 | 2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)acetamide | 822.1 | C | * |

| Cmpd No. | Cmpd Structure | Cmpd Name | MH+ Obs. | DC50 | Y |
|---|---|---|---|---|---|
| 49 | | N-(3-chloro-5-(2,6-dioxopiperidin-3-ylamino)phenyl)-2-(4-(4-(3-(4-cyano-3-(trifluoromethyl)phenyl)-5,5-dimethyl-4-oxo-2-thioxoimidazolidin-1-yl)-2-ethylphenoxy)piperidin-1-yl)acetamide | 810.2 | B | ** |

| Cmpd No. | Cmpd Structure | Cmpd Name | MH+ Obs. | DC50 | Y |
|---|---|---|---|---|---|
| 50 | | 2-(4-(4-(3-(4-cyano-3-(trifluoromethyl)phenyl)-5,5-dimethyl-4-oxo-2-thioxoimidazolidin-1-yl)-2-ethylphenoxy)piperidin-1-yl)-N-(3-(2,6-dioxopiperidin-3-ylamino)phenyl)acetamide | 776.2 | B | ** |

| Cmpd No. | Cmpd Structure | Cmpd Name | MH+ Obs. | DC50 | Y |
|---|---|---|---|---|---|
| 51 | | N-(3-chloro-5-(2,6-dioxopiperidin-3-ylamino)phenyl)-2-(4-(4-(3-(6-cyano-5-(trifluoromethyl)pyridin-3-yl)-5,5-dimethyl-4-oxo-2-thioxoimidazolidin-1-yl)-2-ethylphenoxy)piperidin-1-yl)acetamide | 811.2 | C | * |

TABLE 1-continued

| Cmpd No. | Cmpd Structure | Cmpd Name | MH+ Obs. | DC50 | Y |
|---|---|---|---|---|---|
| 52 | | 2-(4-(4-(3-(6-cyano-5-(trifluoromethyl)pyridin-3-yl)-5,5-dimethyl-4-oxo-2-thioxoimidazolidin-1-yl)-2-ethylphenoxy)piperidin-1-yl)-N-(5-(2,6-dioxopiperidin-3-ylamino)-2-fluorophenyl)acetamide | 795.2 | B | *** |

TABLE 1-continued

| Cmpd No. | Cmpd Structure | Cmpd Name | MH+ Obs. | DC50 | Y |
|---|---|---|---|---|---|
| 53 | | 2-(4-(4-(3-(6-cyano-5-(trifluoromethyl)pyridin-3-yl)-5,5-dimethyl-4-oxo-2-thioxoimidazolidin-1-yl)-2-ethylphenoxy)piperidin-1-yl)-N-(3-(2,6-dioxopiperidin-3-ylamino)phenyl)acetamide | 777.2 | C | ** |
| 54 Diast 1 | | 2-((R)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-(2,6-dioxopiperidin-3-ylamino)phenyl)acetamide | 845.3 | C | * | or or

TABLE 1-continued

| Cmpd No. | Cmpd Structure | Cmpd Name | MH+ Obs. | DC50 | Y |
|---|---|---|---|---|---|
| 55 Diast 2 | | 2-((S)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-(2,6-dioxopiperidin-3-ylamino)phenyl)acetamide | 845.3 | B | * |
| 56 | | 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)acetamide | 835.4 | B | * |

TABLE 1-continued

| Cmpd No. | Cmpd Structure | Cmpd Name | MH+ Obs. | DC50 | Y |
|---|---|---|---|---|---|
| 57 | (structure) | 2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)acetamide | 834.4 | B | * |

TABLE 1-continued

| Cmpd No. | Cmpd Structure | Cmpd Name | MH+ Obs. | DC$_{50}$ | Y |
|---|---|---|---|---|---|
| 58 |  | 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)acetamide | 823.3 | C | * |

TABLE 1-continued
| Cmpd No. | Cmpd Structure | Cmpd Name | MH+ Obs. | DC50 | Y |
|---|---|---|---|---|---|
| 59 Diast 1 | 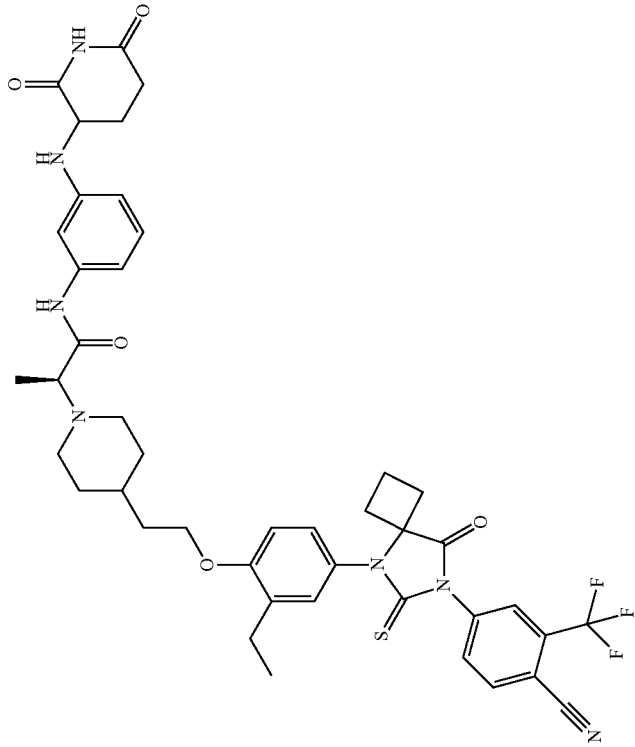 | (2S)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide | 852.1 (M + Na+) | B | ** |
or TABLE 1-continued

| Cmpd No. | Cmpd Structure | Cmpd Name | MH+ Obs. | DC50 | Y |
|---|---|---|---|---|---|
| 60 Diast 2 | | (2R)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide | 852.1 (M + Na+) | B | ** |
| 61 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4-methylpiperidin-1-yl)-N-(3-(2,6-dioxopiperidin-3-ylamino)phenyl)acetamide | 819.2 | C | * |

TABLE 1-continued

| Cmpd No. | Cmpd Structure | Cmpd Name | MH+ Obs. | DC50 | Y |
|---|---|---|---|---|---|
| 62 Diast 1 | 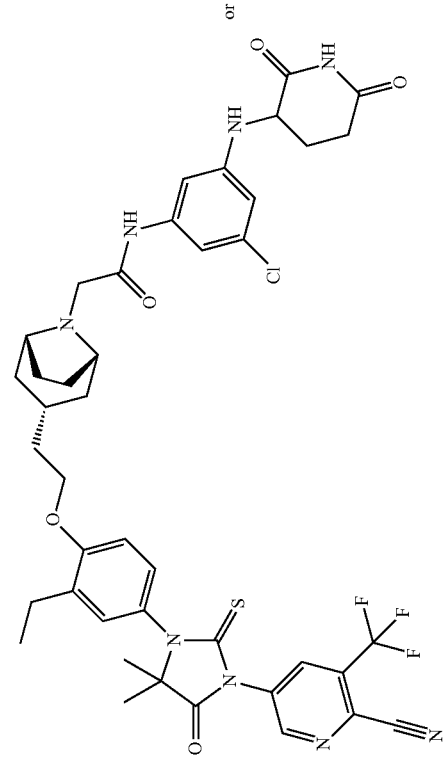 | N-(3-chloro-5-(2,6-dioxopiperidin-3-ylamino)phenyl)-2-((1R,3s,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)acetamide | 865.0 | C | * |
| | or | or | | | |
| 63 Diast 2 | 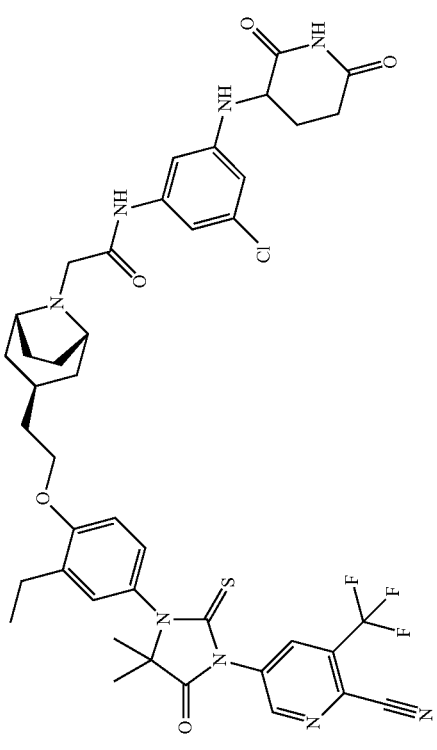 | N-(3-chloro-5-(2,6-dioxopiperidin-3-ylamino)phenyl)-2-((1R,3r,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)acetamide | 865.0 | C | ** |

TABLE 1-continued

| Cmpd No. | Cmpd Structure | Cmpd Name | MH+ Obs. | DC50 | Y |
|---|---|---|---|---|---|
| 64 | 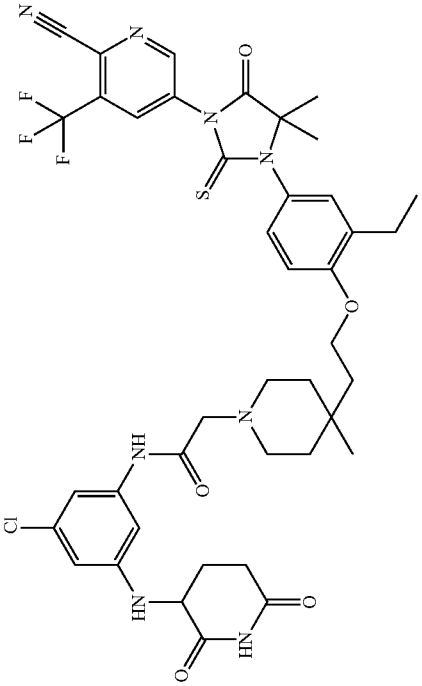 | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4-methylpiperidin-1-yl)acetamide | 853.2 | B | * |
| 65 Diast 1 | 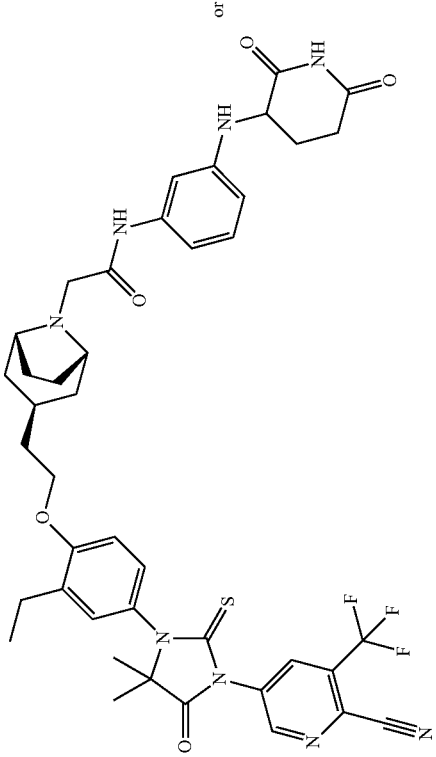 | 2-((1R,3r,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)-N-(3-(2,6-dioxopiperidin-3-ylamino)phenyl)acetamide | 831.0 | C | * | or

TABLE 1-continued

| Cmpd No. | Cmpd Structure | Cmpd Name | MH+ Obs. | DC50 | Y |
|---|---|---|---|---|---|
| 66 Diast 2 | | 2-((1R,3s,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)-N-(3-(2,6-dioxopiperidin-3-ylamino)phenyl)acetamide | 831.0 | C | * | or

| 67 Diast 1 | | 2-((1R,3r,5S)-3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-(2,6-dioxopiperidin-3-ylamino)phenyl)acetamide | 843.0 | C | ** | or

TABLE 1-continued

| Cmpd No. | Cmpd Structure | Cmpd Name | MH+ Obs. | DC50 | Y |
|---|---|---|---|---|---|
| 68 Diast 2 | | 2-((1R,3s,5S)-3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-(2,6-dioxopiperidin-3-ylamino)phenyl)acetamide | 843.0 | C | * |
| 69 | | N-(3-chloro-5-(2,6-dioxopiperidin-3-ylamino)phenyl)-2-((1R,5S)-3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)acetamide | 877.0 | B | ** |

TABLE 1-continued
| Cmpd No. | Cmpd Structure | Cmpd Name | MH+ Obs. | DC50 | Y |
|---|---|---|---|---|---|
| 70 | 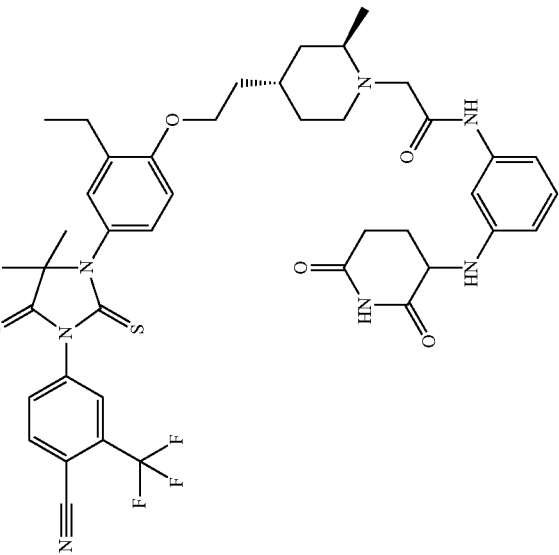 | 2-((2R,4S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide | 818.21 | C | * |

TABLE 1-continued

| Cmpd No. | Cmpd Structure | Cmpd Name | MH+ Obs. | DC50 | Y |
|---|---|---|---|---|---|
| 71 | | 2-((2R,4R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide | 818.2 | C | * |

TABLE 1-continued

| Cmpd No. | Cmpd Structure | Cmpd Name | MH+ Obs. | DC50 | Y |
|---|---|---|---|---|---|
| 72 Diast 1 | 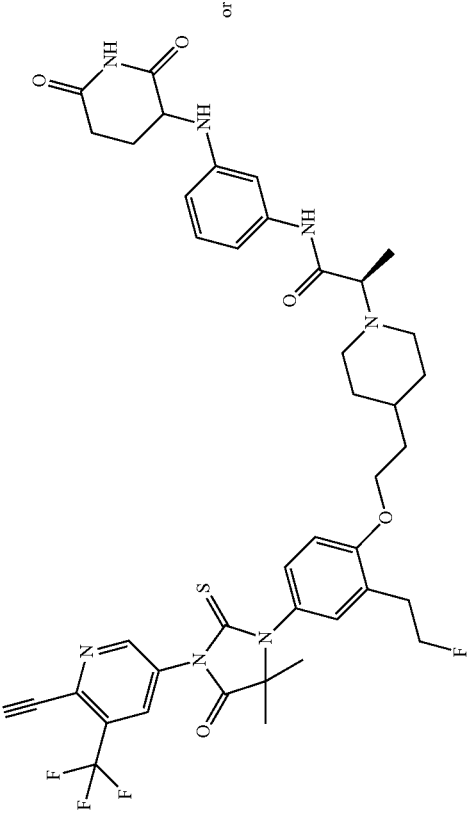 | (2R)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)propanamide or | 837.3 | C | * |
| 73 Diast 2 | 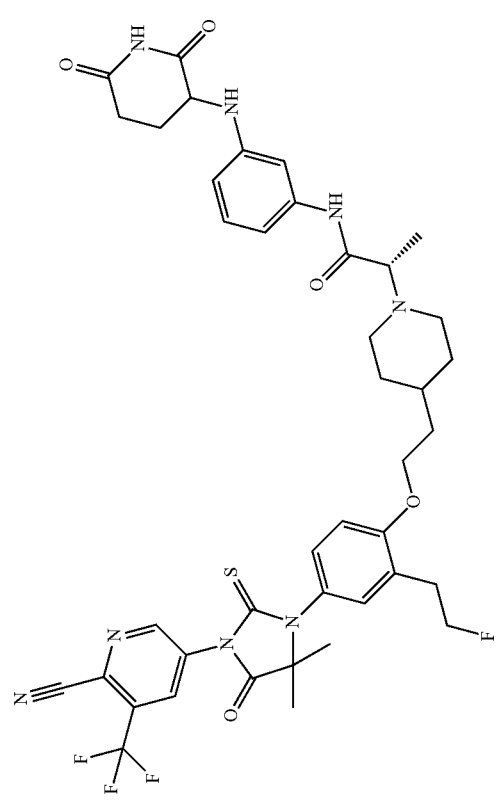 | (2S)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)propanamide | 837.3 | C | * |

TABLE 1-continued

| Cmpd No. | Cmpd Structure | Cmpd Name | MH+ Obs. | DC50 | Y |
|---|---|---|---|---|---|
| 74 Diast 1 | | (2S)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide | 848.4 | B | ** |
| | | or | | | |
| 75 Diast 2 | | (2R)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide | 848.4 | B | ** |

TABLE 1-continued

| Cmpd No. | Cmpd Structure | Cmpd Name | MH+ Obs. | DC50 | Y |
|---|---|---|---|---|---|
| 76 | | 2-((2R,4S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide | 819.2 | C | * |
| 77 | | 2-((2R,4S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(5-(2,6-dioxopiperidin-3-ylamino)-2-fluorophenyl)acetamide | 837.2 | B | * |

TABLE 1-continued

| Cmpd No. | Cmpd Structure | Cmpd Name | MH+ Obs. | $DC_{50}$ | Y |
|---|---|---|---|---|---|
| 78 | (structure) | 2-((2R,4R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide | 819.2 | C | * |

TABLE 1-continued
| Cmpd No. | Cmpd Structure | Cmpd Name | MH+ Obs. | DC50 | Y |
|---|---|---|---|---|---|
| 79 | 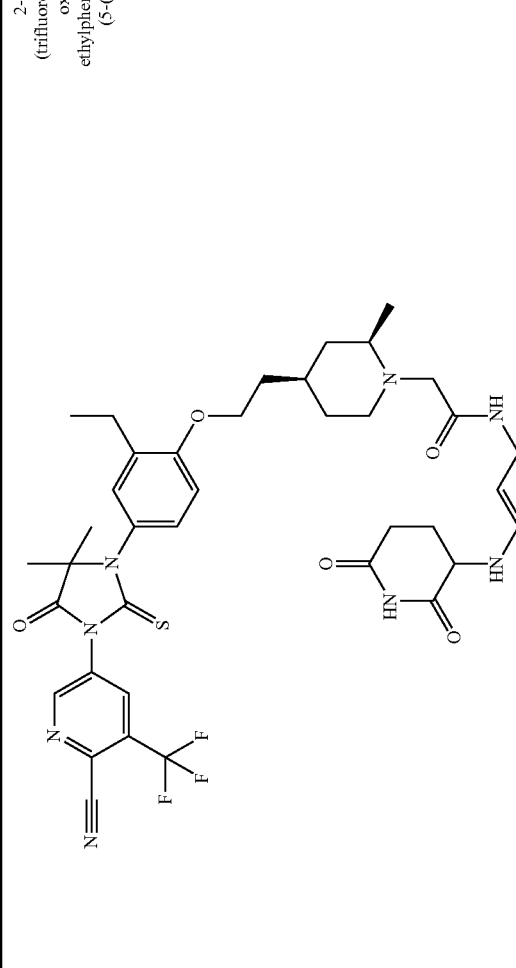 | 2-((2R,4R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(5-(2,6-dioxopiperidin-3-ylamino)-2-fluorophenyl)acetamide | 837.0 | B | ** |

TABLE 1-continued

| Cmpd No. | Cmpd Structure | Cmpd Name | MH+ Obs. | DC50 | Y |
|---|---|---|---|---|---|
| 80 | | 2-(4-((4-(3-(6-cyano-5-(trifluoromethyl)pyridin-3-yl)-5,5-dimethyl-4-oxo-2-thioxoimidazolidin-1-yl)-2-ethylphenoxy)methyl)piperidin-1-yl)-N-(3-(2,6-dioxopiperidin-3-ylamino)phenyl)acetamide | 791.0 | C | ** |
| 81 | | N-(3-chloro-5-(2,6-dioxopiperidin-3-ylamino)phenyl)-2-(4-((4-(3-(6-cyano-5-(trifluoromethyl)pyridin-3-yl)-5,5-dimethyl-4-oxo-2-thioxoimidazolidin-1-yl)-2-ethylphenoxy)methyl)piperidin-1-yl)acetamide | 825.0 | C | ** |

TABLE 1-continued

| Cmpd No. | Cmpd Structure | Cmpd Name | MH+ Obs. | DC50 | Y |
|---|---|---|---|---|---|
| 82 | | 2-((2R,4S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperidin-1-yl)-N-(5-(2,6-dioxopiperidin-3-ylamino)-2-fluorophenyl)acetamide | 836.4 | B | ** |
| 83 Diast 1 | | (2S)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide | 831.3 | C | * | or

TABLE 1-continued

| Cmpd No. | Cmpd Structure | Cmpd Name | MH+ Obs. | DC50 | Y |
|---|---|---|---|---|---|
| 84 Diast 2 | | (2R)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide | 831.3 | C | * |
| 85 Diast 1 | | (2S)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide | 849.3 | B | * | or

TABLE 1-continued

| Cmpd No. | Cmpd Structure | Cmpd Name | MH+ Obs. | DC50 | Y |
|---|---|---|---|---|---|
| 86 Diast 2 | | (2R)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide | 849.3 | B | * |
| 87 | | 2-((1R,3s,5S)-3-(4-(3-(6-cyano-5-(trifluoromethyl)pyridin-3-yl)-5,5-dimethyl-4-oxo-2-thioxoimidazolidin-1-yl)-2-ethylphenoxy)-8-azabicyclo[3.2.1]octan-8-yl)-N-(3-(2,6-dioxopiperidin-3-ylamino)phenyl)acetamide | 803.6 | A | *** |

TABLE 1-continued

| Cmpd No. | Cmpd Structure | Cmpd Name | MH+ Obs. | DC50 | Y |
|---|---|---|---|---|---|
| 88 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-4-fluoropiperidin-1-yl)-N-(3-(2,6-dioxopiperidin-3-ylamino)phenyl)acetamide | 822.3 | C | * |

TABLE 1-continued
| Cmpd No. | Cmpd Structure | Cmpd Name | MH+ Obs. | DC50 | Y |
|---|---|---|---|---|---|
| 89 |  | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4-fluoropiperidin-1-yl)-N-(3-(2,6-dioxopiperidin-3-ylamino)phenyl)acetamide | 823.2 | C | * |

TABLE 1-continued
| Cmpd No. | Cmpd Structure | Cmpd Name | MH+ Obs. | DC50 | Y |
|---|---|---|---|---|---|
| 90 | 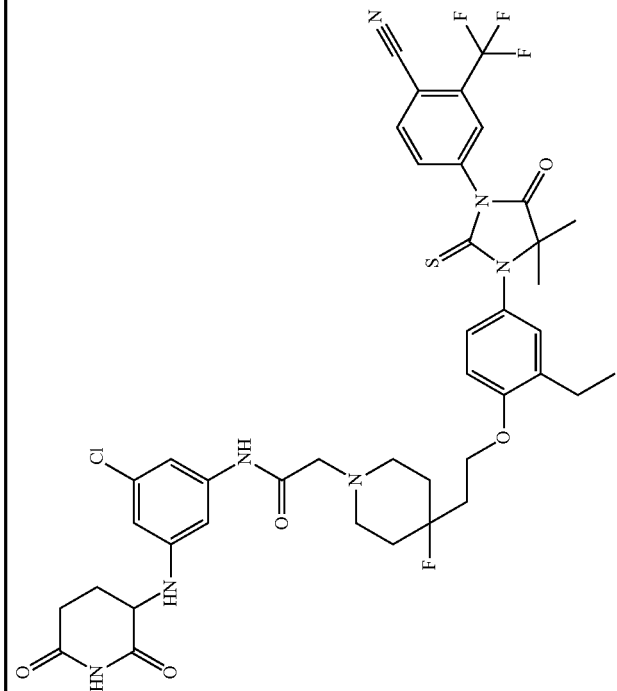 | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-4-fluoropiperidin-1-yl)acetamide | 856.2 | C | * |

TABLE 1-continued

| Cmpd No. | Cmpd Structure | Cmpd Name | MH+ Obs. | DC50 | Y |
|---|---|---|---|---|---|
| 91 | | 2-((2R,4R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2-methylpiperidin-1-yl)-N-(3-(2,6-dioxopiperidin-3-ylamino)phenyl)acetamide | 832.4 | A | ** |
| 92 | | 2-((2S,4S)-4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide | 819.5 | | |
| 93 | | 2-((2S,4R)-4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl)acetamide | 819.3 | | |

TABLE 1-continued

| Cmpd No. | Cmpd Structure | Cmpd Name | MH+ Obs. | DC50 | Y |
|---|---|---|---|---|---|
| 94 | | 2-((2S,4r,6R)-4-(2-((5-(3-(4-cyano-3-(trifluoromethyl)phenyl)-5,5-dimethyl-4-oxo-2-thioxoimidazolidin-1-yl)-3-isopropylpyridin-2-yl)oxy)ethyl)-2,6-dimethylpiperidin-1-yl)-N-(3-((2,6-dioxopiperidin-3-yl)amino)phenyl)acetamide | 846.3 | A | ** |
| 95 | | 2-((2R,4r,6S)-4-((5-(3-(4-cyano-3-(trifluoromethyl)phenyl)-5,5-dimethyl-4-oxo-2-thioxoimidazolidin-1-yl)-3-ethylpyridin-2-yl)oxy)-2,6-dimethylpiperidin-1-yl)-N-(3-((2,6-dioxopiperidin-3-yl)amino)phenyl)acetamide | 804.3 | A | ** |

A number of references have been cited, the disclosures of which are incorporated herein by reference in their entirety.

What is claimed is:

1. A compound of formula (I)

[chemical structure]

or a pharmaceutically acceptable salt thereof,
wherein
$R^N$ is H;
each $R^1$ is independently selected from halogen, CN, and $C_{1-3}$ alkyl;
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;
each $R^4$ is independently selected from substituted or unsubstituted $C_{1-3}$ alkyl;
X is $CR^x$;
$R^x$ is H, halogen, or substituted or unsubstituted $C_{1-3}$ alkyl;
L is —O—, or —O(CH$_2$)$_p$—;
n is 0-4;
m is 0-8;
p is 1-3;
V is

[chemical structure]

wherein
A is N, CH, or $CR^A$;
B is N, CH or $CR^B$;
each $R^A$ is independently selected from halogen, substituted or unsubstituted $C_{1-6}$ alkyl, and substituted and unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-5}$ cycloalkyl or a 3-5 membered heterocyclyl;
a is 0-3; and
b is 0-2.

2. The compound of claim 1, wherein each $R^1$ is independently selected from Cl, F, Br, CN, —CH$_3$, and —CH$_2$CH$_3$.

3. The compound of claim 1, wherein each $R^1$ is independently selected from Cl, F, and CN.

4. The compound of claim 1, wherein n is 0.

5. The compound of claim 1, wherein n is 1.

6. The compound of claim 1, wherein $R^2$ and $R^3$ are each independently selected from H, substituted or unsubstituted methyl, and ethyl, or $R^2$ and $R^3$ and the carbon to which they are attached form a substituted or unsubstituted cyclopropyl, cyclobutyl or cyclopentyl.

7. The compound of claim 1, wherein $R^2$ and $R^3$ are each independently selected from H and methyl, or wherein $R^2$ and $R^3$ and the carbon to which they are attached form an unsubstituted cyclopropyl.

8. The compound of claim 1, wherein $R^2$ and $R^3$ are both H or methyl, or wherein $R^2$ and $R^3$ and the carbon to which they are attached form an unsubstituted cyclopropyl.

9. The compound of claim 1, wherein each $R^4$ is independently selected from substituted or unsubstituted methyl and ethyl.

10. The compound of claim 1, wherein each $R^4$ is independently selected from substituted or unsubstituted methyl.

11. The compound of claim 1, wherein each $R^4$ is independently selected from methyl and CH$_2$OH.

12. The compound of claim 1, wherein m is 0, 1, 2, 3 or 4.

13. The compound of claim 1, wherein m is 0, 1, or 2.

14. The compound of claim 1, wherein $R^x$ is H.

15. The compound of claim 1, wherein $R^x$ is CH$_3$.

16. The compound of claim 1, wherein $R^x$ is F.

17. The compound of claim 1, wherein L is —O—, —O(CH$_2$)—, or —O(CH$_2$(CH$_2$)—.

18. The compound of claim 1, wherein A is CH.

19. The compound of claim 1, wherein B is CH.

20. The compound of claim 1, wherein B is N.

21. The compound of claim 1, wherein a is 0, 1 or 2.

22. The compound of claim 18, wherein each $R^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CH$_2$C(CH$_3$)$_3$, CF$_3$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopopyl, cyclobutyl, and cyclopentyl.

23. The compound of claim 1, wherein each $R^A$ is independently selected from Cl, F, ethyl, isopropyl, CF$_2$CH$_3$, and CH$_2$CH$_2$F.

24. The compound of claim 19, wherein each $R^A$ is independently selected from Cl, F, ethyl, isopropyl, CF$_2$CH$_3$, and CH$_2$CH$_2$F.

25. The compound of claim 20, wherein each $R^A$ is independently selected from Cl, ethyl, isopropyl, CF$_2$CH$_3$ and CH$_2$CH$_2$F.

26. The compound of claim 1, wherein b is 0.

27. The compound of claim 1, wherein $R^C$ is CF$_3$.

28. The compound of claim 1, wherein $R^5$ and $R^6$ are methyl, or $R^5$ and $R^6$, together with the carbon atom to which they are attached, form a cyclopropyl, cyclobutyl, tetrahydrofuranyl, or tetrahydropyranyl.

29. The compound of claim 1, wherein $R^5$ and $R^6$ are methyl, or $R^5$ and $R^6$, together with the carbon atom to which they are attached, form a cyclobutyl.

30. A compound
2-(4-(4-(3-(4-cyano-3-(trifluoromethyl)phenyl)-5,5-dimethyl-4-oxo-2-thioxoimidazolidin-1-yl)-2-fluorophenoxy)piperidin-1-yl)-N-(3-(2,6-dioxopiperidin-3-ylamino)phenyl)acetamide,
2-(4-((4-(3-(4-cyano-3-(trifluoromethyl)phenyl)-5,5-dimethyl-4-oxo-2-thioxoimidazolidin-1-yl)-2-fluorophenoxy)methyl)piperidin-1-yl)-N-(3-(2,6-dioxopiperidin-3-ylamino)phenyl)acetamide,
2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperidin-1-yl)-N-(3-(2,6-dioxopiperidin-3-ylamino)phenyl)acetamide, 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperidin-1-yl)-N-(3-(2,6-dioxopiperidin-3-ylamino)phenyl)acetamide, 2-(4-(2-(2-chloro-4-(3-(6-cyano-5-(trifluoromethyl)pyridin-3-yl)-5,5-dimethyl-4-oxo-2-thioxoimidazolidin-1-yl)phenoxy)ethyl)piperidin-1-yl)-N-(3-(2,6-dioxopiperidin-3-ylamino)phenyl)acetamide, 2-(4-((4-(3-(6-cyano-5-(trifluoromethyl)pyridin-3-yl)-5,5-dimethyl-4-oxo-2-thioxoimidazolidin-1-yl)phenoxy)methyl)piperidin-1-yl)-N-(3-(2,6-dioxopiperidin-3-ylamino)phenyl)acetamide, 2-(4-((2-chloro-4-(3-(6-cyano-5-(trifluoromethyl)pyridin-3-yl)-5,5-dimethyl-4-oxo-2-thioxoimidazolidin-1-yl)phenoxy)methyl)piperidin-1-yl)-N-(3-(2,6-dioxopiperidin-3-ylamino)phenyl)acetamide, 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperidin-1-yl)-N-(3-chloro-5-(2,6-dioxopiperidin-3-ylamino)phenyl)acetamide, 2-(4-((2-chloro-4-(3-(4-cyano-3-(trifluoromethyl)phenyl)-5,5-dimethyl-4-oxo-2-thioxoimidazolidin-1-yl)phenoxy)methyl)piperidin-1-yl)-N-(3-chloro-5-(2,6-dioxopiperidin-3-ylamino)phenyl)acetamide, N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperidin-1-yl)acetamide, 2-(4-((4-(3-(4-cyano-3-(trifluoromethyl)phenyl)-5,5-dimethyl-4-oxo-2-thioxoimidazolidin-1-yl)-2-ethylphenoxy)methyl)piperidin-1-yl)-N-(3-(2,6-dioxopiperidin-3-ylamino)phenyl)acetamide, 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)acetamide, N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide, N-(2-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide, 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(5-(2,6-dioxopiperidin-3-ylamino)-2-fluorophenyl)acetamide, 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)-5-fluorophenyl)acetamide, 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)acetamide, 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(5-(2,6-dioxopiperidin-3-ylamino)-2-fluorophenyl)acetamide, 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)-5-fluorophenyl)acetamide, N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)acetamide, (2R)—N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide, 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)-N-(3-(2,6-dioxopiperidin-3-ylamino)-5-fluorophenyl)acetamide, (2S)—N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide, N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperidin-1-yl)acetamide, (2R)—N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide, (2S)—N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)propanamide, N-(3-chloro-5-(2,6-dioxopiperidin-3-ylamino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)acetamide, N-(3-chloro-5-(2,6-dioxopiperidin-3-ylamino)phenyl)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)acetamide, 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)acetamide, N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(1,1-difluoroethyl)phenoxy)ethyl)piperidin-1-yl)acetamide, (2R)—N-(3-chloro-5-(2,6-dioxopiperidin-3-ylamino)phenyl)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)propanamide, (2S)—N-(3-chloro-5-(2,6-dioxopiperidin-3-ylamino)phenyl)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)propanamide, N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)acetamide, N-(3-chloro-5-(2,6-dioxopiperidin-3-ylamino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)cyclopropanecarboxamide, (2S)—N-(3-chloro-5-(2,6-dioxopiperidin-3-ylamino)phenyl)-2-(4-(2-(4-(7-(6-cyano-5-(trifluoromethyl)

pyridin-3-yl)-8-oxo-6-thioxo-5,7-diazaspiro[3.4]octan-5-yl)-2-ethylphenoxy)ethyl)piperidin-1-yl)propanamide, (2R)—N-(3-chloro-5-(2,6-dioxopiperidin-3-ylamino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)propanamide, (2S)—N-(3-cyano-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide, (2R)—N-(3-cyano-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanamide, N-(3-cyano-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)acetamide, 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-cyano-5-(2,6-dioxopiperidin-3-ylamino)phenyl)acetamide, (2S)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)propanamide, (2R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperidin-1-yl)-N-(3-(2,6-dioxopiperidin-3-ylamino)phenyl)propanamide, 2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)acetamide, (S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((R)-2,6-dioxopiperidin-3-ylamino)phenyl)propanamide, (R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((R)-2,6-dioxopiperidin-3-ylamino)phenyl)propanamide, (S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((S)-2,6-dioxopiperidin-3-ylamino)phenyl)propanamide, (R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperidin-1-yl)-N-(3-((S)-2,6-dioxopiperidin-3-ylamino)phenyl)propanamide, 2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)acetamide, N-(3-chloro-5-(2,6-dioxopiperidin-3-ylamino)phenyl)-2-(4-(4-(3-(4-cyano-3-(trifluoromethyl)phenyl)-5,5-dimethyl-4-oxo-2-thioxoimidazolidin-1-yl)-2-ethylphenoxy)piperidin-1-yl)acetamide, 2-(4-(4-(3-(4-cyano-3-(trifluoromethyl)phenyl)-5,5-dimethyl-4-oxo-2-thioxoimidazolidin-1-yl)-2-ethylphenoxy)piperidin-1-yl)-N-(3-(2,6-dioxopiperidin-3-ylamino)phenyl)acetamide, N-(3-chloro-5-(2,6-dioxopiperidin-3-ylamino)phenyl)-2-(4-(4-(3-(6-cyano-5-(trifluoromethyl)pyridin-3-yl)-5, 5-dimethyl-4-oxo-2-thioxoimidazolidin-1-yl)-2-ethylphenoxy)piperidin-1-yl)acetamide, 2-(4-(4-(3-(6-cyano-5-(trifluoromethyl)pyridin-3-yl)-5,5-dimethyl-4-oxo-2-thioxoimidazolidin-1-yl)-2-ethylphenoxy)piperidin-1-yl)-N-(5-(2,6-dioxopiperidin-3-ylamino)-2-fluorophenyl)acetamide, 2-(4-(4-(3-(6-cyano-5-(trifluoromethyl)pyridin-3-yl)-5,5-dimethyl-4-oxo-2-thioxoimidazolidin-1-yl)-2-ethylphenoxy)piperidin-1-yl)-N-(3-(2,6-dioxopiperidin-3-ylamino)phenyl)acetamide, 2-((R)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-(2,6-dioxopiperidin-3-ylamino)phenyl)acetamide, 2-((S)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperidin-1-yl)-N-(3-(2,6-dioxopiperidin-3-ylamino)phenyl)acetamide, 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)acetamide, 2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)acetamide, 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)acetamide, (2S)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide, (2R)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide, 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4-methylpiperidin-1-yl)-N-(3-(2,6-dioxopiperidin-3-ylamino)phenyl)acetamide, N-(3-chloro-5-(2,6-dioxopiperidin-3-ylamino)phenyl)-2-((1R,3s,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)acetamide, N-(3-chloro-5-(2,6-dioxopiperidin-3-ylamino)phenyl)-2-((1R,3r,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)acetamide, N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4-methylpiperidin-1-yl)acetamide, 2-((1R,3r,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)-N-(3-(2,6-dioxopiperidin-3-ylamino)phenyl)acetamide, 2-((1R,3s,5S)-3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-8-azabicyclo[3.2.1]octan-8-yl)-N-(3-(2,6-dioxopiperidin-3-ylamino)phenyl)acetamide, 2-((1R,3r,5S)-3-(2-(4-(7-(6-cyano-5-(trifluoromethyl) pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-(2,6-dioxopiperidin-3-ylamino)phenyl) acetamide, 2-((1R,3s,5S)-3-(2-(4-(7-(6-cyano-5-(trifluoromethyl) pyridin-3-yl)-8-oxo-6-thioxo-5,7-diazaspiro[3.4]octan-5-yl)-2-ethylphenoxy)ethyl)-8-azabicyclo[3.2.1]octan-8-yl)-N-(3-(2,6-dioxopiperidin-3-ylamino)phenyl) acetamide, N-(3-chloro-5-(2,6-dioxopiperidin-3-ylamino)phenyl)-2-((1R,5S)-3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-8-azabicyclo[3.2.1]octan-8-yl)acetamide, 2-((2R,4S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide, 2-((2R,4R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide, (2R)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)propanamide, (2S)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperidin-1-yl)-N-(3-(2,6-dioxopiperidin-3-ylamino)phenyl)propanamide, (2S)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide, (2R)-2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide, 2-((2R,4S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide, 2-((2R,4S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(5-(2,6-dioxopiperidin-3-ylamino)-2-fluorophenyl) acetamide, 2-((2R,4R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(3-(2,6-dioxopiperidin-3-ylamino)phenyl)acetamide, 2-((2R,4R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperidin-1-yl)-N-(5-(2,6-dioxopiperidin-3-ylamino)-2-fluorophenyl) acetamide, 2-(4-((4-(3-(6-cyano-5-(trifluoromethyl)pyridin-3-yl)-5,5-dimethyl-4-oxo-2-thioxoimidazolidin-1-yl)-2-ethylphenoxy)methyl)piperidin-1-yl)-N-(3-(2,6-dioxopiperidin-3-ylamino)phenyl)acetamide, N-(3-chloro-5-(2,6-dioxopiperidin-3-ylamino)phenyl)-2-(4-((4-(3-(6-cyano-5-(trifluoromethyl)pyridin-3-yl)-5,5-dimethyl-4-oxo-2-thioxoimidazolidin-1-yl)-2-ethylphenoxy)methyl)piperidin-1-yl)acetamide, 2-((2R,4S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperidin-1-yl)-N-(5-(2,6-dioxopiperidin-3-ylamino)-2-fluorophenyl) acetamide, (2S)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide, (2R)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(3-(2,6-dioxopiperidin-3-ylamino)phenyl)propanamide, (2S)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide, (2R)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperidin-1-yl)-N-(5-(2,6-dioxopiperidin-3-ylamino)-2-fluorophenyl)propanamide, 2-((1R,3s,5S)-3-(4-(3-(6-cyano-5-(trifluoromethyl)pyridin-3-yl)-5,5-dimethyl-4-oxo-2-thioxoimidazolidin-1-yl)-2-ethylphenoxy)-8-azabicyclo[3.2.1]octan-8-yl)-N-(3-(2,6-dioxopiperidin-3-ylamino)phenyl)acetamide, 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-4-fluoropiperidin-1-yl)-N-(3-(2,6-dioxopiperidin-3-ylamino)phenyl)acetamide, 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4-fluoropiperidin-1-yl)-N-(3-(2,6-dioxopiperidin-3-ylamino)phenyl)acetamide, N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-4-fluoropiperidin-1-yl)acetamide, 2-((2R,4R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2-methylpiperidin-1-yl)-N-(3-(2,6-dioxopiperidin-3-ylamino)phenyl)acetamide, 2-((2S,4S)-4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl) acetamide, 2-((2S,4R)-4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)-2-methylpiperidin-1-yl)-N-(3-((2,6-dioxopiperidin-3-yl)amino)phenyl) acetamide, 2-((2S,4r,6R)-4-(2-((5-(3-(4-cyano-3-(trifluoromethyl) phenyl)-5,5-dimethyl-4-oxo-2-thioxoimidazolidin-1-yl)-3-isopropylpyridin-2-yl)oxy)ethyl)-2,6-dimethylpiperidin-1-yl)-N-(3-((2,6-dioxopiperidin-3-yl)amino) phenyl)acetamide, 2-((2R,4r,6S)-4-((5-(3-(4-cyano-3-(trifluoromethyl)phenyl)-5,5-dimethyl-4-oxo-2-thioxoimidazolidin-1-yl)-3-ethylpyridin-2-yl)oxy)-2,6-dimethylpiperidin-1-yl)-N-(3-((2,6-dioxopiperidin-3-yl)amino)phenyl)acetamide, or a pharmaceutically acceptable salt thereof.

31. A pharmaceutical composition comprising an effective amount of a compound of claim 1, or a pharmaceutically acceptable salt thereof, and a pharmaceutically acceptable carrier, excipient or vehicle.

32. A method for the treatment of an androgen receptor mediated disease, the method comprising administering to a subject in need thereof an effective amount of a compound of claim 1, wherein the androgen mediated disease is prostate cancer.

33. A method for the treatment of an androgen receptor mediated disease, the method comprising administering to a subject in need thereof an effective amount of the pharmaceutical composition of claim 31, wherein the androgen mediated disease is prostate cancer.

34. The method of claim 32, wherein the prostate cancer is castration resistant prostate cancer (CRPC).

35. The method of claim 33, wherein the prostate cancer is castration resistant prostate cancer (CRPC).

* * * * *